(12) United States Patent
Lashinski et al.

(10) Patent No.: US 11,219,462 B2
(45) Date of Patent: *Jan. 11, 2022

(54) DEVICES, SYSTEMS, AND METHODS FOR TREATING THE LEFT ATRIAL APPENDAGE

(71) Applicant: Laminar, Inc., Santa Rosa, CA (US)

(72) Inventors: Randall T. Lashinski, Windsor, CA (US); Joshua J. Dwork, Santa Rosa, CA (US)

(73) Assignee: Laminar, Inc., Santa Rosa, CA (US)

( * ) Notice: Subject to any disclaimer, the term of this patent is extended or adjusted under 35 U.S.C. 154(b) by 153 days.

This patent is subject to a terminal disclaimer.

(21) Appl. No.: 16/828,782

(22) Filed: Mar. 24, 2020

(65) Prior Publication Data

US 2020/0305887 A1 Oct. 1, 2020

Related U.S. Application Data

(60) Provisional application No. 62/949,338, filed on Dec. 17, 2019, provisional application No. 62/925,155, (Continued)

(51) Int. Cl.
*A61B 17/12* (2006.01)
*A61B 17/00* (2006.01)

(52) U.S. Cl.
CPC .. *A61B 17/12122* (2013.01); *A61B 17/12031* (2013.01); *A61B 17/12145* (2013.01); (Continued)

(58) Field of Classification Search
CPC ........ A61B 17/12022; A61B 17/12027; A61B 17/12031; A61B 17/12036; (Continued)

(56) References Cited

U.S. PATENT DOCUMENTS

| 5,006,106 A | 4/1991 | Angelchik |
| 6,290,674 B1 | 9/2001 | Roue et al. |

(Continued)

FOREIGN PATENT DOCUMENTS

| EP | 3 632 337 | 4/2020 |
| WO | WO 2004/082532 | 9/2004 |

(Continued)

OTHER PUBLICATIONS

U.S. Appl. No. 17/006,660, filed Aug. 28, 2020, Devices, Systems, and Methods for Treating the Left Atrial Appendage.

(Continued)

*Primary Examiner* — Melanie R Tyson
(74) *Attorney, Agent, or Firm* — Knobbe Martens Olson & Bear, LLP

(57) ABSTRACT

Disclosed are embodiments of a device for occluding a left atrial appendage (LAA) and other cavities or openings within a body. Some embodiments of the device can include an implant configured to be deployed within the LAA or other cavity, configured to be expanded or moved against a wall portion of the LAA or other cavity, and configured to twist at least a portion of the LAA or other cavity when the implant is rotated. Thereafter, one or more securing elements, staples, sutures, or other fasteners can be implanted in the gathered tissue to hold the tissue in the gathered state, thereby occluding the opening of the LAA or other cavity. In some embodiments, the opening of the LAA or other cavity can be occluded by elongating or otherwise reshaping the opening using an implant device, and securing the opening in the occluded state.

30 Claims, 104 Drawing Sheets

Related U.S. Application Data filed on Oct. 23, 2019, provisional application No. 62/894,501, filed on Aug. 30, 2019, provisional application No. 62/880,552, filed on Jul. 30, 2019, provisional application No. 62/866,405, filed on Jun. 25, 2019, provisional application No. 62/854,162, filed on May 29, 2019, provisional application No. 62/853,672, filed on May 28, 2019, provisional application No. 62/849,713, filed on May 17, 2019, provisional application No. 62/828,351, filed on Apr. 2, 2019, provisional application No. 62/824,948, filed on Mar. 27, 2019, provisional application No. 62/497,352, filed on Mar. 25, 2019.

(52) U.S. Cl.
CPC ............... *A61B 2017/00292* (2013.01); *A61B 2017/00367* (2013.01); *A61B 2017/00477* (2013.01); *A61B 2017/00632* (2013.01); *A61B 2017/12054* (2013.01); *A61B 2017/12095* (2013.01)

(58) Field of Classification Search
CPC .......... A61B 17/1204; A61B 17/12099; A61B 17/12113; A61B 17/12122; A61B 17/12131; A61B 17/12168; A61B 17/12172; A61B 17/12177; A61B 17/0057; A61B 17/08; A61B 17/0649; A61B 17/064; A61B 17/0644; A61B 2017/00575; A61B 2017/00632; A61B 2017/00646; A61B 2017/00654; A61B 2017/1205; A61B 2017/12054; A61B 2017/12095; A61B 2017/081

See application file for complete search history.

(56) References Cited

U.S. PATENT DOCUMENTS

| | | |
|---|---|---|
| 6,463,331 B1 | 10/2002 | Edwards |
| 6,652,556 B1 | 11/2003 | VanTassel et al. |
| 6,773,440 B2 | 8/2004 | Gannoe et al. |
| 6,969,396 B2 | 11/2005 | Krolik et al. |
| 7,025,756 B2 | 4/2006 | Frazier et al. |
| 7,044,134 B2 | 5/2006 | Khairkhahan et al. |
| 7,115,110 B2 | 10/2006 | Frazier et al. |
| 7,122,043 B2 | 10/2006 | Greenhalgh et al. |
| 7,128,073 B1 | 10/2006 | van der Burg et al. |
| 7,226,458 B2 | 6/2007 | Kaplan et al. |
| 7,320,665 B2 | 1/2008 | Vijay |
| 7,357,815 B2 | 4/2008 | Shaoulian et al. |
| 7,442,207 B2 | 10/2008 | Rafiee |
| 7,566,336 B2 | 7/2009 | Corcoran et al. |
| 7,645,285 B2 | 1/2010 | Cosgrove et al. |
| 7,648,532 B2 | 1/2010 | Greenhalgh et al. |
| 7,655,040 B2 | 2/2010 | Douk et al. |
| 7,695,510 B2 | 4/2010 | Bloom et al. |
| 7,722,641 B2 | 5/2010 | van der Burg et al. |
| 7,727,249 B2 | 6/2010 | Rahmani |
| 7,736,392 B2 | 6/2010 | Starkebaum |
| 7,758,639 B2 | 7/2010 | Mathis |
| 7,780,683 B2 | 8/2010 | Roue et al. |
| 7,828,716 B2 | 11/2010 | Burton et al. |
| 7,984,717 B2 | 7/2011 | Tropsha et al. |
| 8,070,671 B2 | 12/2011 | Deem et al. |
| 8,097,015 B2 | 1/2012 | Devellian |
| 8,197,496 B2 | 6/2012 | Roue et al. |
| 8,236,050 B2 | 8/2012 | Bolling et al. |
| 8,287,557 B2 | 10/2012 | To et al. |
| 8,323,309 B2 | 12/2012 | Khairkhahan et al. |
| 8,512,403 B2 | 8/2013 | Navia et al. |
| 8,523,897 B2 | 9/2013 | van der Burg et al. |
| 8,551,161 B2 | 10/2013 | Dolan |
| 8,603,137 B2 | 12/2013 | Voss et al. |
| 8,690,911 B2 | 4/2014 | Miles et al. |
| 8,758,395 B2 | 6/2014 | Kleshinski et al. |
| 8,764,793 B2 | 7/2014 | Lee |
| 8,771,297 B2 | 7/2014 | Miller et al. |
| 8,777,926 B2 | 7/2014 | Chang et al. |
| 8,784,469 B2 | 7/2014 | Kassab |
| 8,784,482 B2 | 7/2014 | Rahdert et al. |
| 8,840,641 B2 | 9/2014 | Miles et al. |
| 8,845,711 B2 | 9/2014 | Miles et al. |
| 8,968,284 B2 | 3/2015 | Thomas et al. |
| 9,089,311 B2 | 7/2015 | Fortson et al. |
| 9,186,152 B2 | 11/2015 | Campbell et al. |
| 9,220,487 B2 | 12/2015 | Davis et al. |
| 9,314,249 B2 | 4/2016 | Kreidler et al. |
| 9,326,857 B2 | 5/2016 | Carledge et al. |
| 9,358,009 B2 | 6/2016 | Yock et al. |
| 9,427,220 B2 | 8/2016 | Whitman et al. |
| 9,554,804 B2 | 1/2017 | Erzberger et al. |
| 9,572,584 B2 | 2/2017 | Miles et al. |
| 9,592,058 B2 | 3/2017 | Erzberger et al. |
| 9,597,086 B2 | 3/2017 | Larsen et al. |
| 9,615,926 B2 | 4/2017 | Lashinski et al. |
| 9,649,115 B2 | 5/2017 | Edmiston et al. |
| 9,662,117 B2 | 5/2017 | Forsell |
| 9,675,360 B2 | 6/2017 | Baker |
| 9,693,781 B2 | 7/2017 | Miles et al. |
| 9,717,488 B2 | 8/2017 | Kassab |
| 9,763,666 B2 | 9/2017 | Wu et al. |
| 9,795,480 B2 | 10/2017 | Bolling et al. |
| 9,795,481 B2 | 10/2017 | Callas et al. |
| 9,808,253 B2 | 11/2017 | Li et al. |
| 9,826,980 B2 | 11/2017 | Figulla et al. |
| 9,883,864 B2 | 2/2018 | Miles et al. |
| 9,918,719 B2 | 3/2018 | Konstantino et al. |
| 9,937,042 B2 | 4/2018 | Cabiri et al. |
| 10,064,628 B2 | 9/2018 | Edmiston et al. |
| 10,098,640 B2 | 10/2018 | Bertolero et al. |
| 10,143,478 B2 | 12/2018 | Forbes |
| 10,238,398 B2 | 3/2019 | Hughett, Sr. et al. |
| 10,278,705 B2 | 5/2019 | Amin et al. |
| 10,299,799 B1 | 5/2019 | DeMeritt |
| 10,307,165 B2 | 6/2019 | Henderson et al. |
| 10,307,620 B2 | 6/2019 | Burdette |
| 10,386,990 B2 | 8/2019 | Shikham et al. |
| 10,405,866 B2 | 9/2019 | Chakraborty et al. |
| 10,420,564 B2 | 9/2019 | Miles et al. |
| 10,433,998 B2 | 10/2019 | Keren et al. |
| 10,441,258 B2 | 10/2019 | Corcoran et al. |
| 10,531,878 B2 | 1/2020 | Slaughter et al. |
| 10,537,332 B2 | 1/2020 | Edmiston et al. |
| 10,582,929 B2 | 3/2020 | Miles et al. |
| 10,582,930 B2 | 3/2020 | Miles et al. |
| 10,624,648 B2 | 4/2020 | Li et al. |
| 10,631,969 B2 | 4/2020 | Edmiston et al. |
| 10,695,070 B2 | 6/2020 | Miles et al. |
| 10,709,432 B2 | 7/2020 | Ma |
| 10,758,241 B1 * | 9/2020 | Lashinski ........ A61B 17/12168 |
| 2003/0040771 A1 | 2/2003 | Hyodoh et al. |
| 2003/0057156 A1 | 3/2003 | Peterson et al. |
| 2003/0181942 A1 | 9/2003 | Sutton et al. |
| 2005/0004652 A1 | 1/2005 | van der Burg et al. |
| 2005/0288722 A1 | 12/2005 | Eigler et al. |
| 2008/0294175 A1 | 11/2008 | Bardsley et al. |
| 2008/0319254 A1 | 12/2008 | Nikolic et al. |
| 2009/0171386 A1 | 7/2009 | Amplatz et al. |
| 2009/0209986 A1 | 8/2009 | Stewart et al. |
| 2010/0185235 A1 | 7/2010 | Kassab et al. |
| 2011/0054515 A1 | 3/2011 | Bridgeman et al. |
| 2011/0178537 A1 | 7/2011 | Whitman |
| 2012/0221042 A1 | 8/2012 | Schwartz et al. |
| 2012/0265296 A1 | 10/2012 | McNamara et al. |
| 2012/0283585 A1 | 11/2012 | Werneth et al. |
| 2012/0316584 A1 | 12/2012 | Miles et al. |
| 2013/0197570 A1 | 8/2013 | Ebata et al. |
| 2014/0018841 A1 | 1/2014 | Peiffer et al. |
| 2014/0135817 A1 | 5/2014 | Tischler et al. |
| 2015/0005809 A1 | 1/2015 | Ayres et al. |
| 2015/0005810 A1 | 1/2015 | Center et al. |

(56) References Cited

U.S. PATENT DOCUMENTS

| | | |
|---|---|---|
| 2015/0209049 A1 | 7/2015 | Bernstein et al. |
| 2016/0058434 A1 | 3/2016 | Delaloye et al. |
| 2016/0278749 A1 | 9/2016 | Javois et al. |
| 2017/0095256 A1 | 4/2017 | Lindgren et al. |
| 2017/0224354 A1 | 8/2017 | Tischler et al. |
| 2017/0258475 A1 | 9/2017 | Mellmann et al. |
| 2017/0340336 A1 | 11/2017 | Osypka |
| 2018/0055496 A1 | 3/2018 | Hou et al. |
| 2018/0235640 A1 | 8/2018 | Slaughter et al. |
| 2018/0289487 A1 | 10/2018 | Alexander et al. |
| 2018/0310926 A1 | 11/2018 | Delaloye et al. |
| 2019/0069901 A1 | 3/2019 | Forbes |
| 2019/0083075 A1 | 3/2019 | Onushko et al. |
| 2019/0167242 A1 | 6/2019 | Rowe et al. |
| 2019/0183512 A1 | 6/2019 | Subramaniam et al. |
| 2019/0192754 A1 | 6/2019 | Kassab et al. |
| 2019/0209179 A1 | 7/2019 | Subramaniam et al. |
| 2019/0209180 A1 | 7/2019 | Kealey et al. |
| 2019/0321176 A1 | 10/2019 | Lashinski et al. |
| 2019/0374229 A1 | 12/2019 | Anderson et al. |
| 2020/0038004 A1 | 2/2020 | Corcoran et al. |
| 2020/0107837 A1 | 4/2020 | Slaughter et al. |
| 2020/0155164 A1 | 5/2020 | Edmiston et al. |
| 2020/0214714 A1 | 7/2020 | Li et al. |
| 2021/0113212 A1 | 4/2021 | Lashinski et al. |

FOREIGN PATENT DOCUMENTS

| | | |
|---|---|---|
| WO | WO 2018/0178979 | 10/2018 |
| WO | WO 2018/178979 | 10/2018 |
| WO | WO 2019/212894 | 11/2019 |
| WO | WO 2020/074738 | 4/2020 |

OTHER PUBLICATIONS

U.S. Appl. No. 17/180,121, filed Feb. 19, 2021, Devices, Systems, and Methods for Treating the Left Atrial Appendage.
U.S. Appl. No. 17/208,435, filed Mar. 22, 2021, Devices, Systems, and Methods for Occluding Cavities Within the Body.
U.S. Appl. No. 17/368,715, filed Jul. 6, 2021, Devices, Systems, and Methods for Treating the Left Atrial Appendage.
U.S. Appl. No. 16/863,995, now U.S. Pat. No. 10,758,241, filed Apr. 30, 2020, Devices, Systems, and Methods for Treating the Left Atrial Appendage.
U.S. Appl. No. 17/006,600, filed Aug. 28, 2020, Devices, Systems, and Methods for Treating the Left Atrial Appendage.
U.S. Appl. No. 63/049,077, filed Jul. 7, 2020, Devices, Systems, and Methods for Treating the Left Atrial Appendage.
U.S. Appl. No. 63/072,035, filed Aug. 28, 2020, Devices, Systems, and Methods for Treating the Left Atrial Appendage.
U.S. Appl. No. 63/171,011, filed Apr. 5, 2021, Devices, Systems, and Methods for Treating the Left Atrial Appendage.
U.S. Appl. No. 63/072,856, filed Aug. 31, 2020, Devices, Systems, and Methods for Treating the Left Atrial Appendage.
Search Report and Written Opinion for PCT Application No. PCT/US2020/024513 dated Jun. 15, 2020; 21 pages.
U.S. Appl. No. 17/180,121, filed Feb. 19, 2021, Lashinski et al.
U.S. Appl. No. 17/208,435, filed Mar. 22, 2021, Lashinski et al.
WATCHMAN® Left Atrial Appendage Closure Device, Patient Information Guide; Boston Scientific; 9 pages.
"Watchman Stroke Device Lawsuit;" https://www.nationalinjuryhelp.com/watchman-stroke-device-lawsuit/; 7 pages.
Densford, Fink, "Prominent cardiologist calls for a halt to Watchman implants;" https://www.massdevice.com/prominent-cardiologist-calls-for-a-halt-to-watchman-implants/; Nov. 10, 2016; 12 pages.
Kelley Drye & Warren LLP, "Texas Court dismisses off-label device marketing FCA case;" Lexology; Oct. 27, 2010; 2 pages.
Perriello, Brad, "Jury hands Covidien's ev3 subsidiary a possible $275M loss;" https://www.massdevice.com/jury-hands-covidiens-ev3-subsidiary-possible-275m-loss/; Aug. 13, 2013; 12 pages.
Rosenthal et al., "What is the efficacy and safety of devices for left atrial appendage (LAA) closure/litigation in atrial fibrillation (Afib) AF)?;" Medscape; Jul. 25, 2019; 2 pages.
WATCHMAN® Left Atrial Appendage Closure Device, Patient Information Guide; Boston Scientific; 7 pages dated as copyrighted 2015.
WATCHMAN® Left Atrial Appendage Closure Device, Product Brochure; 6 pages dated as copyright 2018.
Cardia Delivery System, 1 page, dated as available at http://www.cardia.com/ds.html on Mar. 7, 2019 by the Wayback Machine internet archive (accessed and printed on May 6, 2020).
Cardia Fenestrated Fontan Closure System, 1 page, dated as available at http://www.cardia.com/fontan.html on Feb. 11, 2019 by the Wayback Machine internet archive (accessed and printed on May 6, 2020).
Ultrasept Cribriform Device, 1 page, dated as available at http://www.cardia.com/cribriform.html on Feb. 11, 2019 by the Wayback Machine internet archive (accessed and printed on May 6, 2020).
Ultrasept Left Atrial Appendage Closure Device, 1 page, dated as available at http://www.cardia.com/laa.html on Mar. 7, 2019 by the Wayback Machine internet archive (accessed and printed on May 6, 2020).
Ultrasept Patent Foramen Ovale Closure Device, 1 page dated as available at http://www.cardia.com/pfo.html on of Mar. 7, 2019 by the Wayback Machine internet archive (accessed and printed on May 6, 2020).
Ultrasept Atrial Septal Defect Closure Device, http://www.cardia.com/asd.html, 1 page, dated as available as of March 7, 2019by the Wayback Machine internet archive (accessed and printed on May 6, 2020).
U.S. Appl. No. 16/863,995, now U.S. Pat. No. 10,758,241, filed Sep. 1, 2020, Devices, Systems, and Methods for Treating the Left Atrial Appendage.
U.S. Appl. No. 17/180,121, now U.S. Pat. No. 11,123,080, filed Feb. 19, 2021, Devices, Systems, and Methods for Treating the Left Atrial Appendage.
U.S. Appl. No. 17/402,438, filed Aug. 13, 2021, Devices, Systems, and Methods for Treating the Left Atrial Appendage.
EP, 20719075.2, filed Jun. 25, 2021, Devices and Systems for Treating the Left Atrial Appendage.
WO, PCT/US2020/024513, filed Mar. 24, 2020, Devices and Systems for Treating the Left Atrial Appendage.
WO, PCT/US2021/023475, filed Mar. 22, 2021, Devices, Systems, and Methods for Occluding Cavities Within the Body.
U.S. Appl. No. 17/461,718, filed Aug. 30, 2021, Devices, Systems, and Methods for Treating a Tissue of the Heart.
U.S. Appl. No. 63/218,884, filed Jul. 6, 2021, Devices, Systems, and Methods for Treating a Tissue of the Heart.
WO, PCT/US2021/048284, filed Aug. 30, 2021, Devices, Systems, and Methods for Treating a Tissue of the Heart.
WO, PCT/US2021/040563, filed Jul. 6, 2021, Devices, Systems, and Methods for Treating the Left Atrial Appendage.

* cited by examiner

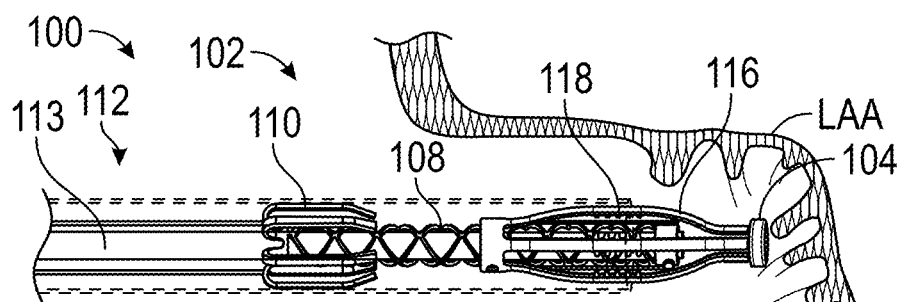
FIG. 8A
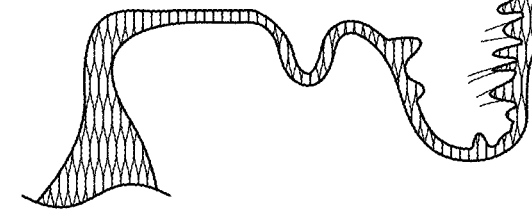
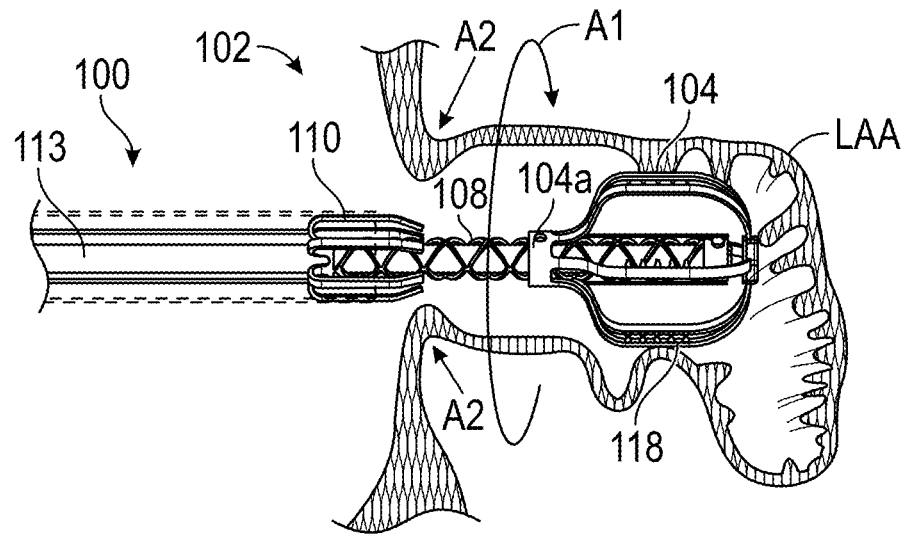
FIG. 8B
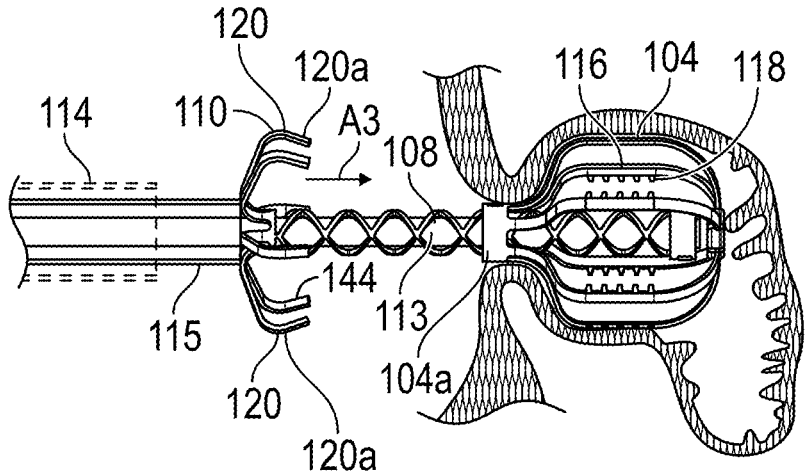
FIG. 8C

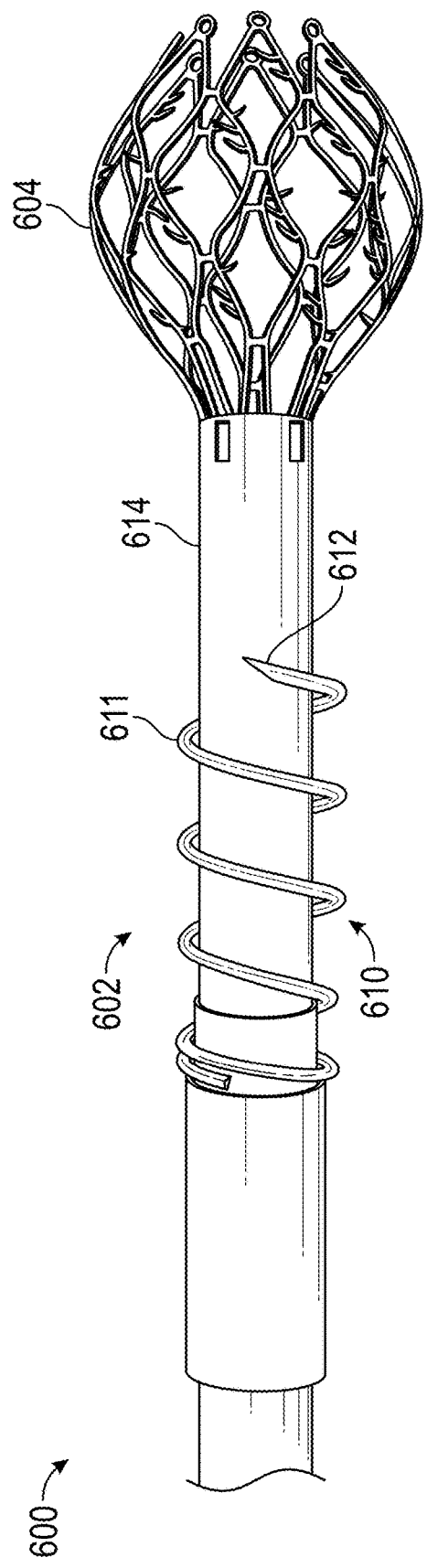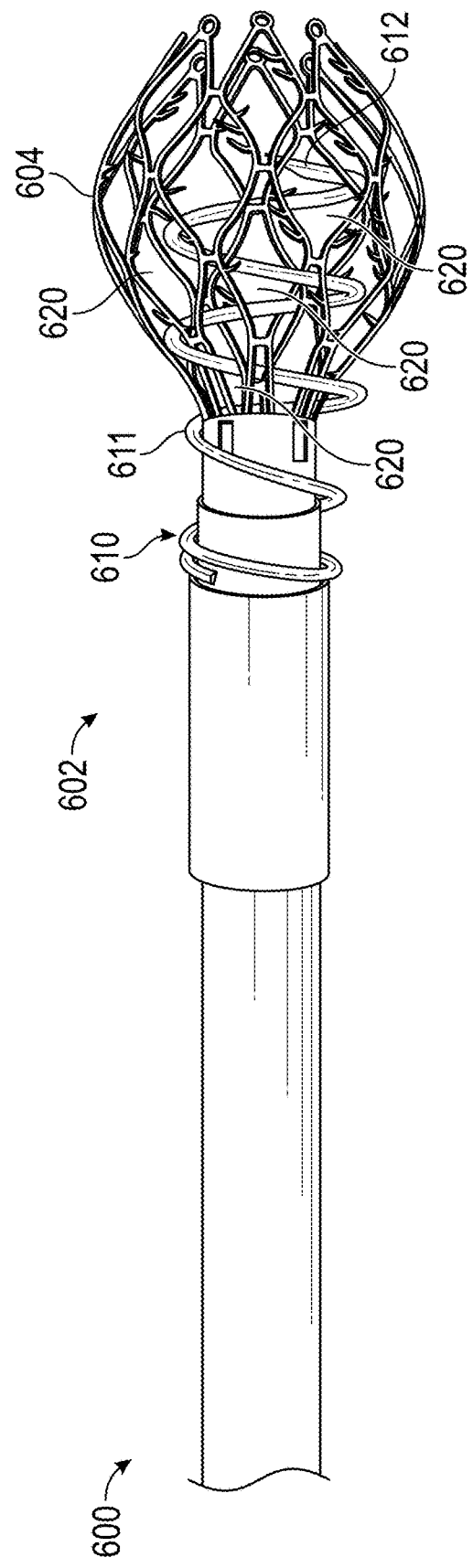
FIG. 22A
FIG. 22B

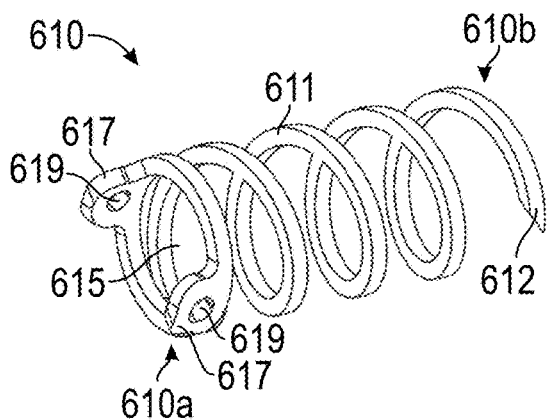
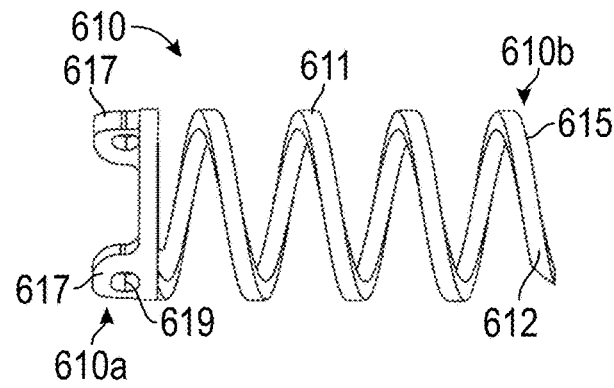
FIG. 23A    FIG. 23B
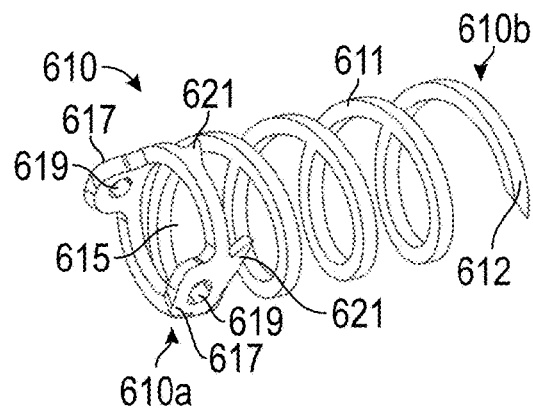
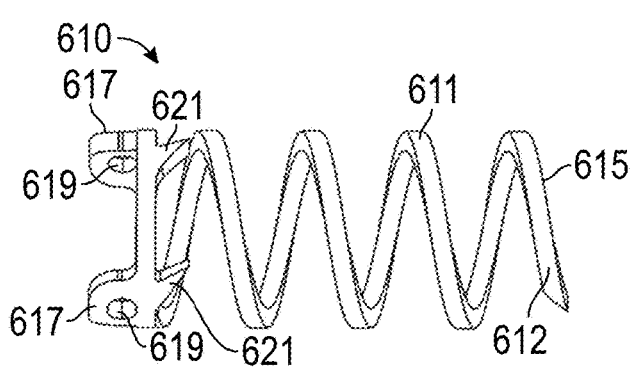
FIG. 23C    FIG. 23D
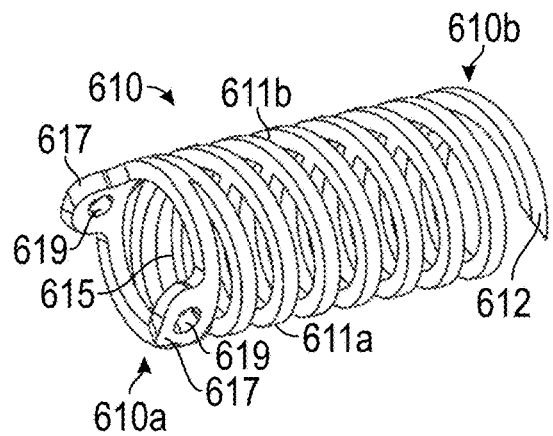
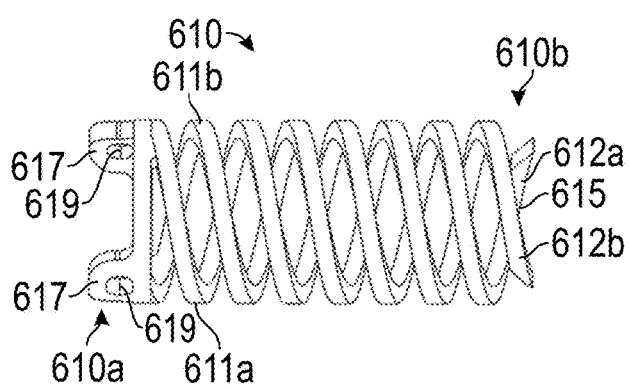
FIG. 23E    FIG. 23F

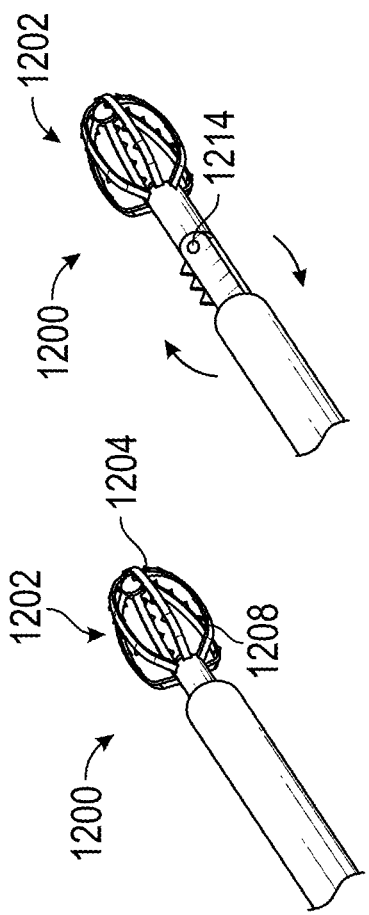
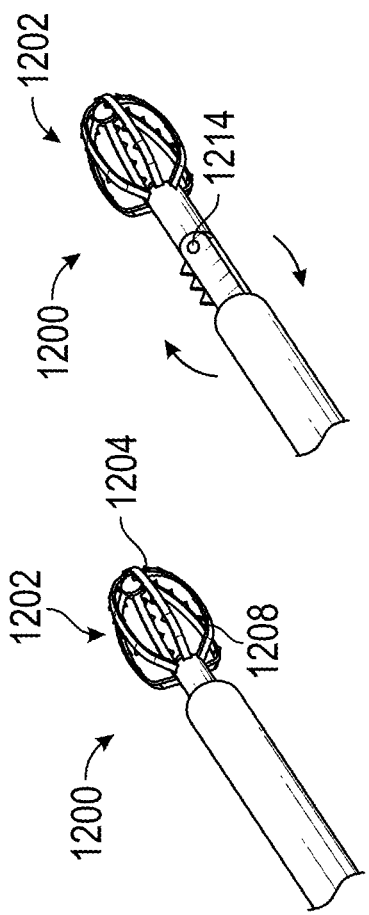
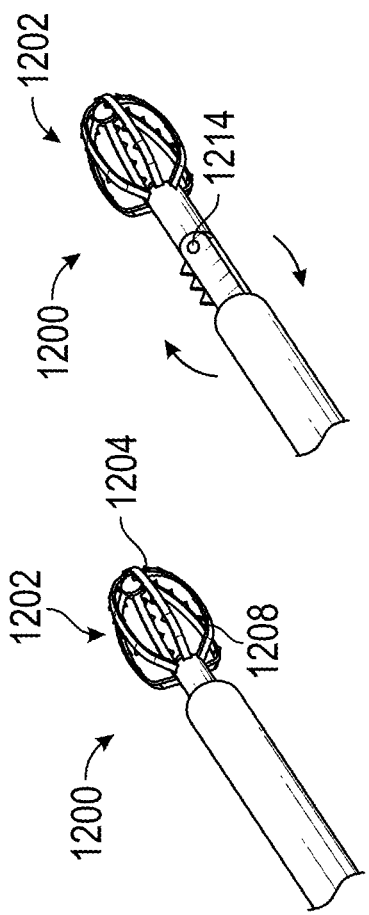
FIG. 49A  FIG. 49B  FIG.49C  FIG. 49D
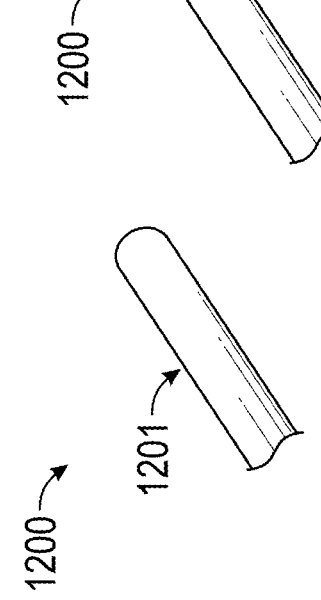
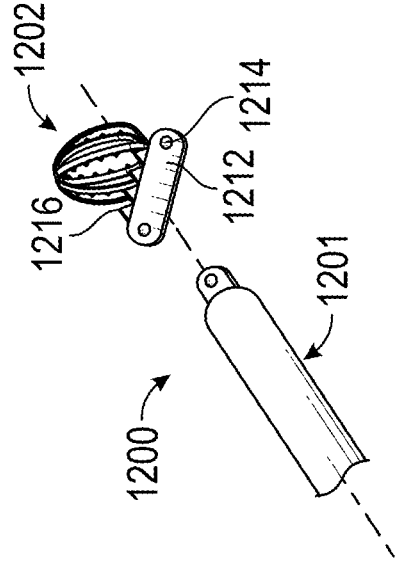
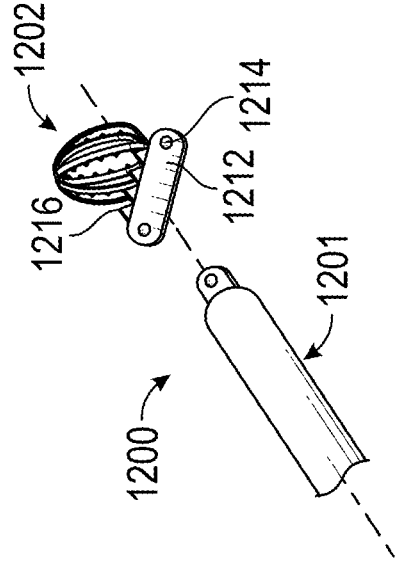
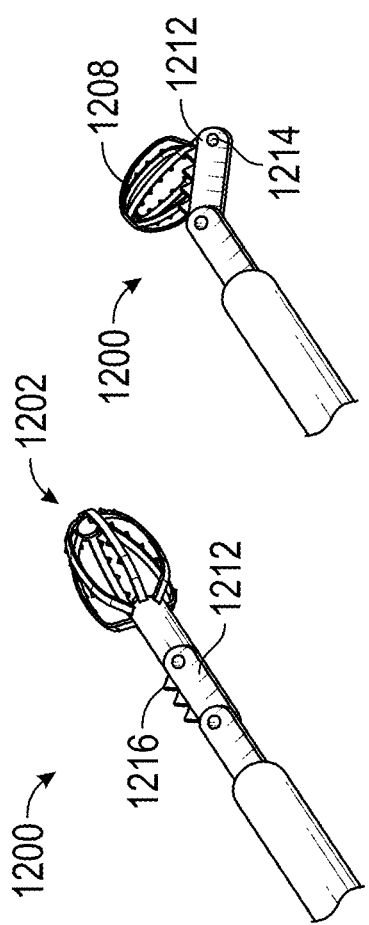
FIG. 49E  FIG. 49F  FIG. 49G

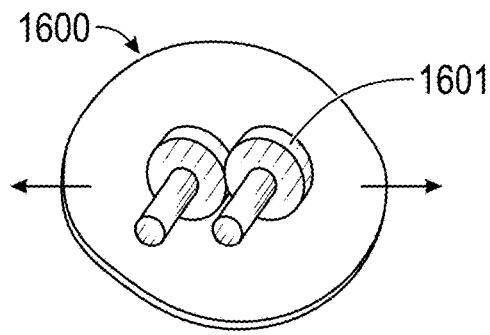
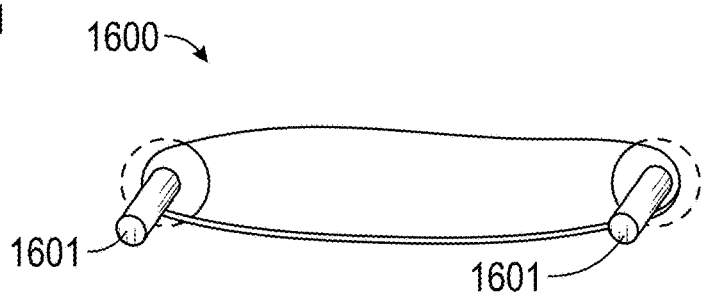
FIG. 66A  FIG. 66B
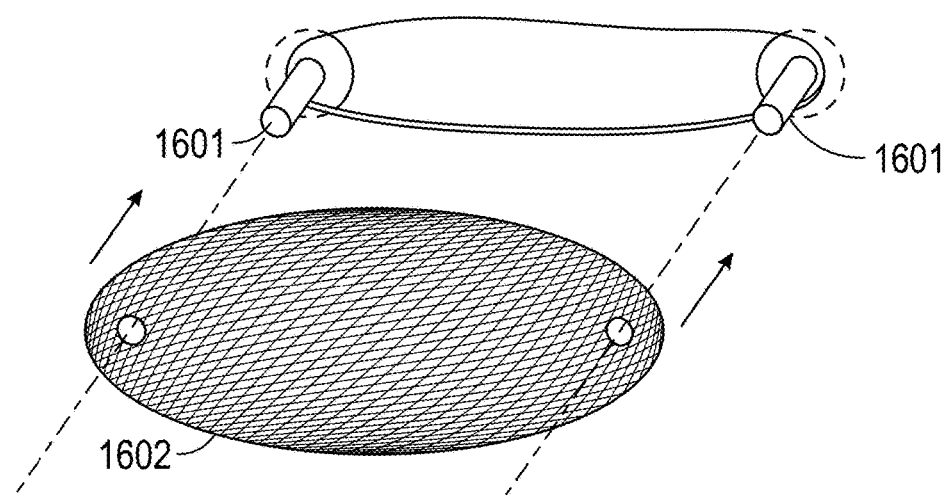
FIG. 66C
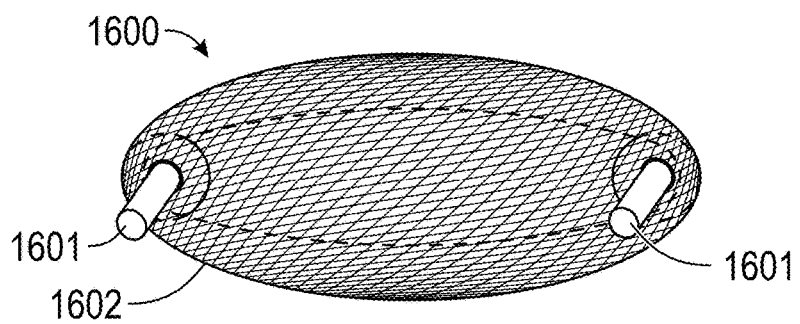
FIG. 66D

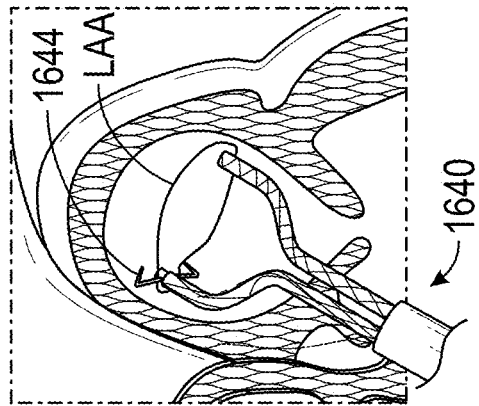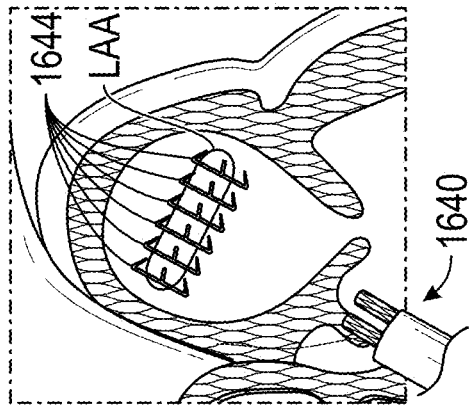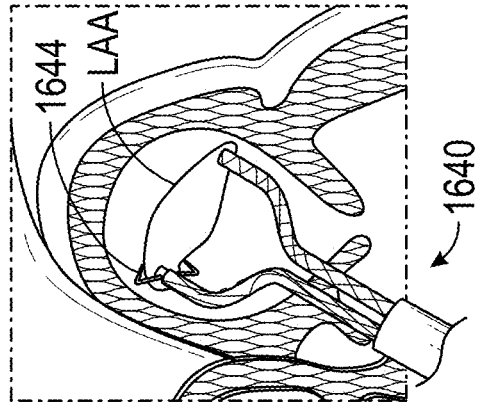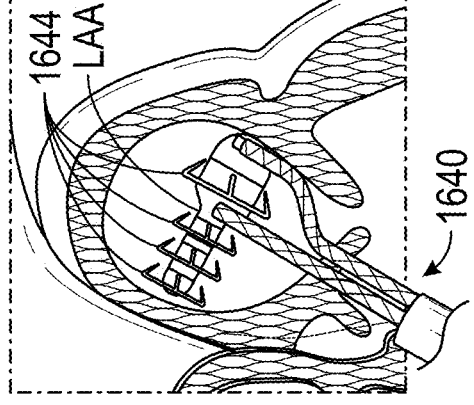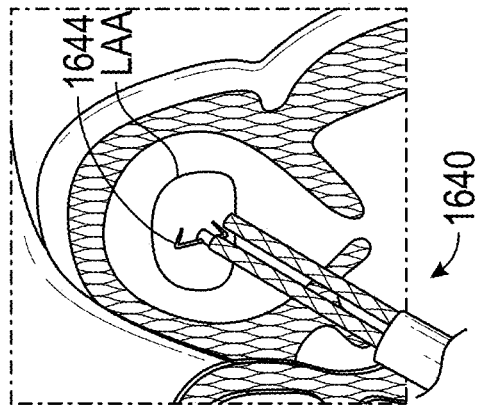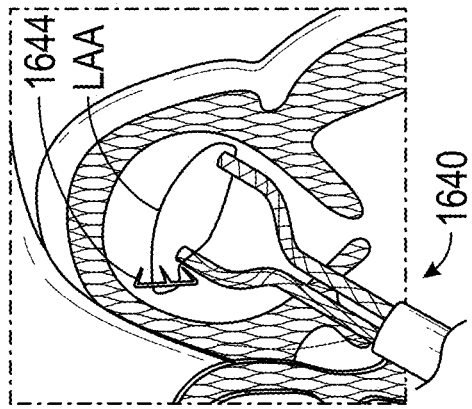

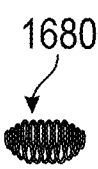
FIG. 77A
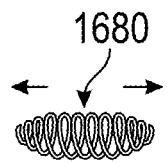
FIG. 77B
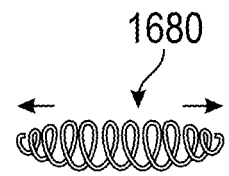
FIG. 77C
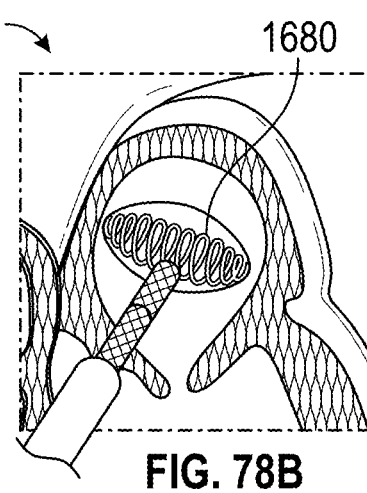
FIG. 78A
FIG. 78B
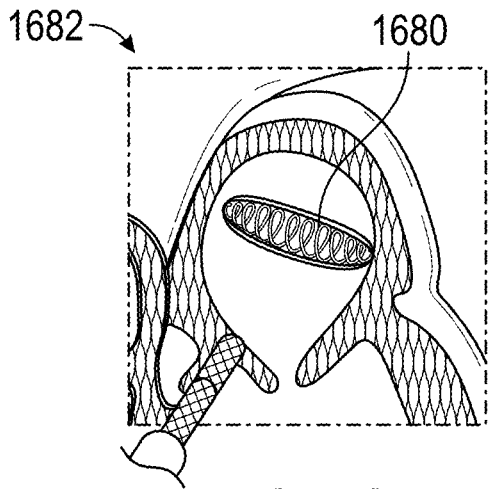
FIG. 78C
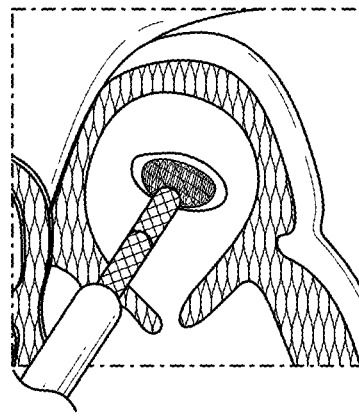
FIG. 79A
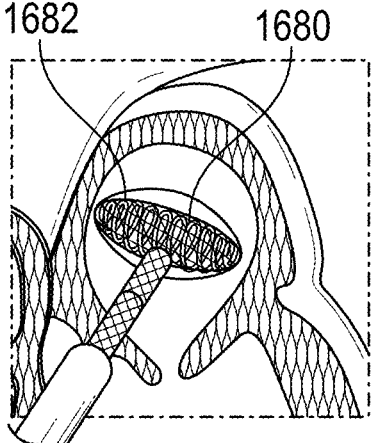
FIG. 79B
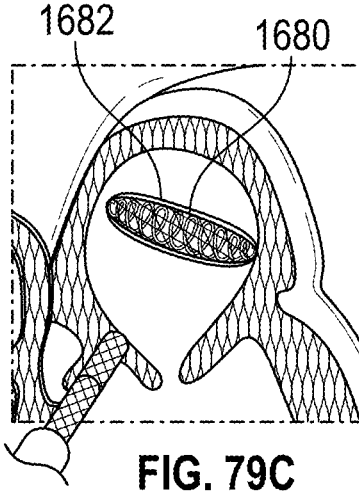
FIG. 79C

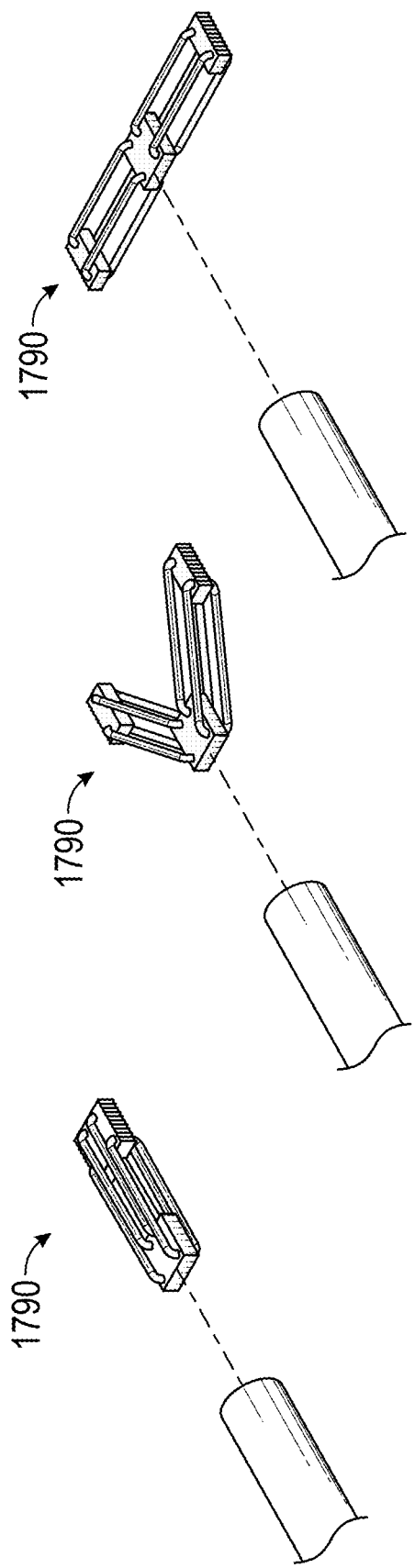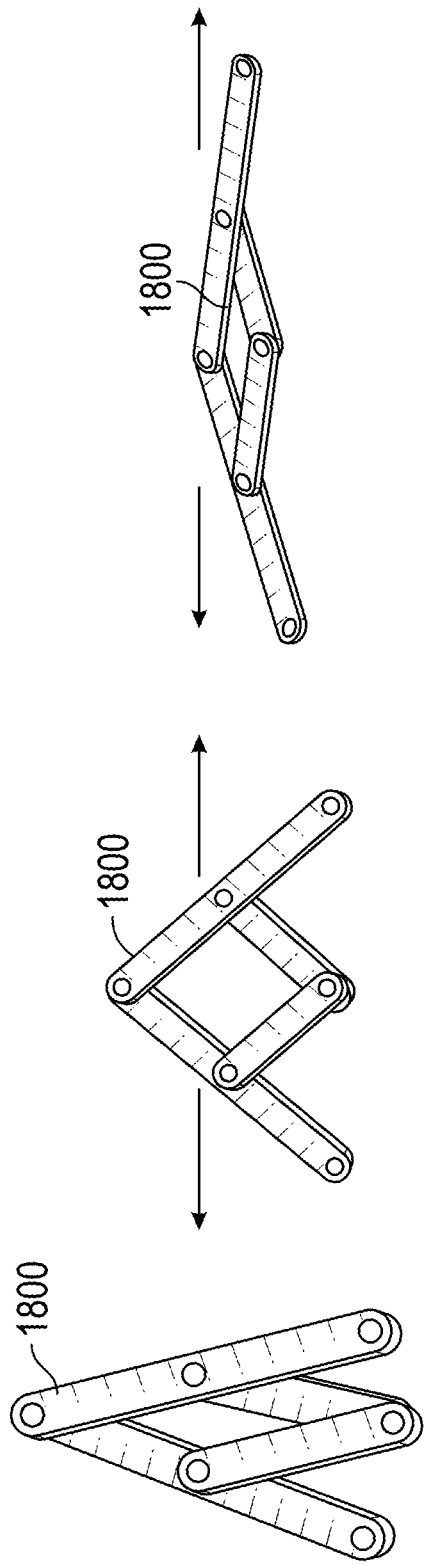

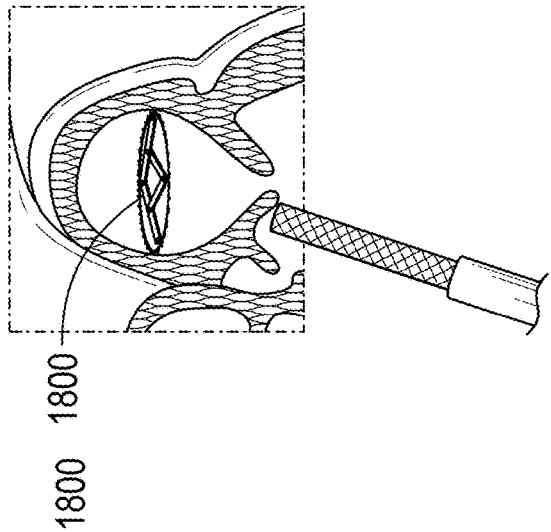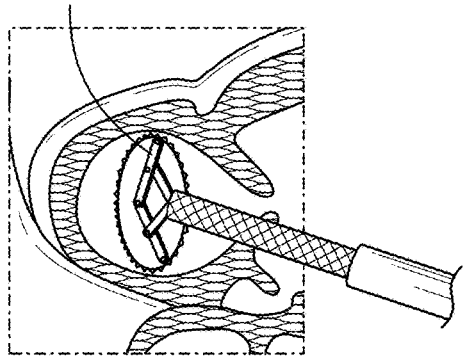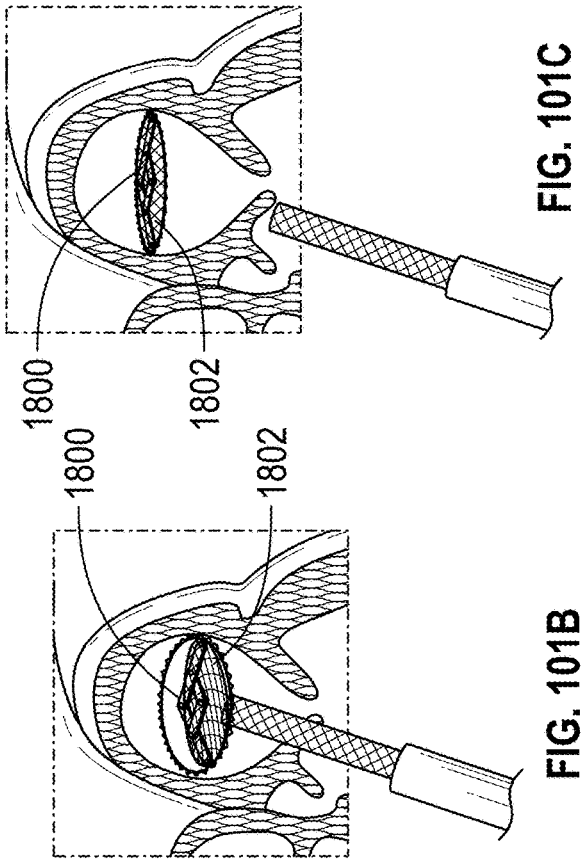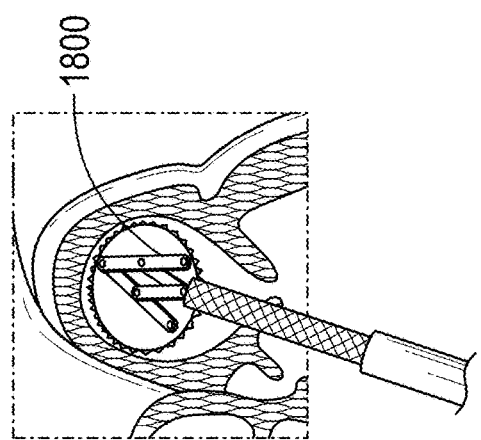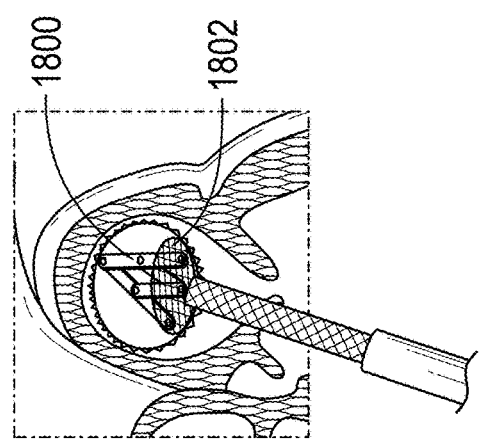

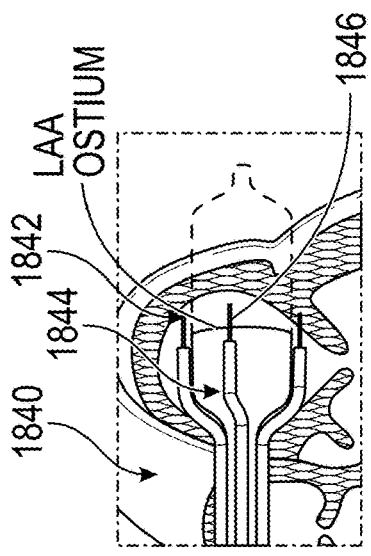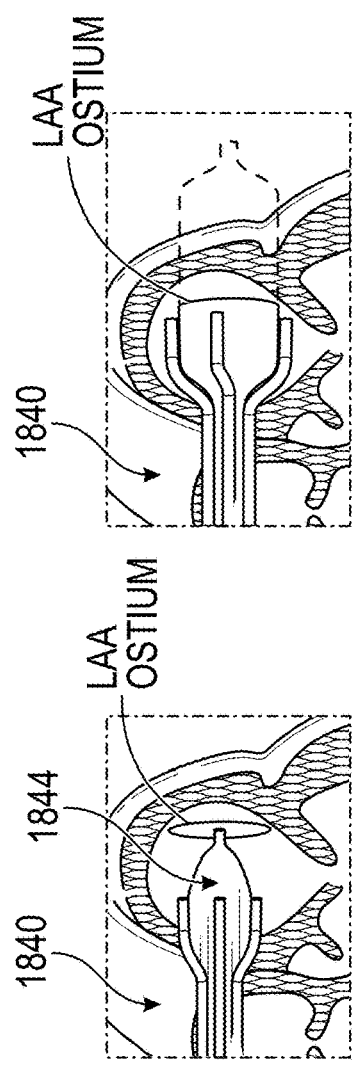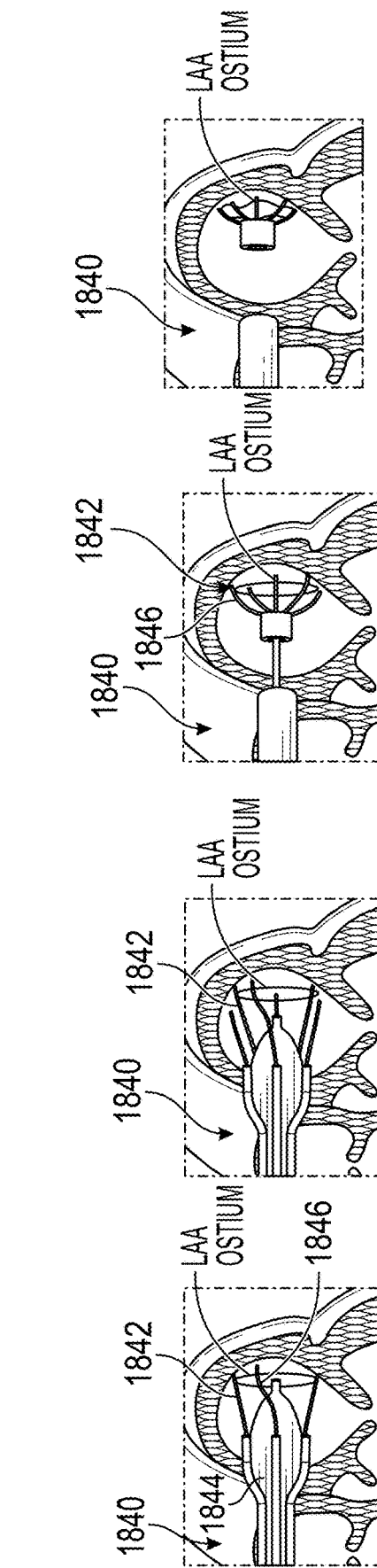

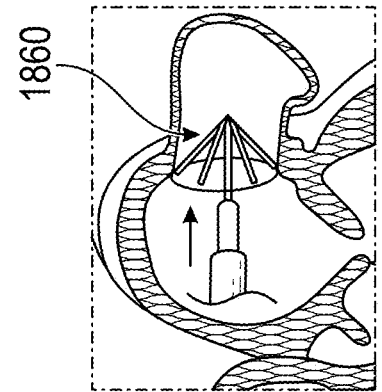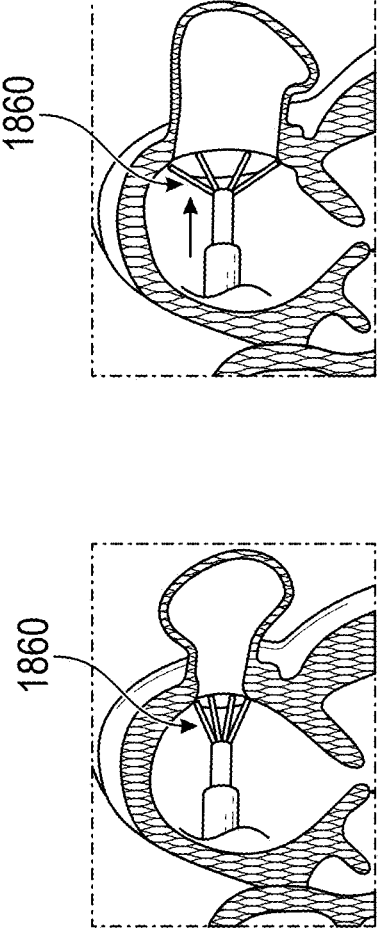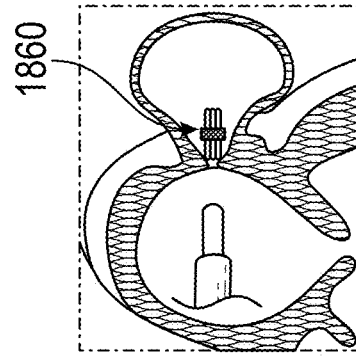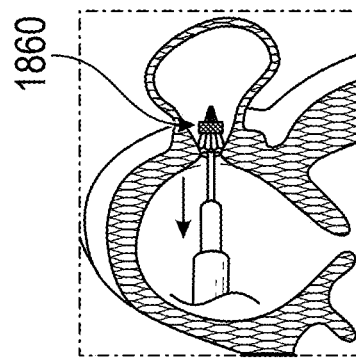
FIG. 110A  FIG. 110B  FIG. 110C  FIG. 110D  FIG. 110E

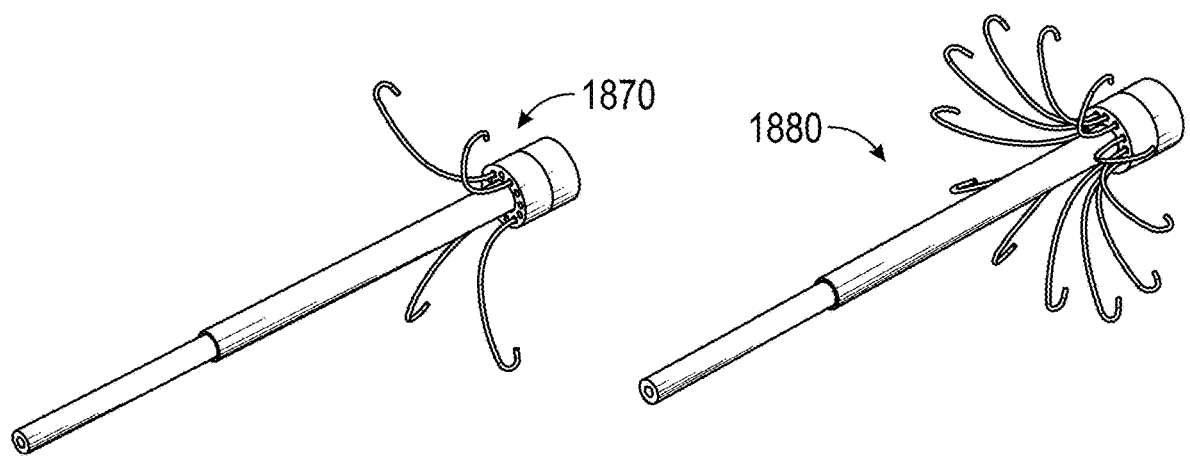
FIG. 111
FIG. 112
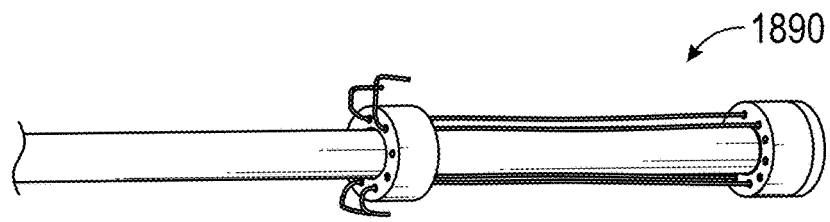
FIG. 113A
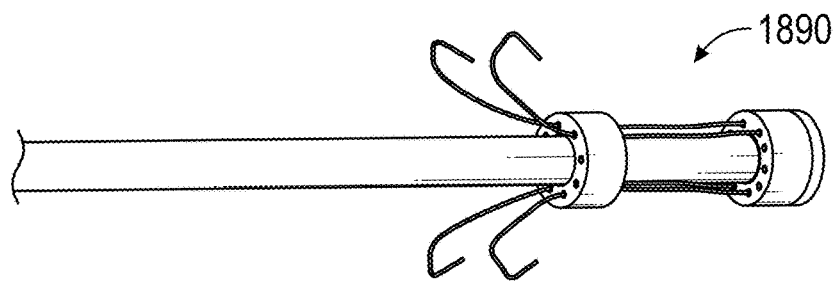
FIG. 113B
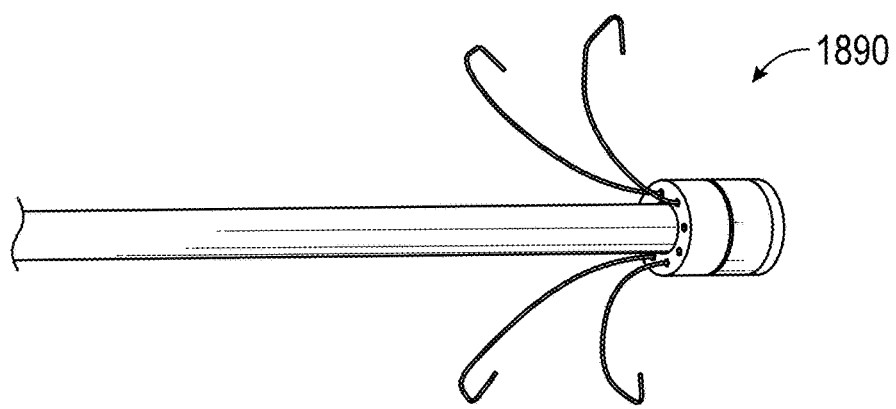
FIG. 113C

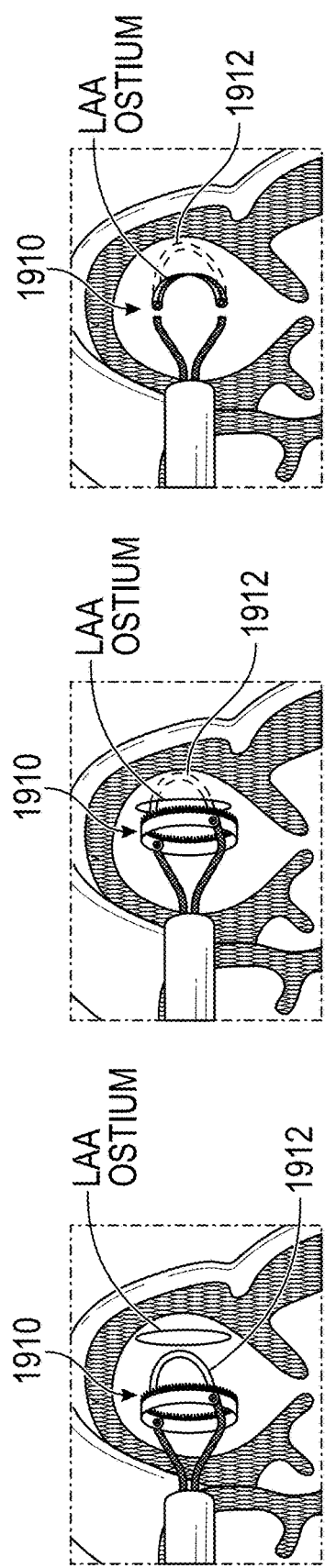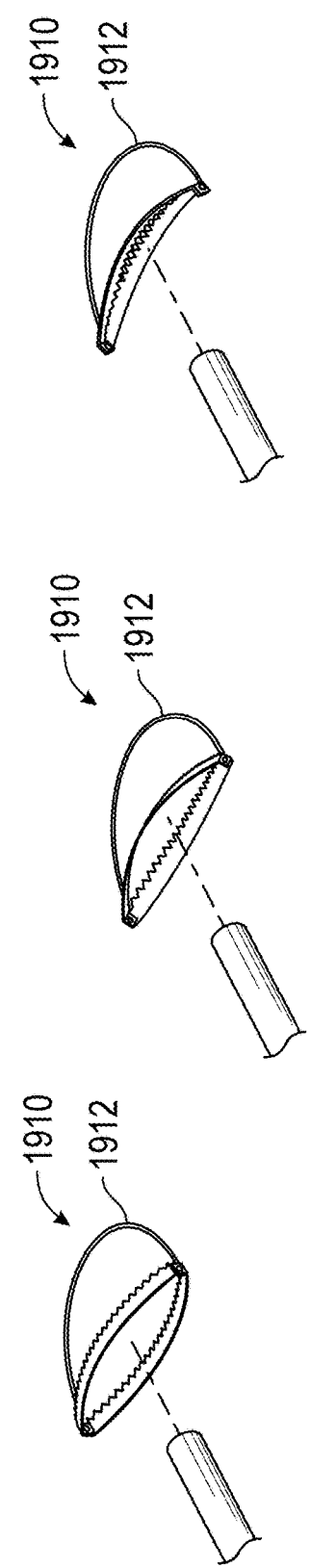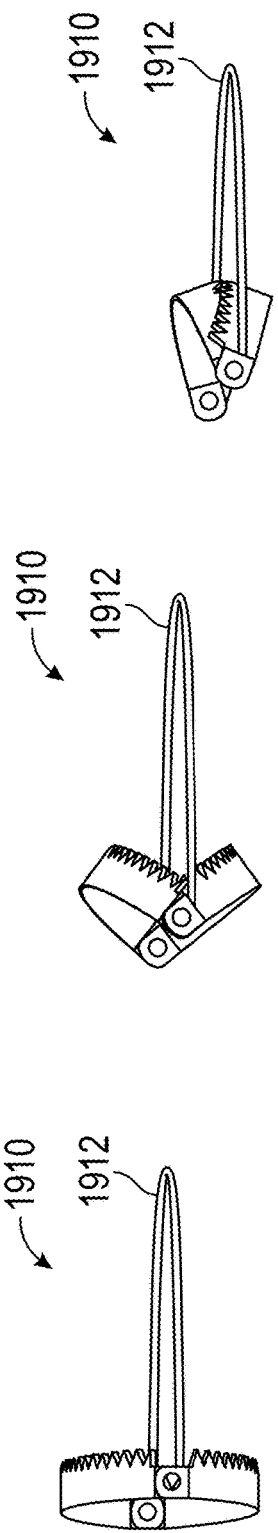

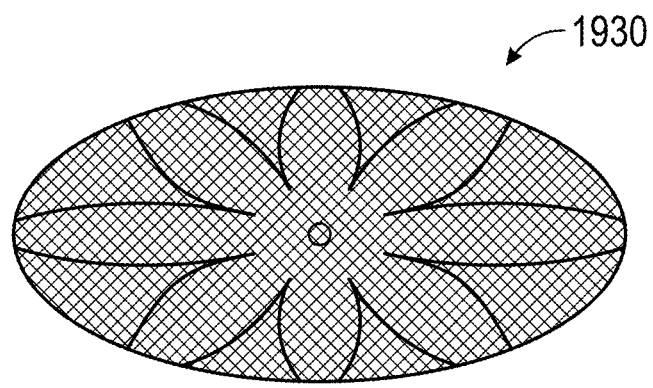
FIG. 120A
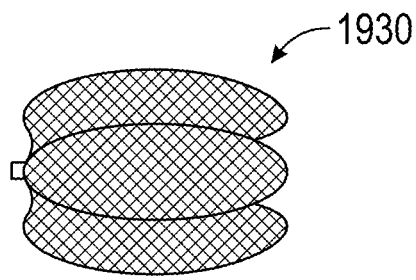
FIG. 120B
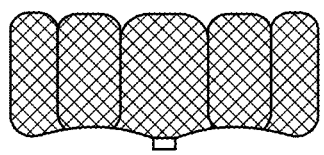
FIG. 120C
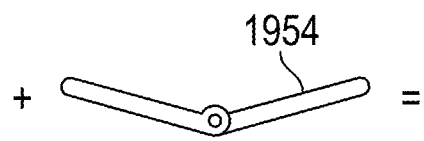
FIG. 121A
FIG. 121B
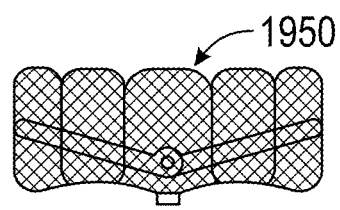
FIG. 121C

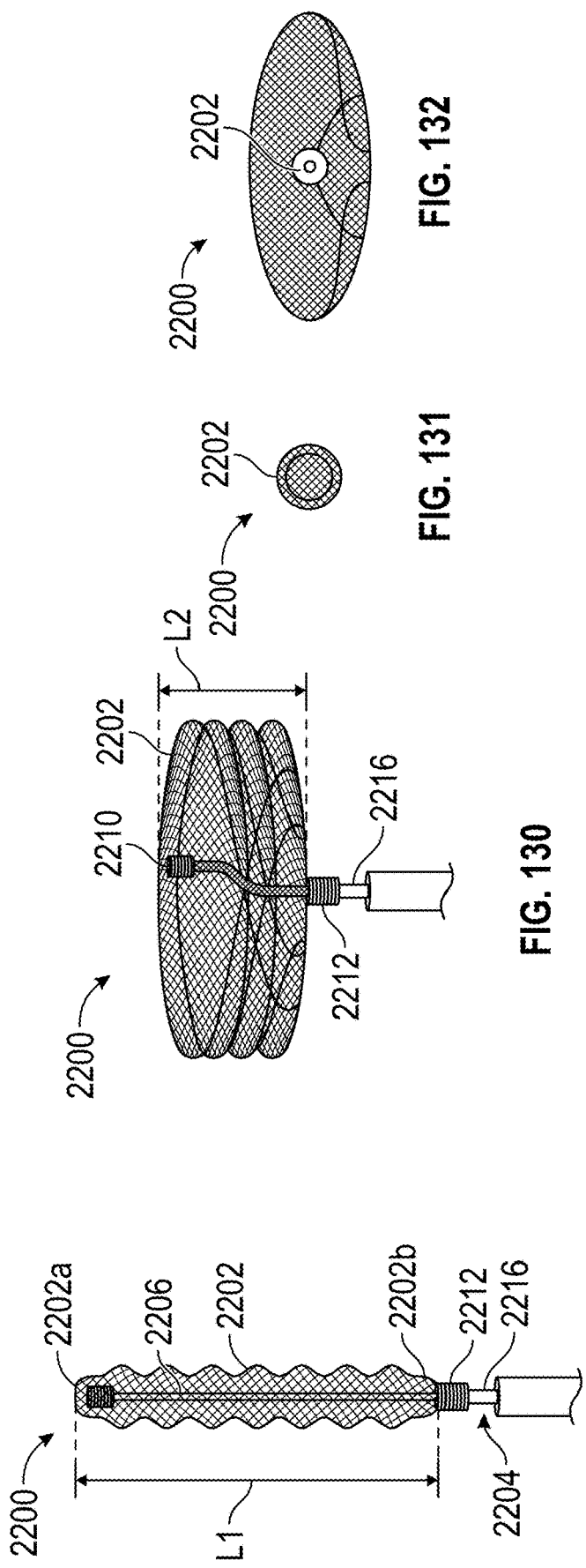

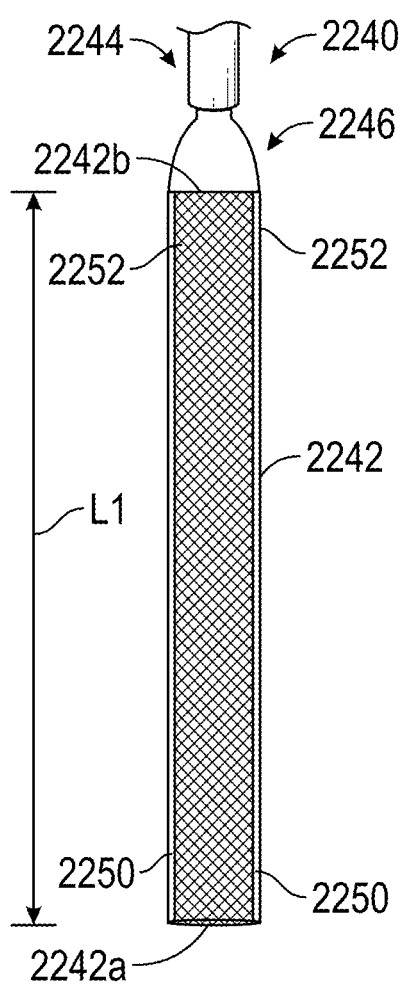 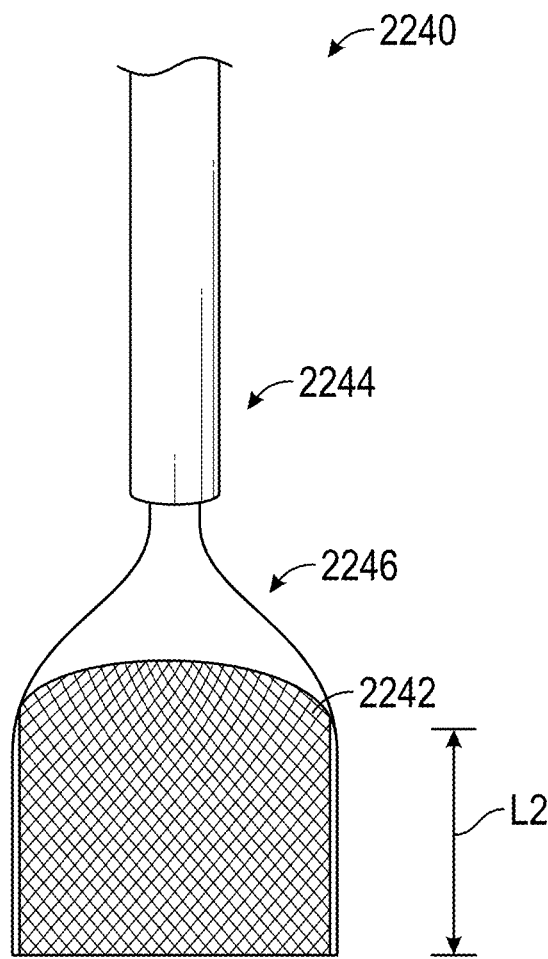
FIG. 133  FIG. 134
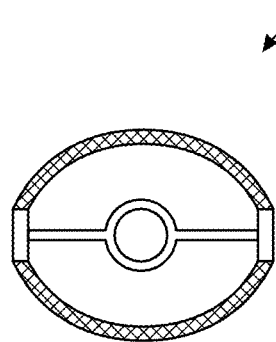 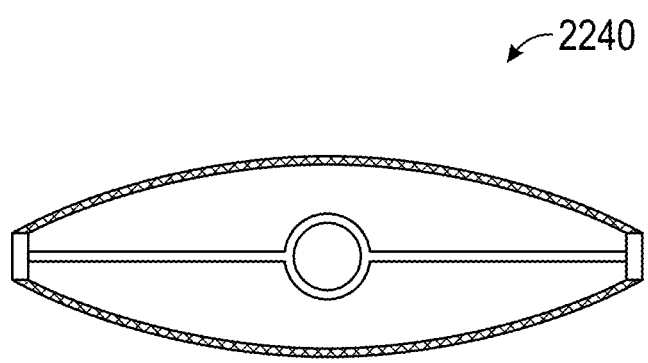
FIG. 135  FIG. 136

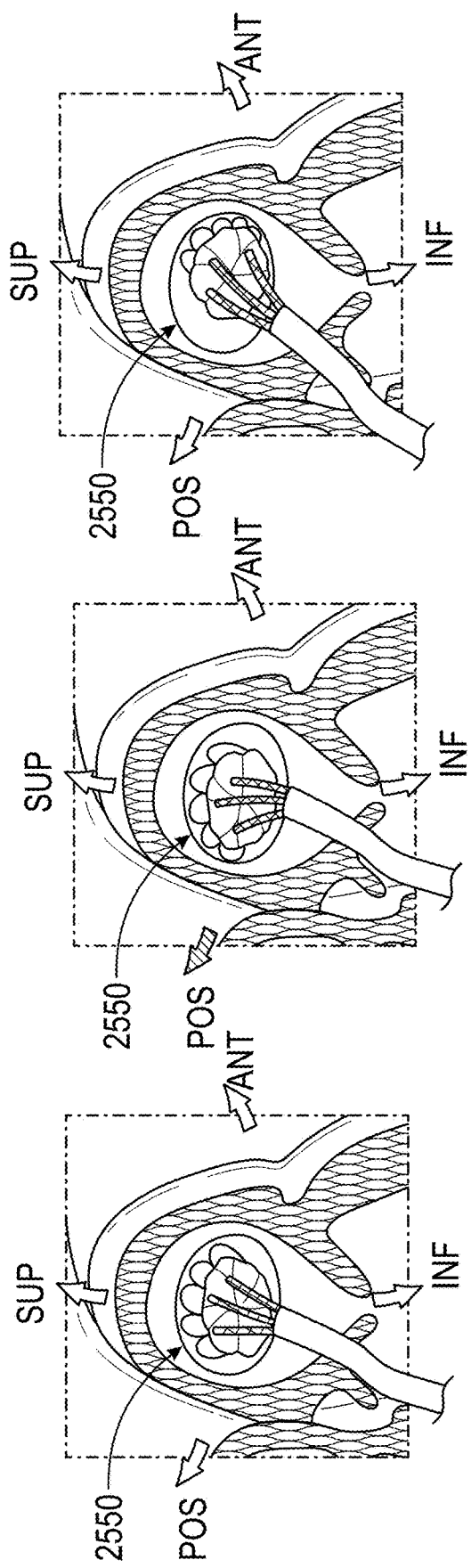
FIG. 152A
FIG. 152B
FIG. 152C
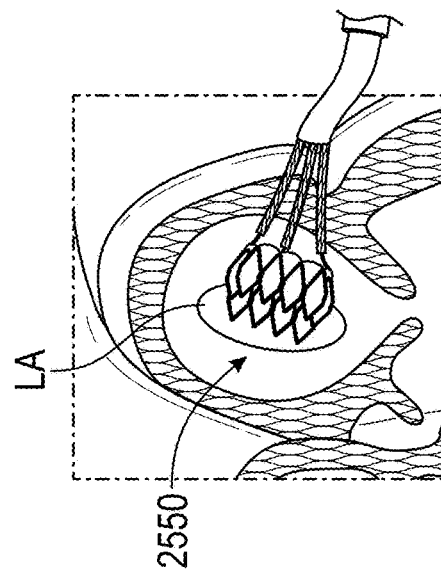
FIG. 153A
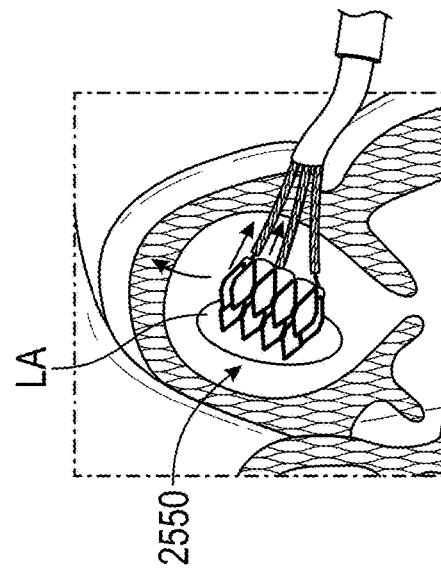
FIG. 153B

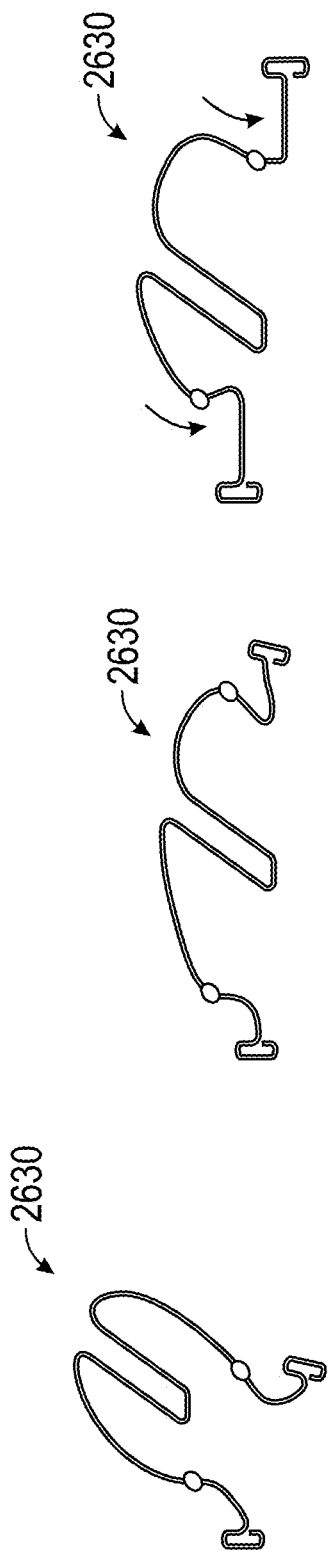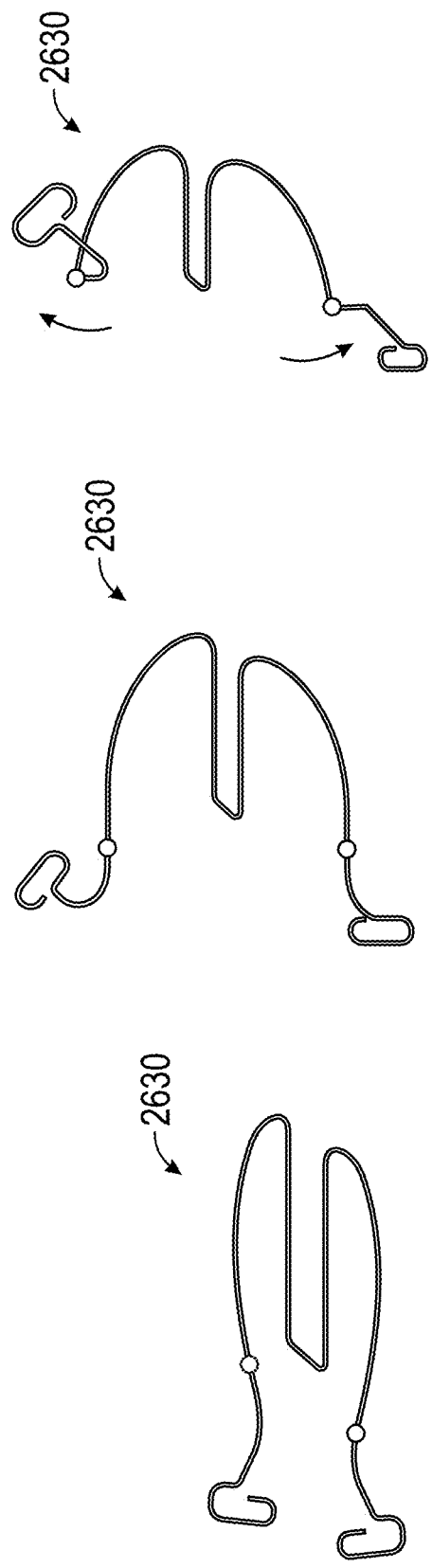

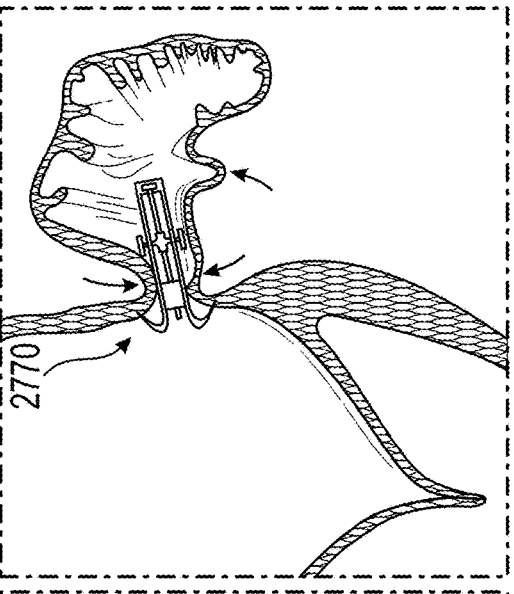
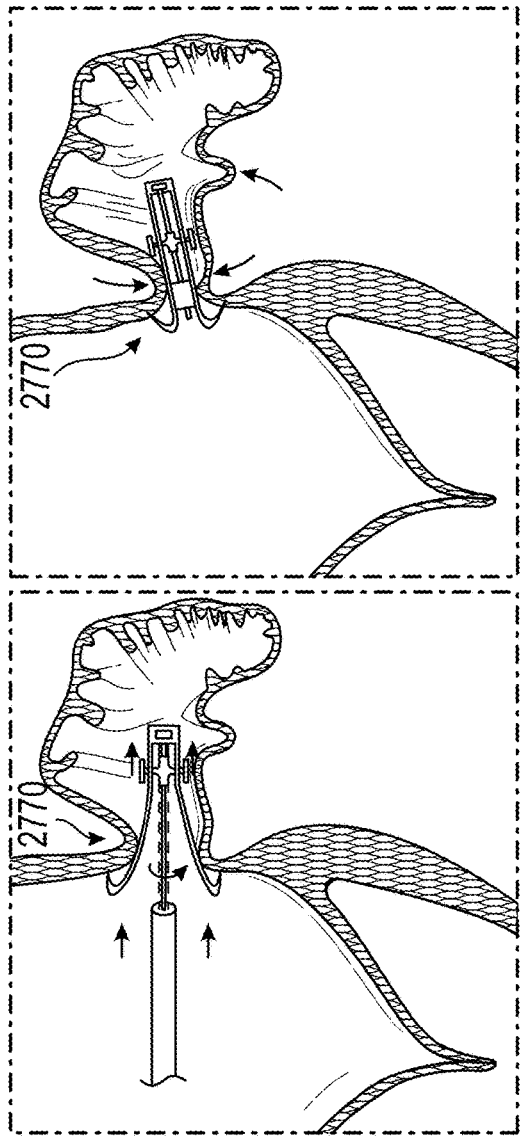
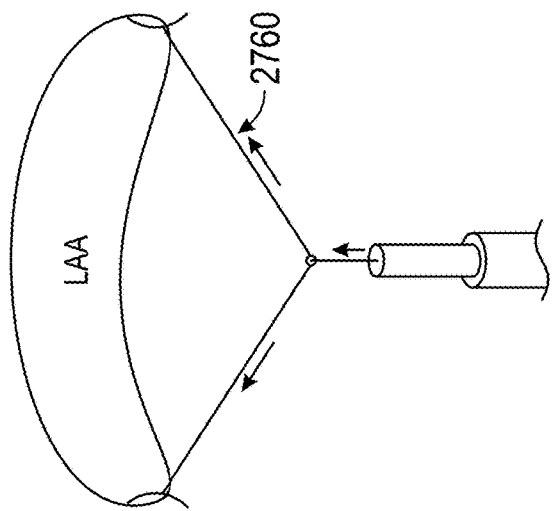
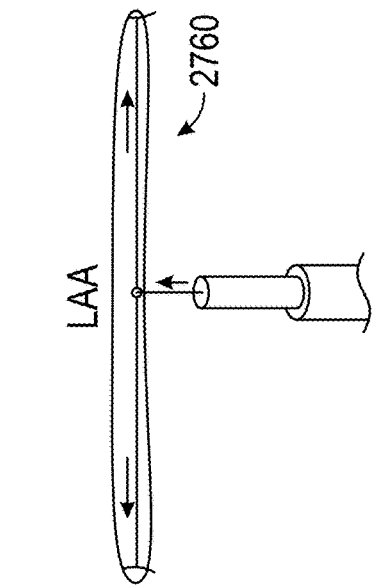

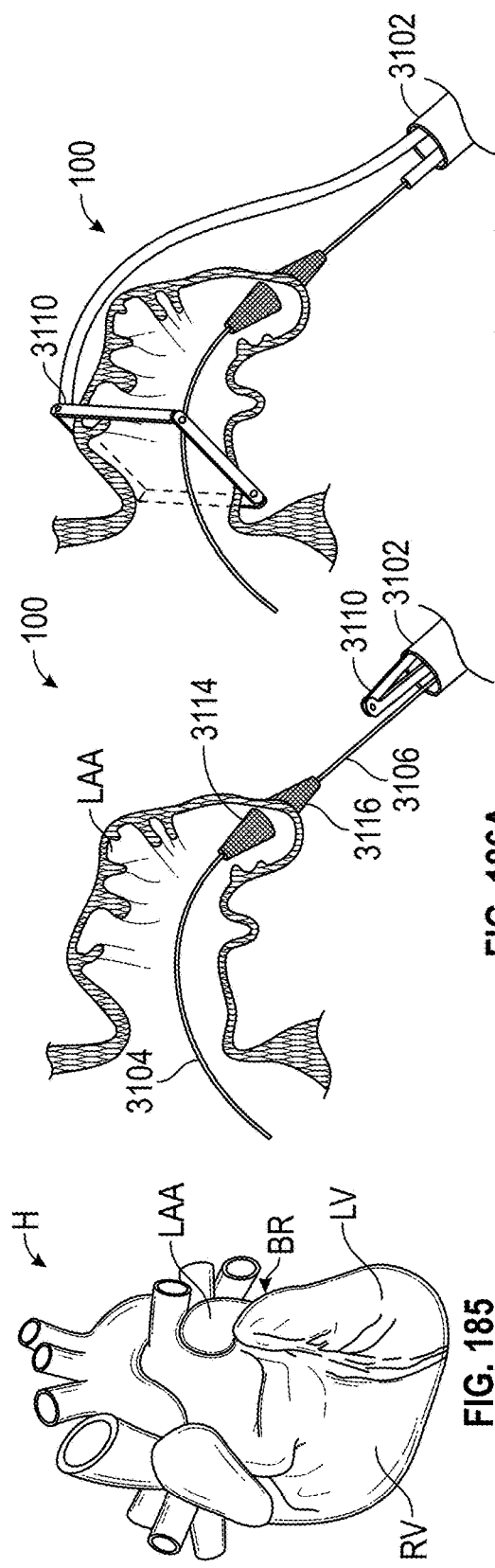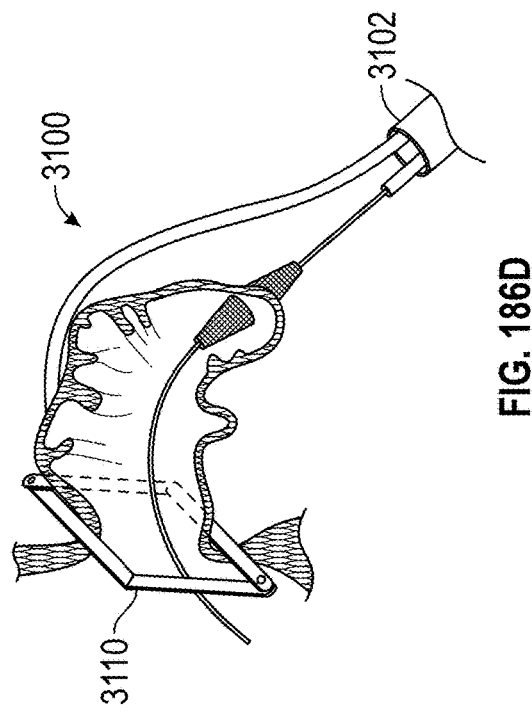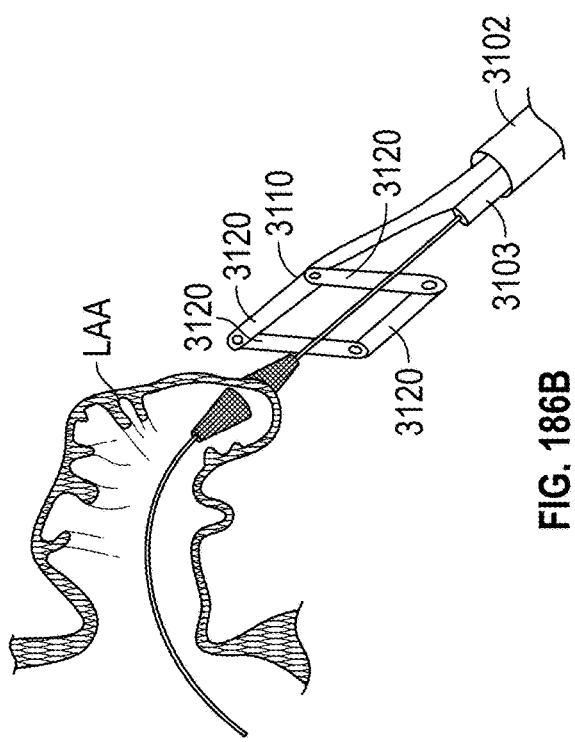

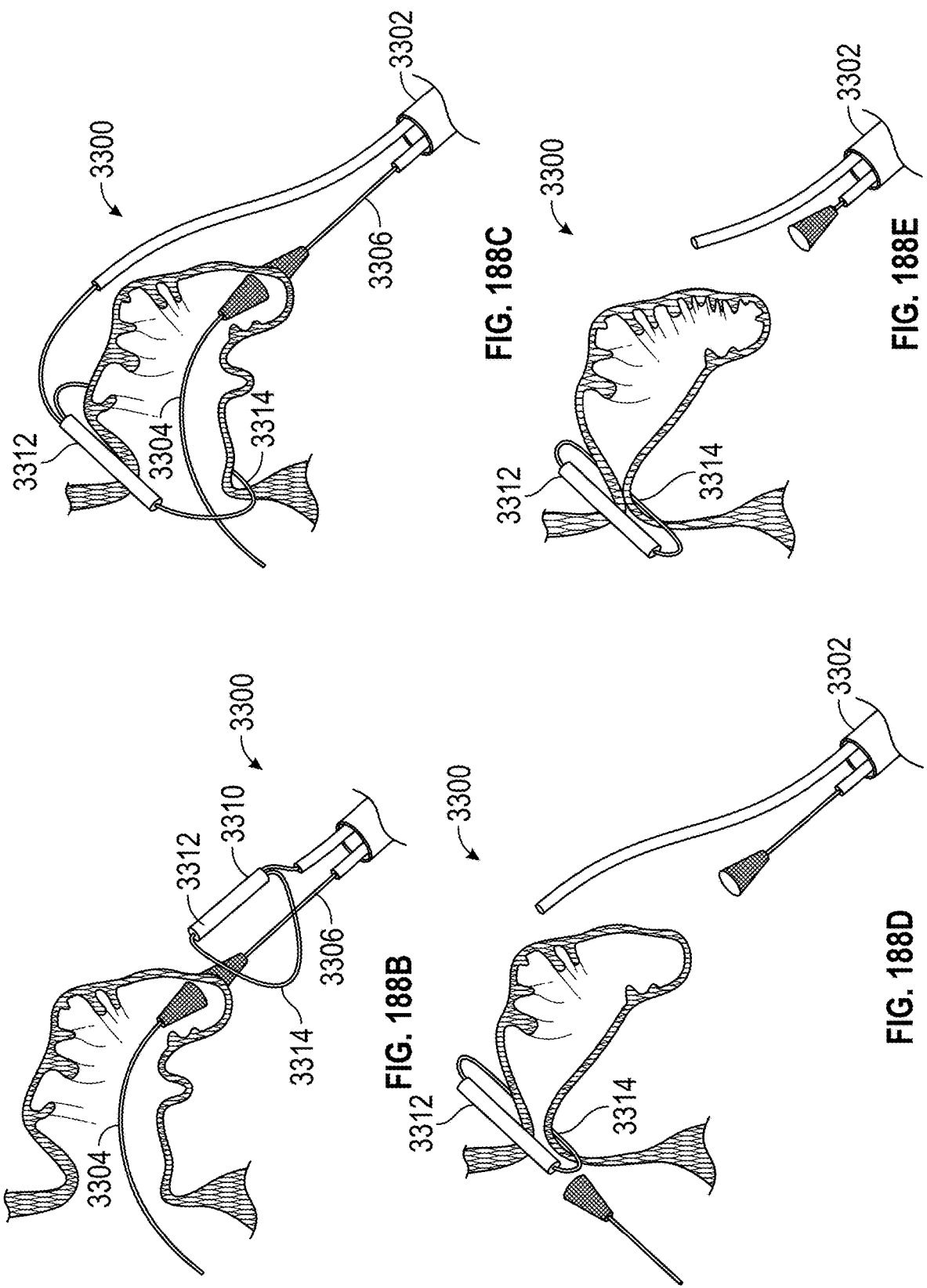

DEVICES, SYSTEMS, AND METHODS FOR TREATING THE LEFT ATRIAL APPENDAGE

PRIORITY CLAIM AND INCORPORATION BY REFERENCE

The present application claims priority from U.S. Patent Application No. 62/497,352, filed on Mar. 25, 2019, titled LEFT ATRIAL APPENDAGE DEVICE AND TECHNIQUES, U.S. Patent Application No. 62/824,948, filed on Mar. 27, 2019, titled LEFT ATRIAL APPENDAGE CLOSURE DEVICE AND TECHNIQUES, U.S. Patent Application No. 62/828,351, filed on Apr. 2, 2019, titled LEFT ATRIAL APPENDAGE CLOSURE DEVICE AND TECHNIQUES, U.S. Patent Application No. 62/849,713, filed on May 17, 2019, titled LEFT ATRIAL APPENDAGE CLOSURE DEVICE AND METHODS OF USING SAME, U.S. Patent Application No. 62/853,672, filed on May 28, 2019, titled LEFT ATRIAL APPENDAGE CLOSURE DEVICE AND METHODS OF USING SAME, U.S. Patent Application No. 62/854,162, filed on May 29, 2019, titled LEFT ATRIAL APPENDAGE CLOSURE DEVICE AND METHODS OF USING SAME, U.S. Patent Application No. 62/866,405, filed on Jun. 25, 2019, titled LEFT ATRIAL APPENDAGE CLOSURE DEVICE AND METHODS OF USING SAME, U.S. Patent Application No. 62/880,552, filed on Jul. 30, 2019, titled LEFT ATRIAL APPENDAGE CLOSURE DEVICES AND METHODS, U.S. Patent Application No. 62/894,501, filed on Aug. 30, 2019, titled DEVICES, SYSTEMS, AND METHODS FOR CLOSING THE LEFT ATRIAL APPENDAGE, U.S. Patent Application No. 62/925,155, filed on Oct. 23, 2019, titled DEVICES, SYSTEMS, AND METHODS FOR CLOSING THE LEFT ATRIAL APPENDAGE, U.S. Patent Application No. 62/949,338, filed on Dec. 17, 2019, titled DEVICES, SYSTEMS, AND METHODS FOR TREATING THE LEFT ATRIAL APPENDAGE, the contents of each of these priority applications are hereby incorporated by reference herein in their entirety as if fully set forth herein. The benefit of priority is claimed under the appropriate legal basis including, without limitation, under 35 U.S.C. § 119(e). Any and all applications for which a foreign or domestic priority claim is identified in the Application Data Sheet as filed with the present application are hereby incorporated by reference herein in their entirety and made a part of this specification.

FIELD OF THE DISCLOSURE

Embodiments of the present disclosure relate to devices, apparatuses, and methods for closing or occluding a left atrial appendage.

BACKGROUND

Left atrial appendage (LAA) closure has been typically performed in high-risk patients due to possible stroke risk. LAA closure techniques are generally performed to block emboli from exiting the LAA. Typical surgical closure includes stitching the opening closed via left atrium entry. Other techniques include the application of external clamps such as ATRICLIP manufactured by Atricure where a Nitinol device is used to clamp the appendage without opening the left atrium to exclude the appendage from left atrium blood circulation.

Other solutions have used a plug to close the appendage from the inside of the left atrium. Such plugs can be constructed from a laser cut Nitinol tube expanded to a semi-spherical shape. The portion exposed to the left atrium can be covered with cover—such as a thin micron membrane made from polyethylene terephthalate. The membrane can act as a blood barrier to prevent flow from flowing through and between one or more struts of the plug. Typical sizes range between approximately 20 mm and 35 mm in diameter and approximately 20 mm and 40 mm in depth. The device can have anchors protruding from an outer surface of the device intended to engage the wall of the appendage and prevent movement post deployment. The device can be delivered via venous access through the groin and a transseptal crossing into the left atrium where a guide catheter and coaxial delivery catheter are positioned proximal to the left atrial appendage. The implant for appendage exclusion is typically positioned at the distal most portion of the delivery catheter. The device is typically positioned and deployed using fluoroscopy and echocardiography for guidance. Typical issues with conventional devices include complicated pre-procedural sizing algorithms used to determine the appropriate device size, migration of the implant, leakage around or through the implant, and/or fracture of the implant, all which may exacerbate the thrombus and stroke problem the device was designed to reduce. A typical drug regimen associated with conventional LAA treatment devices includes warfarin anticoagulation for 45 days (approximately 6 weeks) followed by dual antiplatelet therapy (DAPT) for six months post-procedure and aspirin thereafter. Another procedure typically required with conventional LAA treatment devices includes a follow up transesophageal echogram at six weeks following the procedure. The incidence of device-related thrombus in patients with LAA imaging has been reported to be 7.2% per year.

SUMMARY OF SOME EXEMPLIFYING EMBODIMENTS

The systems, methods and devices of this disclosure each have several innovative aspects, implementations, or aspects, no single one of which is solely responsible for the desirable attributes disclosed herein.

Disclosed herein are embodiments of devices and systems for treating an LAA that can include an implant comprising a contact member configured to move between a first state and a second state, and a securing element, wherein the contact member is configured to move from the first state to the second state so that at least a portion of the contact member engages a wall portion of the LAA after the contact member has been advanced into the LAA, the contact member is configured to rotate at least in a first direction from a first rotational position to a second rotational position, the contact member is configured to twist at least a portion of the LAA when the contact member is rotated from the first rotational position to the second rotational position, and the securing element is configured to prevent a rotation of the implant in a second direction when the securing element is in an operable state, wherein the second direction is opposite to the first direction.

Also disclosed herein are embodiments of devices and systems for treating an LAA can include an implant configured to move between a first state and a second state, a catheter configured to advance the implant into the LAA when the implant is in the first state and to cause the implant to move from the first state to the second state so that an outside surface of the implant moves against an inner wall surface of the LAA after the implant has been advanced into the LAA, wherein the catheter is configured to rotate the implant in a first direction from a first rotational position to a second rotational position so that the implant can twist at least a portion of the LAA when the implant is in the second state.

Also disclosed herein are embodiments of devices and systems for drawing a first tissue surface toward a second tissue surface, including a contact member configured to expand from a first state to a second state and a securing element configured to move from a first state to a second state, wherein the contact member can be configured to expand from the first state to the second state so that at least a portion of the contact member engages at least a distal portion of the first tissue surface and at least a distal portion of the second tissue surface, the contact member can be configured to rotate at least in a first direction from a first rotational position to a second rotational position, wherein the rotation of the contact member in the first direction causes at least a proximal portion of the first tissue surface to twist and to move toward a proximal portion of the second tissue surface, and wherein the securing element is configured to prevent a rotation of the implant in a second direction when the securing element is in an operable state and engaged with a tissue portion adjacent to and/or comprising the proximal portions of the first and second tissue surfaces, wherein the second direction is opposite to the first direction. Further, in any device and/or system embodiments disclosed herein, the device can be configured to occlude or close a cavity in a body having the first and second tissue surfaces, the first and second tissue surfaces can be tissue surfaces within any cavity within the body, and/or wherein the rotation of the contact member further causes the proximal portion of the second tissue surface to twist and to move toward the proximal portion of the first tissue surface.

Any embodiments of the devices and systems disclosed herein can include, in additional embodiments, one or more of the following features, components, and/or details, in any combination with any of the other features, components, and/or details of any other embodiments disclosed herein: wherein the implant is self-expandable such that the implant automatically expands from the first state to the second state when a restraint is removed from the implant; wherein the contact member is self-expandable such that at least a portion of the contact member automatically expands from the first state to the second state when a restraint is removed from the contact member; wherein the implant is substantially collapsed when the implant is in the first state and is expanded when the implant is in the second state such that a size of the implant is bigger when the implant is in the second state than when the implant is in the first state; wherein the contact member is biased to remain in the second state after deployment into the LAA; wherein the contact member is configured to be rotated in a clockwise or a counter-clockwise direction; wherein the device is configured to cause a tissue of the left atrium and/or the LAA to constrict around an outer surface of a body portion of the implant when the contact member is rotated to the second rotational position, and the securing element is configured to engage with the tissue that has constricted around the outer surface of the body portion of the implant to prevent rotation of the implant in the second direction; wherein the securing element has a plurality of tissue anchors configured to engage with an internal wall of the heart adjacent to the LAA; wherein the securing element has a helical shape and is configured to rotate about a body portion of the implant during the implantation procedures; wherein the implant is configured to rotate in a first direction from the first rotational position to the second rotational position; wherein the implant is configured to prevent rotation of the implant in a second direction after the implant has been fully deployed, wherein the second direction is opposite to the first direction; wherein the contact member has a plurality of tissue anchors on an outside surface thereof; wherein the plurality of tissue anchors on the outside surface of the contact member are configured to engage an inner wall surface of the LAA after the contact member has been moved to the second state; wherein the implant comprises a securing element configured to engage with a tissue portion of the heart adjacent to the LAA; wherein the second rotational position is at least one-quarter of a complete rotation relative to the first rotational position; wherein the second rotational position is at least one-half of a complete rotation relative to the first rotational position; and/or wherein the second rotational position is from approximately one-quarter of a complete rotation to one or more complete rotations relative to the first rotational position.

Further, any embodiments of the devices and systems disclosed herein can include, in additional embodiments, one or more of the following features, components, and/or details, in any combination with any of the other features, components, and/or details of any other embodiments disclosed herein: further comprising a catheter selectively coupled with the contact member and configured to exert a torque on the contact member to rotate the contact member from the first rotational position until a threshold predetermined torque level is reached; wherein a threshold predetermined torque level is from approximately 0.25 in-oz of torque to approximately 10 in-oz of torque; wherein a threshold predetermined torque level is from approximately 0.5 in-oz of torque to approximately 5 in-oz of torque; further comprising a retention member configured to bias the securing element toward a tissue wall of the LAA; further comprising a retention member configured to bias the securing element toward the contact member; further comprising a retention member configured to couple the securing element with the contact member; wherein the retention member comprises a threaded shaft; wherein the device is configured such that a rotation of the retention member in a first direction causes the securing element to move toward the contact member; wherein the contact member is configured to rotate at least in a first direction from a first rotational position to a second rotational position when a torque is applied to the contact member; wherein the device is configured such that the contact member can be removed from the LAA after the securing element has been deployed to the operable state of the securing element; wherein the device is configured such that the contact member can be removed from the LAA after the securing element has been deployed to the operable state of the securing element, and wherein the securing element is configured to prevent a rotation of the tissue of the left atrium and/or the LAA that has been constricted as a result of the rotation of the contact member from the first rotational position to the second rotational position; wherein only a portion of the securing element extends into the left atrium after deployment of the device, and all other portions of the device are internal to the LAA after deployment of the device; wherein only approximately 10% or less of an overall length of the deployed device extends into the left atrium after deployment of the device; wherein the device is configured for use by a surgical robot device or system; a surgical robotic device, comprising one or more robotic arms and wherein the device of any embodiments disclosed herein is configured for use by the surgical robotic device; wherein the contact member and the securing element are integrally formed and/or monolithically formed;

wherein the device is configured to cause a tissue of the left atrium and/or the LAA to constrict around an outer surface of a body portion of the implant when the contact member is rotated to the second rotational position, and the securing element is configured to compress the tissue that has constricted around the outer surface of the body portion of the implant between a distal surface of the securing element and the contact member to prevent rotation of the implant in the second direction.

Some embodiments of devices and systems for closing or occluding a left atrial appendage (LAA) disclosed herein can include an implant configured to move between a first state and a second state and a catheter configured to advance the implant into the left atrial appendage when the implant is in the first state, wherein the implant can be configured to move from the first state to the second state so that at least a portion of the implant engages a wall portion of the left atrial appendage after the implant has been advanced into the left atrial appendage, and wherein the implant can be configured to twist at least a portion of the left atrial appendage when the implant is rotated from a first rotational position to a second rotational position when the implant is in the second state. In any embodiments disclosed herein, the twisting movement or step can be accomplished by a torque catheter.

Any embodiments of the devices and systems disclosed herein can, in additional embodiments, include one or more of the following features or details, in any combination: wherein the implant is configured to automatically rotate from the first rotational position to the second rotational position after the implant is in the second state; wherein the implant can be configured to be triggered or activated to thereafter automatically rotate from the first rotational position to the second rotational position; wherein the device has a spring that is coupled with the implant, the spring being configured to automatically rotate the implant when the spring is released or activated; wherein the implant can be self-expandable such that the implant automatically expands from the first state to the second state when a restraint is removed from the implant; wherein the implant can be self-expandable such that at least a portion of the implant automatically expands from the first state to the second state when the implant is advanced past a distal end of an outer sleeve of the catheter; wherein the implant is substantially collapsed when the implant is in the first state and can be expanded when the implant is in the second state such that a size of the implant can be bigger when the implant is in the second state than when the implant is in the first state; wherein the implant can be biased to remain in the second state after deployment into the left atrial appendage; wherein the implant can be configured to be rotated in a clockwise or a counter-clockwise direction; wherein the implant can include a securing element configured to engage with an internal wall of the heart outside of the left atrial appendage; wherein the implant can include a securing element configured to engage with an internal wall of the heart outside of the left atrial appendage, wherein the securing element has a helical shape and is configured to rotate about a body portion of the implant during the implantation procedures; wherein the implant can include a corkscrew shaped securing element configured to engage with an internal wall of the heart outside of the left atrial appendage; wherein the implant can include a securing element having a corkscrew tissue anchor to engage the internal wall of the heart and/or LAA tissue; wherein the implant can include a securing element having a plurality of tissue anchors configured to engage with an internal wall of the heart adjacent to the left atrial appendage; wherein the implant can be configured to prevent the implant from rotating back to the first rotational position after the implant has been fully deployed; wherein the implant can be configured to rotate in a first direction from the first rotational position to the second rotational position, and the implant can be configured to prevent rotation of the implant in a second direction after the implant has been fully deployed, the second direction being opposite to the first direction.

Any embodiments of the devices and systems disclosed herein can, in additional embodiments, include one or more of the following features or details, in any combination: wherein the implant has a plurality of tissue anchors on an outside surface thereof; wherein the plurality of tissue anchors on the outside surface of the implant configured to engage an inner wall surface of the left atrial appendage after the implant has been moved to the second state; wherein the implant can include a securing element configured to engage with a tissue portion of the heart adjacent to the left atrial appendage; wherein the second rotational position can be at least one-quarter or approximately one-quarter of a complete rotation (i.e., 90 degrees or approximately 90 degrees) relative to the first rotational position; wherein the second rotational position can be at least one-half or approximately one-half of a complete rotation (i.e., 180 degrees or approximately 180 degrees) relative to the first rotational position; wherein the second rotational position can be from one-quarter or approximately one-quarter of a complete rotation (i.e., 90 degrees or approximately 90 degrees) to one or more or approximately one or more complete rotations (i.e., 360 degrees or approximately 360 degrees or more) relative to the first rotational position; wherein the catheter can be configured to exert a torque on the implant to rotate the implant from the first rotational position until a threshold predetermined torque level is reached; wherein a threshold predetermined torque level can be from 0.25 or approximately 0.25 in-oz of torque to 10 or approximately 10 in-oz of torque; and/or wherein a threshold predetermined torque level can be from 0.5 or approximately 0.5 in-oz of torque to 5 or approximately 5 in-oz of torque.

Any embodiments of the devices and systems disclosed herein can include an implant having a contact member configured to move between a first state and a second state and a catheter configured to advance the contact member into the LAA when the contact member is in the first state and to cause the contact member to move from the first state to the second state so that an outside surface of the contact member expands against an inner wall surface of the LAA after the contact member has been advanced into the LAA, wherein the catheter is configured to exert a torque on the contact member when at least a portion of the catheter is rotated until a predetermine torque level is reached to rotate the contact member from a first rotational position to a second rotational position so that the contact member can twist at least a portion of the LAA.

Any embodiments of the devices and systems disclosed herein can include an expandable implant configured to move between a first state and a second state, a catheter configured to advance the implant into the left atrial appendage when the implant is in the first state and to cause the implant to move from the first state to the second state so that an outside surface of the implant expands against at least a portion of an inner wall surface of the left atrial appendage after the implant has been advanced into the left atrial appendage. In any embodiments of the device for closing or occluding an LAA disclosed herein, the catheter can be configured to exert a torque on the implant to rotate the implant from a first rotational position to a second rotational position so that the implant can twist at least a portion of the left atrial appendage until a predetermine torque level is reached, or in some embodiments, until the user decides to stop, whichever comes first.

Also disclosed herein are devices and systems for treating the LAA, which include a device configured to be inserted into the LAA and to engage the LAA tissue while the device is rotated to a rotated position to close the blood communication between the LAA and the left atrium. In any embodiments of the apparatus, the device can be configured to be selectively lockable in the rotated position to at least substantially maintain the device in the rotated position after implantation, the device can include a securing element configured to engage a tissue surface adjacent to the LAA to maintain the device in the rotated position after implantation, the device can be round, spherical, or disc shaped when the device is in a deployed state in the LAA, the device can be expandable from a first collapsed state to a second expanded state, and/or the device can be self-expanding from a first collapsed state to a second expanded state.

Also disclosed herein are embodiments of methods for treating the LAA, including engaging a tissue of the LAA, and rotating the tissue of the LAA to close or occlude a blood communication between the LAA and a left atrium. In any embodiments of the methods disclosed herein, rotating the tissue of the LAA to close or occlude the blood communication between the LAA and the left atrium can include rotating the tissue of the LAA to close or occlude the ostium of the LAA. Further, any embodiments of the methods disclosed herein can further include securing the LAA in a rotated position to hold the LAA in a closed or occluded state.

Any embodiments of a method of closing or occluding an LAA disclosed herein can include advancing a deployment device having an implant into the left atrial appendage, wherein the implant can be configured to be moved from a first state to a second state. In some embodiments, at least a portion of the implant can be enlarged in a radial direction when the implant is in the second state as compared to the first state. The method can further include moving the implant from the first state to the second state within the left atrial appendage so as to move at least a portion of an outside wall of the implant or one or more tissue anchors extending away from an outer surface of the implant against at least a portion of an inner wall surface of the left atrial appendage, rotating the implant from a first rotational position to a second rotational position to twist the left atrial appendage, and preventing the implant from rotating back to the first rotational position.

Any embodiments of methods of closing or occluding an LAA disclosed herein can, in some additional embodiments, include one or more of the following steps, in any combination and in any combination with any of the other steps, features, or other details of any other embodiments: wherein the implant is self-expanding and wherein moving the implant from the first state to the second state comprises advancing the implant out of a distal end of the deployment device; wherein engaging a wall portion on an inside of the LAA comprises engaging a wall portion on an inside of the LAA with one or more tissue anchors positioned on an outside surface of the implant; wherein preventing the implant from rotating back to the first rotational position comprises engaging a tissue wall with an anchor element to prevent relative movement between the implant and the tissue wall; wherein preventing the implant from rotating back to the first rotational position comprises engaging a tissue wall with an anchor element, and wherein the anchor element is configured to be secured to the implant to prevent a rotation between the implant and the anchor element; wherein preventing the implant from rotating back to the first rotational position comprises engaging a tissue wall of the heart with an anchor element, wherein the anchor element is rotationally fixed relative to the implant and configured to prevent the implant from rotating back to the first rotational position; wherein preventing the implant from rotating back to the first rotational position comprises engaging a tissue of the heart outside of the closed portion of the LAA with an anchor element, wherein the anchor element is rotationally fixed relative to the implant and configured to prevent the implant from rotating back to the first rotational position; wherein the anchor element comprises a plurality of tissue anchors on at least one surface thereof configured to engage with the internal wall of the heart outside of the LAA; wherein rotating the implant from the first rotational position to the second rotational position to twist the LAA comprises rotating the implant until an ostium of the LAA is substantially or completely closed; wherein rotating the implant from the first rotational position to the second rotational position to twist the LAA comprises rotating the implant at least approximately 90 degrees in either direction from the first rotational position; wherein rotating the implant from the first rotational position to the second rotational position to twist the LAA comprises rotating the implant at least approximately 180 degrees in either direction from the first rotational position; wherein rotating the implant from the first rotational position to the second rotational position to twist the LAA comprises rotating the implant from approximately 90 degrees to approximately 360 degrees in either direction from the first rotational position; wherein rotating the implant from the first rotational position to the second rotational position to twist the LAA comprises rotating the implant from approximately 90 degrees to approximately 180 degrees in either direction from the first rotational position; wherein rotating the implant from the first rotational position to the second rotational position to twist the LAA comprises exerting a torque on the implant to rotate the implant in either direction from the first rotational position until a threshold predetermined torque level is reached, holding the implant in the second rotational position, and securing the implant in approximately the second rotational position relative to a tissue surface surrounding the LAA; wherein a maximum predetermined torque level is from approximately 0.25 in-oz of torque to approximately 10 in-oz of torque; and/or wherein a maximum predetermined torque level is from approximately 0.5 in-oz of torque to approximately 5 in-oz of torque.

Any embodiments of the methods of closing or occluding an LAA disclosed herein can, in some additional embodiments, include one or more of the following steps, in any combination and in any combination with any of the other steps, features, or other details of any other embodiments: wherein the implant is self-expanding and wherein moving the implant from the first state to the second state can include advancing the implant out of a distal end of the deployment device; wherein engaging a wall portion on an inside of the left atrial appendage can include engaging at least a portion of a wall portion on an inside of the left atrial appendage or surrounding the left atrial appendage with one or more tissue anchors positioned on an outside surface of the implant; wherein preventing the implant from rotating back to the first rotational position can include engaging a tissue wall outside of the left atrial appendage with an anchor element; wherein the anchor element can be rotationally fixed to the implant to prevent relative movement between the anchor element and the implant; wherein preventing the implant from rotating back to the first rotational position can include engaging a tissue wall of the heart with an anchor element; wherein the anchor element can be rotationally fixed relative to the implant and configured to prevent the implant from rotating back to the first rotational position; wherein preventing the implant from rotating back to the first rotational position can include engaging an internal wall of the heart outside of the left atrial appendage with an anchor element; wherein the anchor element can be rotationally fixed relative to the implant and configured to prevent the implant from rotating back to the first rotational position; wherein the anchor element can include a plurality of tissue anchors on at least one surface thereof configured to engage with the internal wall of the heart outside of the left atrial appendage; and/or wherein rotating the implant from the first rotational position to the second rotational position to twist the left atrial appendage can include rotating the implant until an ostium of the LAA can be substantially or completely closed or occluded, or collapsed about an outer surface of the implant.

Any embodiments of the methods of closing or occluding an LAA disclosed herein can, in any additional embodiments, include one or more of the following steps, in any combination and in any combination with any of the other steps, features, or other details of any other embodiments: wherein rotating the implant from the first rotational position to the second rotational position to twist the left atrial appendage can include rotating the implant at least one-quarter or approximately one-quarter of a complete rotation (i.e., 90 degrees or approximately 90 degrees) relative to the first rotational position; wherein rotating the implant from the first rotational position to the second rotational position to twist the left atrial appendage can include rotating the implant at least one-half or approximately one-half of a complete rotation (i.e., 180 degrees or approximately 180 degrees) in either direction from the first rotational position; wherein rotating the implant from the first rotational position to the second rotational position to twist the left atrial appendage can include rotating the implant from one-quarter or approximately one-quarter of a complete rotation (i.e., 90 degrees or approximately 90 degrees) to one full turn or approximately one full turn (i.e., 360 degrees or approximately 360 degrees), or to more than one full turn (i.e., more than 360 degrees) in either direction from the first rotational position; wherein rotating the implant from the first rotational position to the second rotational position to twist the left atrial appendage can include rotating the implant from one-quarter or approximately one-quarter of a complete rotation (i.e., 90 degrees or approximately 90 degrees) to one-half of a full turn or approximately one-half of a full turn (i.e., 180 degrees or approximately 180 degrees), or to more than one full turn (i.e., more than 360 degrees) in either direction from the first rotational position; wherein rotating the implant from the first rotational position to the second rotational position to twist the left atrial appendage can include exerting a torque on the implant to rotate the implant in either direction from the first rotational position until a threshold predetermined torque level is reached; wherein rotating the implant from the first rotational position to the second rotational position to twist the left atrial appendage can include holding the implant in the second rotational position; wherein rotating the implant from the first rotational position to the second rotational position to twist the left atrial appendage can include securing the implant in approximately the second rotational position relative to a tissue surface surrounding the left atrial appendage; wherein a maximum predetermined torque level can be from approximately 0.25 in-oz of torque to approximately 10 in-oz of torque; and/or wherein a maximum predetermined torque level can be from approximately 0.5 in-oz of torque to approximately 5 in-oz of torque.

Some embodiments of an implant for deployment within a cavity or vessel disclosed herein include an expandable body, a plurality of tissue anchors on an outside surface of the expandable body configured to engage with an inner wall surface of the cavity or vessel, and an anchor element coupled with the expandable body configured to engage with a tissue surface adjacent to the inner wall surface of the cavity or vessel.

Any embodiments of the devices and systems disclosed herein can include an expandable implant having a plurality of tissue anchors on an outside surface thereof, the expandable implant being configured to move between a first state in which the implant is substantially collapsed and a second state in which at least a portion of the implant is expanded, and a catheter configured to advance the implant into the left atrial appendage when the implant is in the first state and to cause the implant to move from the first state to the second state so that at least some of the plurality of tissue anchors engage an inner wall surface of the left atrial appendage after the implant has been advanced into the left atrial appendage. In some embodiments, the catheter can be configured to rotate the implant in a first direction from a first rotational position to a second rotational position so that the implant can twist the wall of the left atrial appendage.

Some embodiments of the devices and systems for closing or occluding an LAA disclosed herein can include an implant configured to move between a first state and a second state, and a catheter configured to advance the implant into the left atrial appendage when the implant is in the first state and to cause the implant to move from the first state to the second state so that an outside surface of the implant moves against an inner wall surface of the left atrial appendage after the implant has been advanced into the left atrial appendage. In some embodiments, the catheter can be configured to rotate the implant in a first direction from a first rotational position to a second rotational position so that the implant can twist at least a portion of the left atrial appendage when the implant is in the second state.

Any embodiments of the methods of treating the left atrial appendage disclosed herein can include engaging a tissue of the left atrial appendage and rotating the tissue of the left atrial appendage to close or significantly close, or inhibit or substantially inhibit, a blood communication between the left atrial appendage and a left atrium. Any embodiments of the method(s) disclosed herein can include, in additional embodiments, one or more of the following features, components, steps, and/or details, in any combination with any of the other features, components, steps, and/or details of any other treatment method embodiments disclosed herein: further including rotating the tissue of the left atrial appendage to close the blood communication between the left atrial appendage and the left atrium can include rotating the tissue of the left atrial appendage to close the ostium of the left atrial appendage, and/or further including securing the left atrial appendage in a rotated position to hold the left atrial appendage in a closed state.

Some embodiments of apparatuses for treating the left atrial appendage disclosed herein can include a device configured to be inserted into the left atrial appendage and to engage the left atrial appendage tissue while the device is rotated to a rotated position to close the blood communication between the left atrial appendage and the left atrium. In some embodiments, the device can be configured to be locked in the rotated position to maintain the device in the rotated position after implantation, wherein the device can include a securing element configured to engage a tissue surface adjacent to the left atrial appendage to maintain the device in the rotated position after implantation, wherein the device can be round, spherical, or disc shaped when the device is in a deployed state in the left atrial appendage, wherein the device can be expandable from a first collapsed state to a second expanded state, and/or wherein the device can be self-expanding from a first collapsed state to a second expanded state.

Disclosed herein are additional embodiments of implants for treatment of an LAA, such additional embodiments being configured to elongate an opening of the LAA or stretch the opening of the LAA. In any such implant embodiments disclosed herein, the implant can include a frame that is expandable from a collapsed state to an expanded state, the frame including a wall having an elongated shape along an entire length of the frame in at least the expanded state, and an opening extending through the frame in an axial direction from a proximal end to a distal end of the frame, the opening being surrounded by the wall. In any embodiments disclosed herein, the frame can be configured to define a first width in a first direction from a first portion across the opening of the frame to a second portion that is greater than a second width in a second direction that is perpendicular to the first direction.

Additionally, any embodiments of the implants for treatment of the LAA disclosed herein can include, in additional embodiments, one or more of the following features, components, and/or details, in any combination with any of the other features, components, and/or details of any other embodiments disclosed herein: a first apex extension that extends away from the proximal end of the frame at the first portion of the wall, wherein the first apex extension can be configured to bias the proximal end of the frame to approximately align with the outside edge of the ostium; a first apex extension that extends away from the proximal end of the frame at the first portion of the wall, wherein the first apex extension can be configured to prevent the frame from passing completely through an ostium of the LAA; a first apex extension that extends away from the proximal end of the frame at the first portion of the wall, wherein the first apex extension can be configured to overlap an outside surface of a wall portion surrounding an ostium of the LAA when the implant is in an operable position within the LAA; a second apex extension that extends away from the proximal end of the frame at the second portion of the wall of the frame; a second apex extension that extends away from the proximal end of the frame at the second portion of the wall, wherein the second apex extension can be configured to bias the proximal end of the frame to approximately align with the outside edge of the ostium; a second apex extension that extends away from the proximal end of the frame at the second portion of the wall, wherein the second apex extension can be configured to prevent the frame from passing completely through an ostium of the LAA; and/or a second apex extension that extends away from the proximal end of the frame at the second portion of the wall of the frame, wherein the second apex extension can be configured to overlap an outside surface of a wall portion surrounding an ostium of the LAA when the implant is in an operable position within the LAA.

Any implant embodiments disclosed herein can include, in additional embodiments, one or more of the following features, components, and/or details, in any combination with any of the other features, components, and/or details of any other embodiments disclosed herein: wherein the first width of the opening of the frame is at least approximately two times the second width of the frame, but no more than approximately ten times the second width of the opening of the frame, when the implant is in a naturally expanded state outside of the body; wherein the first width of the opening of the frame is from approximately two times to approximately five times the second width of the opening of the frame, when the implant is in a naturally expanded state outside of the body; wherein the first width of the opening of the frame is from approximately two times to approximately four times the second width of the opening of the frame, when the implant is in a naturally expanded state outside of the body; wherein the first width of the opening of the frame is from approximately three times to approximately four times the second width of the opening of the frame, when the implant is in a naturally expanded state outside of the body; wherein a ratio of the first width of the opening of the frame to the second width of the opening of the frame when the implant is in a naturally expanded state outside of the body is at least approximately 2 to 1; wherein a ratio of the first width of the opening of the frame to the second width of the opening of the frame when the implant is in a naturally expanded state outside of the body is from approximately 2 to 1 to approximately 5 to 1; wherein a ratio of the first width of the opening of the frame to the second width of the opening of the frame when the implant is in a naturally expanded state outside of the body is from approximately 3 to 1 to approximately 4 to 1; and/or wherein a ratio of the first width of the opening of the frame to the second width of the opening of the frame when the implant is in a naturally expanded state outside of the body is approximately 3.5 to 1.

Any implant embodiments disclosed herein can include, in additional embodiments, one or more of the following features, components, and/or details, in any combination with any of the other features, components, and/or details of any other embodiments disclosed herein: wherein the first width of the opening of the frame is at least approximately two times the second width of the opening of the frame, but no more than approximately ten times the second width of the opening of the frame, when the implant is in a deployed state in the LAA; wherein the first width of the opening of the frame is from approximately two times to approximately five times the second width of the opening of the frame, when the implant is in a deployed state in the LAA; wherein the first width of the opening of the frame is from approximately two times to approximately four times the second width of the opening of the frame, when the implant is in a deployed state in the LAA; wherein the first width of the opening of the frame is from approximately three times to approximately four times the second width of the opening of the frame, when the implant is in a deployed state in the LAA; wherein a ratio of the first width of the opening of the frame of the frame to the second width of the opening of the frame when the implant is in a deployed state in the LAA is at least approximately 2 to 1; wherein a ratio of the first width of the frame to the second width of the frame when the implant is in a deployed state in the LAA is from approximately 2 to 1 to approximately 5 to 1; wherein a ratio of the first width of the frame to the second width of the frame when the implant is in a deployed state in the LAA is from approximately 3 to 1 to approximately 4 to 1; and/or wherein a ratio of the first width of the frame to the second width of the frame when the implant is in a deployed state in the LAA is approximately 3.5 to 1.

Any implant embodiments disclosed herein can include, in additional embodiments, one or more of the following features, components, and/or details, in any combination with any of the other features, components, and/or details of any other embodiments disclosed herein: wherein the implant can be configured to change a shape of the ostium so that a first width of the ostium is at least approximately two times the second width of the ostium, but no more than approximately ten times the second width of the ostium, when the implant is in a deployed state in the LAA; wherein the implant can be configured to change a shape of the ostium so that a first width of the ostium is from approximately two times to approximately five times the second width of the ostium, when the implant is in a deployed state in the LAA; wherein the implant can be configured to change a shape of the ostium so that a first width of the ostium is from approximately two times to approximately four times the second width of the ostium, when the implant is in a deployed state in the LAA; wherein the implant can be configured to change a shape of the ostium so that a first width of the ostium is from approximately three times to approximately four times the second width of the ostium, when the implant is in a deployed state in the LAA; wherein the implant can be configured to change a shape of the ostium so that a ratio of the first width of the ostium to the second width of the ostium when the implant is in a deployed state in the LAA is at least approximately 2 to 1; wherein the implant can be configured to change a shape of the ostium so that a ratio of the first width of the ostium to the second width of the ostium when the implant is in a deployed state in the LAA is from approximately 2 to 1 to approximately 5 to 1; wherein the implant can be configured to change a shape of the ostium so that a ratio of the first width of the ostium to the second width of the ostium when the implant is in a deployed state in the LAA is from approximately 3 to 1 to approximately 4 to 1; wherein the implant can be configured to change a shape of the ostium so that a ratio of the first width of the ostium to the second width of the ostium when the implant is in a deployed state in the LAA is approximately 3.5 to 1; further including an anchoring element configured to anchor the frame to the LAA located at least at the first portion and the second portion of the frame; wherein the frame comprises grip features on an outside surface of the frame at least at the first portion and the second portion of the frame configured to inhibit a movement of the frame relative to a tissue surface of the ostium of the LAA; including a first coarse region and a second coarse region on an outside surface of the frame at the first portion and the second portion of the frame, respectively, the first and second coarse regions being configured to inhibit a movement of the frame relative to a tissue surface of the ostium of the LAA; further including a cover coupled with the frame, the cover at least partially covering the opening in the frame; further including a cover coupled with the frame, the cover completely covering the opening in the frame; further including a cover coupled with the frame, the cover completely covering the opening in the frame, wherein the cover comprises a mesh material; and/or wherein the first and second end portions of the frame are configured to spread a first portion of an ostium of the LAA apart from a second portion of the ostium that is opposite to the first portion so as to elongate the ostium of the LAA in the first direction.

Further, in any implant embodiments disclosed herein, the implant can include a frame that is expandable from a collapsed state to an expanded state, the frame including a wall having an elongated shape along an entire length of the frame in at least the expanded state, and an opening extending through the frame in an axial direction from a proximal end to a distal end of the frame, the opening being surrounded by the wall. In some embodiments, the elongated shape can define a first width in a first direction from a first portion of the frame across the opening of the frame to a second portion of the frame when the implant is an operable position that is at least two times greater than a second width in a second direction that is normal to the first direction, and the proximal end of the frame is flared outwardly at least at the first portion and the second portion of the frame. In any embodiments disclosed herein, the first width can be from approximately two times greater to approximately five times greater than the second width, the first width can be from approximately three times greater to approximately five times greater than the second width, the first width can be from approximately three times greater to approximately four times greater than the second width, and/or the first and second portions of the frame can be configured to spread a first portion of an ostium of the LAA apart from a second portion of the ostium that is opposite to the first portion so as to elongate the ostium of the LAA in the first direction.

Additionally, any implant, device and/or system embodiments disclosed herein can be adapted and/or used for treatment of any opening, chamber, or cavity in a body. Any implant embodiments disclosed herein can include a frame that is expandable from a collapsed state to an expanded state, the frame including a wall continuously surrounding an opening extending through the frame, a plurality of openings extending through the wall, and a first recess in a first portion of the wall, and a second recess in a second portion of the wall, wherein the first recess and the second recess can each be configured to receive an edge of a wall of the opening of the body therein when the implant is expanded against the wall of the opening, the first and second recesses being configured to bias the edge of the opening of the body to remain in the first and second recesses. In any embodiments disclosed herein, the recess can have a curved profile. Further, the first and second portions of the wall of the frame can be configured to spread a first portion of an ostium of the opening apart from a second portion of the ostium that is opposite to the first portion so as to elongate the ostium of the opening.

In any embodiments disclosed herein, the implant can include: a frame that is expandable from a first state to a second state, the frame having a first portion that is moveable in a first direction when the frame is expanded from the first state to the second state, a second portion coupled with the first portion, the second portion being moveable in a second direction when the frame is expanded from the first state to the second state, the second direction being opposite to the first direction, a length in a lengthwise direction (also referred to herein as a first direction) between an end of the first portion and an end of the second end portion, a width in a widthwise direction (also referred to herein as a second direction) that is perpendicular to the lengthwise direction, and a height in a heightwise direction (also referred to herein as a third direction) that is perpendicular to the lengthwise direction and the widthwise direction.

Any embodiments of the implants disclosed herein can include, in additional embodiments, one or more of the following features, components, and/or details, in any combination with any of the other features, components, and/or details of any other embodiments disclosed herein: wherein the frame is advanceable through a delivery catheter when the frame is in the first state; wherein the length of the frame increases when the frame is expanded from the first state to the second state; and/or wherein the width and the height of the frame remain generally constant when the frame is expanded from the first state to the second state.

Additional embodiments of implants for treating an LAA are also disclosed herein. In any implant embodiments disclosed herein, the implant can include a frame that is expandable from a first state to a second state, the frame having a middle portion, a first end portion coupled with the middle portion, the first end portion being expandable in a first direction when the frame is expanded from the first state to the second state, a second end portion coupled with the middle portion, the second end portion being expandable in a second direction when the frame is expanded from the first state to the second state, the second direction being opposite to the first direction, a length in a lengthwise direction between the first end portion and the second end portion, and/or a width in a widthwise direction that is perpendicular to the lengthwise direction.

Any implant embodiments disclosed herein can include, in additional embodiments, one or more of the following features, components, and/or details, in any combination with any of the other features, components, and/or details of any other embodiments disclosed herein: wherein the frame is advanceable through a delivery catheter when the frame is in the first state; wherein the length of the frame increases when the frame is expanded from the first state to the second state; and/or wherein the width of the frame remains approximately constant when the frame is expanded from the first state to the second state; wherein the implant includes a frame that is expandable from a first state to a second state; wherein the frame has a middle portion, a first end portion coupled with the middle portion, the first end portion being expandable in a first direction when the frame is expanded from the first state to the second state, a second end portion coupled with the middle portion, the second end portion being expandable in a second direction when the frame is expanded from the first state to the second state, the second direction being opposite to the first direction, a length in a lengthwise direction between the first end portion and the second end portion, and a width in a widthwise direction that is perpendicular to the lengthwise direction; wherein the frame is advanceable through a delivery catheter when the frame is in the first state; wherein the length of the frame increases when the frame is expanded from the first state to the second state; wherein the first and second end portions of the frame are configured to spread a first portion of an ostium of the LAA apart from a second portion of the ostium that is opposite to the first portion so as to elongate the ostium of the LAA in the lengthwise direction; further including a clip configured to hold two or more portions of tissue of the LAA together; further including at least one cushion coupled with at least one of the first end portion and the second end portion of the frame; wherein the frame can be configured to increase in size in the lengthwise direction without increasing in size in any other direction; wherein the frame is self-expandable from the first state to the second state; wherein the second stage portion comprises a hinge mechanism for constricting or closing the opening of the LAA; further including at least one of a passive activation mechanism and an active activation mechanism to activate the hinge mechanism; wherein at least a portion of the frame can be configured to be contractible in the lengthwise direction so as to decrease a length of the frame in the lengthwise direction; wherein the frame comprises a length of wire having a U-shape configured to allow cantilever bending near the middle portion of the frame; wherein the frame comprises a torsion spring wire-form near the middle portion of the frame; wherein the frame comprises multiple U-shape cantilever sections or torsion spring forms; wherein the frame is formed from a round wire, a wire strip, or a sheet that is laser cut; and/or wherein the frame comprises at least one of a polymer, a composite material, a metal, and a super-elastic shape memory alloy.

In any implant embodiments disclosed herein, the implant can include a frame that is expandable from a first state to a second state, the frame having a middle portion, a first end portion coupled with the middle portion, the first end portion being expandable in a first direction when the frame is expanded from the first state to the second state, a second end portion coupled with the middle portion, the second end portion being expandable in a second direction when the frame is expanded from the first state to the second state, the second direction being opposite to the first direction, a length in a lengthwise direction between the first end portion and the second end portion, and a width in a widthwise direction that is perpendicular to the lengthwise direction. In any embodiments disclosed herein, the frame can be advanceable through a delivery catheter when the frame is in the first state; the length of the frame can increase when the frame is expanded from the first state to the second state; and/or the frame can be configured to increase a size of an ostium of the LAA in the lengthwise direction and to decrease a size of the ostium of the LAA in the widthwise direction when the frame is expanded from the first state to the second state.

In any embodiments disclosed herein, the implant can be adapted for use in closing, restricting, tightening, and/or occluding any vessel, opening, chamber, or cavity in a body, and can include a frame that is expandable from a first state to a second state, the frame having a middle portion including a proximal portion, a first portion extending distally away from the proximal portion, and a second portion extending distally away from the proximal portion, a first leg coupled with the first end of the middle portion, the first leg being expandable in a first direction when the frame is expanded from the first state to the second state, a second leg coupled with the second end of the middle portion, the second leg being expandable in a second direction when the frame is expanded from the first state to the second state, the second direction being opposite to the first direction, a length in a lengthwise direction between the first end portion and the second end portion, and a width in a widthwise direction that is perpendicular to the lengthwise direction.

Any implant embodiments disclosed herein can include, in additional embodiments, one or more of the following features, components, and/or details, in any combination with any of the other features, components, and/or details of any other embodiments disclosed herein: wherein the first leg and the second leg are integrally formed with the middle portion; wherein the frame is advanceable through a delivery catheter when the frame is in the first state; wherein the length of the frame increases when the frame is expanded from the first state to the second state; wherein the frame can be configured to increase a size of an ostium of the LAA in the lengthwise direction and to decrease a size of the ostium of the LAA in the widthwise direction when the frame is expanded from the first state to the second state so as to draw a first wall of the LAA closer to a second wall of the LAA; wherein the first and second legs are configured to spread a first portion of an ostium of the LAA apart from a second portion of the ostium that is opposite to the first portion so as to elongate the ostium of the LAA in the lengthwise direction; further including a clip configured to hold two or more portions of tissue of the LAA together; further including at least one cushion coupled with at least one of the first and second legs; wherein the frame can be configured to increase in size in the lengthwise direction without increasing in size in any other direction; wherein the frame is self-expandable from the first state to the second state; further including an anchoring element to anchor one or more walls of the opening of the LAA to another wall of the opening of the LAA; wherein the implant comprises a hinge mechanism for constricting or closing the opening of the LAA; further including at least one of a passive activation mechanism and an active activation mechanism to activate the hinge mechanism; wherein at least a portion of the frame can be configured to be contractible in the lengthwise direction so as to decrease a length of the frame in the lengthwise direction; wherein the frame comprises a length of wire having a U-shape configured to allow cantilever bending near the middle portion of the frame; wherein the frame comprises a torsion spring wire-form near the middle portion of the frame; wherein the frame comprises multiple U-shape cantilever sections or torsion spring forms; wherein the frame is formed from a round wire, a wire strip, or a sheet that is laser cut; and/or wherein the frame comprises at least one of a polymer, a composite material, a metal, and a super-elastic shape memory alloy.

Disclosed herein are embodiments of devices for treating a left atrial appendage that include an implant having a contact member and a catheter configured to advance the contact member into the left atrial appendage and to cause the contact member to move against an inner wall surface of the left atrial appendage, wherein the catheter is configured to exert a torque on the contact member when at least a portion of the catheter is rotated until a predetermine torque level is reached to rotate the contact member from a first rotational position to a second rotational position so that the contact member can twist at least a portion of the left atrial appendage. In any embodiments disclosed herein, the contact member can be configured to be moved against the inner wall surface of the left atrial appendage without changing a state or shape of the contact member, and/or the contact member can be configured to be movable or expandable from a first state to a second state.

Disclosed herein are embodiments of devices for reducing an opening of the left atrial appendage that include a contact member and a securing element, wherein the contact member is configured to engage a tissue surface of the left atrial appendage, the contact member is configured to rotate at least a portion of the left atrial appendage in a first direction from a first rotational position to a second rotational position and to cause the opening of the left atrial appendage to reduce in size from a first size to a second size, and/or the securing element is configured to engage with at least a portion of tissue adjacent to the opening of the left atrial appendage and to prevent the opening of the left atrial appendage from expanding to the first size. In any embodiments disclosed herein, the contact member can be configured to engage a tissue surface on an outside surface of the left atrial appendage. Further, in any embodiments disclosed herein, the contact member can be configured to engage the tissue surface of the left atrial appendage without changing a state or shape of the contact member.

Additional embodiments of implants for treating the LAA are also disclosed herein. In any embodiments disclosed herein, the implant can include a frame that is expandable from a first state to a second state, the frame having a middle portion, a first end portion coupled with the middle portion, the first end portion being expandable in a first direction when the frame is expanded from the first state to the second state, a second end portion coupled with the middle portion, the second end portion being expandable in a second direction when the frame is expanded from the first state to the second state, the second direction being opposite to the first direction, a length in a lengthwise direction (also referred to herein as a first direction) between the first end portion and the second end portion, and a width in a widthwise direction that is normal to the lengthwise direction.

Any implant embodiments disclosed herein can include, in additional embodiments, one or more of the following features, components, and/or details, in any combination with any of the other features, components, and/or details of any other embodiments disclosed herein: including a clip coupled with a proximal portion of the middle portion; including a clip configured to hold two or more portions of tissue of the LAA together; wherein the first end portion and the second end portion are integrally formed with the middle portion; wherein the frame is advanceable through a delivery catheter when the frame is in the first state; wherein the length of the frame increases when the frame is expanded from the first state to the second state; wherein the frame can be configured to increase a size of an ostium of the LAA in the lengthwise direction and to decrease a size of the ostium of the LAA in the widthwise direction when the frame is expanded from the first state to the second state so as to draw a first wall of the LAA closer to a second wall of the LAA; wherein the clip can be configured to be closeable so as to secure a portion of the first wall with a portion of the second wall when the frame is in the second state; wherein the first and second end portions of the frame are configured to spread a first portion of an ostium of the LAA apart from a second portion of the ostium that is opposite to the first portion so as to elongate the ostium of the LAA in the lengthwise direction; further including at least one cushion coupled with at least one of the first end portion and the second end portion of the frame; wherein the frame can be configured to increase in size in the lengthwise direction without increasing in size in any other direction; wherein the frame is self-expandable from the first state to the second state; further including a means for constricting or closing the opening of the LAA; wherein the implant comprises a hinge mechanism for constricting or closing the opening of the LAA; further including at least one of a passive activation mechanism and an active activation mechanism to activate the hinge mechanism; further including a means for contracting at least a portion of the frame in the lengthwise direction so as to decrease a length of the frame in the lengthwise direction; wherein the frame comprises a length of wire having a U-shape configured to allow cantilever bending near the middle portion of the frame; wherein the frame comprises a torsion spring wire-form near the middle portion of the frame; wherein the frame comprises multiple U-shape cantilever sections or torsion spring forms; wherein the frame is formed from a round wire, a wire strip, or a sheet that is laser cut; and/or wherein the frame comprises at least one of a polymer, a composite material, a metal, and a super-elastic shape memory alloy.

Also disclosed herein are additional embodiments of closure or occlusion devices for an LAA. In any embodiments disclosed herein, the device can include a delivery catheter and an implant that is advanceable through the delivery catheter when the implant is in a first state, wherein the implant has a first expandable portion and a second expandable portion, wherein the first and the second expandable portions of the implant are each independently expandable to a second state, and wherein the implant can be configured to block an opening of the LAA when the first and second expandable portions of the implant are in the second state.

Any embodiments of the devices and systems disclosed herein can include, in additional embodiments, one or more of the following features, components, and/or details, in any combination with any of the other features, components, and/or details of any other embodiments disclosed herein: wherein the first expandable portion is a distal portion of the implant and the second expandable portion is a proximal portion of the implant; further including a removable restraint surrounding only a proximal portion of the implant when the implant is in a pre-deployed state; wherein at least one of the first expandable portion and the second expandable portion is self-expanding; wherein the implant can be configured such that the first expandable portion is expanded before the second expandable portion is expanded; and/or any features, components, and/or details of any implant embodiments disclosed herein.

Disclosed herein are additional embodiments of closure or occlusion devices for an LAA, including an implant that is selectively expandable from a first state to a second state and a cover coupled with the implant, wherein the implant can be configured to be expanded against a wall of an opening of the LAA when the implant is in the second state, wherein a size of the implant is greater in the second state than in the first state, wherein at least a portion of the cover is positioned adjacent to an outside surface of the implant and is selectively movable between at least a first state and a second state, wherein the cover can be configured to have a plurality of folds or wrinkles in a portion of the cover adjacent to the outside surface of the implant when the cover is in the second state, and wherein the implant can be configured to block an opening of the LAA when the implant is in the second state.

Any embodiments of the devices disclosed herein can include, in additional embodiments, one or more of the following features, components, and/or details, in any combination with any of the other features, components, and/or details of any other embodiments disclosed herein: wherein the cover can be configured such that at least one or more of the plurality of folds or wrinkles is positioned between the outside surface of at least a portion of the implant and at least a portion of the wall of the opening of the LAA when the implant and the cover are in the second state; further including a pull wire coupled with the cover and configured to move the cover from the first state to the second state upon withdrawal of the pull wire; and/or wherein the implant is also selectively contractible from the second state to the first state.

Any embodiments of the devices disclosed herein can include, in additional embodiments, one or more of the following features, components, and/or details, in any combination with any of the other features, components, and/or details of any other embodiments disclosed herein: wherein the device further includes a delivery catheter; wherein the device further includes an implant of any of the implant embodiments disclosed herein that is advanceable through the delivery catheter when the implant is in a first state; wherein the implant includes a first stage portion and a second stage portion that are each independently deployable to at least a second operable or deployed state; wherein the first stage portion is configured to be at least partially deployed before a second stage portion is deployed; wherein the first stage portion is configured to be positioned near a distal end portion of the LAA; wherein the second stage portion is configured to constrict an opening of the LAA when the second stage portion is in the second state; wherein second stage portion is configured to close the opening of the LAA when the second stage portion is in the second state; wherein second stage portion is configured to fold one or more tissue portions surrounding or adjacent to the opening of the LAA when the second stage portion is in the second state; wherein the second stage portion is configured to twist one or more portions of tissue surrounding the opening of the LAA to constrict or close the opening of the LAA when the second stage portion is in a second state; wherein the second stage portion comprises a means for constricting or closing the opening of the LAA; wherein the second stage portion comprises a hinge mechanism for constricting or closing the opening of the LAA; further including at least one of a passive activation mechanism and an active activation mechanism to activate the hinge mechanism; and/or wherein at least one of the first stage portion and the second stage portion is self-expanding.

Disclosed herein are embodiments of methods of constricting, occluding, closing, or otherwise treating an LAA (hereinafter collectively referred to treatment methods). Any embodiments of such methods can be used to deploy or implant any embodiments of the implants or devices disclosed herein. Any embodiments of the methods disclosed herein can include advancing a delivery catheter having an implant coupled therewith into the heart, advancing a distal tip of the delivery catheter near an ostium of the LAA, and/or elongating the LAA in a first direction by at least expanding the implant in the first direction so that a ratio of a size of the ostium of the LAA in the first direction relative to a size of the ostium of the LAA in a second direction that is perpendicular to the first direction is at least 2 to 1. The method can also include withdrawing the delivery catheter with the implant positioned in the LAA.

Any embodiments of the methods disclosed herein can include, in additional embodiments, one or more of the following features, components, steps, and/or details, in any combination with any of the other features, components, steps, and/or details of any other treatment method embodiments disclosed herein: wherein elongating the LAA in the first direction by at least expanding the implant in the first direction so that the ratio of the size of the ostium of the LAA in the first direction relative to the size of the ostium of the LAA in the second direction is from approximately 2 to 1 to approximately 5 to 1; wherein elongating the LAA in the first direction by at least expanding the implant in the first direction so that the ratio of the size of the ostium of the LAA in the first direction relative to the size of the ostium of the LAA in the second direction is from approximately 3 to 1 to approximately 4 to 1; wherein elongating the LAA in the first direction by at least expanding the implant in the first direction so that the ratio of the size of the ostium of the LAA in the first direction relative to the size of the ostium of the LAA in the second direction is approximately 3.5 to 1; further including a clip configured to hold two or more portions of tissue of the opening together; further including at least one cushion coupled with the frame; wherein the frame can be configured to increase in size in the first direction without increasing in size in any other direction; wherein the frame is self-expandable; further including a catheter for implanting the implant; wherein the implant comprises a hinge mechanism for constricting or closing the opening; including at least one of a passive activation mechanism and an active activation mechanism to activate the hinge mechanism; wherein at least a portion of the frame is further configured to be contractible in a first direction so as to decrease a length of the frame in the first direction; wherein the frame comprises a length of wire having a U-shape configured to allow cantilever bending near the middle portion of the frame; wherein the frame comprises a torsion spring wire-form near the middle portion of the frame; wherein the frame comprises multiple U-shape cantilever sections or torsion spring forms; wherein the frame is formed from a round wire, a wire strip, or a sheet that is laser cut; and/or wherein the frame comprises at least one of a polymer, a composite material, a metal, and a super-elastic shape memory alloy.

Any embodiments of the methods disclosed herein can include: advancing a delivery catheter having an implant therein into the heart, advancing a distal tip of the delivery catheter near an ostium of the LAA, elongating the LAA in a first direction by at least partially expanding at least a portion of the implant in the first direction, clipping a first wall portion of the LAA to a second wall portion of the LAA, and/or removing the catheter. In other embodiments, any embodiments of the method(s) disclosed herein can include, in additional embodiments, one or more of the following features, components, steps, and/or details, in any combination with any of the other features, components, steps, and/or details of any other embodiments disclosed herein: positioning the implant to achieve apposition in a first direction and/or a second direction; evaluating a position and/or an orientation of the implant, constricting at least a portion of the implant, and repositioning at least a portion of the implant relative to the LAA; and/or recapturing all or a portion of the implant and repositioning the implant.

Disclosed herein are additional embodiments of treatment methods that include advancing a distal tip of a catheter having an implant therein into the heart, at least partially deploying a distal portion of the implant; positioning the partially expanded implant to the appropriate implant depth and angulation; deploying the proximal portion of the implant adjacent to an ostium of the LAA; and/or removing the catheter. Any embodiments of the method(s) disclosed herein can include, in additional embodiments, one or more of the following features, components, steps, and/or details, in any combination with any of the other features, components, steps, and/or details of any other embodiments disclosed herein: evaluating a position and/or an orientation of at least one of the proximal and distal portions of the implant before removing the catheter; determining if the position and/or orientation of the implant is desirable before removing the catheter; restraining at least one of the proximal portion and the distal portion of the implant after at least partially deploying the distal portion of the implant; restraining at least one of the proximal portion and the distal portion of the implant after deploying the proximal portion of the implant adjacent to an ostium of the LAA; repositioning the partially expanded implant to the appropriate implant depth and angulation; wherein the device is self-expanding; wherein deploying at least one of the proximal portion and the distal portion of the implant comprises removing a restraint from at least one of the proximal portion and the distal portion of the implant; wherein deploying at least one of the proximal portion and the distal portion of the implant comprises releasing a suture from at least one of the proximal portion and the distal portion of the implant; wherein deploying at least one of the proximal portion and the distal portion of the implant comprises removing a tension tether from at least one of the proximal portion and the distal portion of the implant; wherein deploying the proximal portion of the implant comprises activating a mechanical linkage mechanism to expand at least one of the proximal portion and the distal portion of the implant; including a proximal restraint that has a frame configured to selectively restrain the proximal portion of the implant in a restrained state; and/or wherein the catheter is steerable.

Additional embodiments of any methods disclosed herein can include: advancing a distal tip of a delivery catheter having an implant therein into the heart; advancing the distal tip of the delivery catheter near an ostium of the LAA; expanding a first stage portion of the implant to at least a partially expanded state; moving the first stage portion of the implant to a desired implant depth and angulation; positioning the implant to achieve apposition in a first direction and/or a second direction; activating a portion of the implant to reduce a size of the opening of the LAA adjacent to the ostium of the LAA; and/or removing the catheter.

Any embodiments of the methods disclosed herein can include, in additional embodiments, one or more of the following features, components, steps, and/or details, in any combination with any of the other features, components, steps, and/or details of any other embodiments disclosed herein: wherein activating a portion of the implant to reduce the size of the opening of the LAA adjacent to the ostium of the LAA comprises folding a tissue surrounding the opening of the LAA so as to reduce a size of the opening of the LAA; wherein activating a portion of the implant to reduce the size of the opening of the LAA comprises folding a tissue surrounding the opening of the LAA to close the opening of the LAA; wherein activating a portion of the implant to reduce the size of the opening of the LAA comprises linearizing the opening of the LAA; wherein activating a portion of the implant to reduce the size of the opening of the LAA comprises stretching the opening of the LAA; twisting one or more portions of tissue surrounding the opening of the LAA to constrict or close the opening of the LAA when the second stage portion is in a second state; activating at least a portion of the implant to close the opening of the LAA after positioning the implant to achieve apposition in a first direction and/or a second direction; activating a means for folding a portion of tissue to fold a tissue surrounding the opening of the LAA to reduce a size of the opening of the LAA; activating a tissue folding mechanism of the implant to fold a tissue surrounding the opening of the LAA to close the opening of the LAA; reversing the tissue folding mechanism after evaluating the opening of the LAA and reactivating the tissue folding mechanism of the implant to fold a tissue surrounding the opening of the LAA to close the opening of the LAA; evaluating a position and/or an orientation of the implant, constricting at least a portion of the implant and repositioning at least a portion of the implant relative to the LAA; constricting the first stage portion of the implant after evaluating the position and/or the orientation of the implant, repositioning at least a portion of the implant relative to the LAA, and expanding the first stage portion of the implant to at least the partially expanded state; recapturing all or a portion of the implant and repositioning the implant; wherein expanding the distal portion of the implant to at least a partially expanded state comprises advancing the distal portion of the implant past the distal tip of the deployment catheter; and/or wherein at least the distal portion of the implant is self-expanding.

Disclosed herein are additional embodiments of treatment methods that include advancing a deployment device having an implant into the left atrial appendage, moving at least a portion of an outside surface of the implant or one or more tissue anchors extending away from an outer surface of the implant against an inner wall surface of the left atrial appendage, rotating the implant from a first rotational position to a second rotational position to twist the left atrial appendage, and preventing the implant from rotating back to the first rotational position. In any embodiments, the method can include moving at least a portion of an outside surface of the implant or one or more tissue anchors extending away from an outer surface of the implant against an inner wall surface of the left atrial appendage without changing a shape or size of the implant, and/or moving the implant from a first state to a second state, and wherein at least a portion of the implant is enlarged in a radial direction when the implant is in the second state as compared to the first state.

Disclosed herein are additional embodiments of devices and systems for closing an LAA that can include a clamp device having a first member and a second member and be configured to move between a closed position and an open position, a first guide device configured to be advanceable into the LAA, and a second guide device configured to be advanceable into a pericardial space outside of the LAA and moved so that an end portion of the second guide device is in approximate axial alignment with an end portion of the first guide device. In any embodiments disclosed herein, at least one of the first and second members of the clamp device can be substantially rigid; the clamp device can have an opening sized so that the clamp device can be passed over the LAA when the clamp device is in the open position; and/or at least one of the first and second members of the clamp device can be configured to substantially flatten and close a portion of the LAA when the clamp device is moved to the closed position. In any additional embodiments disclosed herein, the clamp device can include only the first member and the second member. In additional embodiments, the clamp device can further include a third member and a fourth member connected together in an end to end arrangement and defining an opening in the clamp device that is sized and configured to pass over an outside surface of the LAA. In any additional embodiments disclosed herein, the device can further include a delivery catheter having an outer sheath and a guide lumen, the guide lumen configured to receive and track over the second guide device. Additionally, the first member of the clamp device can be rigid and the second member of the clamp device can comprise a suture.

Disclosed herein are additional embodiments of methods of closing or occluding an LAA. In any embodiments disclosed herein, the method can include advancing a first guide device into the LAA, advancing a second guide device into a pericardial space outside of the LAA, approximately aligning an end portion of the second guide device with an end portion of the first guide device, advancing a delivery catheter over the second guide device, advancing a clamp device having a first member and a second member from the delivery catheter, opening the clamp device from a closed position to an open position, advancing the clamp device over an outside surface of the LAA toward a neck portion of the LAA, and/or substantially flattening and closing the neck portion of the LAA by closing the clamp device from the open position to the closed position.

Any embodiments of the methods of closing or occluding the LAA can include, in additional embodiments, one or more of the following features, components, steps, and/or details, in any combination with any of the other features, components, steps, and/or details of any other embodiments disclosed herein: wherein moving the clamp device from the closed position to the open position comprises advancing the clamp device past a distal end of the delivery catheter so that the clamp device can automatically move to the open position; wherein the delivery catheter has a guide lumen, the guide lumen being configured to receive and track over the second guide device; wherein the delivery catheter has an outer sheath; wherein at least one of the first and second members of the clamp device is substantially rigid; wherein at least one of the first and second members of the clamp device has a substantially planar contact surface, the contact surface being the surface configured to contact an outside surface of the LAA; wherein the delivery catheter has an outer sheath; wherein the clamp device comprises a least four substantially rigid members connected together in an end to end arrangement and defining an opening in the clamp device that is sized and configured to pass over an outside surface of the LAA; and/or wherein the clamp device comprises at least one rigid member and at least one flexible member interconnected with the at least one rigid member.

Additionally, any implant and/or device or system embodiments disclosed herein can be adapted and/or used for treatment of any tissue condition in a body that is desired to be occluded, restricted, or closed. For example and without limitation, some embodiments of the devices and systems for treating a tissue condition disclosed herein can include an implant comprising a contact member that can be (but is not required to be) configured to move between a first state and a second state and a securing element, wherein the contact member can be configured to move from the first state to the second state so that at least a portion of the contact member engages a wall portion of the tissue condition after the contact member has been advanced into the tissue condition, the contact member can be configured to rotate at least in a first direction from a first rotational position to a second rotational position, the contact member can be configured to twist at least a portion of the tissue of the tissue condition in the first direction when the contact member is rotated from the first rotational position to the second rotational position, and/or the securing element can be configured to prevent a rotation of at least a portion of the tissue of the tissue condition in a second direction when the securing element is in an operable state, wherein the second direction is opposite to the first direction. In any embodiments, the tissue condition can be a cavity, a chamber, an opening, a passageway, a tear in the tissue, two adjacent or adjoining tissue surfaces, or otherwise.

Further, some embodiments of the devices and systems for treating a tissue condition disclosed herein can include an implant having a contact member that can be (but is not required to be) configured to move between a first state and a second state, a catheter configured to advance the contact member into the tissue condition when the contact member is in the first state and to cause the contact member to move from the first state to the second state so that an outside surface of the contact member engages at least one wall surface of the tissue condition after the contact member has been advanced into or adjacent to the tissue condition, wherein the catheter is configured to exert a torque on the contact member when at least a portion of the catheter is rotated until a predetermine torque level is reached to rotate the contact member from a first rotational position to a second rotational position so that the contact member can twist at least a portion of the tissue condition. In any embodiments, the tissue condition can be a cavity, a chamber, an opening, a passageway, a tear in the tissue, two adjacent or adjoining tissue surfaces, or otherwise.

Further, some embodiments of the devices and systems for treating a tissue condition disclosed herein can include a method of treating a tissue condition, comprising advancing a deployment device having an implant into or adjacent to the tissue condition, wherein the implant can be (but is not required to be) configured to be moved from a first state to a second state, and wherein at least a portion of the implant can be enlarged in a radial direction when the implant is in the second state as compared to the first state, moving the implant from the first state to the second state within the tissue condition so as to move at least a portion of an outside surface of the implant or one or more tissue anchors extending away from an outer surface of the implant against at least one wall surface of the tissue condition, rotating the implant from a first rotational position to a second rotational position to twist the tissue condition, and/or preventing the implant from rotating back to the first rotational position.

Additionally, any implant and/or device or system embodiments disclosed herein can be adapted and/or used for treatment of any tissue condition in a body that is desired to be occluded, reshaped, restricted, or closed. For example and without limitation, some embodiments of the devices and systems for treating a tissue condition disclosed herein can include an implant comprising a contact member that is configured to engage a wall portion of the tissue condition after the contact member has been advanced into the tissue condition, the contact member can be configured to rotate at least in a first direction from a first rotational position to a second rotational position, the contact member can be configured to twist at least a portion of the tissue of the tissue condition in the first direction when the contact member is rotated from the first rotational position to the second rotational position, and/or the securing element can be configured to prevent a rotation of at least a portion of the tissue of the tissue condition in a second direction when the securing element is in an operable state, wherein the second direction is opposite to the first direction. In any embodiments, the tissue condition can be a cavity, a chamber, an opening, a passageway, a tear in the tissue, two adjacent or adjoining tissue surfaces, or otherwise.

Further, some embodiments of the devices and systems for treating a tissue condition disclosed herein can include an implant having a contact member, a catheter configured to advance the contact member into the tissue condition so that the contact member engages at least one wall surface of the tissue condition after the contact member has been advanced into or adjacent to the tissue condition, wherein the catheter is configured to exert a torque on the contact member when at least a portion of the catheter is rotated until a predetermine torque level is reached to rotate the contact member from a first rotational position to a second rotational position so that the contact member can twist at least a portion of the tissue condition. In any embodiments, the tissue condition can be a cavity, a chamber, an opening, a passageway, a tear in the tissue, two adjacent or adjoining tissue surfaces, or otherwise.

Further, some embodiments of the devices and systems for treating a tissue condition disclosed herein can include a method of treating a tissue condition, comprising advancing a deployment device having an implant into or adjacent to the tissue condition, and wherein at least a portion of the implant engages a wall surface of the tissue condition, rotating the implant from a first rotational position to a second rotational position to twist the tissue condition, and/or preventing the implant from rotating back to the first rotational position.

BRIEF DESCRIPTION OF THE DRAWINGS

FIG. 8A shows the embodiment of the implant device of FIG. 2A, showing the contact member being advanced further distally into the LAA.

FIG. 8B shows the embodiment of the implant device of FIG. 2A, showing the contact member being rotated to twist the LAA and cause a neck or opening of the LAA to constrict around a portion of the implant device.

FIG. 8C shows the embodiment of the implant device of FIG. 2A, showing the securing element of the embodiment of the implant device being advanced toward the contact member of the implant device.

FIG. 22A shows a side view of another embodiment of a treatment system wherein the contact member is in a second, expanded state and the retention member is in a first, retracted state.

FIG. 22B shows a side view of the treatment system of FIG. 22 wherein the contact member is in the second state and the retention member is in a second, deployed state.

FIG. 23A shows an isometric view of another embodiment of a securing element.

FIG. 23B shows a side view of the embodiment of the securing element shown in FIG. 23A.

FIG. 23C shows an isometric view of another embodiment of a securing element.

FIG. 23D shows a side view of the embodiment of the securing element shown in FIG. 23C.

FIG. 23E shows an isometric view of another embodiment of a securing element.

FIG. 23F shows a side view of the embodiment of the securing element shown in FIG. 23E.

FIGS. 49A-49G show another embodiment of a treatment system for closing or occluding an LAA.

FIGS. 66A-66D show an embodiment of an implant device and a method for occluding the LAA.

FIGS. 70A-70F show another embodiment of a device and a method for occluding the LAA.

FIGS. 77A-77C show an embodiments of a device and a method for occluding the LAA.

FIGS. 78A-78C show an embodiments of a device and a method for occluding the LAA.

FIGS. 79A-79C show an embodiments of a device and a method for occluding the LAA.

FIGS. 98A-98C show an embodiment of a method for deploying the embodiment of the device shown in FIGS. 95A-95C.

FIGS. 99A-99C show an embodiment of a device for treating the LAA.

FIGS. 100A-100C show an embodiment of a method for using the device shown in FIGS. 99A-99C for occluding the LAA.

FIGS. 101A-101C show an embodiment of a method for using another embodiment of a device for occluding the LAA.

FIGS. 107A-107G show another embodiment of a device and an embodiment of a method for using such device for treating the LAA.

FIGS. 109A-109C show another embodiment of a device and an embodiment of a method for using such device for treating the LAA.

FIGS. 110A-110E show another embodiment of a device and an embodiment of a method for using such device for treating the LAA.

FIG. 111 shows another embodiment of a device for treating the LAA.

FIG. 112 shows another embodiment of a device for treating the LAA.

FIGS. 113A-113C show an embodiment of a device for treating the LAA.

FIGS. 114A-114C show an embodiment of a device for treating the LAA.

FIGS. 115A-115C show another embodiment of a device and an embodiment of a method for using such device for treating the LAA.

FIGS. 116A-116C show an embodiment of a device for treating the LAA.

FIGS. 117A-117C show an embodiment of a device for treating the LAA.

FIGS. 118A-118D show another embodiment of a device and an embodiment of a method for using such device for treating the LAA.

FIGS. 119A-119D show another embodiment of a device and an embodiment of a method for using such device for treating the LAA.

FIGS. 120A-120C show an embodiment of a device for treating the LAA.

FIGS. 121A-121C show another embodiment of a device for treating the LAA.

Figure 122:
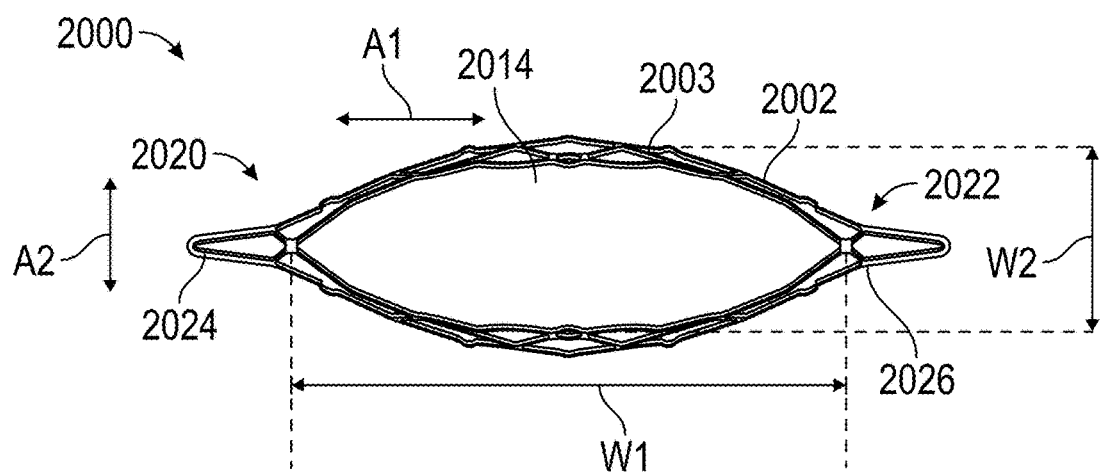

FIG. 122 shows another embodiment of a device for treating the LAA from a downward looking view.

Figure 123:
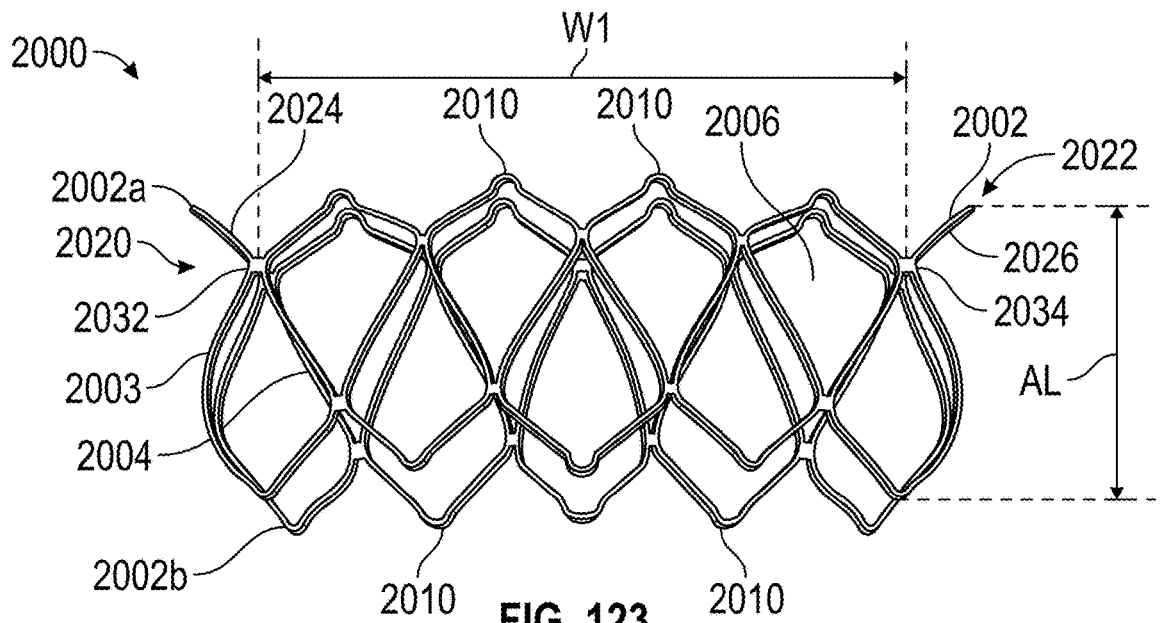

FIG. 123 shows the embodiment of the device of FIG. 122 from a side looking view.

Figure 124:
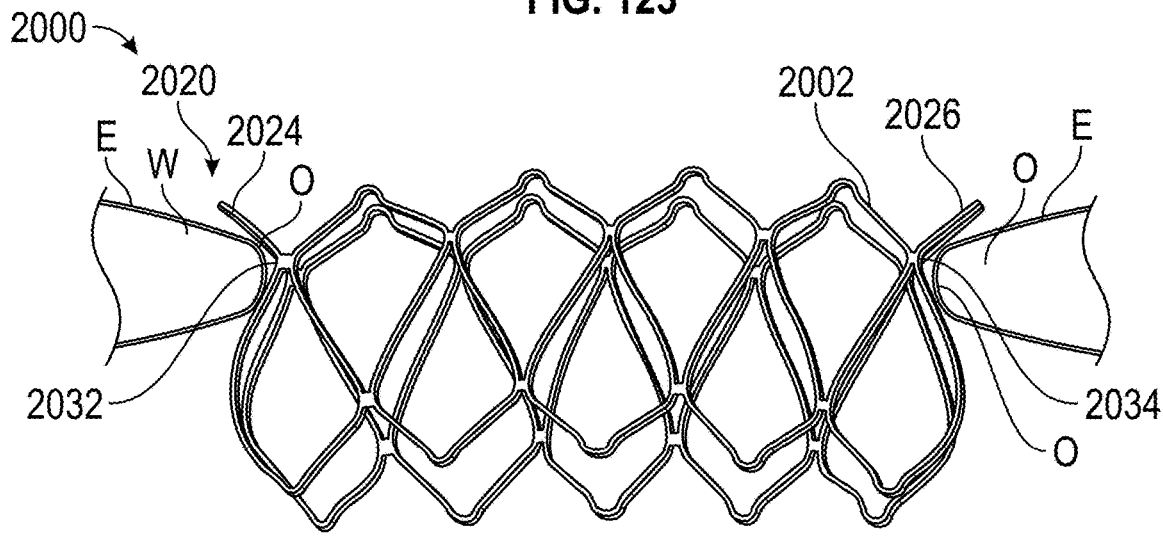

FIG. 124 shows a side view of the embodiment of the device of FIG. 122, showing the device relative to an ostium of the LAA.

Figure 125:
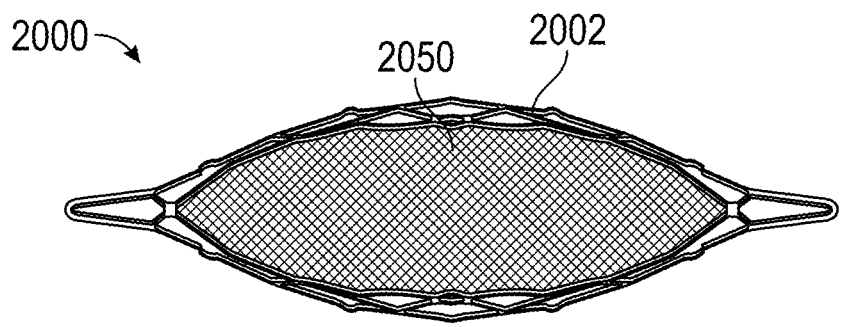

FIG. 125 shows a top view of another embodiment of a device for treating the LAA.

Figure 126:
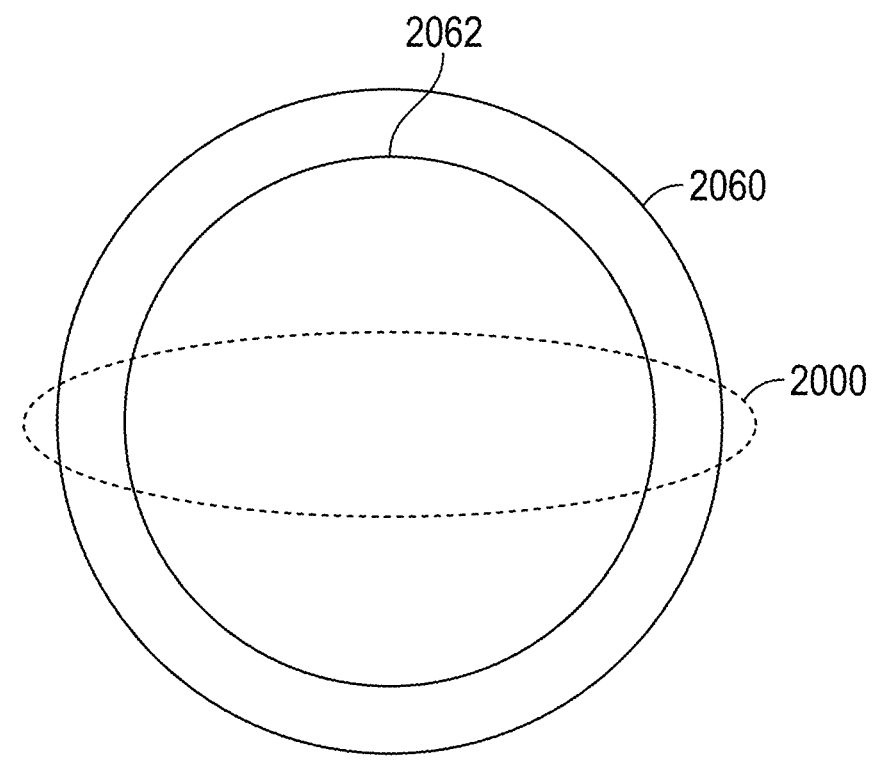

FIG. 126 illustrates an overall cross-sectional area of some embodiments of devices disclosed herein relative to conventional devices for treating the LAA.

Figure 127:
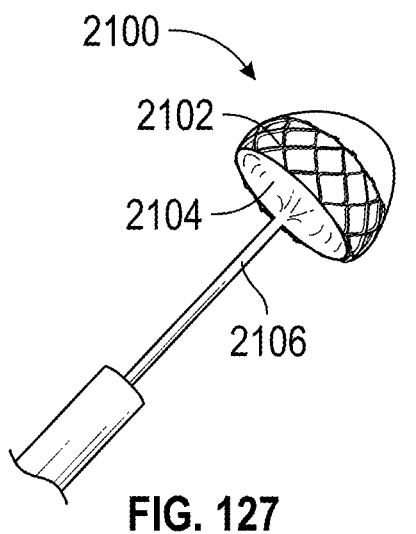

FIG. 127 shows another embodiment of a device for treating the LAA.

Figure 128:
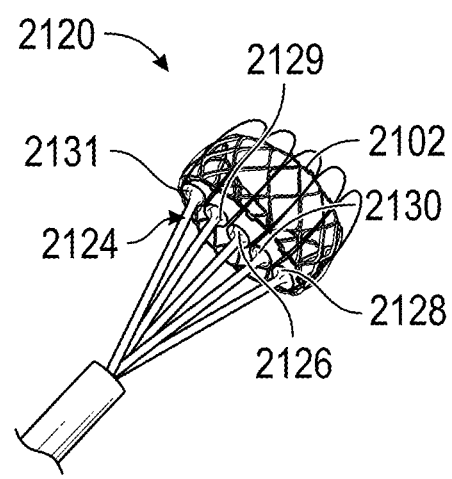
Figures 137A, 137B, 137C, 137D:
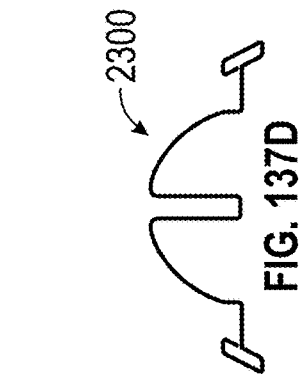

FIG. 128 shows another embodiment of a device for treating the LAA.

FIG. 129 shows a side view of another embodiment of a device for treating the LAA, showing the device in an extended state.

FIG. 130 shows a side view of the embodiment of the device shown in FIG. 129, showing the device in a contracted state.

FIG. 131 shows an end view of the embodiment of the device shown in FIG. 129, showing the device in an extended state.

FIG. 132 shows an end view of the embodiment of the device shown in FIG. 129, showing the device in a contracted state.

FIG. 133 shows a side view of another embodiment of a device for treating the LAA, showing the device in an extended state.

FIG. 134 shows a side view of the embodiment of the device shown in FIG. 133, showing the device in a contracted state.

FIG. 135 shows an end view of the embodiment of the device shown in FIG. 133, showing the device in an extended state.

FIG. 136 shows an end view of the embodiment of the device shown in FIG. 133, showing the device in a contracted state.

FIGS. 137A-137D show an embodiment of a device for treating the LAA.

Figures 138A, 138B, 138C:
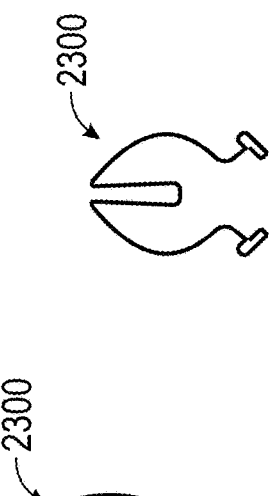
Figures 139A, 139B, 139C, 139D, 139E:
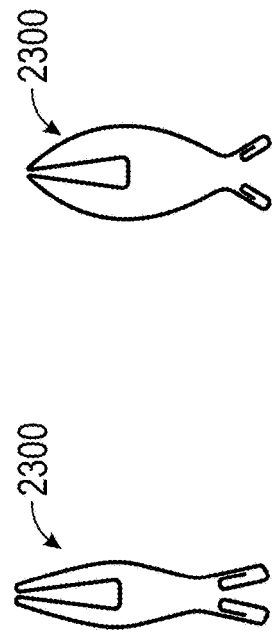
Figure 140A:
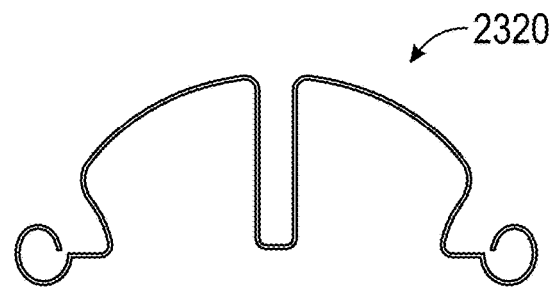
Figure 140B:
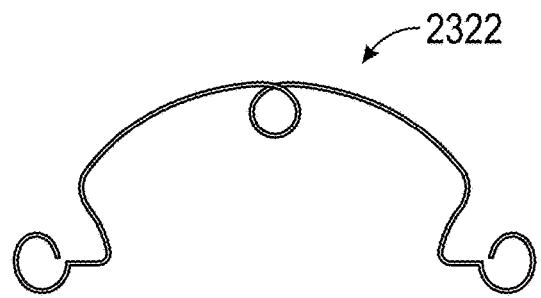
Figure 140C:
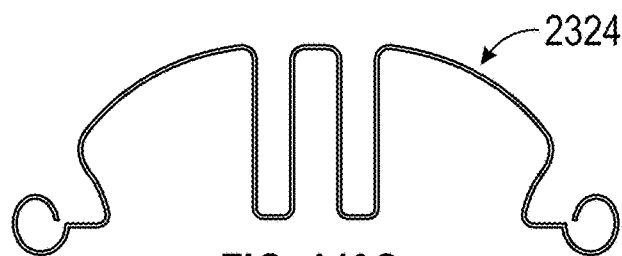
Figure 140D:
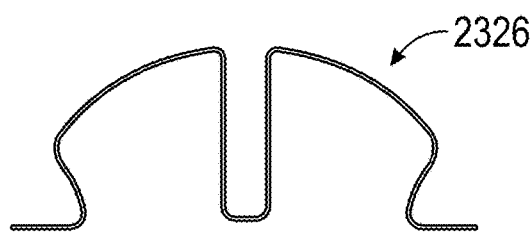
Figure 140E:
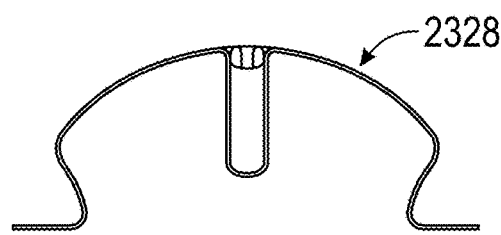
Figure 140F:
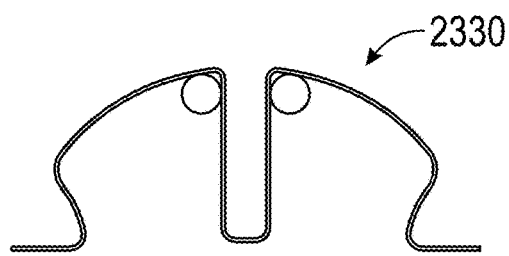
Figure 140G:
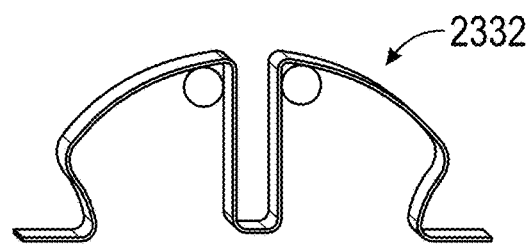
Figure 141A:
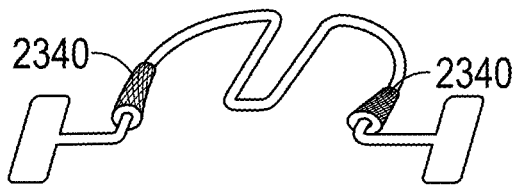
Figure 141B:
Figure 141C:
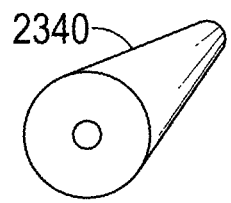
Figure 141D:
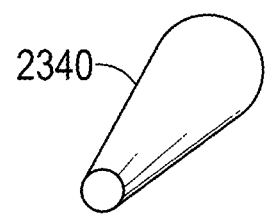
Figure 141E:
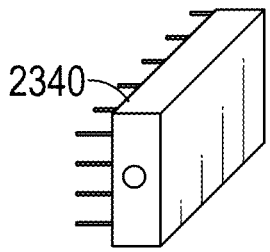
Figure 141F:
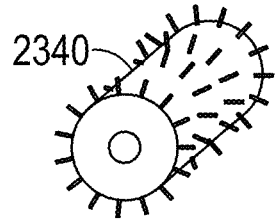
Figure 141G:
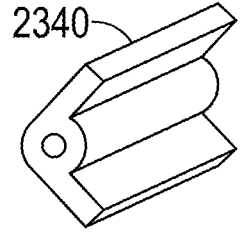
Figure 141H:
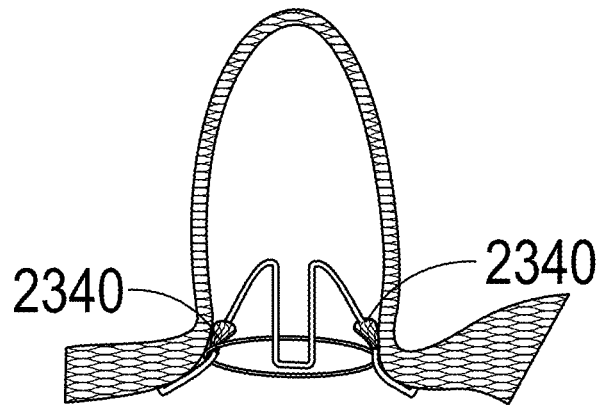
Figure 142A:
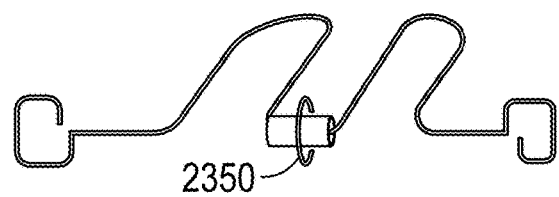
Figure 142B:
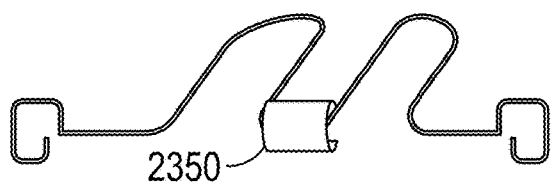
Figure 142C:
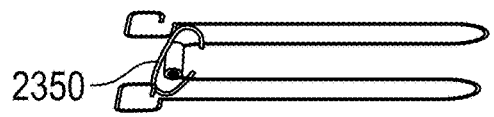
Figure 142D:
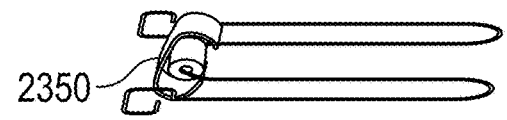
Figure 142E:
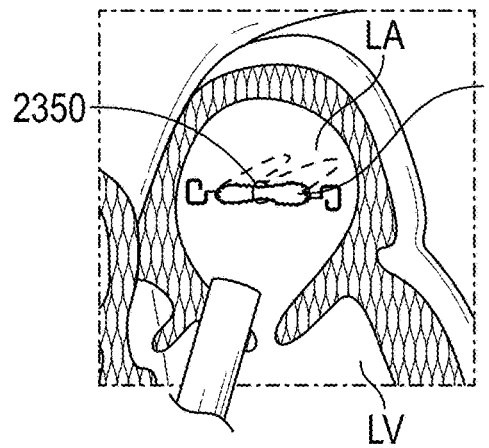
Figure 142F:
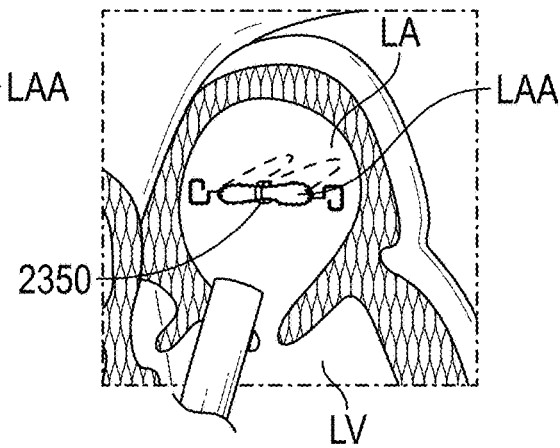
Figure 143A:
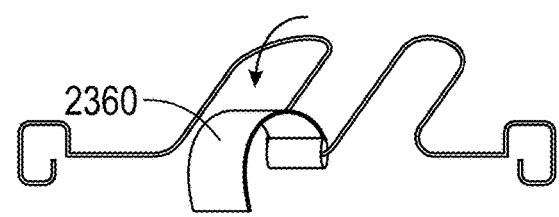
Figure 143B:
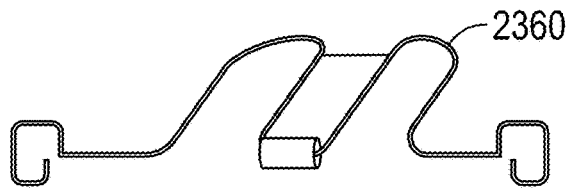
Figures 143C, 143D:
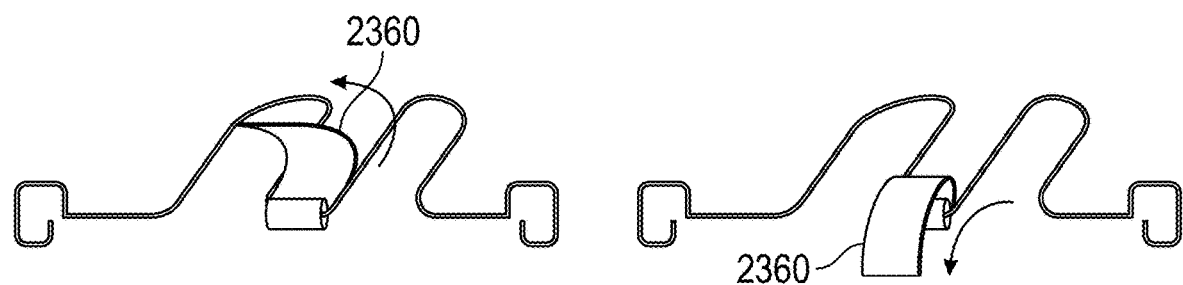
Figure 143E:
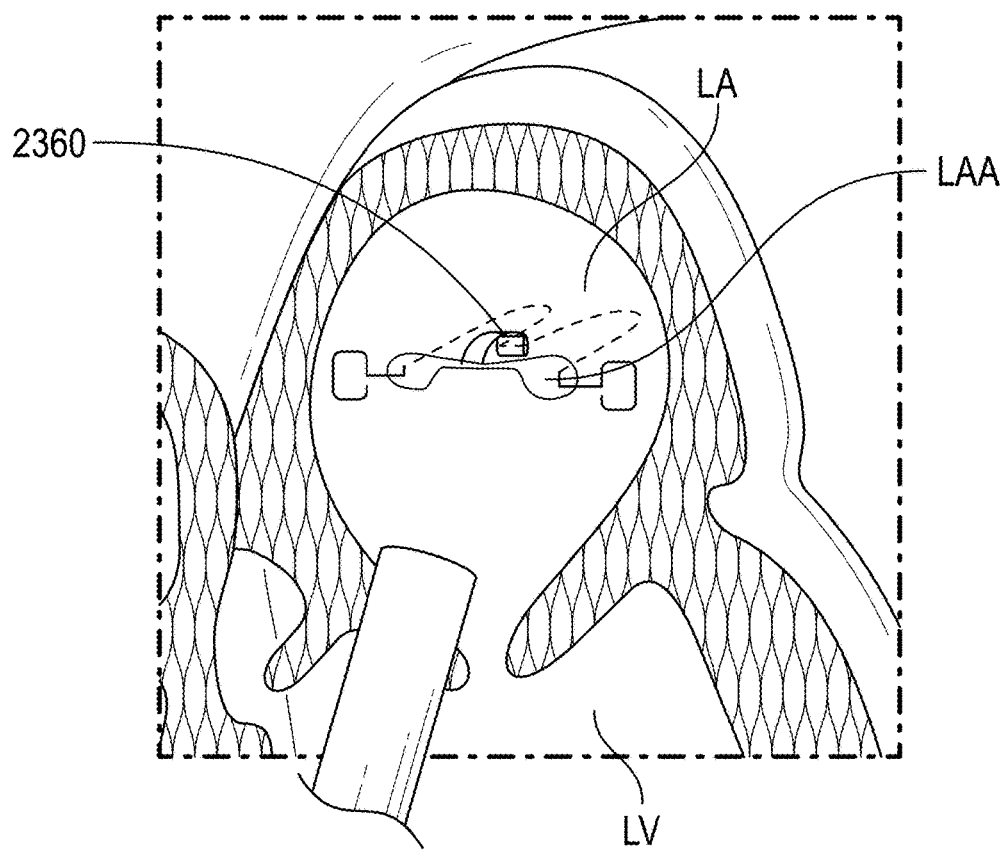
Figures 144A, 144B:
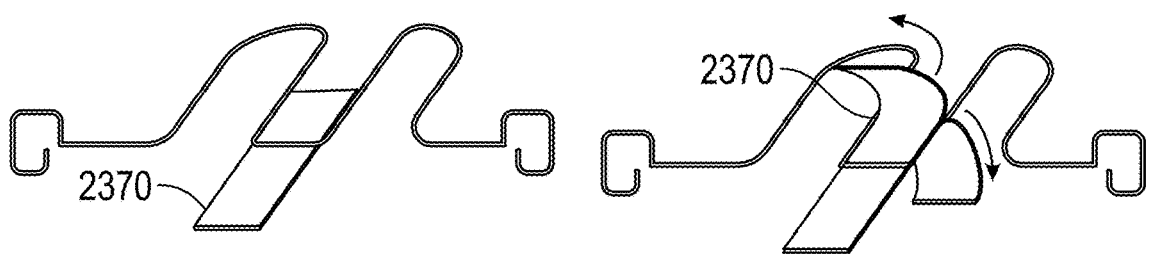
Figure 144C:
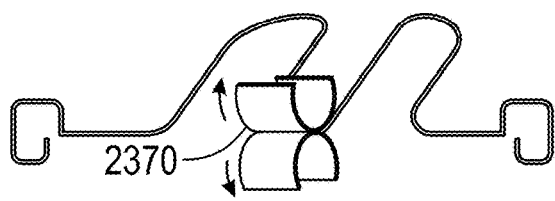
Figure 144D:
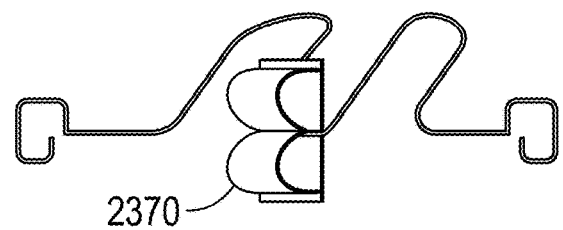
Figure 144E:
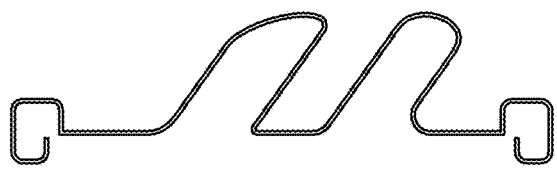
Figure 144F:
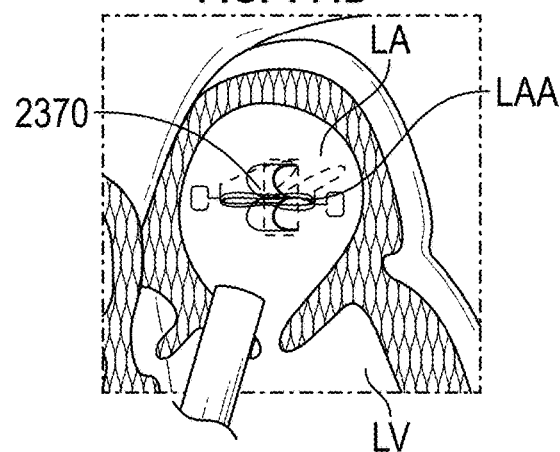
Figure 145A:
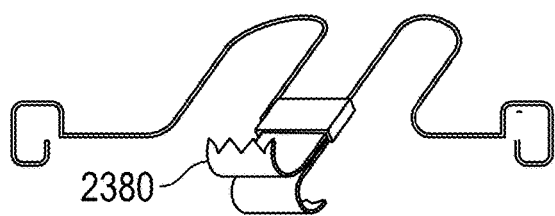
Figure 145B:
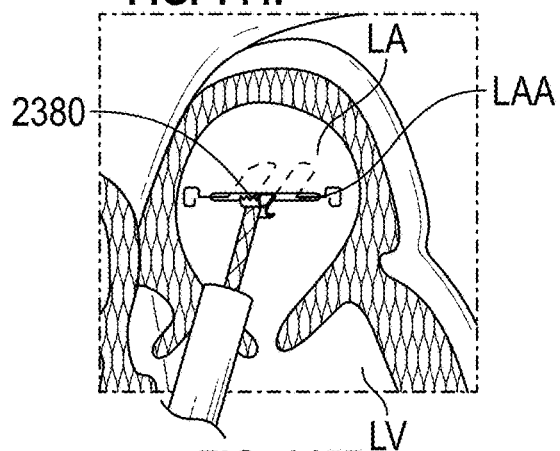
Figure 145C:
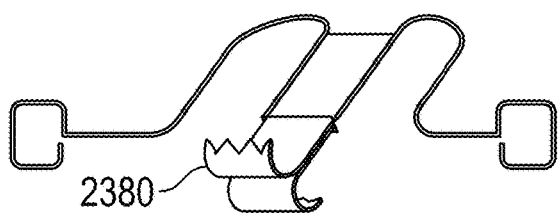
Figure 145D:
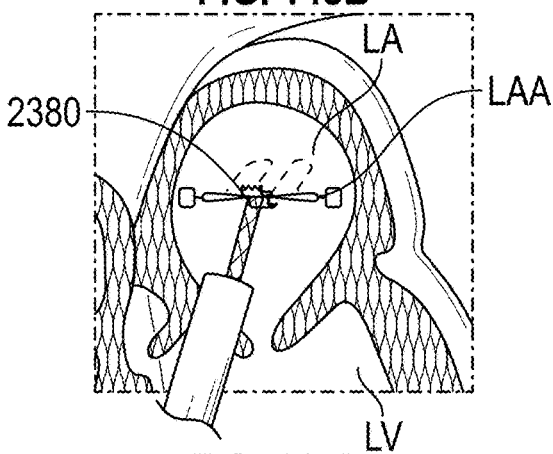

FIGS. 138A-138C show an embodiment of a method for implanting the embodiment of the device shown in FIGS. 137A-137D.

FIGS. 139A-139E show another embodiment of a device and an embodiment of a method for using such device for treating the LAA.

FIGS. 140A-140G show additional embodiments of devices for treating the LAA.

FIGS. 141A-141H show additional embodiments of devices for treating the LAA.

FIGS. 142A-142F show additional embodiments of devices and methods of using such devices for treating the LAA.

FIGS. 143A-143E show another embodiment of a device and a method of using such device for treating the LAA.

FIGS. 144A-144F show another embodiment of a device and a method of using such device for treating the LAA.

FIGS. 145A-145D show another embodiment of a device and a method of using such device for treating the LAA.

Figure 146B:
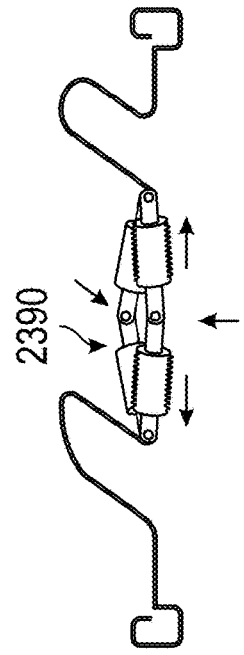
Figure 146A:
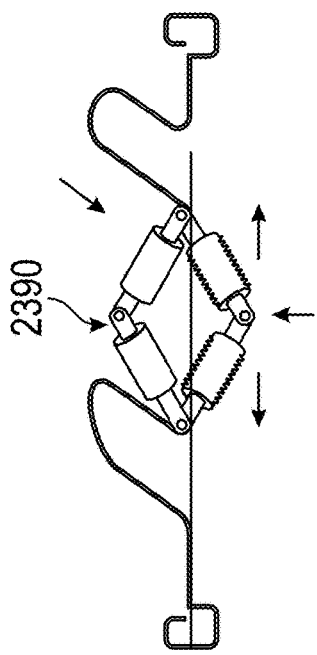
Figure 146C:
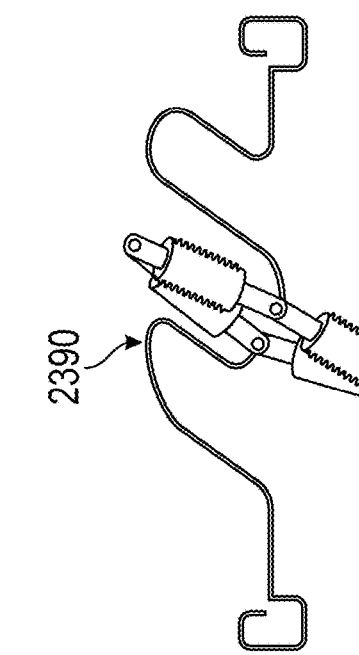

FIGS. 146A-146C show an embodiment of a device for treating the LAA.

Figure 147B:
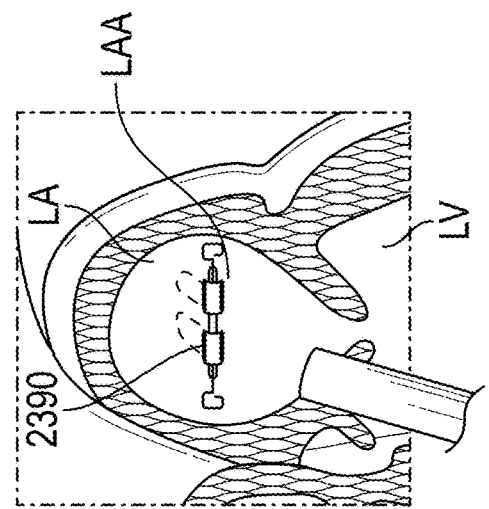
Figure 147A:
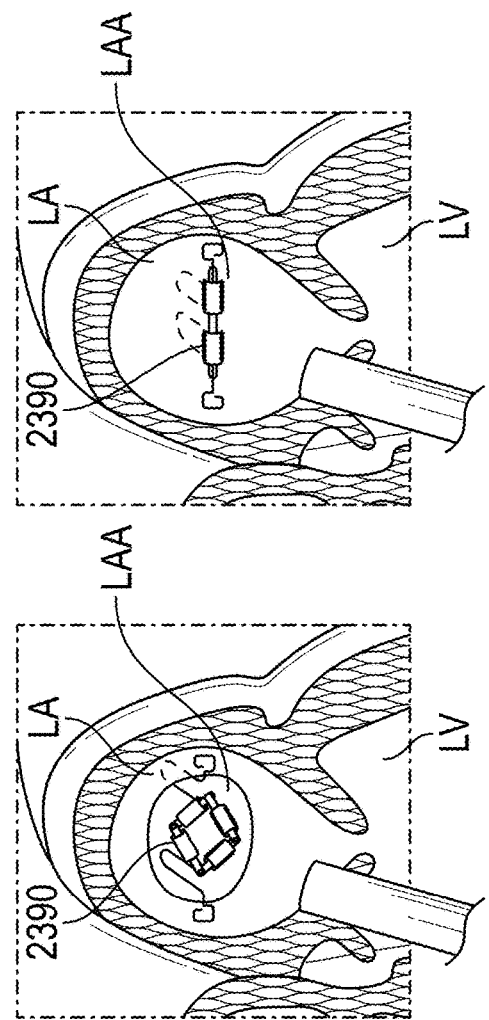

FIGS. 147A-147B show an embodiment of a method of using the device of FIGS. 146A-146C.

Figure 148A:
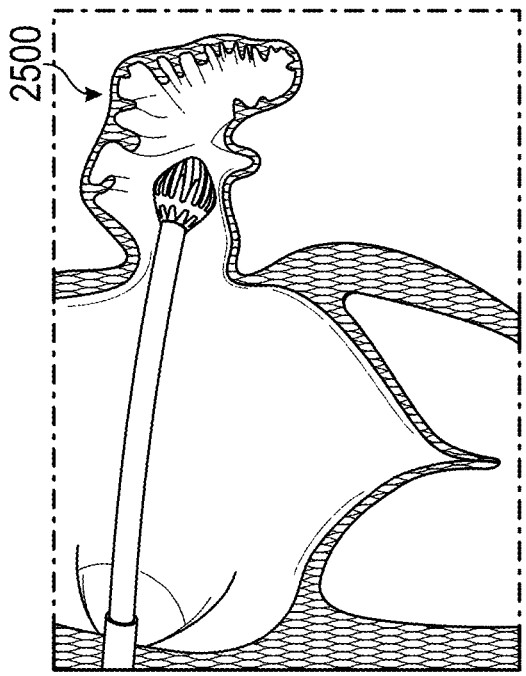
Figure 148B:
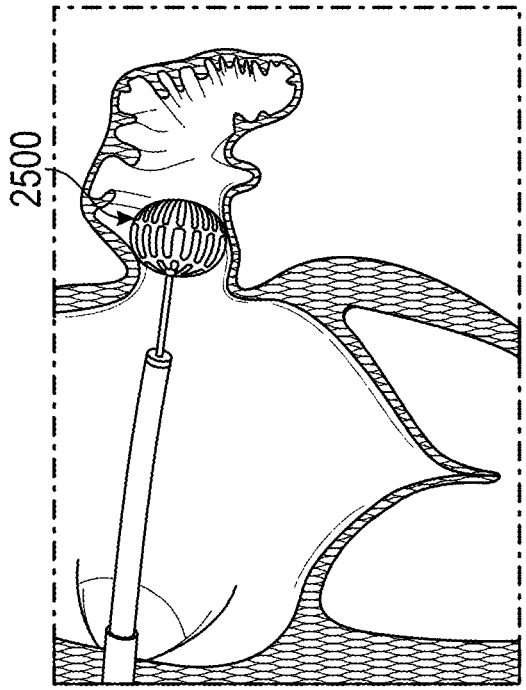

FIGS. 148A-148B show another embodiment of a device and a method of using such device for treating the LAA.

Figure 149A:
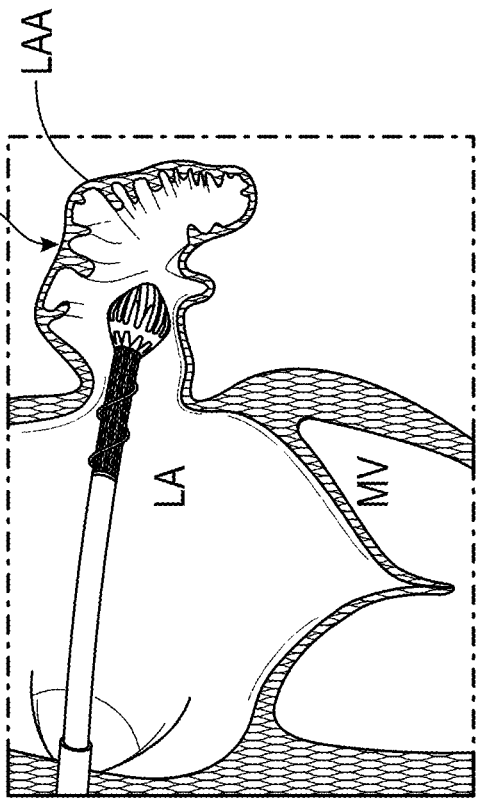
Figure 149B:
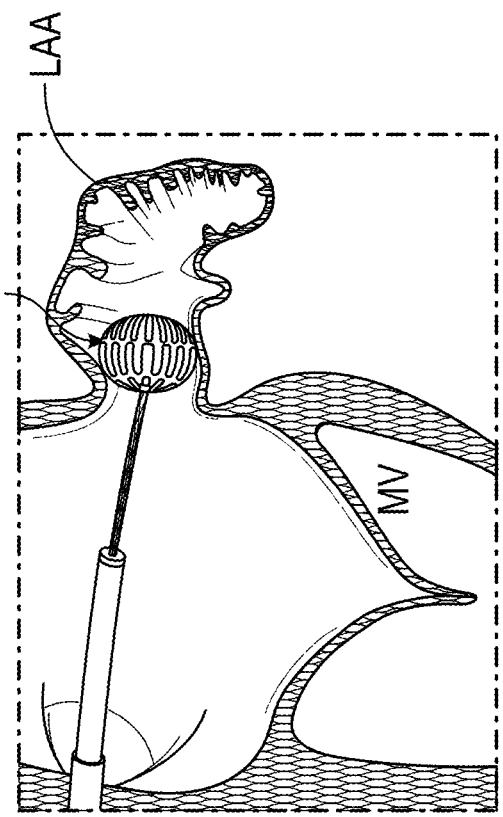

FIGS. 149A-149B show another embodiment of a device and a method of using such device for treating the LAA.

Figure 150B:
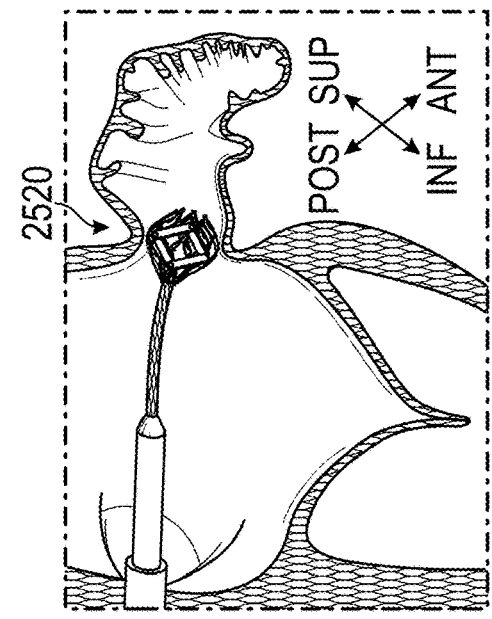
Figure 150A:
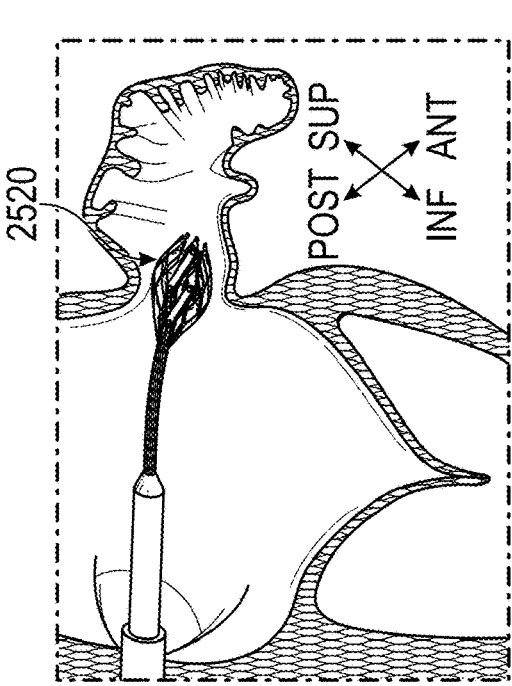
Figure 150C:
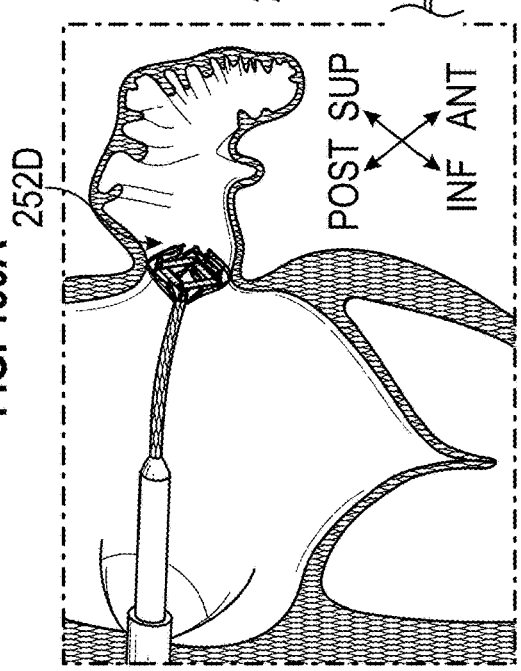

FIGS. 150A-150C show another embodiment of a device and a method of using such device for treating the LAA.

Figure 151A:
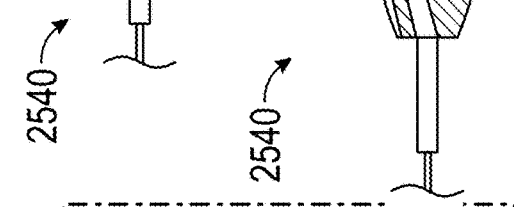
Figure 151B:
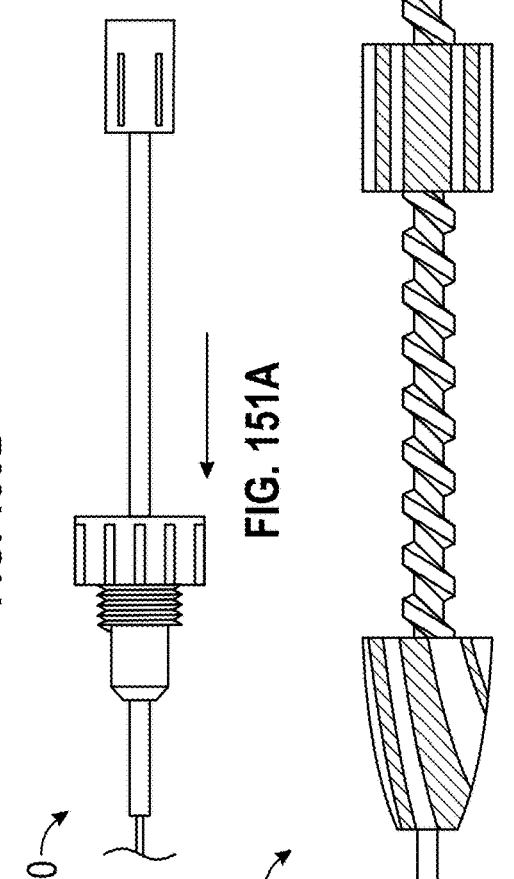

FIGS. 151A-151B show embodiments of portions of delivery devices that can be used with some embodiments of the implant devices disclosed herein.

FIGS. 152A-152C show embodiments of delivery devices having steering mechanisms and implant devices and methods of using such devices.

FIGS. 153A-153B show embodiments of delivery devices having steering mechanisms and implant devices and methods of using such devices.

Figure 154A:
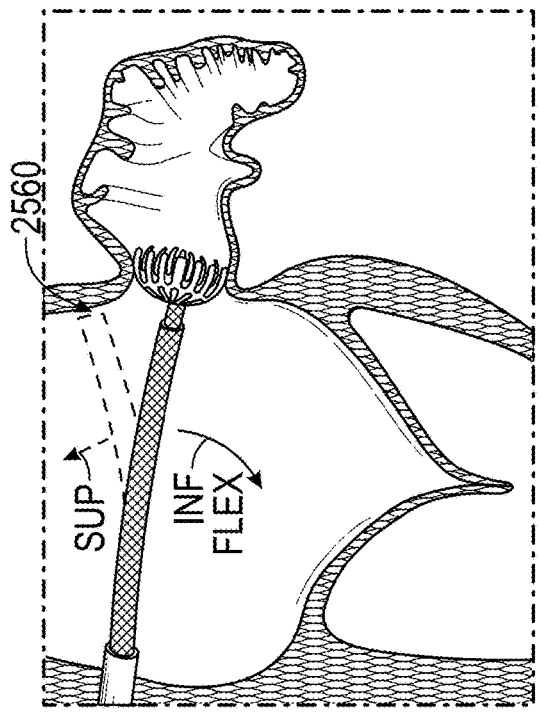
Figure 154B:
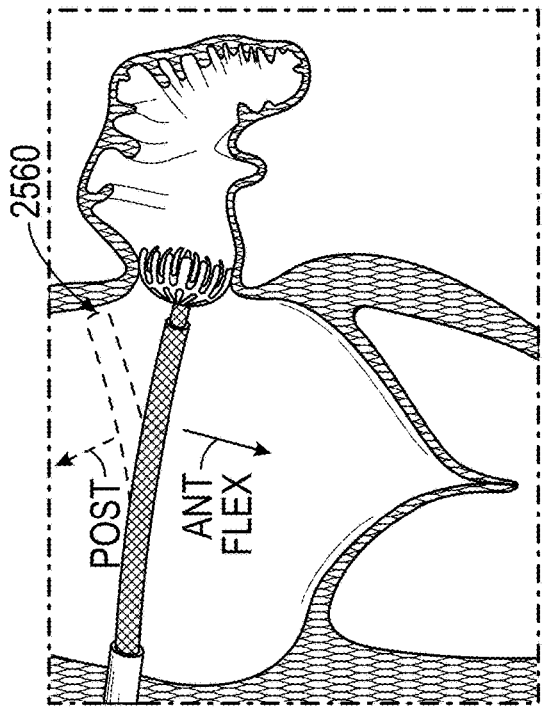

FIGS. 154A-154B show embodiments of delivery devices having steering mechanisms and implant devices and methods of using such devices.

Figure 155A:
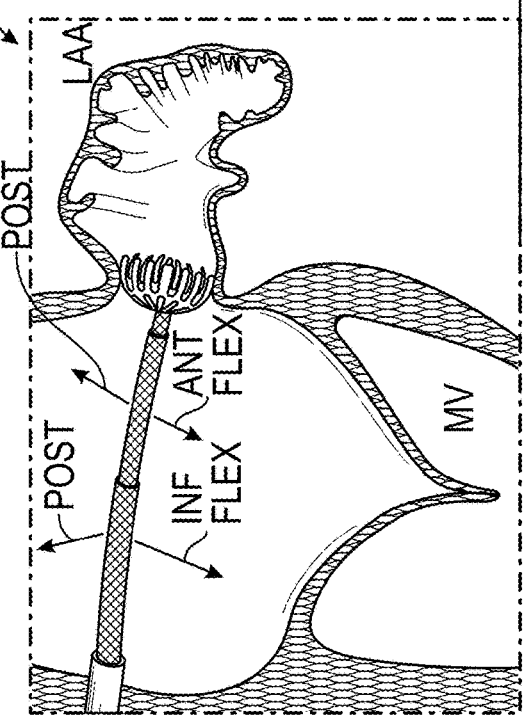
Figure 155B:
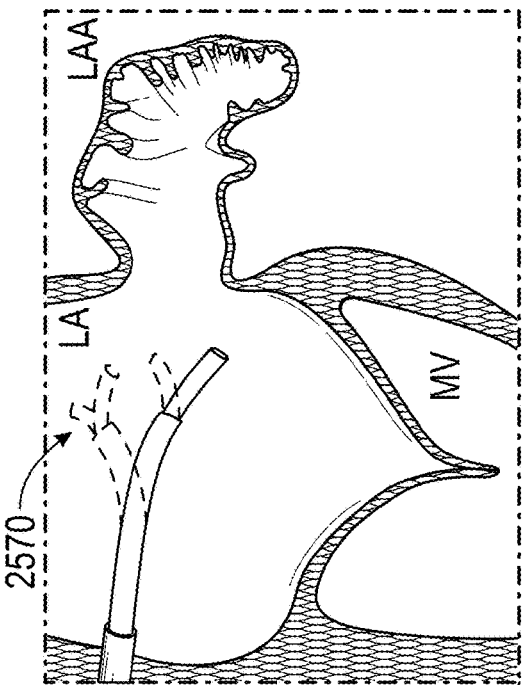

FIGS. 155A-155B show embodiments of delivery devices having steering mechanisms and implant devices and methods of using such devices.

FIGS. 156A-156D show embodiments of implant devices having sealing elements for treating the LAA.

Figure 157A:
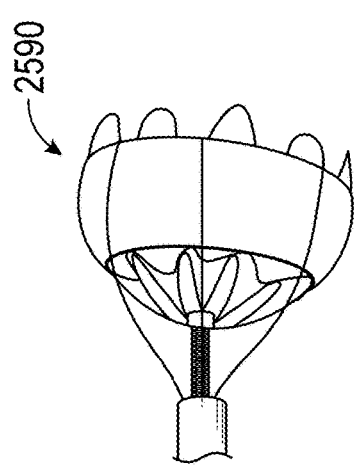
Figure 157B:
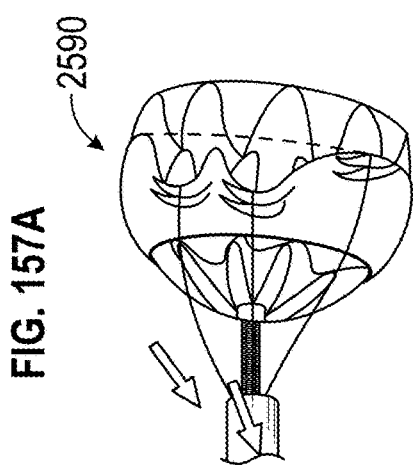
Figure 157C:
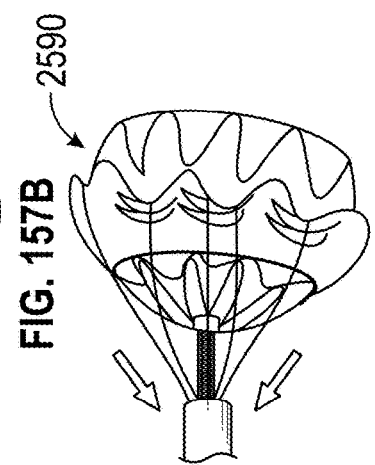
Figure 156B:
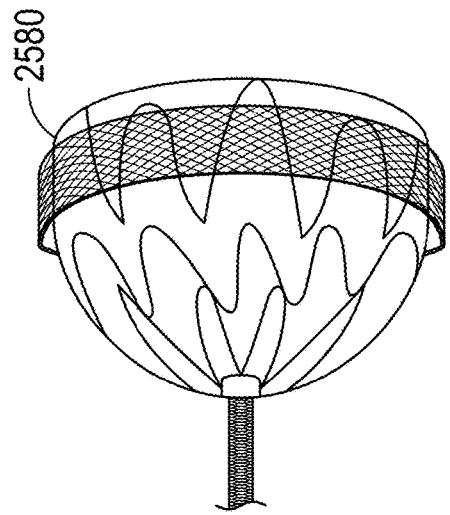
Figure 156D:
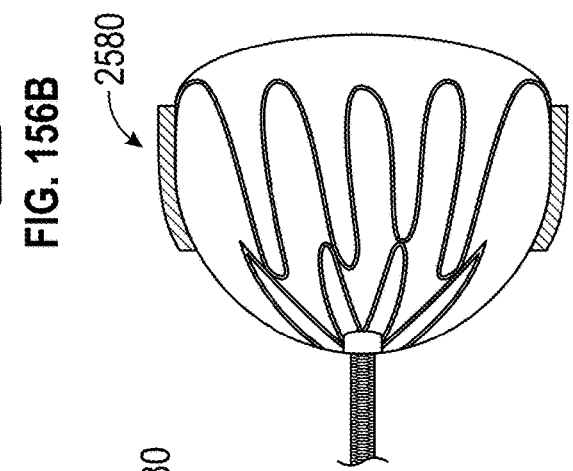
Figure 156A:
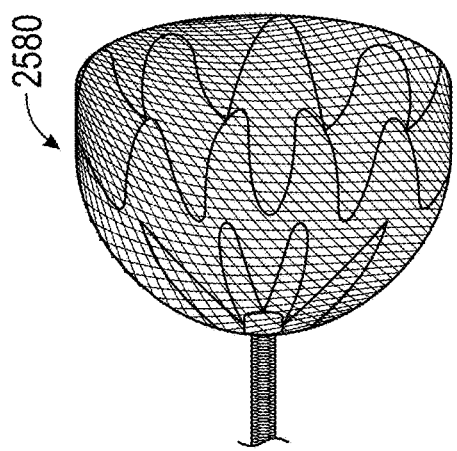
Figure 156C:
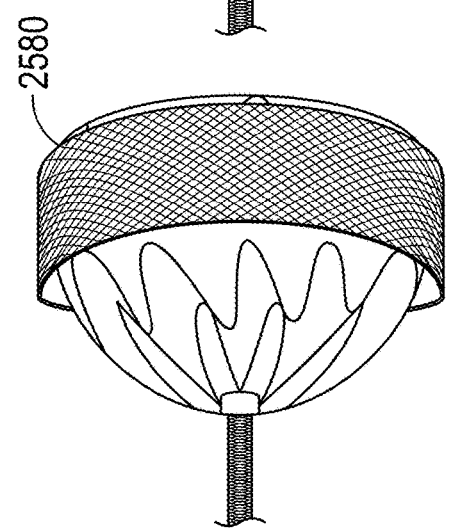

FIGS. 157A-157C show embodiments of implant devices having cover elements for treating the LAA.

Figure 158A:
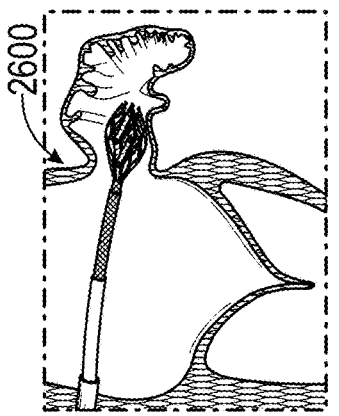
Figure 158B:
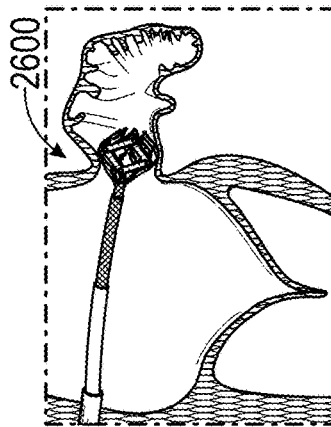
Figure 158C:
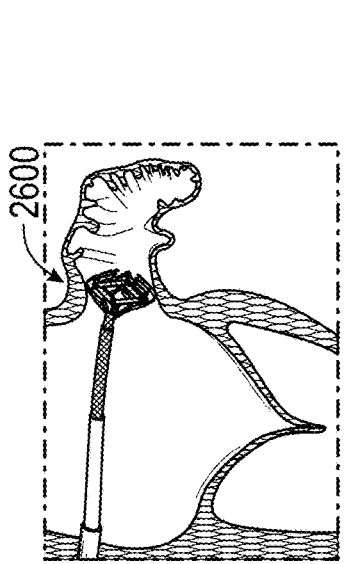

FIGS. 158A-158C show another embodiment of a device and a method of using such device for treating the LAA.

Figure 159A:
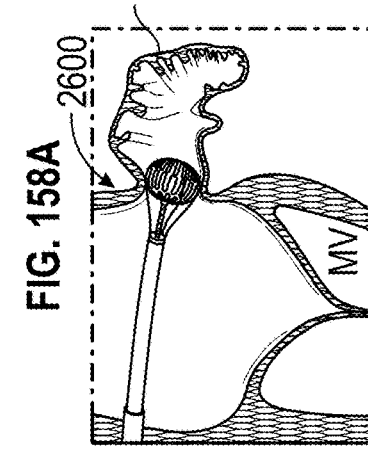
Figure 159B:
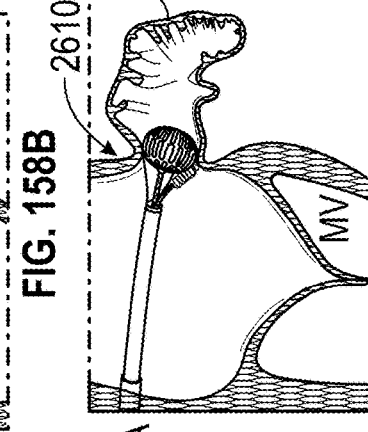
Figure 160A:
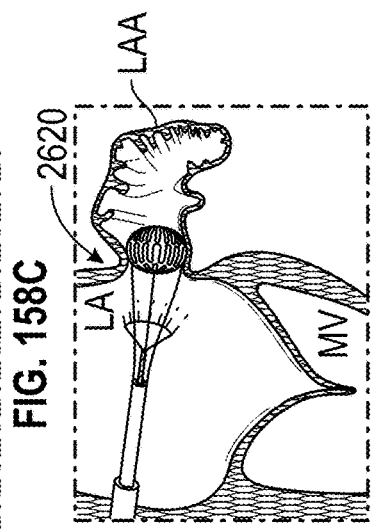
Figure 160B:
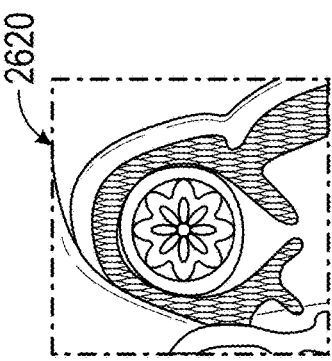
Figure 160C:
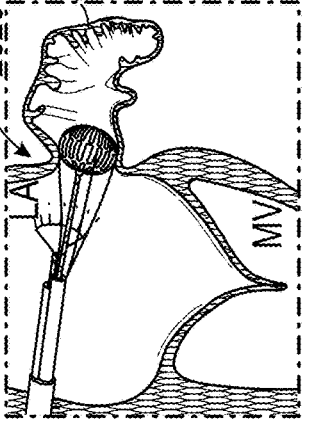
Figure 160D:
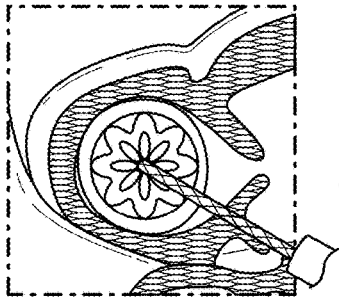
Figure 163A:
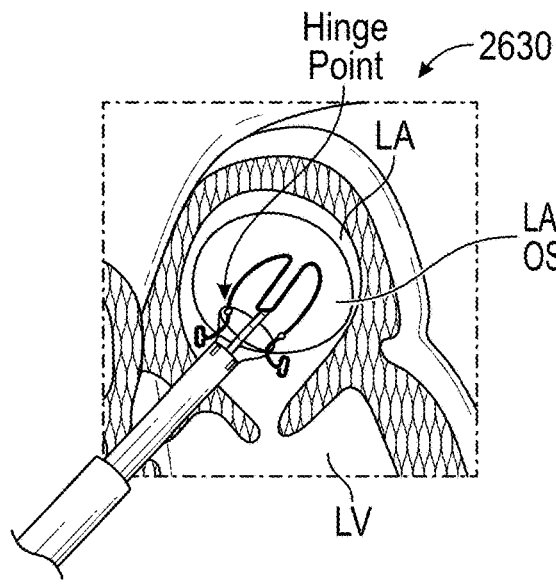
Figure 163B:
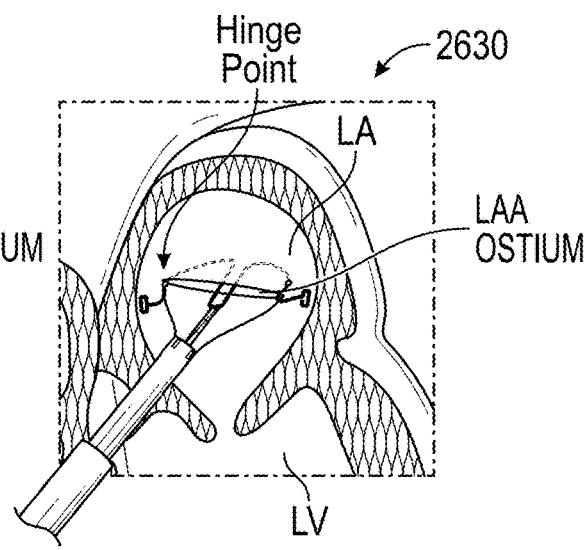
Figure 163C:
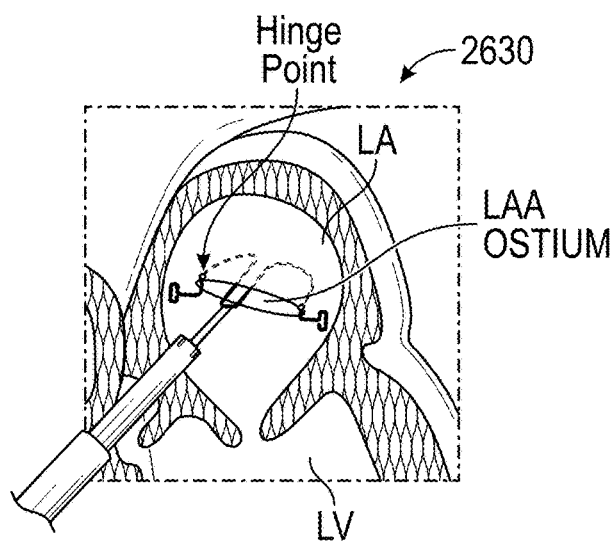
Figure 163D:
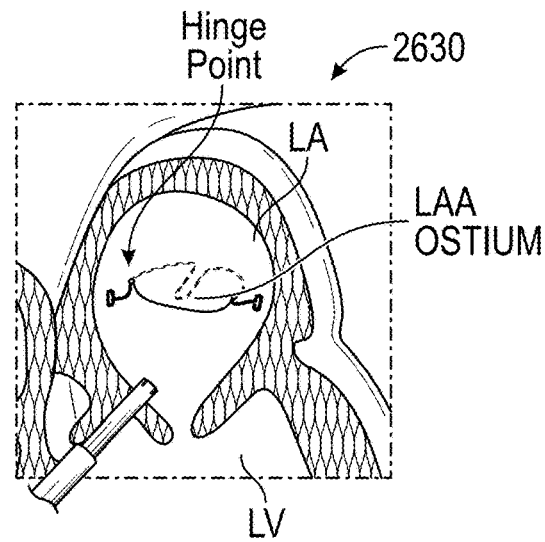

FIGS. 159A-159B show another embodiment of a device and a method of using such device for treating the LAA.

FIGS. 160A-160D show another embodiment of a device and a method of using such device for treating the LAA.

FIGS. 161A-161C show an embodiment of a device for treating the LAA.

FIGS. 162A-162C show an embodiment of a device for treating the LAA.

FIGS. 163A-163D show another embodiment of a device and a method of using such device for treating the LAA.

Figure 164A:
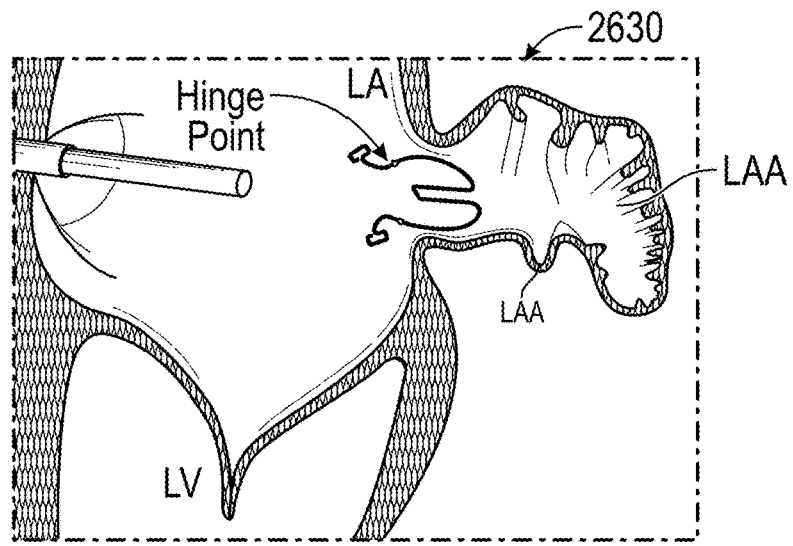
Figure 164B:
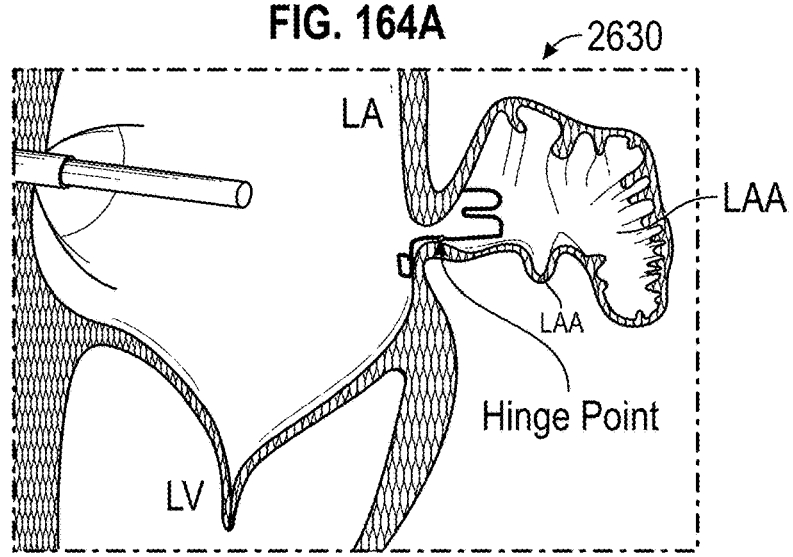
Figure 164C:
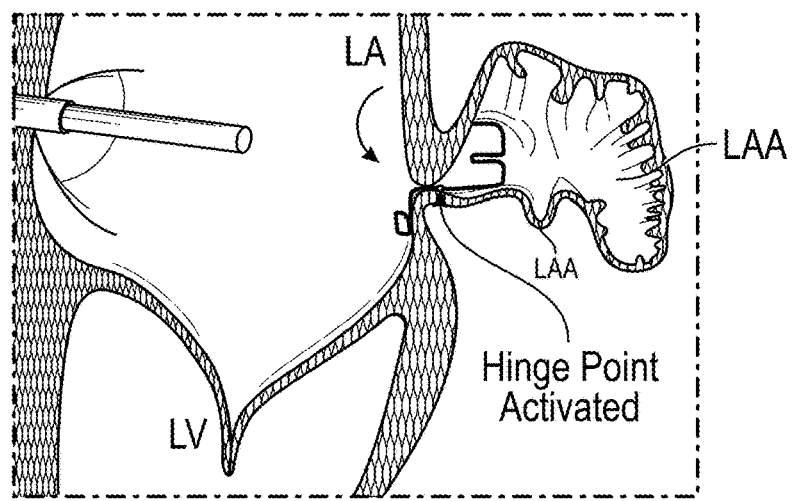

FIGS. 164A-164C show another embodiment of a device and a method of using such device for treating the LAA.

Figure 165A:
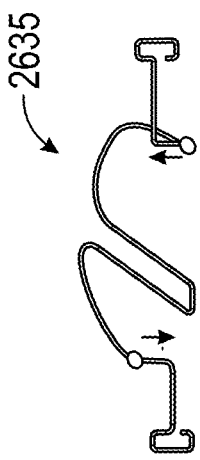
Figure 165B:
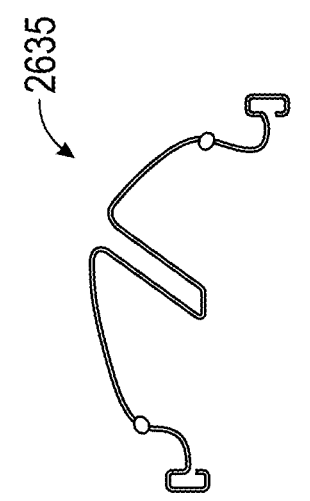
Figure 165C:
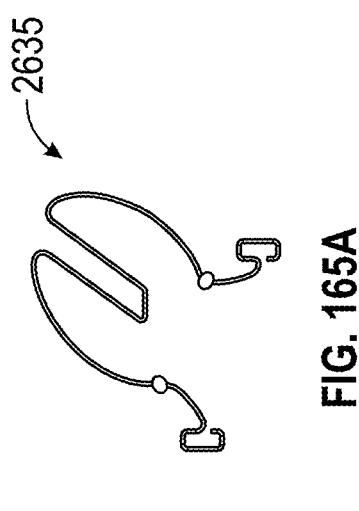

FIGS. 165A-165C show an embodiment of a device for treating the LAA.

Figure 166A:
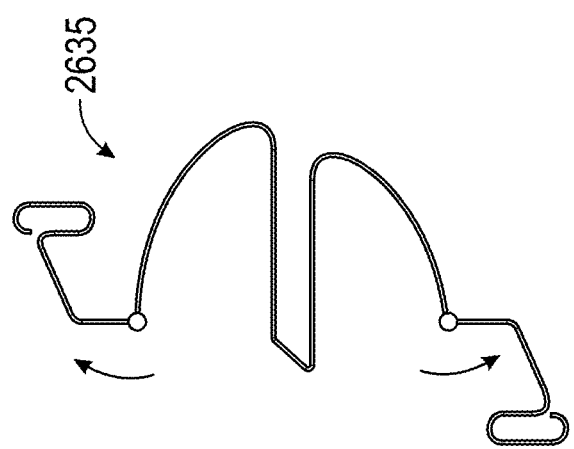
Figure 166B:
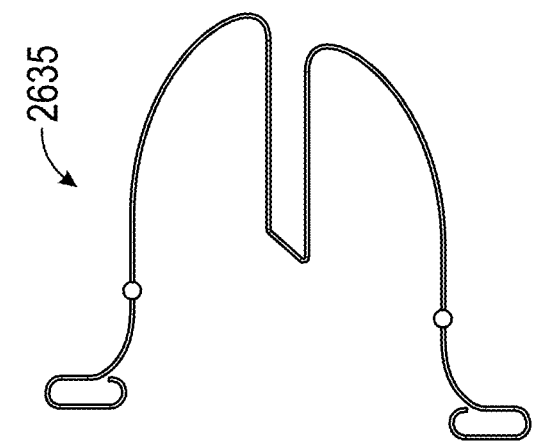
Figure 166C:
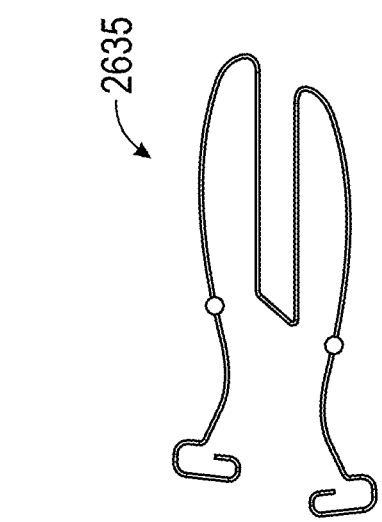
Figure 167A:
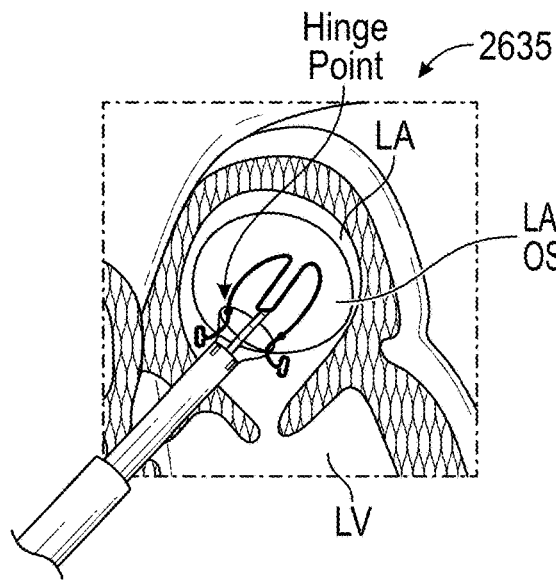
Figure 167B:
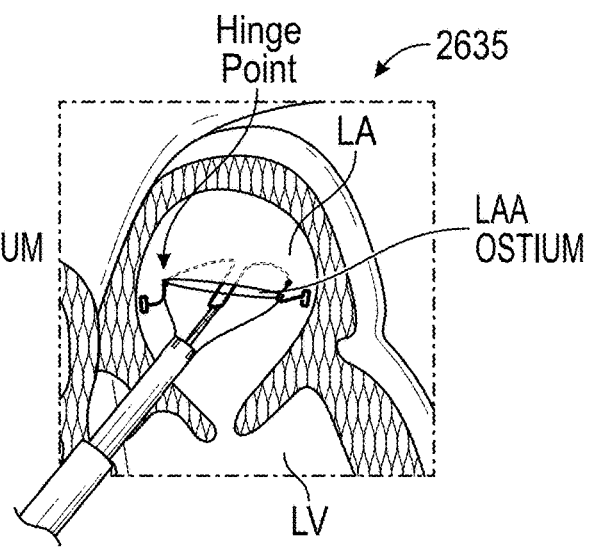
Figure 167C:
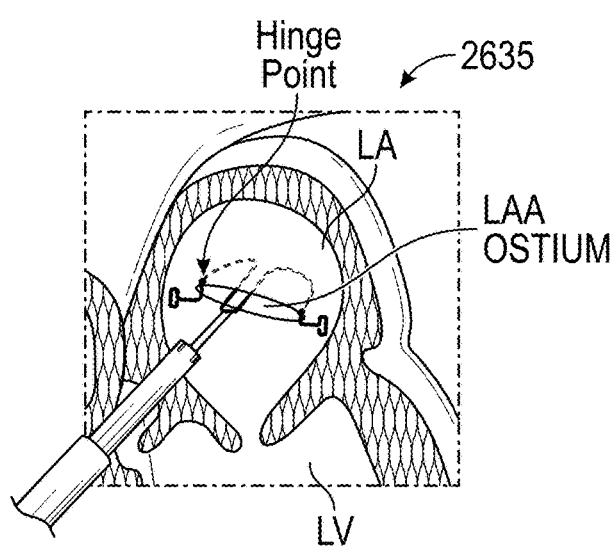
Figure 167D:
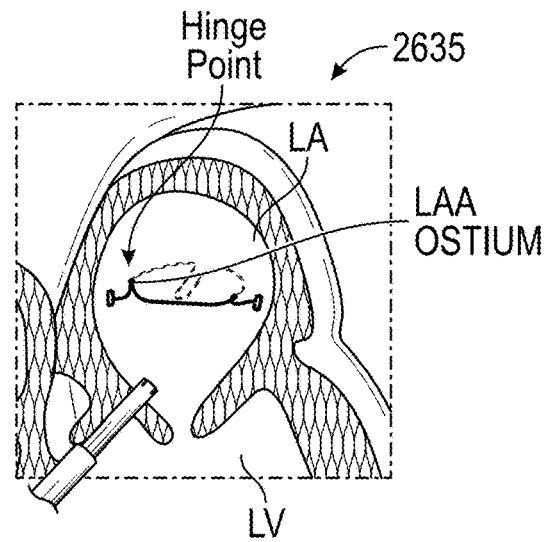

FIGS. 166A-166C show an embodiment of a device for treating the LAA.

FIGS. 167A-167D show another embodiment of a device and a method of using such device for treating the LAA.

Figure 168:
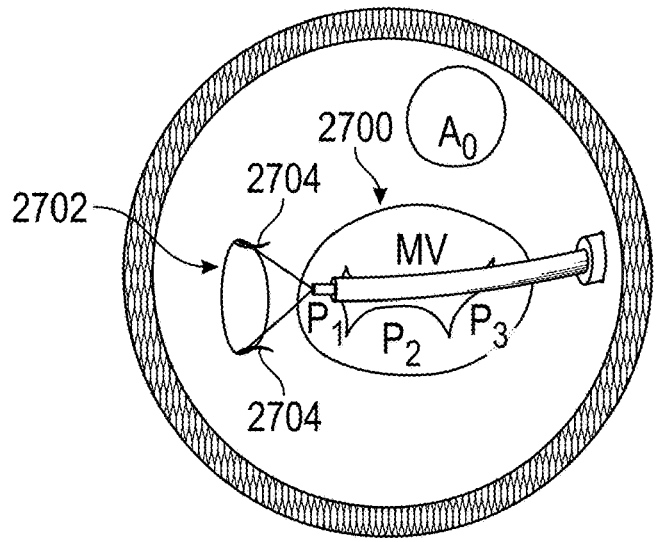
Figure 169:
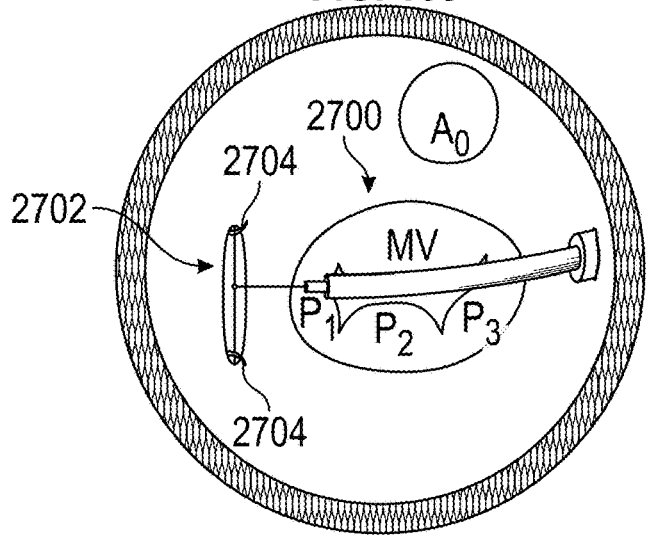
Figure 170:
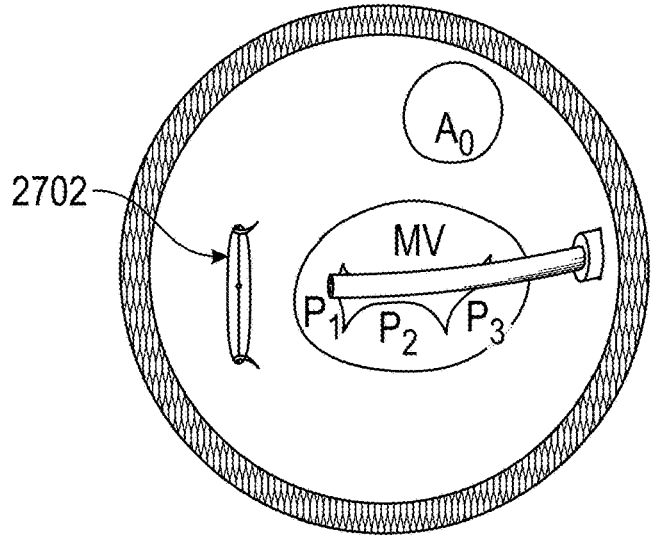

FIGS. 168-170 show an embodiment of a treatment system and an embodiment of a method of treating the LAA.

FIGS. 171A-171D show an embodiment of a treatment system and method of using such device to treat the LAA.

Figure 172A:
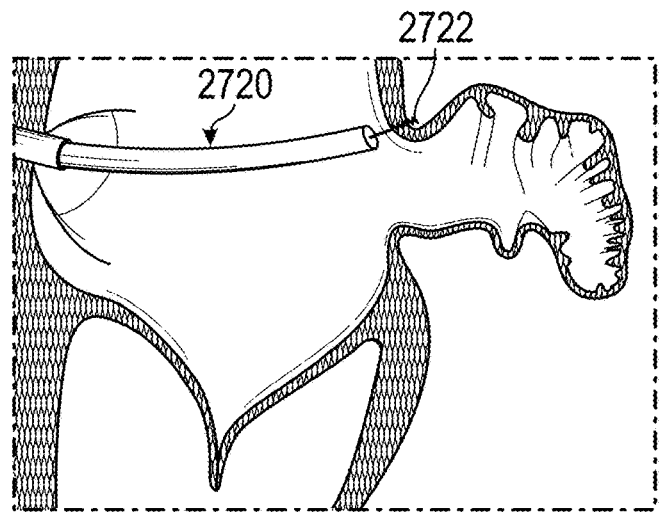
Figure 172B:
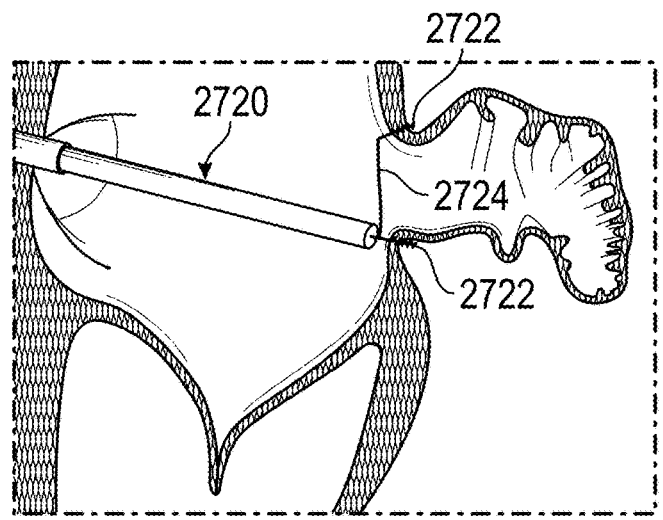
Figure 172C:
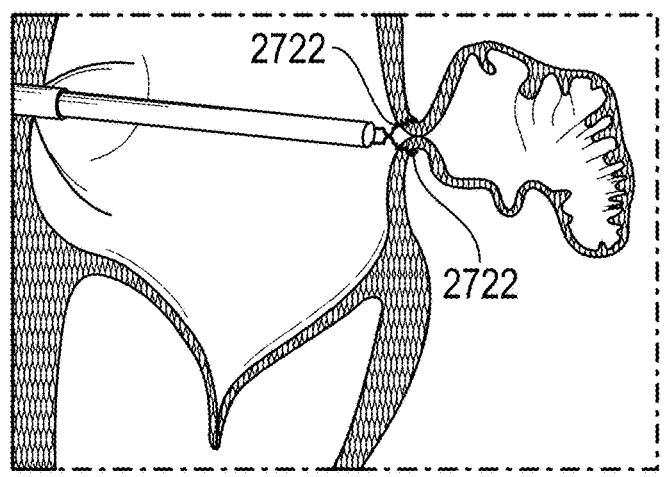

FIGS. 172A-172C show an embodiment of a treatment system and method of using such device to treat the LAA.

FIGS. 173A-173D show additional embodiments of tissue anchors that can be used with any implant devices or systems disclosed herein.

Figure 174:
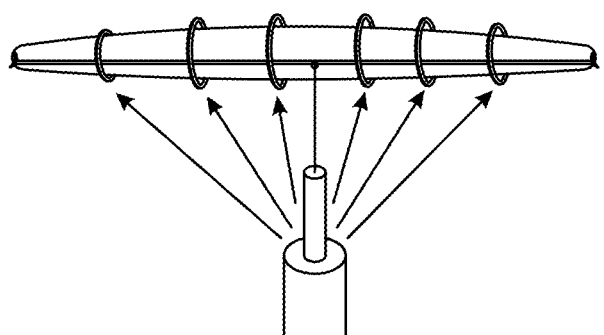

FIG. 174 shows an embodiment of a device for treating the LAA.

FIGS. 175A-175D show additional embodiments of implant devices for treating the LAA.

FIGS. 176A-176D show an embodiment of a treatment system and method of using such device to treat the LAA.

FIG. 177 shows the left atrium.

FIGS. 178A-178B show an embodiment of a treatment system and method of using such device to treat the LAA.

FIGS. 179A-179B show an embodiment of a treatment system and method of using such device to treat the LAA.

FIGS. 180A-180D show an embodiment of a device for treating the LAA.

FIGS. 181A-181D show an embodiment of a device for treating the LAA.

FIGS. 182A-182F show an embodiment of a treatment system and method of using such device to treat the LAA.

FIGS. 183A-183E show an embodiment of a treatment system and method of using such device to treat the LAA.

Figure 184:
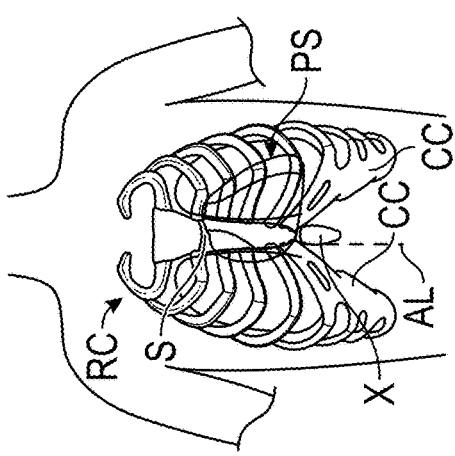

FIG. 184 is an anterior view of a heart illustrating the right ventricle, the left ventricle, and the LAA.

FIG. 185 illustrates the heart, located within the pericardial space located beneath the patient's rib cage.

FIGS. 186A-186F show an embodiment of a treatment system and method of using such device to treat the LAA.

FIGS. 187A-187E show an embodiment of a treatment system and method of using such device to treat the LAA.

FIGS. 188A-188E show an embodiment of a treatment system and method of using such device to treat the LAA.

DETAILED DESCRIPTION OF THE SOME EXEMPLIFYING EMBODIMENTS

Described herein are novel devices, systems, and methods for closing or occluding an LAA. Some embodiments comprise a method that includes advancing a delivery system to the LAA, advancing and deploying an expandable element (which can be, in some embodiments, covered with barbs, texture, or other tissue engaging features or, alternatively, can be smooth) and which can have a generally spherical or orb shaped shape into the left atrial appendage, allowing the expandable element to engage distally and/or radially with inner wall surfaces of the LAA, applying a rotation to the inner catheter member connected to the expandable element to twist the LAA to close and/or occlude the LAA at or near the ostium. By occluding the LAA, some embodiments disclosed herein can effectively eliminate or significantly or nearly completely eliminate a communication of blood or other matter between the left atrium and the LAA. Any methods of deployment disclosed herein can also include deployment of a securing element (which is also referred to herein as a locking element or anchoring element) that is configured to inhibit or prevent the unwinding of the expandable element relative to the LAA and the LA ostial tissue, thereby inhibiting or preventing the untwisting of the LAA.

The devices, systems, and methods disclosed herein can be used, or can be adapted, for other applications within the body or on the surface of the body of any human, animal, reptile, or other living being. Other applications include, without limitation, closing openings in other tissues aside from the LAA, occluding or closing openings, passageways, and/or chambers within the heart or other organs, occluding or closing holes or other slits or openings in vessels and passageways, and/or treating other conditions.

The clinical benefit of some embodiments is a resultant implant which is not in direct blood contact with the left atrial blood or flow except a possible portion of the securing feature. The securing element of any embodiments can be configured to limit the exposure of the securing element to the blood within the left atrium (i.e., to limit the amount of the securing element that projects into the left atrium). In some embodiments, the entire implant can be surrounded by tissue of the LAA tissue so that no portion, or only a minimal portion (for example, less than 10% of the surface area, or less than 40% of the surface area) of the implant is exposed to blood flow within the left atrium. This can have clinical benefits to the patient as there should be post drug regiment required. Any of the devices used in any of the methods described here may be advanced under any of a variety of visualization techniques, e.g., fluoroscopic visualization, ultrasound, etc.

The implant of any embodiments disclosed herein can have an expandable atraumatic shape with tissue gripping features located on the outer edges of the shape, coupled to a securing and or ratcheting feature which can hold the initial or final closed position of the implant. The implant of any embodiments disclosed herein can be configured to grip the internal tissue of the LAA with radial force as well. In some embodiments a vacuum or suction can be provided by the catheter or any component thereof to draw a tissue portion of the LAA or atrium toward the implant. The implant of any embodiments disclosed herein can have an atraumatic shape that can be spherical, dome shaped, or comprise a coil of wire in the shape of a disk, can have expanded cut pattern in the shape of a stent, or anything else which can have rounded edges. In some embodiments, the barbs (which can be tissue anchors) on the outer edges or surface of the implant can comprise metal hooks, plastic cleats, rough texture of some material or surface features, a coating or activated adhesive which grips the inside surface of the LAA. Additionally, in any embodiments disclosed herein, the tissue anchors can be positioned on or adjacent to an end portion of the implant to engage with an end portion of the LAA. In any embodiments, the barbs can be directional allowing for tissue engagement in one rotational direction and a disengagement in the opposite rotational direction for a possible repositioning, resizing, or removal from the LAA.

The rotation used to twist closed or occluded (completely or substantially) the LAA for any embodiments disclosed herein may be as little as a quarter of a turn (i.e., revolution), a half turn, a complete turn, up to as much as multiple turns for deeper or longer LAAs. The securing feature or element (also referred to herein as an anchoring element) in any embodiments disclosed herein can have a single arm or multiple arms which can be connected to the implant body that is positioned and rotated within the closed or substantially closed LAA. The securing feature or element can also be configured to engage tissue adjacent to the ostium of the LAA. In any embodiments, the securing element can have multiple arms or members, can have an annular ring, can have a disk, or any other suitable shaped surface anchor configured to couple non-twisted tissue to the twisted implant. In some embodiments, the securing element can also have a small diameter ring which can be configured to clamp to or engage with the tissue which contacts to the center hub of the implant (adjacent to the ostium of the LAA) or it can also have a clip which folds and clips the implant to the side of the wall of the left atrium (LA).

In some embodiments disclosed herein, the device can be configured to restrict an opening of the LAA by reducing a cross-sectional area of the opening of the LAA by at least 95%, or by at least 90%, or by from at least approximately 80% to approximately 100% as compared to a cross-sectional area of the opening of the LAA before the device was implanted (including a blockage effect from the device). Further, in some embodiments, the method can include rotating the implant from the first rotational position to the second rotational position to twist the LAA until an ostium of the LAA is at least 95% blocked and/or restricted, or at least 90% blocked and/or restricted, or at least 80% blocked and/or restricted, or from approximately 70% blocked and/or restricted to approximately 100% blocked and/or restricted. Additionally, any embodiments disclosed herein can include implanting two or more implants of any of the implant embodiments disclosed herein in the LAA. For example and without limitation, any of the implant embodiments disclosed herein can be configured to be deployed or implanted in the LAA to improve the occlusion of implants already implanted in the LAA, including any implants that fit within any of the foregoing ranges of less than complete occlusion. In some embodiments, one or more additional implants or devices can be implanted adjacent to, over, around, or otherwise with an existing implant to improve a level of occlusion of the LAA.

Alternatively, in any embodiments disclosed herein, the securing element can be configured to merely compress the tissue of the left atrium and/or the left atrial appendage that has constricted around an outer surface of a body portion of the implant between a distal surface of the securing element and the contact member to prevent rotation of the implant in the second direction, i.e., after the contact member has been rotated to the second rotational position, without penetrating into such tissue. For example and without limitation, in any embodiments disclosed herein, the securing element can have a body portion that is smooth an nonobtrusive or nonpenetrating, e.g., so that the securing element does not have any tissue penetrating features on it that extend toward the tissue surfaces. In other embodiments, the arms (or, at least, the portions of the arms that extend in the axial direction when the securing element is in the second state) or other tissue penetrating portions of the securing element can be short, such as from approximately 1 mm to approximately 5 mm in length, or from approximately 1 mm to approximately 3 mm in length, or from approximately 1 mm to approximately 2 mm in length, or of any values or ranges of values between any of the foregoing ranges.

Figure 1A:
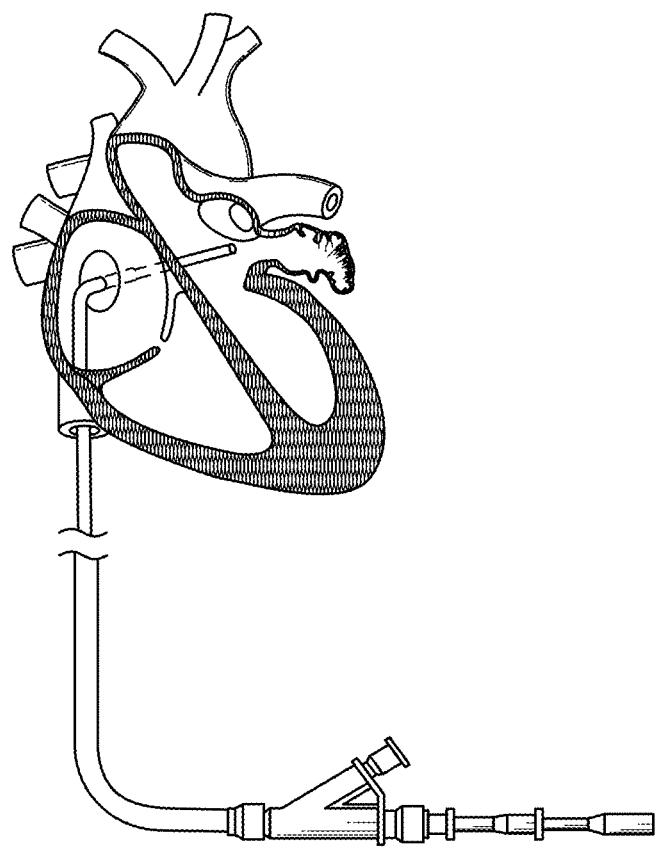
FIG. 1A illustrates a path through the venous system via femoral vein and a transseptal puncture into the left atrium that can be used to access the left atrial appendage (LAA).
Figure 1B:
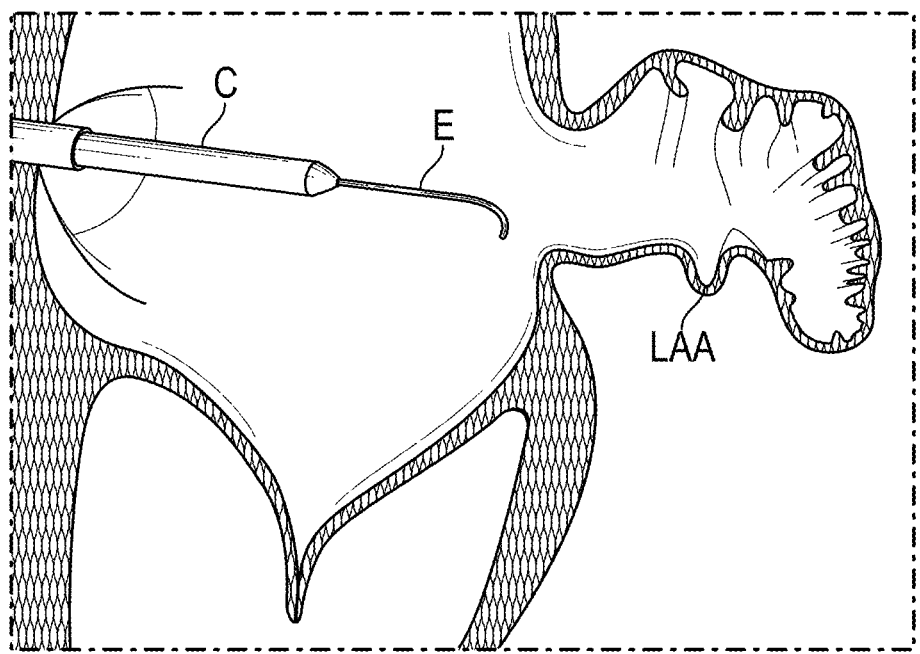
FIG. 1B shows a section view of a left atrium, showing a guidewire advancing toward the LAA.
Figure 2A:
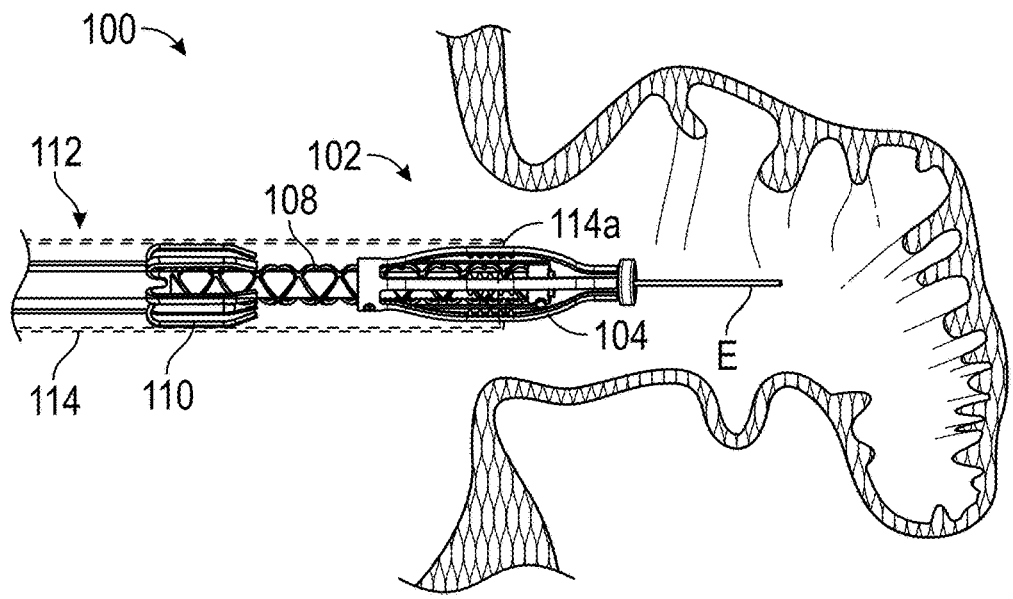
FIG. 2A shows an embodiment of treatment system having an implant device being advanced through a catheter into the LAA, the implant device being in a collapsed state and restrained within an outer tube of the catheter.

FIGS. 1A and 1B show a section view of a left atrium, showing a guidewire G advancing from a catheter C toward the left atrial appendage LAA. FIG. 2A shows an embodiment of an occlusion system 100 for occluding or closing the opening of the LAA. In any embodiments disclosed herein, the occlusion system (including the embodiment of the occlusion system 100) can be configured to rotate and twist the LAA so as to cause a neck or a portion of the LAA adjacent to the opening of the LAA to constrict and substantially or fully close about an outside surface of a portion of the implant device, thereby causing the opening of the LAA to be occluded. In any embodiments of the occlusion system, including the embodiment of the occlusion system 100, the system can have an implant device 102 having a contact member 104 (also referred to herein as a contact element or an expandable implant member), a securing element or securing element 110 (also referred to as a securing member), and a retention member 108. The implant device 102 can be configured to be advanced through a catheter 112 into the LAA. The embodiment of the implant device 102 shown in FIG. 2A is shown in a collapsed state and restrained within an outer sleeve 114 of the catheter 112. As shown, the implant device 102 can be advanced distally out of the catheter 112 past a distal end 114a of the outer sleeve 114 by advancing a portion of or member of the catheter, such as without limitation a core member 113 of the catheter 112, so that the contact member 104 of the implant device 102 can be advanced into the LAA and/or deployed within the LAA.

Figure 2B:
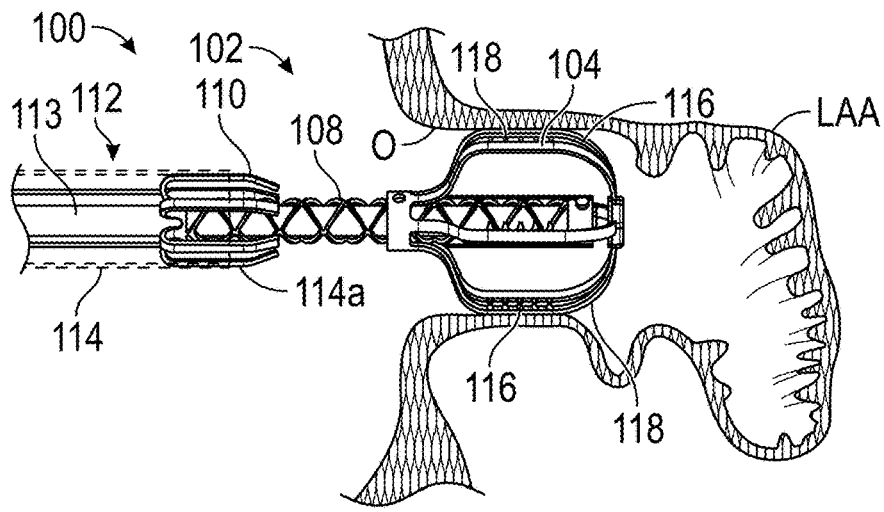
FIG. 2B shows the embodiment of the treatment system of FIG. 2A, showing the contact member being expanded within the LAA.

Alternatively, the catheter 112 having the implant device 102 therein can be advanced into a desired position within the LAA and, while holding the implant device 102 in a stationary axial position by maintaining the core member 113 of the catheter 112 in a stationary axial position, the outer sleeve 114 of the catheter 112 can be retracted or withdrawn so as to expose and/or unrestrain the contact member 104 of the implant device 102. In any embodiments disclosed herein, the contact member 104 can be self-expanding in a radial direction so that, when a restraint is removed from the contact member 104, the contact member 104 can expand against an inner surface or wall of the LAA automatically. In other embodiments, the contact member 104 can be mechanically expandable, such as by a balloon expander, so as to expand against inside surface or wall of the LAA. FIG. 2B illustrates the contact number 104 after it has been expanded against an inside wall of the LAA distal to an ostium or opening O of the LAA.

Alternatively, in any embodiments disclosed herein, the contact member can be configured to remain in a first state within the catheter, during the entire treatment procedure, and/or thereafter. For example and without limitation, in any embodiments disclosed herein, the contact member can be configured such that the contact member is deployed from the catheter and advanced into contact with a tissue surface of an inside wall of the LAA, engage the tissue surface of the inside wall of the LAA, and cause the LAA to twist when a torque and/or rotation is applied to the contact member, all without changing the state of the contact member. Alternatively, in any embodiments disclosed herein, a contact member can be configured to be advanced into the pericardial space around an outside of the LAA to engage an outside surface of the LAA and to and cause the LAA to twist when a torque and/or rotation is applied to the contact member.

In any embodiments disclosed herein, including the embodiment illustrated in FIG. 2B, the contact member 104 can have a plurality of arms or struts 116 that are each configured to self-expand in a radial direction when a restraint has been removed from an outside surface of the contact member 104. For example without limitation, any embodiments of the contact member disclosed herein can have six struts 116, or between six and ten struts, or from less than six to more than ten struts.

Further, in any embodiments, the contact member 104 can have a plurality of teeth, cleats, barbs, nubs, texture, studs, anchors or other tissue engaging features 118 or other similar features configured to penetrate or engage the tissue of the LAA that are configured to penetrate into a tissue within the LAA when the contact member 104 is expanded against the tissue of the LAA and/or when the contact member 104 is rotated or twisted within the LAA. Note that teeth, cleats, barbs, nubs, texture, studs, anchors and other tissue engaging features or features configured to grip or engage the tissue when torque is applied to the expanded contact member will be collectively referred to herein as tissue anchors, which use of this term is meant to describe and include any of the foregoing features individually and/or any combination of these features.

The tissue anchors 118 can be integrally formed with the struts, on the struts, added to the struts, or otherwise coupled with or supported by the struts. The tissue anchors 118 can be circumferentially facing (as shown, can be radially facing so as to penetrate or engage the tissue at an orthogonal angle relative to the tissue surface of the LAA, at an angle relative to the line that is tangential to the outer surface of the contact member 104, or otherwise. In some embodiments, each strut 116 can support a plurality of tapered tissue anchors facing in a circumferential direction, as illustrated in FIG. 2B. All of the tissue anchors can face in a similar orientation relative to each of the struts, such as in the circumferential direction relative to each strut. In the illustrated embodiment, each strut 104 has five tissue anchors 118. In this embodiment, when the contact member 104 is rotated in a first direction (indicated by arrow A1 in FIG. 2C, which can be in the clockwise or the counterclockwise direction), one or more or all of the struts 116 and one or more or all of the tissue anchors 118 can engage the tissue of the LAA and cause the LAA to twist or rotate in the first direction A1. The twisting or rotation of the LAA in the first direction from a first rotational position to a second rotational position results in the opening or ostium O of the LAA constricting in a radial direction (represented or identified by arrows A2 in FIG. 2C) so that the opening O of the LAA is caused to move or constrict around an outside surface of a proximal portion 104a of the contact member 104. An operator can twist or rotate the contact member 104 by twisting or rotating the core member 113 of the catheter 112. The tightening or constriction of the opening O of the LAA around an outside surface of the proximal portion 104a of the contact member 104 or other portion of the implant device can result in the occlusion, or substantial occlusion, or substantial closing off of the interior portion of the LAA from the remaining chambers within the heart, thereby substantially reducing the health risks associated with an open LAA.

In some embodiments, as in the illustrated embodiment, the securing element 110 can be maintained in a collapsed or first state such as by being restrained by the outer sleeve 114 of the catheter 112 while the contact member 104 is being deployed and rotated to prevent the securing element 110 from contacting tissue within the heart and potentially lacerating or otherwise damaging such tissue. An intermediary sleeve or tube 115 can be coupled with the securing element 110 and can be used to manipulate and control a position and/or an orientation of the securing element 110, including holding a proximal end portion 110a of the securing element in a fixed axial position while a distally directed force is exerted on the contact member 104 to maintain the retention member in the first, extended state. In any implant device embodiments disclosed herein, the securing element (including, for example and without limitation, securing element 110) can be keyed, indexed, or otherwise rotationally fixed to the contact member (including, for example and without limitation, contact member 104) so that the securing element cannot rotate relative to the contact member and the contact member cannot rotate relative to the securing element. In this configuration, the securing element can prevent or substantially prevent or inhibit the contact member and the LAA from rotating back toward the first rotational position.

Figure 2C:
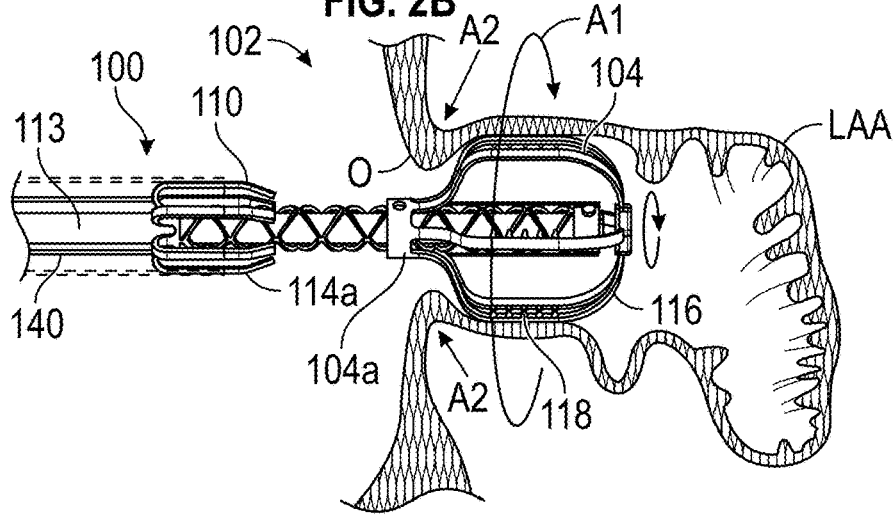
FIG. 2C shows the embodiment of the treatment system of FIG. 2A, showing the contact member being rotated to twist the LAA and cause a neck or opening of the LAA to constrict around a portion of the implant device.
Figure 2D:
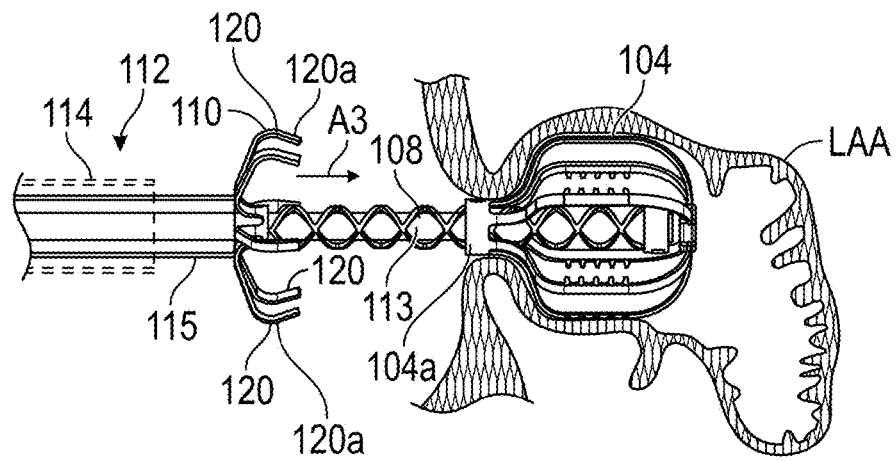
FIG. 2D shows the embodiment of the treatment system of FIG. 2A, showing the securing element of the embodiment of the implant device being advanced toward the contact member of the implant device.
Figure 2E:
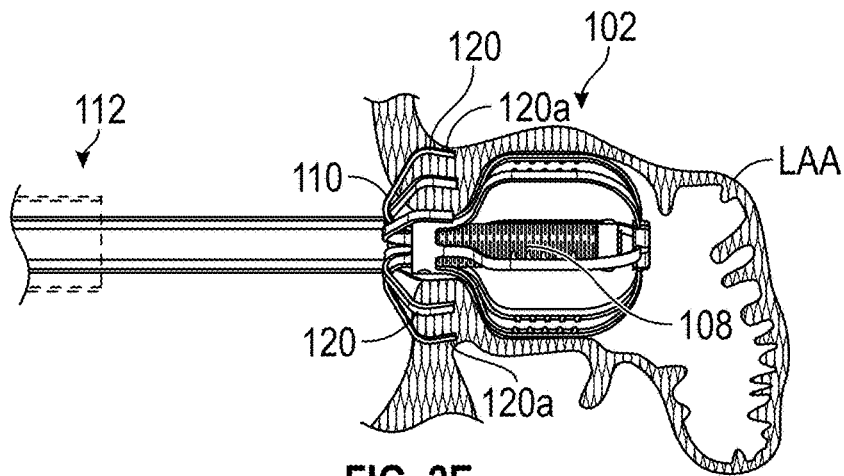
FIG. 2E shows the securing element of the treatment system of FIG. 2A engaged with the patient's tissue surrounding the proximal portion of the contact member of the implant device.
Figure 2F:
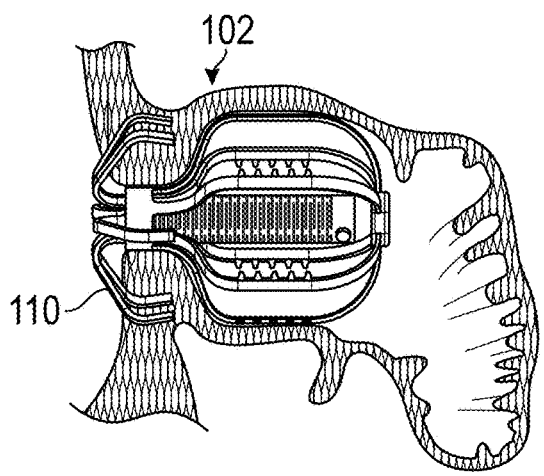
FIG. 2F shows the implant device of FIG. 2A disengaged and removed from the catheter.

With reference to FIG. 2D, with the contact member 104 having been rotated to the second rotational position and maintained in the second rotational position such that the opening O of the LAA remains constricted around a proximal portion 104a of the contact member 104 or other portion of the implant device and the LAA is generally occluded from the remainder of the heart chambers, the catheter tube member 115 can then be advanced in a distal direction (represented by arrow A3 as shown in FIG. 2D) or the outer sleeve 114 can be withdrawn in a proximal direction so that the securing element of 110 can be exposed so that it can self-expand from a first, collapsed state (as shown in FIG. 2C) to a second, expanded or open state (as shown in FIG. 2D). In the second state, a plurality of struts or members 120 of the securing element 110 can expand in a generally radial direction so as to open up to a larger overall diameter or profile. Additionally, because each of the one or more members 120 of the securing element 110 can have end portions 120a that extend in a generally distal axial direction (but can be slightly angled inwardly), as the securing element 110 is advanced in the axial direction, the distal portions 120a of each of the one or more members 120 can penetrate into and/or engage with a tissue portion of the heart, as shown in FIG. 2E. The tissue portion that the one or more members 120 can penetrate into or engage with can include portions of the tissue comprising the left atrium and/or portions of the tissue comprising the LAA. As mentioned above, the contact member 104 can be held in generally a stationary axial position using the core member 113 while the securing element 110 is advanced distally toward the contact member 104. The retention member 108 can thereafter be unrestrained so that it can maintain the securing element 110 in the second position wherein the securing element 110 is engaged with the tissue of the heart, as shown in FIG. 2E. In some embodiments, the securing element can be biased toward a smaller size in the axial direction, such as with a spring member or similar. For example, the retention member 108 can be formed by laser cutting openings within a cylindrical tube, such as a hypo tube made of an elastic material, such as Nitinol. Thereafter, with reference to FIG. 2F, the implant device 102 can be disengaged from the catheter 112 and the catheter 112 can be retracted and removed from the patient's body. With the securing element 110 engaged with the patient's tissue, as illustrated in FIG. 2F, the LAA is prevented from rotating to the first rotational position, which is the untwisted or relaxed position. In this configuration, the implant device 102 can secure and maintain the LAA in a substantially or completely occluded or substantially or completely closed state.

The retention member 108 can thereafter be unrestrained (for example, released) so that it can retract, to maintain the securing element 110 in the second position wherein the securing element 110 is engaged with the tissue of the heart, as shown in FIG. 2E. In some embodiments, the securing retention member 108 can be biased toward a smaller size length or size in the axial direction, such as with a spring member or similar. For example, the retention member 108 can be formed by laser cutting openings within a cylindrical tube, such as a hypo tube made of an elastic material, such as Nitinol.

Thereafter, with reference to FIG. 2F, the implant device 102 can be disengaged from the catheter 112 and the catheter 112 can be retracted and removed from the patient's body. With the securing element 110 engaged with the patient's tissue, as illustrated in FIG. 2F, the LAA is prevented or, at least, inhibited or biased from rotating to the first rotational position, which is the untwisted or relaxed position. In this configuration, the implant device 102 can secure and maintain the LAA in a substantially or completely occluded or substantially or completely closed state.

Any of the components of any of the implant embodiments disclosed herein can be made from Nitinol or any other elastic or super elastic material, including any other shape memory materials, or any mechanically expandable material such as stainless steel or otherwise. In any embodiments disclosed herein, the contact member (such as contact member 104) can have a spherical, cylindrical, or other shape, such as the shape of an elongated bullet, a stent, a mushroom, or other non-round or non-cylindrical shape or any of the shapes described or shown with respect to any of the embodiments disclosed herein. In any embodiments disclosed herein, the contact member may comprise a series of interconnected struts (that can, but are not required to, form a diamond shaped pattern across all or a portion of the surface of the contact member), or may be made from a series of ribs or paddles which form the expandable device.

Figure 3:
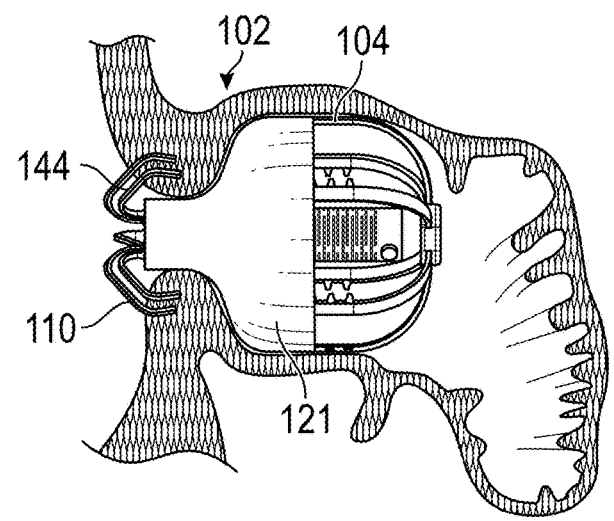
FIG. 3 shows an embodiment of an implant device having a cover member surrounding at least a portion of the implant device.

With reference to FIG. 3, the securing element of any device embodiments disclosed herein, including without limitation the securing element 110, can have an outer size (such as an outer diameter of the arms 144 of the securing element) that is significantly smaller than an outer size (such as an outer diameter) of the contact member 104. For example and without limitation, the securing element of any device embodiments disclosed herein can have an outer size that is approximately one-half of an outer size of the contact member 104, or from approximately 30% to approximately 80% of an outer size of the contact member 104, or from approximately 50% to approximately 60% of an outer size of the contact member 104. In any embodiments, the outer size of the securing element can be similar to or approximately the same as, or even larger than, the outer size of the contact member 104.

As also shown in FIG. 3, any embodiments of the implant device 102 disclosed herein can also have a cover member 121 that can provide an additional seal or barrier around an outside surface of the contact member 104 and/other portions of the implant device 102 to provide an additional barrier to the implant device 102. In some embodiments, the cover can be located or positioned on or against an inside surface or portion of the contact member of the implant. This can improve the seal or occlusion that the implant device 102 creates in the LAA. In some embodiments, the cover member 121 can cover substantially or completely all of the contact member 102 of the implant device.

Figure 4:
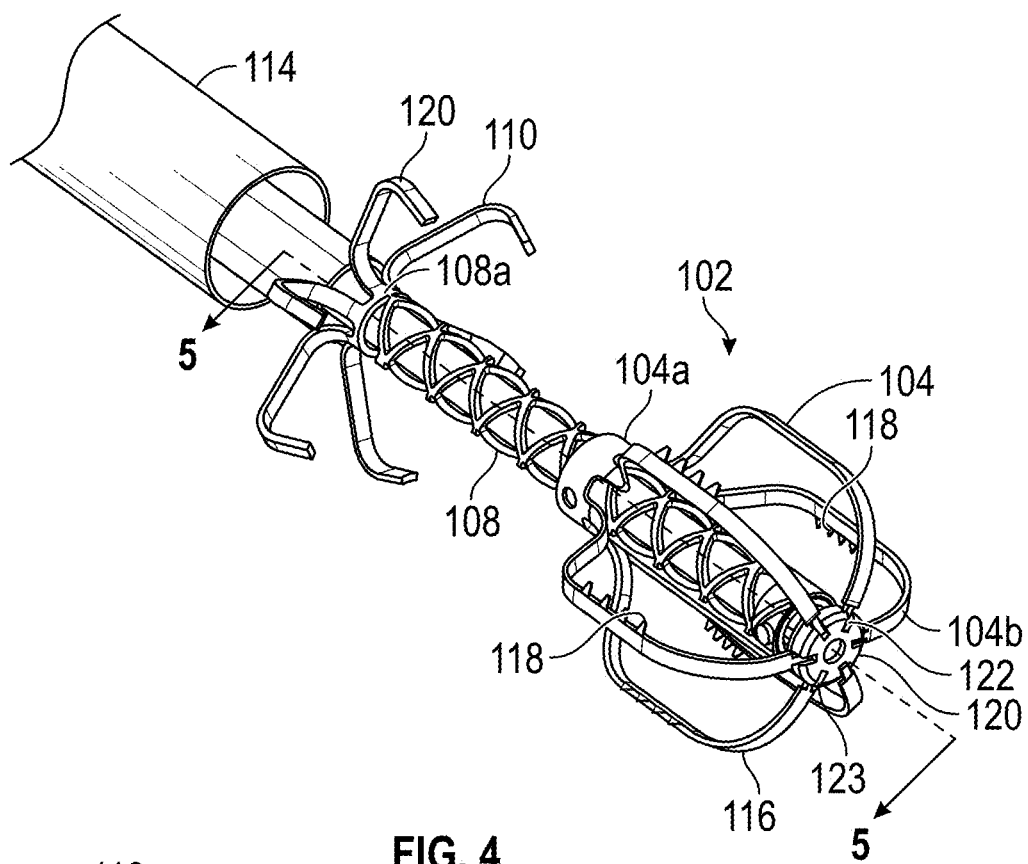
FIG. 4 shows the implant device of FIG. 2A wherein the contact member is in a second, expanded state, the retention member is in a first, extended state, and the securing element is in a second, open state.
Figure 5:
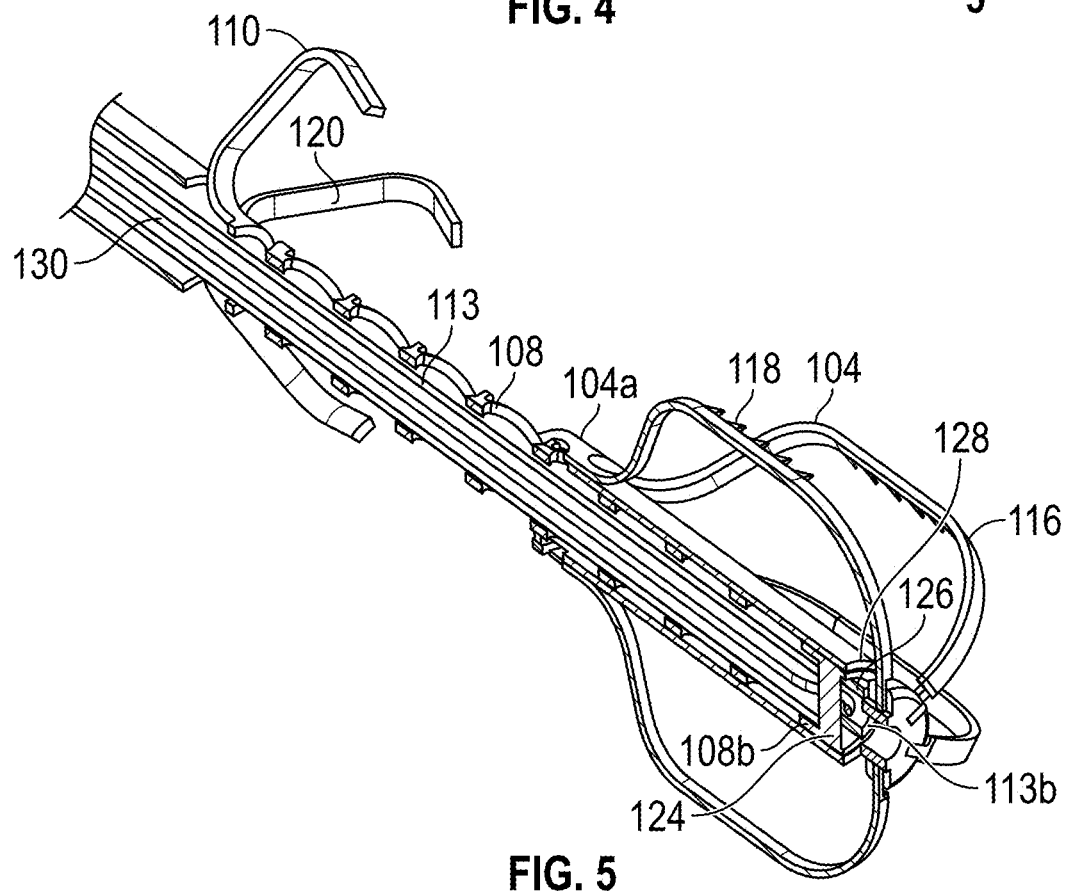
FIG. 5 is a section view of the implant device shown in FIG. 2A, taken through line 5-5 of FIG. 4.
Figure 6:
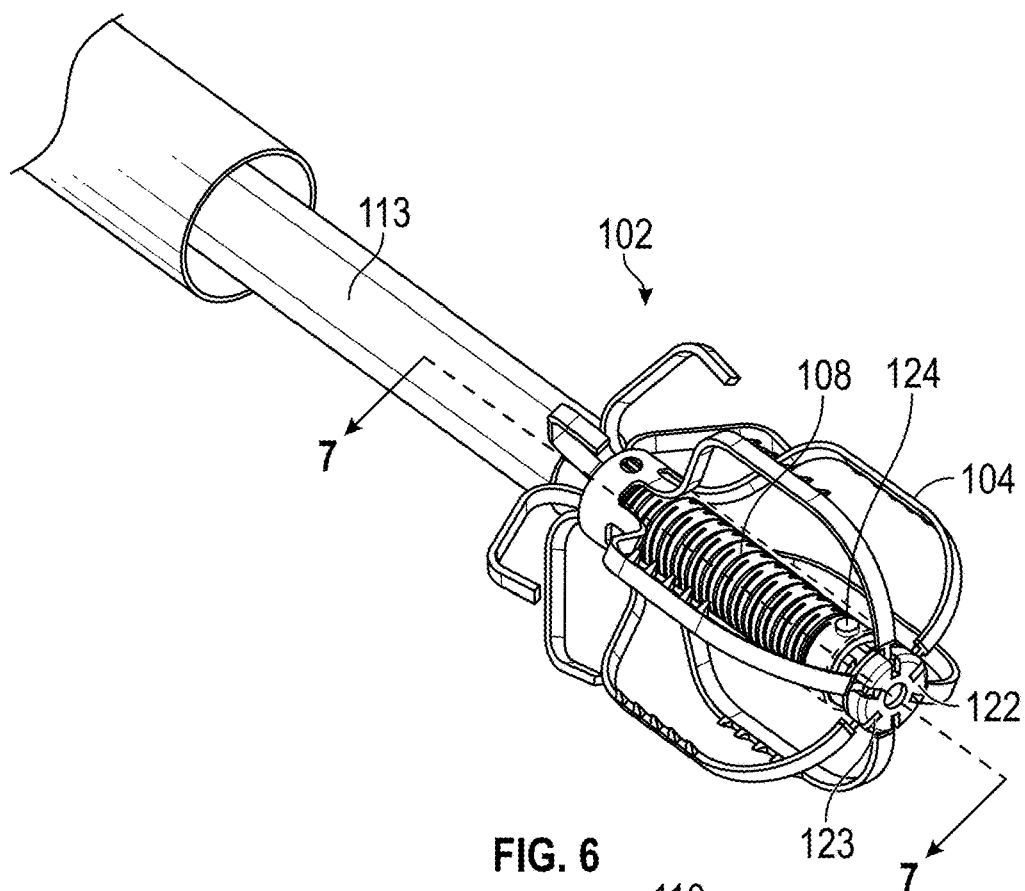
FIG. 6 shows the implant device of FIG. 2A wherein the contact member is in a second, open state, the retention member is in a second, contracted state, and the securing element is in a second, open state.

Further details regarding the implant system 100 will now be described, with reference to FIGS. 4-7. FIG. 4 shows the contact member 104 in the second, expanded state, the retention member 108 (also referred to herein as a biasing member) in the first, extended state, and the securing element 110 in the second, open state. In any embodiments disclosed herein, the retention member can be an axial spring-like member or other axially resilient member. In some embodiments, the contact member 104 can have a continuous and uninterrupted circumference at a proximal end 104a that each of the strut members 116 extend distally away from. Each of the strut members 116 can be preformed into a curved shape such that the strut members 116 are biased to expand to the second state when no external restraint or constraint is applied to the outside surface of the contact member 104 (for example, when in a relaxed state). At a distal end, each of the strut members 116 can, but are not required to, couple with a hub member 122. With reference to FIGS. 5-6, the hub member 122 can have a plurality of receptacles 123 configured to receive and constrain distal end portions 116b of each of the strut members 116. Additionally, each of the receptacles 123 can be configured to permit the distal end portions 116b of each of the strut members 116 to rotate relative to the hub member 122 so that the distal end portions 116b of the strut members 116 can extend generally radially away from the hub member 123 when the contact member 104 is in the second, expanded state. The hub member 123 can be configured to permit the distal end portions 116b of each of the strut members 116 to rotate relative to the hub member 122 without resistance or significant resistance. The distal ends of each of the strut members 116 can have a tab or other feature (such as a T shaped termination or other increased width) 119 that locks into, is secured by, or is otherwise engaged by each of the receptacles 123 so as to axially constrain the end portion of each of the strut members 116, while allow rotation about the end portion.

Figure 7:
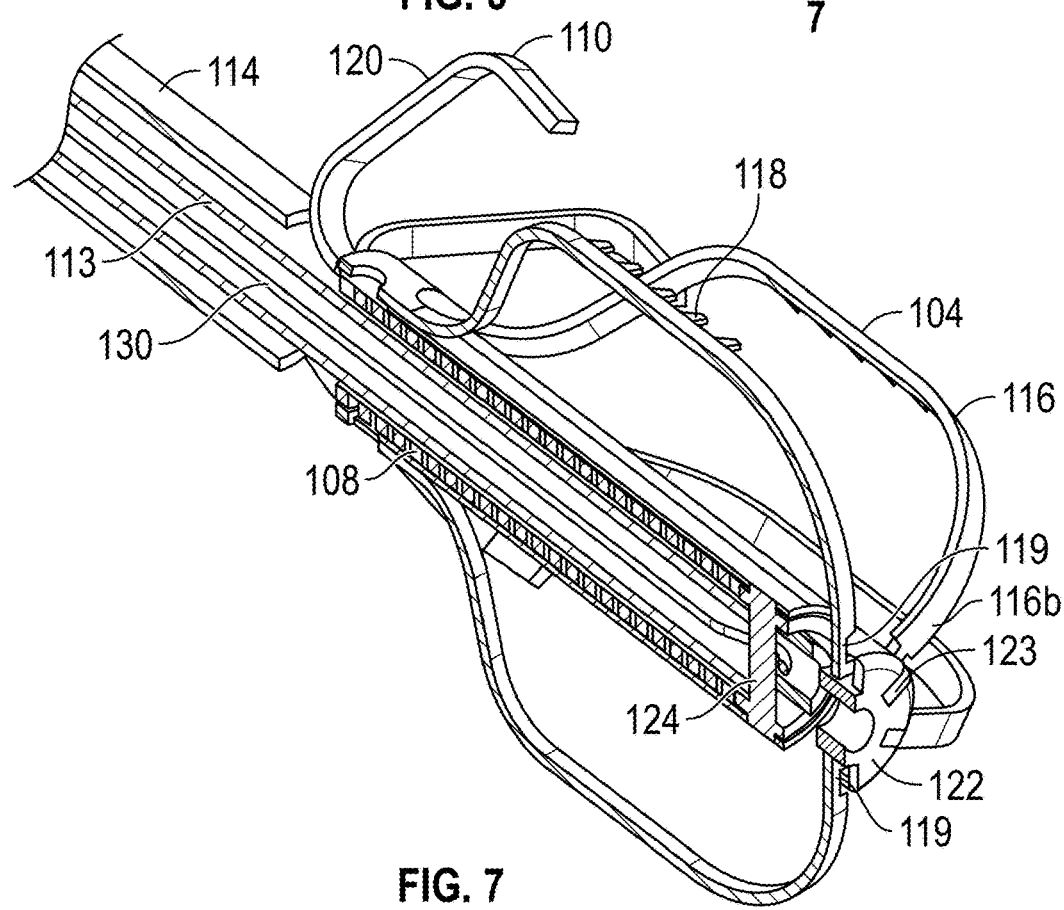
FIG. 7 is a section view of the implant device shown in FIG. 2A, taken through line 7-7 of FIG. 6.

In some embodiments, as in the embodiment illustrated in FIG. 4, the retention member 108 and the securing element 110 can be integrally formed. For example and without limitation, the retention member 108 and the securing element can be laser cut from a single length of tube material, for example, from an elastic or shape memory material, and thereafter formed into the desired shape using conventional or suitable processes. In other embodiments, the securing element 110 can be formed separately and coupled with a proximal end 108a of the retention member 108. In the relaxed state (i.e., the state where no external forces are acting thereon), some embodiments of the retention member 108 can be biased to move to the second or collapsed state, as shown in FIGS. 2E, 6, and 7, for example. Further, in the relaxed state, the retention member 110 can be in the second, or open position as also shown in FIG. 2E. Additionally, with reference to FIG. 5, which is an enlarged section view through line 5-5 of FIG. 4, a pin or cross member 124 can be coupled with a distal end 108b of the retention member 108 and can be configured to fit within a slot 126 formed within a distal end 113b of the core member 113. In this embodiment, the core member 113 can be advanced in a distal direction resulting in the advancement of the contact member 104 in a distal direction. Further, a core tube 128 can extend proximally from a distal end 113b of the core member 113 and couple with a proximal end 104a of the contact member 104. The pin 124 can extend through a pair of openings formed in the core tube 128 to secure the core tube 128 to the pin 124 and, hence, the distal end 108b of the retention member 108. The core tube 128 can, therefore, be used to couple the contact member 104 to the retention member 108. Pins, tabs, sutures, ties, protrusions, clips, depressions, detents, or other features can be used to couple a proximal end 104a of the contact member 104 with a proximal end of the core tube 128. Note that the core tube 128 has been omitted from some of the figures for clarity.

Additionally, in any embodiments, the system 100 can be configured so that the implant device 102 is biased or selectively secured in the proximal direction relative to the core member 113. For example and without limitation, as shown in FIG. 5, some embodiments of the implant device 102 can have a suture or thread 130 that extends through an inside of the core member 113 (such as through a lumen of the core member 113) and loops around the pin 124, thereby permitting a user to retract or withdraw the suture to pull the implant device 102 proximally relative to the core member 113. In this configuration, both ends of the suture 130 can extend from a proximal end of the device 100 such that a practitioner can grasp both ends of the suture 130 to exert the biasing force around the pin 124 to maintain the pin against a proximal end of the slot 126 formed within the distal end 113*b* of the core member 113. When the implant device 102 is ready to be released from the core member 113, the practitioner can simply release one end of the suture and withdraw the other end of the suture until the suture no longer forms a loop and/or no longer wraps around the pin 124. After removing the biasing force or retaining force from the suture 130 and/or removing the proximally directed force from the contact member, the core member 124 can be withdrawn relative to the implant device 102, while the contact member remains stationary within the LAA. This may be done after the contact member and the securing element have been fully deployed or implanted into the LAA and/or tissue adjacent to the LAA.

Further, in any embodiments disclosed herein, the pin or cross member 124 can be configured to permit a guidewire to pass through a distal end portion of the implant device 102 without obstruction. For example without limitation, an opening larger than an outside diameter of a guidewire can be formed in the pin 124 to permit a guidewire to pass therethrough, or the pin 124 can be formed in two parts, with a sufficiently large space therebetween.

With reference to FIGS. 8A-8C, in any embodiments, the contact member 104 of the implant device 102 can be advanced as far into the LAA is desired by the surgeon, or as is appropriate. For example and without limitation, as shown in FIGS. 8A-8C, the contact member 104 can be advanced into contact with, adjacent to, or near to a distal end of the LAA before the contact member 104 is rotated. This will permit more of the implant to be positioned within the LAA and, in some embodiments, more of the tissue of the LAA to constrict around a body portion or other portion of the implant device 102. This can, in some embodiments, permit the user to rotate the contact member 104 of the implant device 102 to a greater extent, and can also result in less stress on the tissue of the LAA. Any implant device embodiments disclosed herein can be configured to be advanced to any extent within the LAA, including being advanced just past the ostium of the LAA, in the middle portion of the LAA, advanced further into the LAA so as to be into contact with, adjacent to, or near to a distal end of the LAA, before the contact member 104 is rotated.

FIGS. 9A-9I show another embodiment of treatment system 140 for closing or occluding an LAA. In any embodiments disclosed herein, any components, features, or other details of the treatment system 140 or implant device 142 can have any of the components, features, or other details of any other treatment system embodiments or implant device embodiments disclosed herein, including without limitation any of the embodiments of the treatment system 100 or implant device 102 described above, in any combination with any of the components, features, or details of the treatment system 140 or implant device 142 disclosed below. Similarly, any components, features, or other details of any of the other treatment system embodiments or implant device embodiments disclosed herein can have any of the components, features, or other details of any embodiments of the treatment system 140 or implant device 142 disclosed herein in any combination with any of the components, features, or details of the treatment system and/or implant device.

Figure 9A:
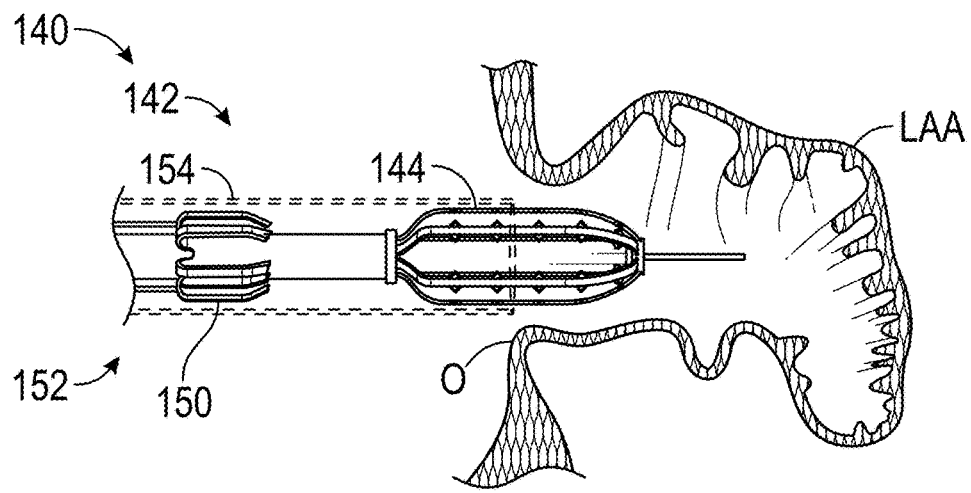
FIG. 9A shows another embodiment of treatment system having an implant device being advanced through a catheter into the LAA, the implant device being in a collapsed state and restrained within an outer tube of the catheter.
Figure 9B:
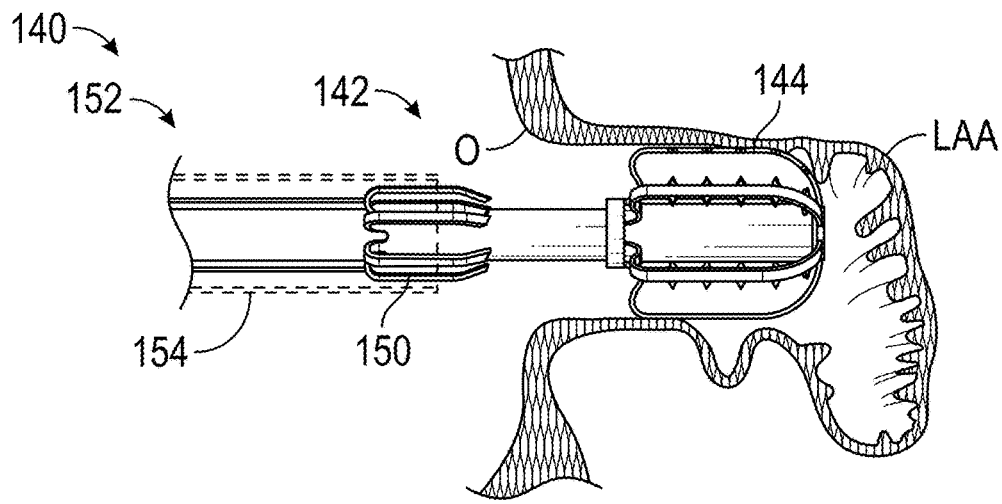
FIG. 9B shows the embodiment of the treatment system of FIG. 9A, showing the contact member being expanded within the LAA.
Figure 9C:
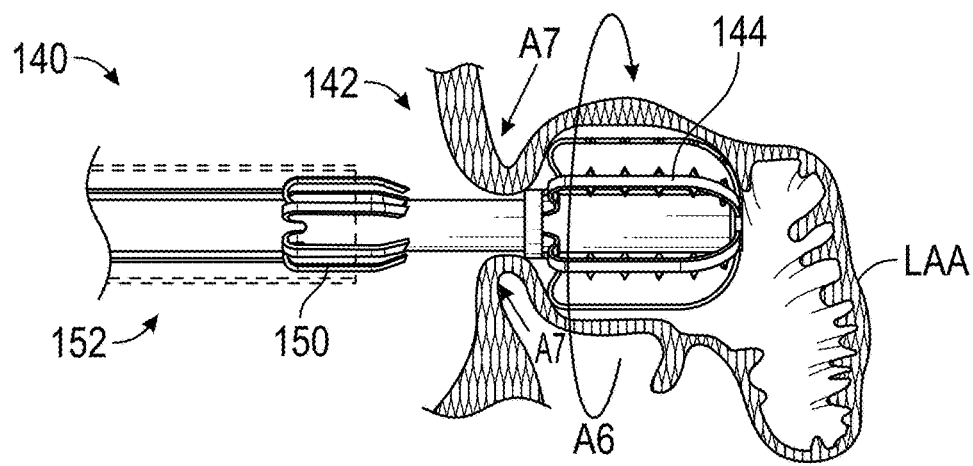
FIG. 9C shows the embodiment of the treatment system of FIG. 9A, showing the contact member being rotated to twist the LAA and cause a neck or opening of the LAA to constrict around a portion of the implant device.
Figure 9D:
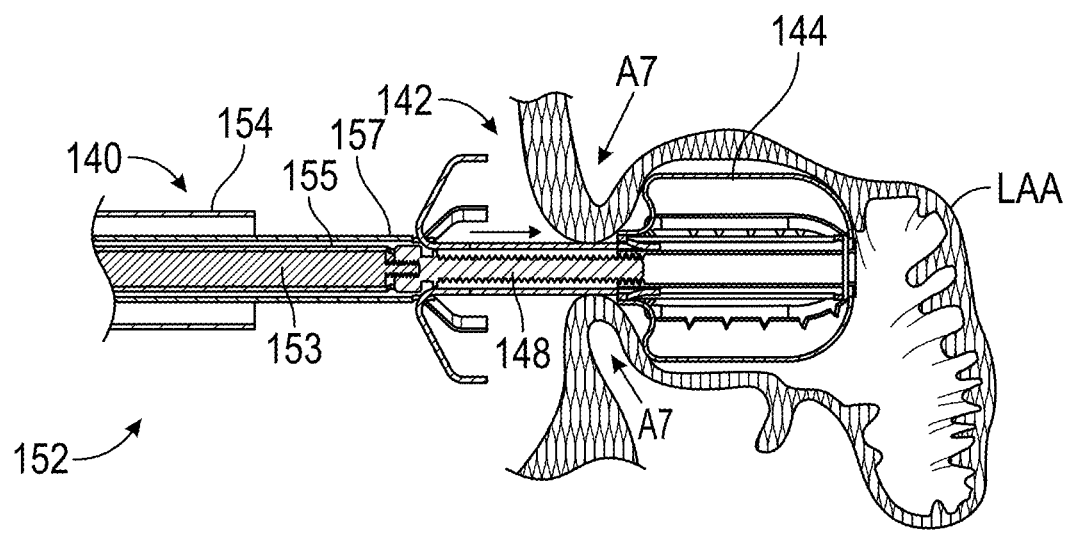
FIG. 9D shows the embodiment of the treatment system of FIG. 9A, showing the securing element of the embodiment of the implant device being advanced toward the contact member of the implant device.

In any embodiments of the occlusion system 140, including the embodiment of the occlusion system 140, the system can have an implant device 142 having a contact member 144 (also referred to herein as a contact element or an expandable implant member), a securing element or securing element 150 (also referred to as a securing member), and a retention member 148. FIG. 9A shows the contact member 144 and the securing element 150 both in a first, contracted or restrained state within an outer sleeve 154 of the catheter 152. The implant device 142 can be advanced distally out of the catheter 152 past a distal end 154*a* of the outer sleeve 154 by advancing a core member 153 of the catheter 152 so that the contact member 144 of the implant device 142 can be deployed within the LAA at any desired depth within the LAA, including near a distal end of the LAA, the middle portion of the LAA, or otherwise by, for example and without limitation, holding the implant device 142 in a stationary axial position by maintaining the core member 153 of the catheter 152 in a stationary axial position and retracting the outer sleeve 154 of the catheter 152. In any embodiments disclosed herein, the contact member 144 can be self-expanding in a radial direction so that, when a restraint is removed from the contact member 144, the contact member 144 can expand against an inner surface or wall of the LAA automatically. In other embodiments, the contact member 144 can be mechanically expandable, such as by a balloon expander, so as to expand against inside surface or wall of the LAA.

In any embodiments, the contact member 144 can have a plurality of arms or struts 156 that are each configured to self-expand in a radial direction when a restraint has been removed from an outside surface of the contact member 144. For example without limitation, any embodiments of the contact member disclosed herein can have six struts 156, or between six and ten struts, or from less than six to more than ten struts. Further, in any embodiments, the contact member 144 can have a plurality of tissue anchors 158 or other similar features configured to penetrate or engage the tissue of the LAA that are configured to penetrate into a tissue within the LAA when the contact member 144 is expanded against the tissue of the LAA and/or when the contact member 144 is rotated or twisted within the LAA.

In this configuration, when the contact member 144 is rotated in a first direction (indicated by arrow A6 in FIG. 9C, which can be in the clockwise or the counterclockwise direction), one or more or all of the struts 156 and one or more or all of the tissue anchors 158 can engage the tissue of the LAA and cause the LAA to twist or rotate in the first direction A6. The twisting or rotation of the LAA in the first direction from a first rotational position to a second rotational position results in the opening or ostium O of the LAA constricting in a radial direction (represented or identified by arrows A7 in FIG. 9C) so that the opening O of the LAA is caused to move or constrict around an outside surface of a proximal portion 144*a* of the contact member 144. An operator can twist or rotate the contact member 144 by twisting or rotating the core member 153 of the catheter 152. The tightening or constriction of the opening O of the LAA around an outside surface of the proximal portion 144*a* of the contact member 144 or other portion of the implant device can result in the occlusion, or substantial occlusion, or substantial closing off of the interior portion of the LAA from the remaining chambers within the heart, thereby substantially reducing the health risks associated with an open LAA. In any embodiments disclosed herein, the implant 142 can be configured to be removed after the securing element is applied to the tissue that has been constricted by the twisting of the contact member so that the only portion of the implant device 142 left in the LAA or the heart is the securing element 150.

Figure 9E:
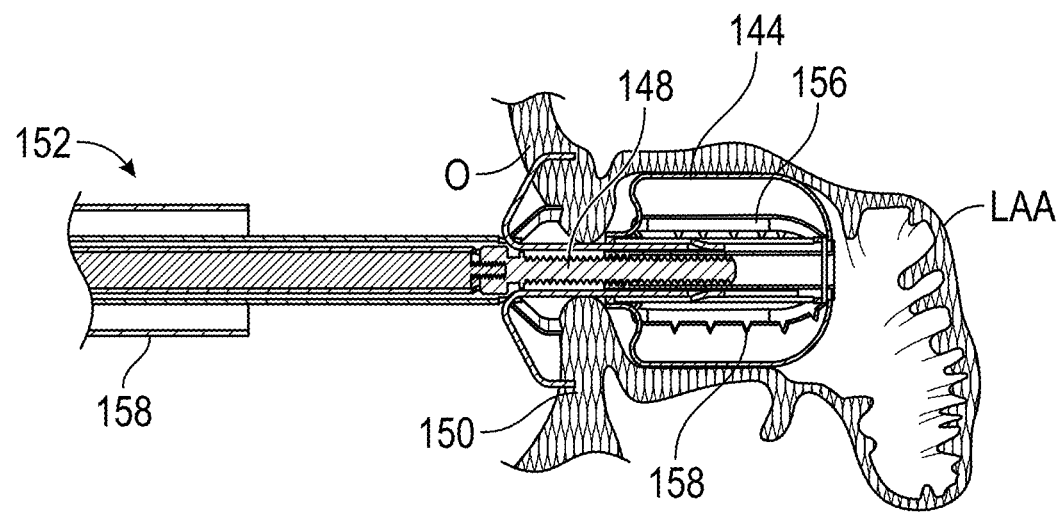
FIG. 9E shows the securing element of the treatment system of FIG. 9A engaged with the patient's tissue surrounding the proximal portion of the contact member of the implant device.
Figure 9F:
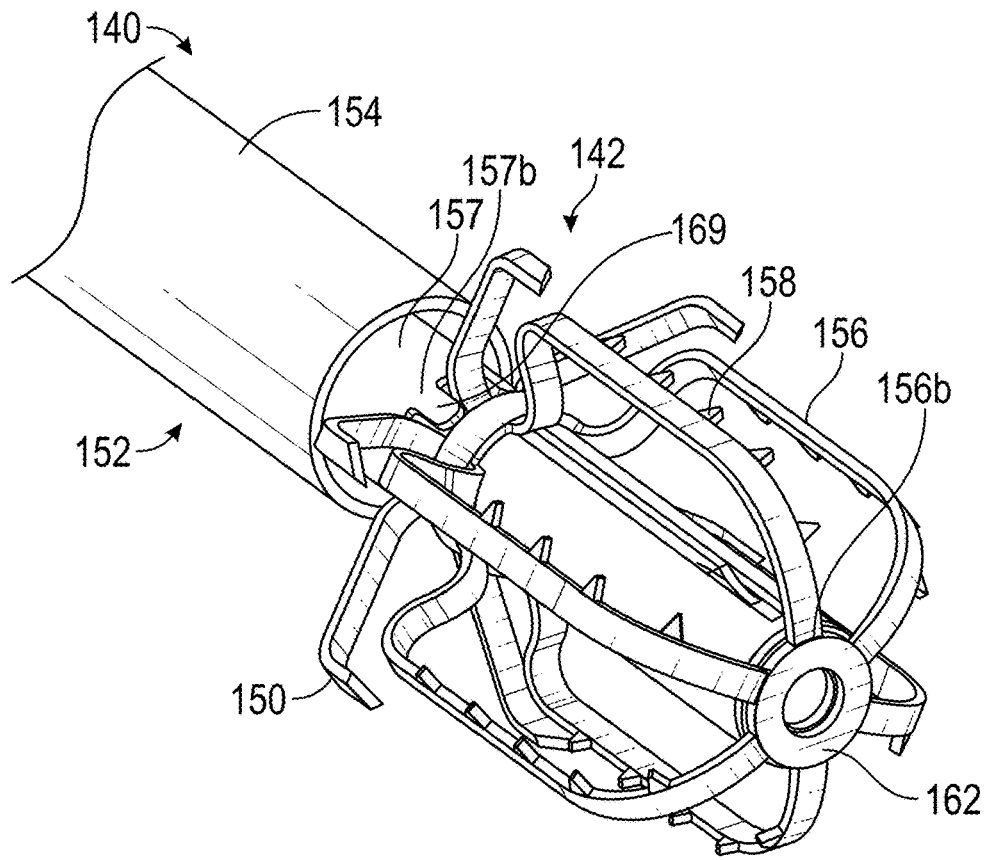
FIG. 9F shows the treatment system of FIG. 9A wherein the contact member is in a second, expanded state, the retention member is in a second, contracted state, and the securing element is in a second, open state.
Figure 9G:
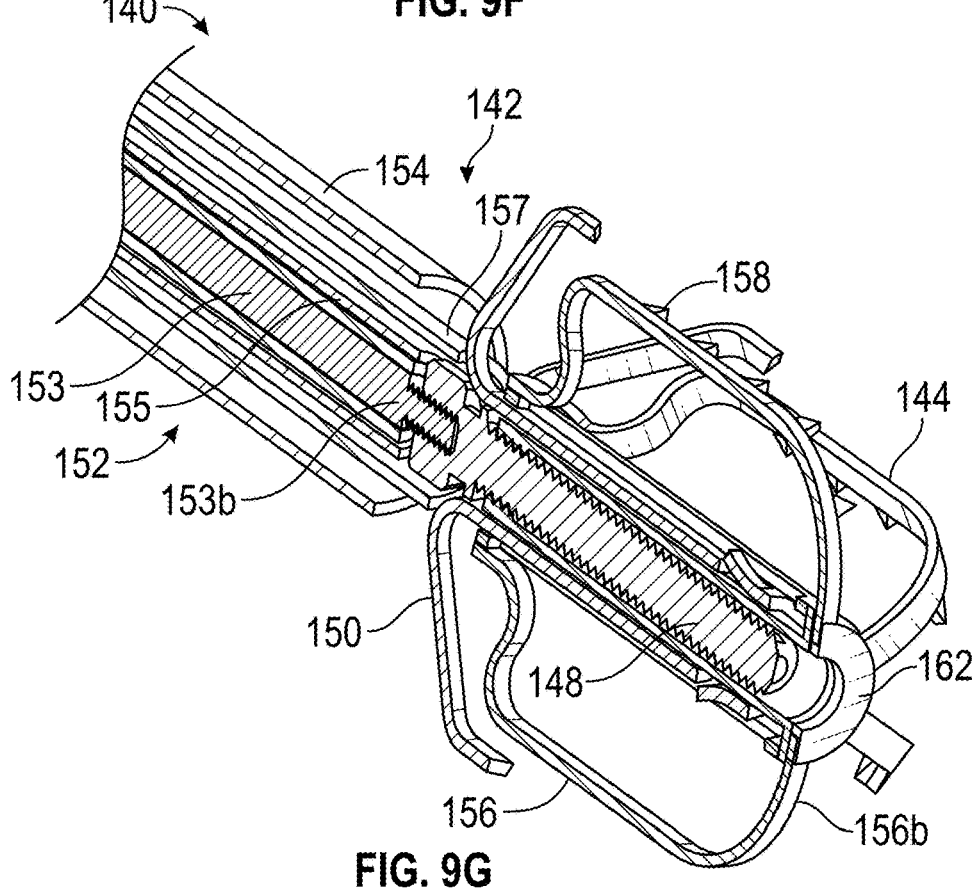
FIG. 9G is a section view of the treatment system shown in FIG. 9A, taken through line 9G-9G of FIG. 9F.
Figure 9H:
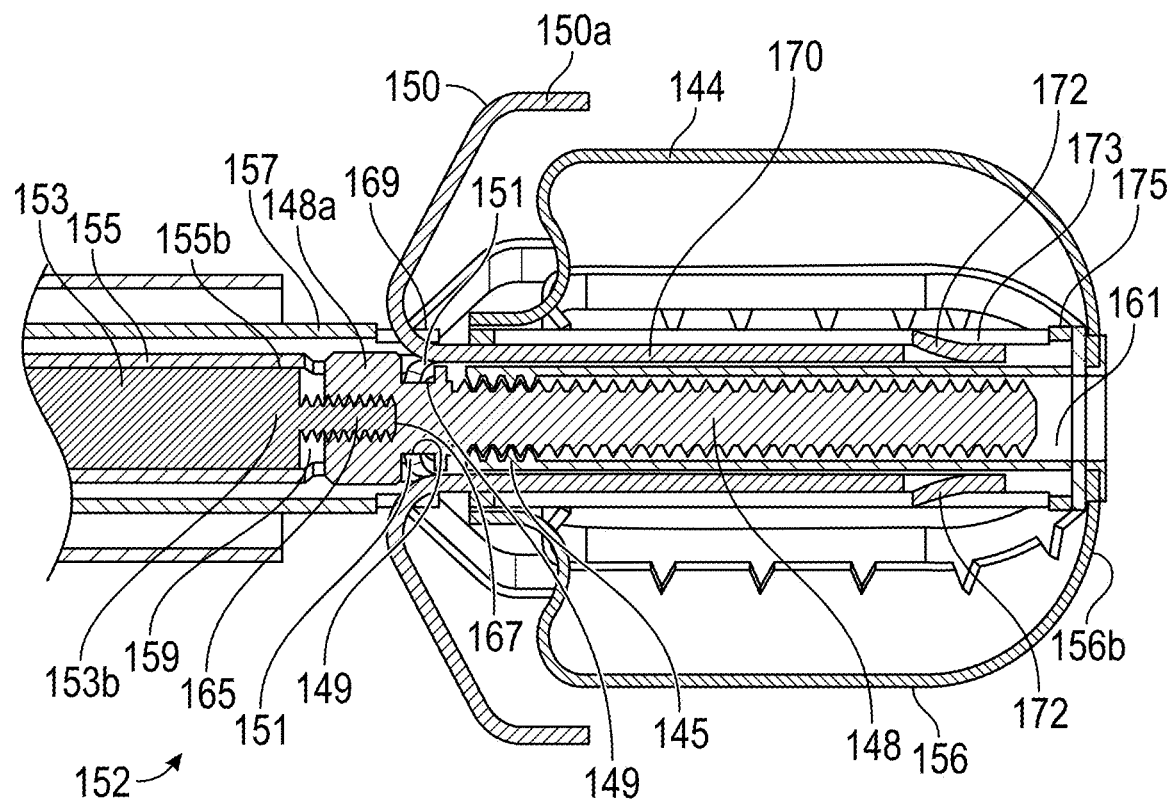
FIG. 9H shows an enlarged side view of the treatment system of FIG. 9A.

The retention member 148 can be used to couple the securing element 150 to the contact member 144 and to also allow a user (such as a surgeon) to move the securing element 150 toward and away from the contact member 144. In any embodiments, the retention member 148 can have helical threads on an outer surface thereof. In any embodiments, the retention member 148 can comprise a threaded shaft. In this configuration, the retention member 148 can be rotated in a first direction to advance the securing element 150 toward the contact member 144, and rotated in a second, opposite direction to move the securing element 150 away from the contact member 144. The retention member 148 can be configured to engage the securing element 150 such that, when the retention member 148 rotates, the securing element 150 moves in an axial direction corresponding to the rotation of the retention member 148. For example and without limitation, the retention member 148 can have an annular recess 149 near a proximal end 148a thereof that is configured to engage or couple with a tab or projection 151 of the securing element 150. In some embodiments, the projection 151 can extend into the annular recess 149 so as to axially lock or engage the securing element 150 with the retention member 148. The interaction of the projection 151 with the annular recess 149, wherein the walls of the annular recess contact and push the projection 151, causes the retention member 148 to move the securing element 150 when the retention member 148 is rotated. In some embodiments, as in the illustrated embodiment, the securing element 150 can have two tabs 151, both engaged with the annular recess 149. The contact member 144 can have a threaded neck portion 145 that threadedly engages the threads of the retention member 148 so that the retention member 148 threads into and out of the threaded neck portion 145. In this configuration, the retention member 148 threads into and out of the contact member 144 to cause the securing element 150 to move relative to the contact member. As shown in FIG. 9H, the retention member 148 is nearly completely threaded into the contact member 144 and into the cavity or space 161 within the contact member 144 such that the securing element 150 is moved toward the contact member 144 about as much as the securing element 150 can be. As the retention member 148 is rotated in the second direction, the retention member 148 will move out of the space 161 within the contact member 144 and move the securing element 150 away from the contact member 144.

With reference to FIG. 9H, an intermediate sleeve 155 can be advanced distally into contact with and engage a proximal end portion 148a of the retention member 148. The intermediate sleeve 155 can be configured such that, when the intermediate sleeve 155 is engaged with the proximal end portion 148a of the retention member 148, the retention member 148 can be rotated in the first or second direction by rotating the intermediate sleeve 155 in the first or second direction. In some embodiments, the intermediate sleeve 155 can be moved axially and rotated independently of the other tubes or sleeves of the catheter 152. For example and without limitation, as shown in FIG. 9H, projections or tabs 159 on a distal end portion 155b of the intermediate sleeve 155 can selectively couple with or be advanced into recesses or depressions 147 formed in the proximal end portion 148a of the retention member 148 that can selectively key or index the intermediate tube 155 with the retention member 148.

Further, in any embodiments, retention member 148 can be used to couple the implant 142 to the delivery catheter 152. For example and without limitation, the core member 153 of the delivery catheter 152 can be coupled with the retention member 148 via a threaded projection 165 at a distal end 153b of the core member 153 that threadedly engages a threaded recess 167 formed in a proximal end portion 148a of the retention member 148. The threaded projection 165 can be formed separately from and coupled with a distal end of the core member 153, or can be formed monolithically therewith. In this configuration, the implant 142 can be removed from the catheter by disengaging the threaded projection 165 from the retention member 148. This can be performed by preventing a rotation of the retention member 148 using the intermediate tube 155 while the core member 153 is being rotated in a second direction so as to withdraw the threaded projection 165 from the recess 167 of the retention member 148.

Further, a second intermediate tube or sleeve 157 can be advanced distally into contact with and engage a proximal end portion 150a of the securing element 150. The second intermediate sleeve 157 can be configured such that, when the second intermediate sleeve 157 is engaged with the proximal end portion 150a of the securing element 150, the securing element 150 can be rotated in the first or second direction by rotating the second intermediate sleeve 157 in the first or second direction. In some embodiments, the second intermediate sleeve 157 can be moved axially and rotated independently of the other tubes or sleeves of the catheter 152. For example and without limitation, as shown in FIG. 9H, projections or tabs 169 on a distal end portion 157b of the second intermediate sleeve 157 can selectively couple with the struts or arms of the securing element 150 so that the second intermediate sleeve 157 can be keyed or indexed to the securing element 150.

Further, in some embodiments, the securing element 150 can be keyed or indexed to the contact member 144 so that the securing element 150 and the contact member 144 rotate dependently and simultaneously. For example, in some embodiments, the securing element 150 can have a body portion 170 having one or more tabs or projections 172 that are configured to extend into a channel or recess 173 formed in a body portion 175 of the contact member 144. One or more channels 173 can be formed in an axial orientation such that the projection(s) 172 of the securing element 150 and the securing element 150 can freely move in an axial direction relative to the contact member 144. However, a narrow width of the channel(s) 173 relative to the projection(s) 172 can prevent the projection(s) 172 and, hence, the securing element 150 from rotating relative to the contact member 144.

In this configuration, the second intermediate sleeve 155 can be coupled with the securing element 150 and can be used to at least rotate the implant 142 in the first or second direction. For example and without limitation, the second intermediate sleeve 155 can be rotated to rotate the contact member 144 to twist the LAA to the desired level of rotation and/or torque. Thereafter, the second intermediate sleeve 155 can be used to maintain the desired rotational position of the contact member 144 by maintaining the second intermediate sleeve 155 in contact with the securing element 150 and in a fixed rotational position, hence holding the contact member 144 in a fixed rotational position while the retention member 148 is rotated in the first direction to advance the securing element 150 toward the contact member 144. Once the securing element 150 is in the desired axial position (for example, engaged with the tissue of the LA/LAA that has constricted as a result of the twisting of the contact member 144), the implant 142 can be removed from the catheter 152 by disengaging the threaded projection 165 from the retention member 148 as described above, and the catheter can be removed from the LA. With the securing element 150 engaged with the patient's tissue, as illustrated in FIG. 9E, the LAA is prevented from rotating to the first rotational position, which is the untwisted or relaxed position. In this configuration, the implant device 142 can secure and maintain the LAA in a substantially or completely occluded or substantially or completely closed state.

Figure 11:
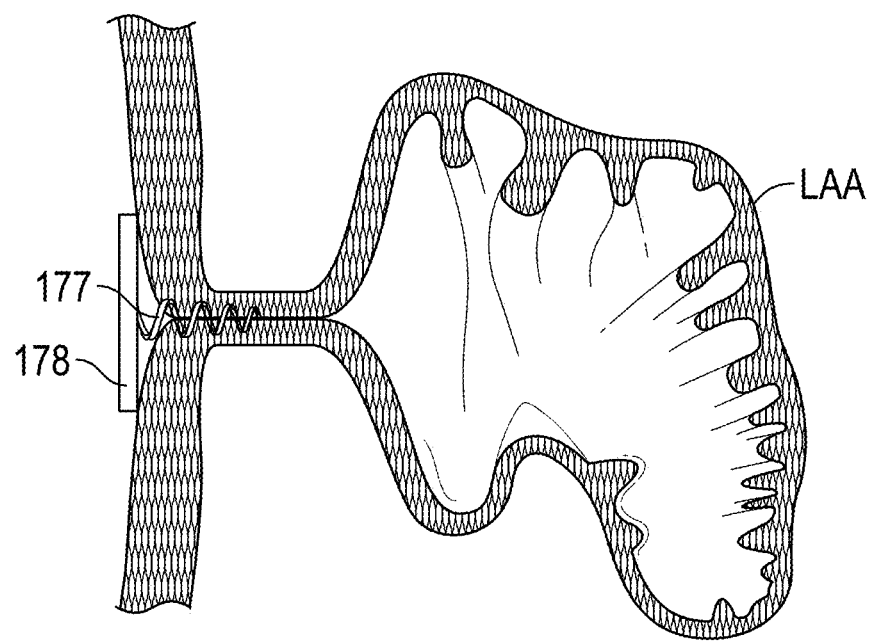
FIG. 11 shows an embodiment of a securing element implanted adjacent to an occluded opening of the LAA.
Figure 12:
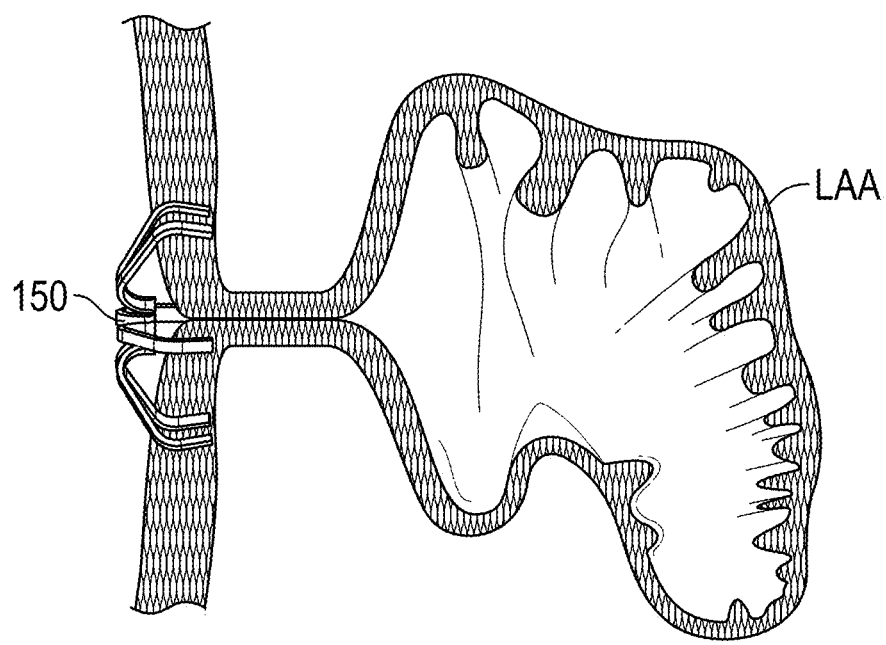
FIG. 12 shows another embodiment of a securing element implanted adjacent to an occluded opening of the LAA.

Further, in any embodiments, the device can be configured such that the contact member 144 can be removed from the patient's LAA after the securing element 150 is engaged with the tissue sufficiently to hold the tissue in a closed or occluded state, for example as shown in FIGS. 11-12, wherein the securing element 177 and the securing element 150 are the only components remaining within the body following the completely of the implant procedure. In this configuration, the implant can have a plug or cover (such as cover 178 coupled with the securing member 177) that can cover the opening in the implant that the contact member (such as contact member 180 or contact member 144) is withdrawn through, or be otherwise configured to plug or cover the opening in the implant that the contact member 144 is withdrawn through. For example and without limitation, a cover member such as cover member 121 can be coupled with the securing element 150 to substantially cover any openings in the implant, or can be coupled with the contact member 144 so as to cover the contact member 144 inside the LAA, in configurations where the contact member 144 remains in the LAA after the securing element 150 has been implanted.

Additionally, in some embodiments, the contact member 144 can have a continuous and uninterrupted circumference at a proximal end 144a that each of the strut members 156 extend distally away from. Each of the strut members 156 can be preformed into a curved shape such that the strut members 156 are biased to expand to the second state when no external restraint or constraint is applied to the outside surface of the contact member 144 (for example, when in a relaxed state). At a distal end, each of the strut members 156 can, but are not required to, couple with a hub member 162. Similar to the hub member 122 described above, the hub member 162 can have a plurality of receptacles (not shown) configured to receive and constrain distal end portions 156b of each of the strut members 156. Additionally, each of the receptacles 163 can be configured to permit the distal end portions 156b of each of the strut members 156 to rotate relative to the hub member 162 so that the distal end portions 156b of the strut members 156 can extend generally radially away from the hub member 163 when the contact member 144 is in the second, expanded state. The hub member 163 can be configured to permit the distal end portions 156b of each of the strut members 156 to rotate relative to the hub member 162 without resistance or significant resistance. In any embodiments, the distal ends of each of the strut members 156 can have a tab or other feature (such as a T shaped termination or other increased width) (not shown) that locks into, is secured by, or is otherwise engaged by each of the receptacles 163 so as to axially constrain the end portion of each of the strut members 156, while allow rotation about the end portion.

Figure 10:
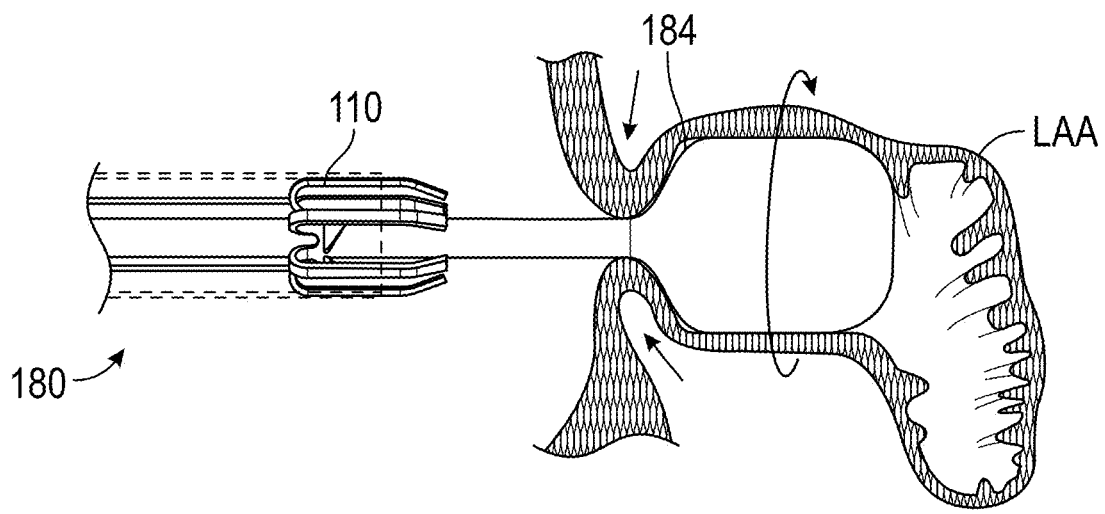
FIG. 10 shows another embodiment of a treatment system for treating the LAA, showing the contact member of the treatment system being expanded within the LAA.
Figure 9I:
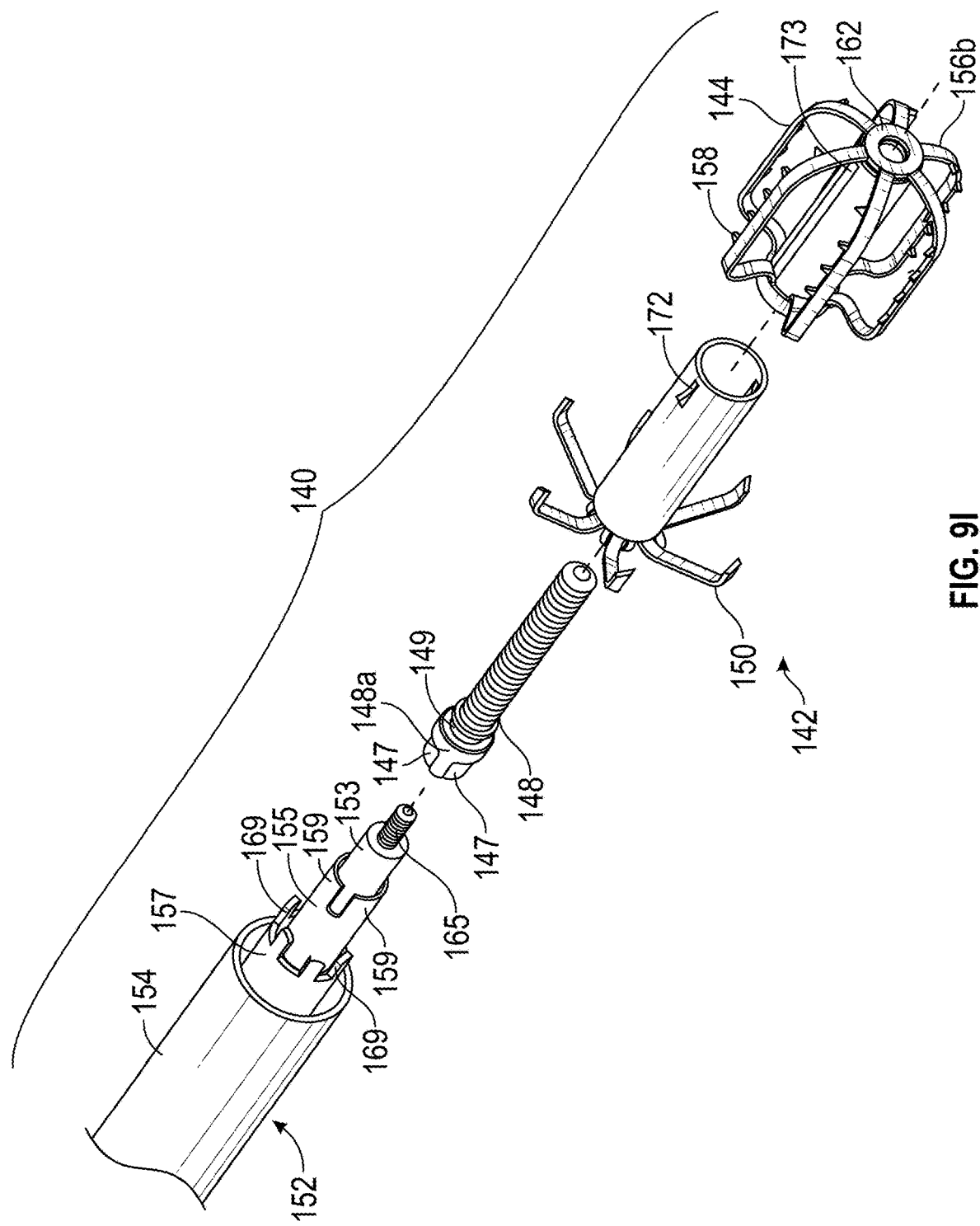
FIG. 9I shows an exploded view of the treatment system of FIG. 9A.

Additionally, as described above, in any embodiments disclosed herein, the implant device can be configured such that the contact member can be removed from the patient's LAA after the securing element engages the tissue to hold the ostium of the LAA in a closed state. For example, with reference to FIG. 10, in any embodiments disclosed herein, the contact member can be an expansion balloon such as expansion balloon 184. The balloon can have a smooth outside surface, or can have dimples, projections, rough texture, tissue anchors, or otherwise to engage the inside surface of the LAA. In some embodiments, the balloon can be a typical expansion balloon such as a balloon used in angioplasty procedures, and can be sized and configured for use in LAA. In these configurations, after the LAA has been rotated and/or torqued to the desired degree and the securing element implanted to hold the opening of the LAA sufficiently closed or constricted, the balloon can be deflated and removed from the LAA, leaving only the securing element to maintain the LAA in the occluded state, as shown in the nonlimiting examples of FIGS. 11-12.

Figure 13:
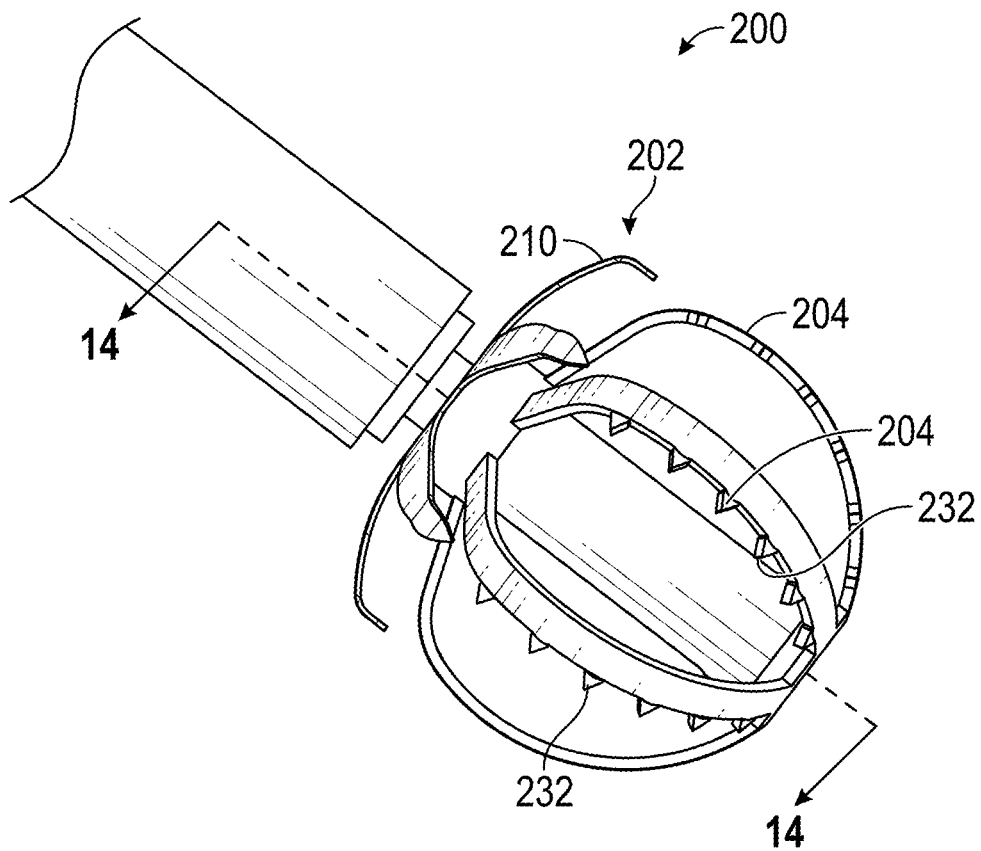
FIG. 13 shows another embodiment of treatment system having an implant device wherein the contact member is in a second, expanded state, the retention member is in a second, contracted state, and the securing element is in a second, open state.
Figure 14:
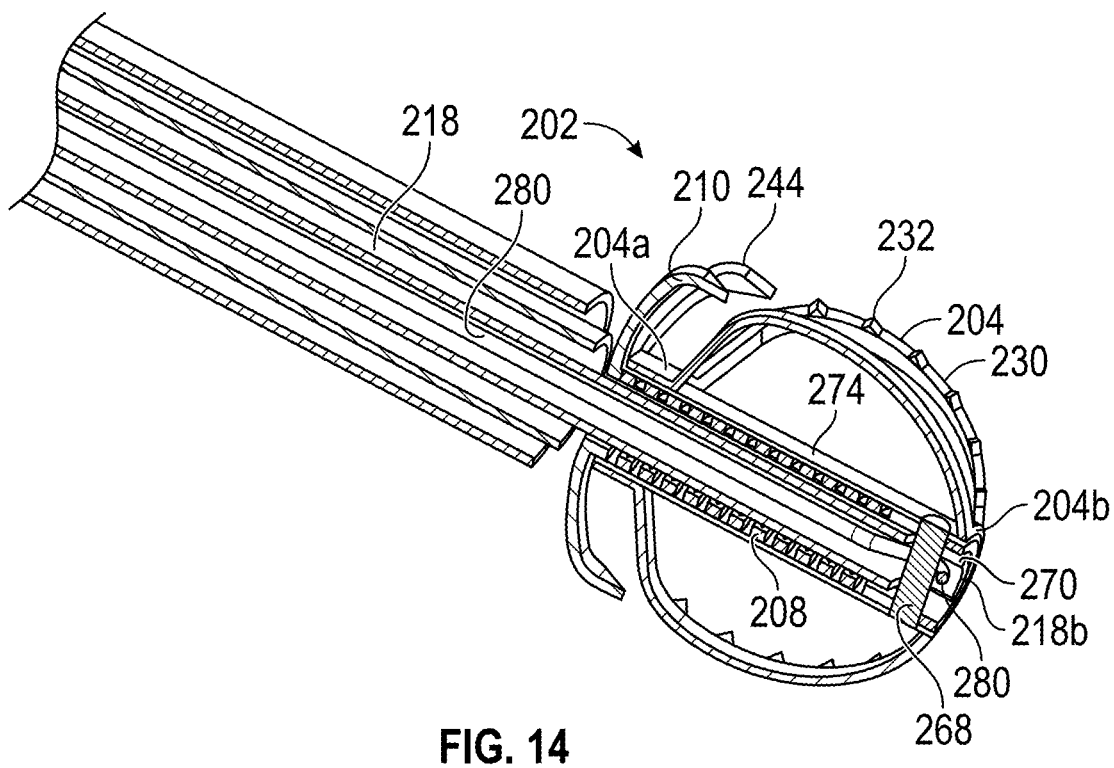
FIG. 14 is a section view of the treatment system shown in FIG. 13, taken through line 14-14 of FIG. 13.

FIG. 13 shows another embodiment of treatment system 200 having an implant device 202, wherein the contact member 204 of the implant device 202 is in a second, expanded state, the retention member 208 is in a second, contracted state, and the securing element 210 is in a second, open state. FIG. 14 is a section view of the embodiment of the treatment system 200 shown in FIG. 13, taken through line 14-14 of FIG. 13. In any embodiments disclosed herein, any components, features, or other details of the treatment system 200 or implant device 202 can have any of the components, features, or other details of any other treatment system embodiments or implant device embodiments disclosed herein, including without limitation any of the embodiments of the treatment system 100 or implant device 102 described above, in any combination with any of the components, features, or details of the treatment system 200 or implant device 202 disclosed below. Similarly, any components, features, or other details of any of the other treatment system embodiments or implant device embodiments disclosed herein can have any of the components, features, or other details of any embodiments of the treatment system 200 or implant device 202 disclosed herein in any combination with any of the components, features, or details of the treatment system and/or implant device.

With reference to FIGS. 13-14, in some embodiments, the contact member 204 can have an annular proximal end portion 204a wherein all of the arms or struts 230 (six being shown) of the contact member 204 extend distally away from the proximal end portion 204a. The struts 230 can have any form of tissue anchors 232 on the struts or attached to the struts, such as any of the tissue anchors 118 described above.

Additionally, in some embodiments, the contact member 204 can have an annular distal end portion 204b wherein all of the arms or struts 230 can be coupled with the annular distal end portion 204b. The contact member 204 can have a bulbous shape, cylindrical shape with a curved distal portion, an elongated spherical shape, or otherwise. In some embodiments, the contact member 204 can be laser cut from a hypotube, or can be formed from different components and welded, brazed, or otherwise coupled together. Each of the strut members 230 can be preformed into a curved shape (which can have a spherical or bulbous shape) and formed such that the strut members 230 are biased to expand to the second state when no external restraint or constraint is applied to the outside surface of the contact member 204.

In some embodiments, as in the illustrated embodiment, the retention member 208 and the securing element 210 can be integrally formed. For example and without limitation, the retention member 208 and the securing element can be laser cut from a single length of tube material, for example, from an elastic or shape memory material such as Nitinol, and thereafter formed into the desired shape. In other embodiments, the securing element 210 can be coupled with a proximal end 208a of the retention member 208. In the relaxed state (i.e., the state where no external forces are acting thereon), some embodiments of the retention member 208 can be biased to move to the second or collapsed state, for example, and the securing element 210 can be in the second, or open state.

Additionally, with reference to FIG. 14, a pin or cross member 268 can be coupled with a distal end 208b of the retention member 208 and can be configured to fit within a slot 270 formed within a distal end 218b of the core member 218. In this embodiment, the core member 218 can be advanced in a distal direction resulting in the advancement of the contact member 204 in a distal direction. Further, a core tube 274 can extend proximally from a distal end 218b of the core member 218 and couple with a proximal end 204a of the contact member 204. The pin 268 can extend through a pair of openings formed in the core tube 274 to secure the core tube 274 to the pin 268 and, hence, the distal end 208b of the retention member 208. The core tube 274 can be, therefore, be used to couple the contact member 204 with the retention member 208. Pins, tabs, sutures, ties, protrusions, clips, depressions, detents, or other features can be used to couple a proximal end 204a of the contact member 204 with a proximal end of the core tube 274.

Additionally, in any embodiments, the system 200 can be configured so that the implant device 202 is biased in the proximal direction relative to the core member 218. For example and without limitation, as shown in FIG. 14, some embodiments of the implant device 202 can have a suture or thread 280 that extends through an inside of the core member 218 (such as through a lumen of the core member 218) and loops around the pin 268, thereby permitting a user to retract or withdraw the suture to pull the implant device 202 proximally relative to the core member 218. In this configuration, both ends of the suture 280 can extend from a proximal end of the device 200 such that a practitioner can grasp both ends of the suture 280 to exert the biasing force around the pin 268 to maintain the pin against a proximal end of the slot 270. When the implant device 202 is ready to be released from the core member 218, the practitioner can simply release one end of the suture and withdraw the other end of the suture until the suture no longer forms a loop or wraps around the pin 268. After removing the biasing force from the suture 280, the core member 268 can be withdrawn relative to the implant device 202. This may be done after the contact member and its securing element have been fully deployed.

Figure 15:
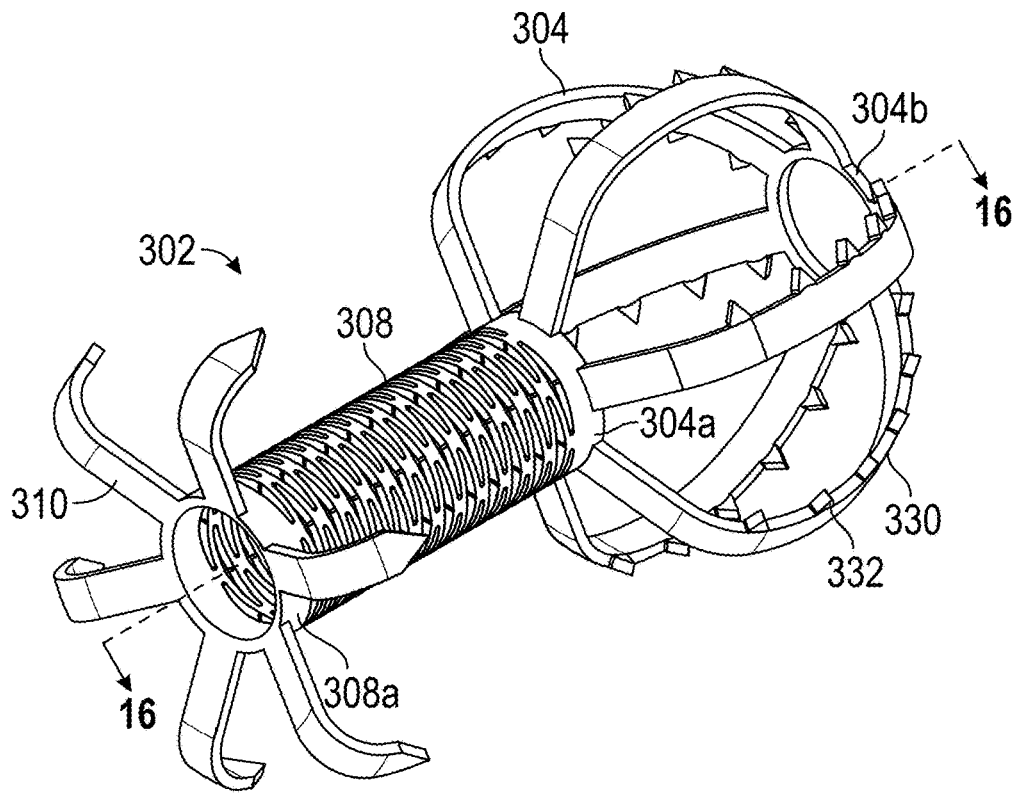
FIG. 15 shows another embodiment of an implant device wherein the contact member is in a second, expanded state, the retention member is in a second, contracted state, and the securing element is in a second, open state.
Figure 16:
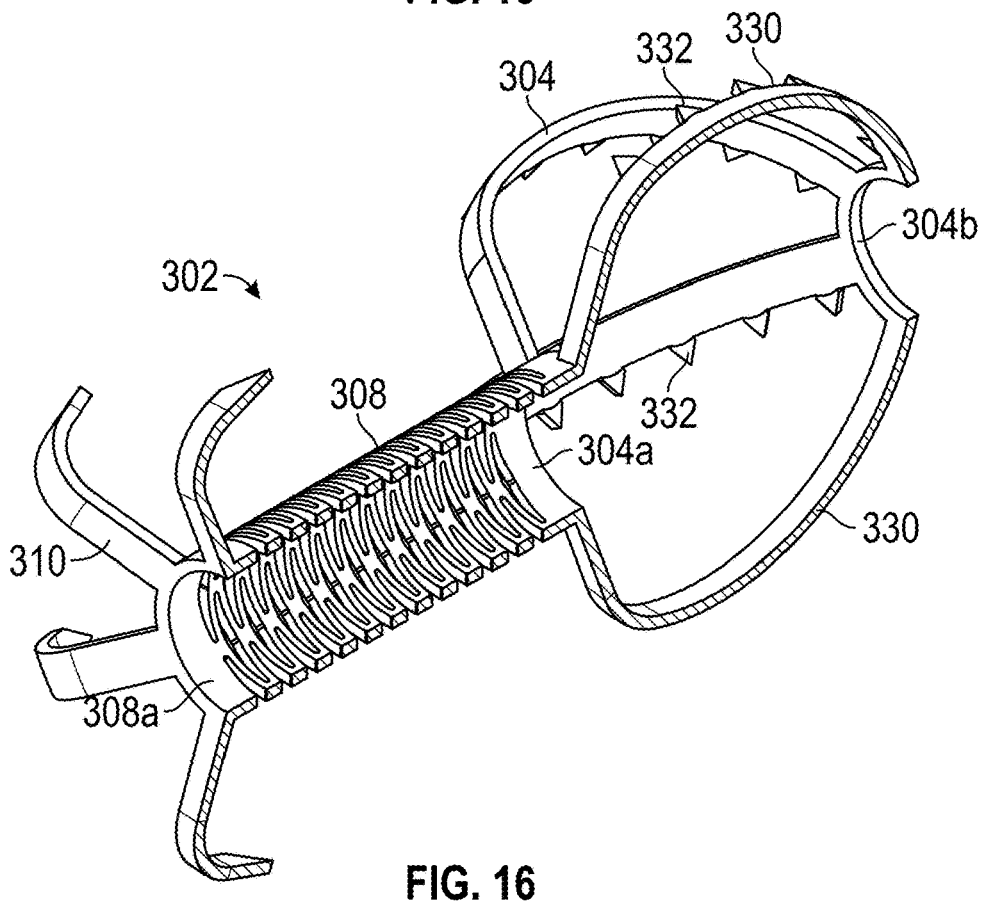
FIG. 16 is a section view of the treatment system shown in FIG. 15, taken through line 16-16 of FIG. 15.

FIG. 15 shows another embodiment of an implant device 302 wherein the contact member 304 is in a second, expanded state, the retention member 308 is in a second, contracted state, and the securing element 310 is in a second, open state. In any embodiments disclosed herein, any components, features, or other details of the treatment system 300 or implant device 302 can have any of the components, features, or other details of any other treatment system or implant device embodiments disclosed herein, including without limitation any of the embodiments of the treatment system 100, 200 or implant device 102, 202 described above, in any combination with any of the components, features, or details of the treatment system 300 or implant device 302 disclosed below. Similarly, any components, features, or other details of any of the other treatment system or implant device embodiments disclosed herein can have any of the components, features, or other details of any embodiments of the treatment system 300 or implant device 302 disclosed herein in any combination with any of the components, features, or details of the treatment system and/or implant device.

In any embodiments, a length of the retention member (including retention member 308) and/or a distance between the securing element and the contact member can be adjusted or varied beyond what is shown and described, for example to accommodate differing anatomy sizes and characteristics of the LA and/or LAA, or to accommodate differing amounts or thicknesses of LAA tissue that has been gathered or twisted up. For example and without limitation, in some embodiments, the length of the retention member, or the distance between the securing element and the contact member, can be approximately the same as a length of the contact member when the retention member is in a relaxed or collapsed state (e.g., in the second state), or can be approximately one-half of the length of the contact member when the retention member is in the second state, or between one-quarter and one-half of the length of the contact member when the retention member is in the second state, or otherwise.

In some embodiments, the contact member 304 can have an annular proximal end portion 304a wherein all of the arms or struts 330 (six being shown) of the contact member 304 extend distally away from the proximal end portion 304a. Additionally, in some embodiments, the contact member 304 can have an annular distal end portion 304b wherein all of the arms or struts 330 can be coupled with the annular distal end portion 304b. In some embodiments, the contact member 304 can be laser cut from a hypotube, or can be formed from different components and welded, brazed, or otherwise coupled together. Each of the strut members 330 can be preformed into a curved shape (which can have a rounded or bulbous shape) and formed such that the strut members 330 are biased to expand to the second state when no external restraint or constraint is applied to the outside surface of the contact member 304. The struts 330 can have any form of tissue anchors 332 on the struts or attached to the struts, such as any of the tissue anchors 118 described above.

In some embodiments, the contact member 304, the retention member 308, and the securing element 310 can be integrally formed, such as being cut from a single length of hypotube, or otherwise. For example and without limitation, the retention member 308 and the securing element can be laser cut from a single length of tube material, for example, from an elastic or shape memory material, and thereafter formed into the desired shape. In other embodiments, the contact member 304, the retention member 308, and/or the securing element 310 can be separately formed and welded, brazed, or otherwise joined together to form a single, unitary component. Because, in some embodiments, a distance between the contact member 304 and the securing element 310 can be large, for example and without limitation, greater than a length of the contact member when the contact member is in the second, expanded state, the contact member 304 can be advanced further distally into the LAA and then rotated so as to twist the opening of the LAA to cause the opening of the LAA to constrict around an outside surface of the retention member. The greater length of the retention member 310 can also accommodate a greater degree of twisting or rotation, or a greater number of rotations or twists of the LAA before the securing element is engaged.

An intermediary sleeve or tube (not shown) can be coupled with the securing element 310 and can be used to manipulate and control a position and/or an orientation of the securing element 310, including holding a proximal end portion 310*a* of the securing element in a fixed axial position while a distally directed force is exerted on the contact member 304 to maintain the retention member 310 in the first, extended state. Additionally, a core member (not shown) can engage a distal end portion 304*b* of the contact member 304*b* to allow a distally directed force to be exerted on the contact member 304. Pins, tabs, sutures, ties, protrusions, clips, depressions, detents, or other features can be used to selectively (i.e., reversibly) couple the contact member 304 to the core member.

After the desired degree of twisting of the LAA has been performed, the securing element 310 can be moved to the second, expanded state by, for example, advancing the securing element 310 out of a distal end of a tube of the delivery catheter and allowed to expand to the second state of the securing element. Thereafter, while maintaining the contact member 304 in the desired axial and rotational position (for example, the second rotational position), the securing element 310 can be advanced into the tissue that has constricted around an outside surface of the implant so as to secure the tissue in the twisted and/or constricted state. In some embodiments, this can be achieved or performed simply by holding the contact member in the desired position and allowing the retention member 308 to retract to its retracted or relaxed state, thereby causing the securing element 310 to advance into the tissue. When the deployment is complete, a user may disengage the core member from the contact member 304 so that the core member may be withdrawn. As with the other embodiments, the implant device 304 can be selectively biased or secured in the proximal direction relative to a delivery catheter, such as with a suture or thread 380 that extends through an inside of the catheter and loops around a pin, tab, or other feature of the implant device and released by disengaging or removing the suture or other retaining device.

Figure 17:
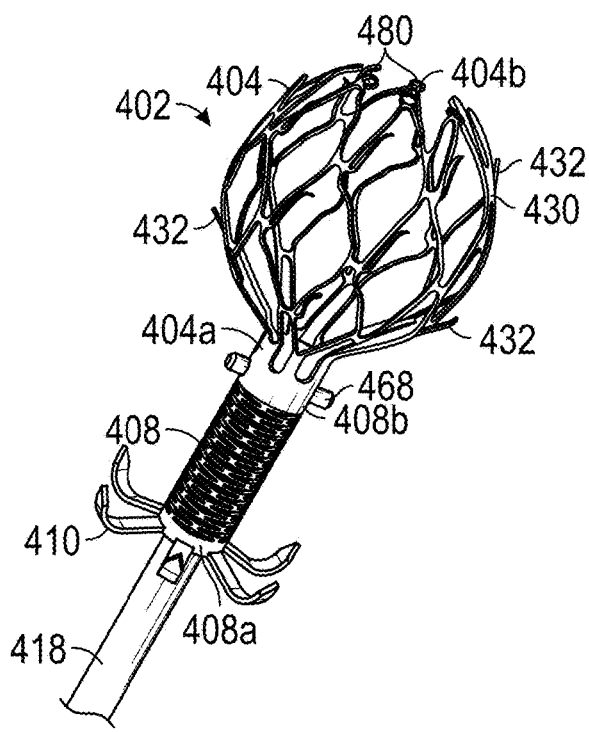
FIG. 17 shows another embodiment of a treatment system wherein the contact member is in a second, expanded state, the retention member is in a second, contracted state, and the securing element is in a second, open state.
Figure 18:
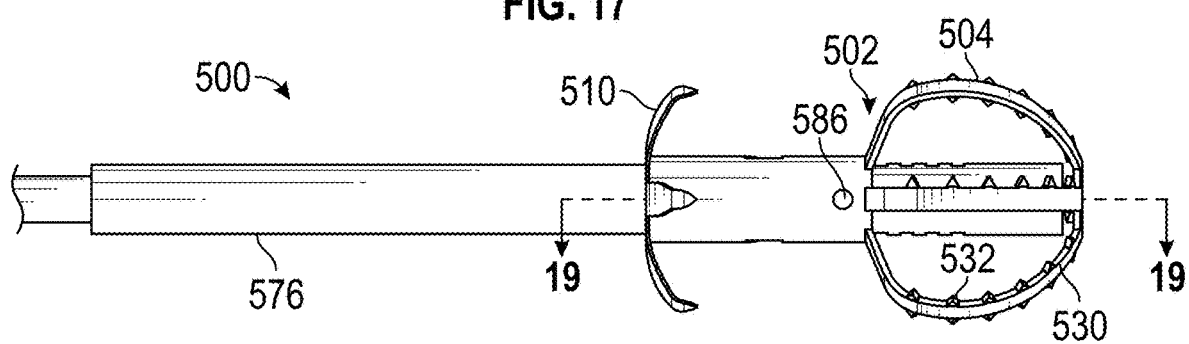
FIG. 18 shows a side view of another embodiment of a treatment system wherein the contact member is in a second, expanded state, the retention member is in a second, contracted state, and the securing element is in a second, open state.

FIG. 17 shows another embodiment of an implant device 402 wherein the contact member 404 is in a second, expanded state, the retention member 408 is in a second, contracted state (or in at least partially contracted or retracted state), and the securing element 410 is in a second, open state. Any embodiments of the treatment system 400 or implant device 402 can have any of the components, features, or other details of any other treatment system or implant device embodiments disclosed herein, including without limitation any of the embodiments of the treatment system 100, 200, 300 or implant device 102, 202, 302 described above, in any combination with any of the components, features, or details of the treatment system 400 or implant device 402 disclosed below. Similarly, any components, features, or other details of any of the other treatment system or implant device embodiments disclosed herein can have any of the components, features, or other details of any embodiments of the treatment system 400 or implant device 402 disclosed herein, in any combination, with any of the components, features, or details of the treatment system or implant device embodiments disclosed herein.

The contact member 404 can have an annular proximal end portion 404*a* and a distal portion 404*b* having a plurality of openings or rings 480. The struts or links 430 of the contact member 404 can form a web-like pattern so as to form a curved, bulbous, elongated bulbous, spherical or other shaped contact member. The struts 430 can have a plurality of tissue anchors or protrusions 432 coupled with the struts or links 430 at a plurality of locations about the contact member 404, such as any of the tissue anchors 118 described above. As in any of the embodiments disclosed herein, the tissue anchors 432 can be, but are not required to be, integrally formed with the struts 430. The struts or links 430 can form a generally diamond shaped pattern about the surface of the contact member. The contact member 404 can have a generally spherical or bulbous shape.

Additionally, with reference to FIG. 17, a pin or cross member 468 can be coupled with the implant device 402, for example and without limitation, at a distal end 408*b* of the retention member 408, or between the retention member 410 and the contact member 404. The pin 468 can be configured to engage an end portion of a core member 418 of the catheter, or a feature formed within a distal end portion of the core member of the catheter to selectively couple the implant device 402 with the core member of the catheter, just as with the other embodiments disclosed herein.

Additionally, similar to the other embodiments of the system disclosed above, some embodiments of the implant device 402 can have a suture or thread 480 that loops around or otherwise engages the pin 468, thereby permitting a user to retract or withdraw the suture to pull the implant device 402 proximally relative to the core member 418. After removing the biasing force from the suture 480, the core member 468 can be withdrawn relative to the implant device 402. This may be done after the implant and its securing element have been fully deployed.

In some embodiments, the contact member 404, the retention member 408, and/or the securing element 410 can be integrally formed, such as being laser cut from a single length of hypotube, or otherwise. For example and without limitation, the retention member 408 and the securing element can be laser cut from a single length of tube material, for example, from an elastic or shape memory material, and thereafter formed into the desired shape. In other embodiments, the contact member 404, the retention member 408, and/or the securing element 410 can be separately formed and welded, brazed, or otherwise joined together to form a single, unitary component. Because, in some embodiments, a distance between the contact member 404 and the securing element 410 can be large, the contact member 404 can be advanced further distally into the LAA and then rotated so as to twist the opening of the LAA to cause the opening of the LAA to constrict around an outside surface of the retention member. The greater length of the retention member 410 can also accommodate a greater number of rotations or twists of the LAA before the securing element is engaged.

An intermediary sleeve or tube (not shown) can be coupled with the securing element 410 and can be used to manipulate and control a position and/or an orientation of the securing element 410, including holding a proximal end portion 410*a* of the securing element in a fixed axial position while a distally directed force is exerted on the contact member 404 to maintain the retention member 410 in the first, extended state. Deployment of the device 402 can include any combination of the steps described with respect to any of the other embodiments disclosed herein.

FIGS. 18-21 show another embodiment of a treatment system 500 having an implant device 502 wherein the contact member 504 is in a second, expanded state, the retention member 508 is in a second, contracted state, and the securing element 510 is in a second, open state. Any embodiments of the treatment system 500 or implant device 502 can have any of the components, features, or other details of any other treatment system or implant device embodiments disclosed herein, including without limitation any of the embodiments of the treatment system 100, 200, 300, 400 or implant device 102, 202, 302, 402 described above, in any combination with any of the components, features, or details of the treatment system 500 or implant device 502 disclosed herein. Similarly, any components, features, or other details of any of the other treatment system or implant device embodiments disclosed herein can have any of the components, features, or other details of any embodiments of the treatment system 500 or implant device 502 disclosed herein, in any combination, with any of the components, features, or details of the treatment system or implant device embodiments disclosed herein.

The contact member 504 can have a plurality of struts or links 530 that can have a plurality of tissue anchors 532 thereon at a plurality of locations about the contact member 504, such as any of the tissue anchors 118 described above. As in any of the embodiments disclosed herein, the tissue anchors 532 can be, but are not required to be, integrally formed with the struts 530. The contact member 504 can have a generally spherical or bulbous shape, or the shape of any of the other embodiments disclosed herein.

Similar to other embodiments described above, any embodiments of the treatment system 500 can have a suture or thread 580 that extends through an inside of the core member 518 (such as through a lumen of the core member 518) and loops around a pin 568 or other retention member that is coupled with the contact member 504, thereby permitting a user to retract or withdraw the suture 580 to pull the contact member 504 proximally relative to the securing element 510 and to keep the implant 502 engaged with the delivery catheter. In this configuration, both ends of the suture 580 can extend from a proximal end of the device 500 such that a practitioner can grasp both ends of the suture 580 to exert a proximally directed force around the pin 568 to pull the contact member 504 toward the securing element 510 and to keep the pin 568 positioned within a slot 570 of the core member 518. Additionally, a slot 574 formed in the cylindrical body portion 572 of the securing element 510 can be sized so that the cylindrical body portion 572 of the securing element 510 can be moved axially in a proximal and distal direction relative to the pin 568, between a proximal end 574a of the slot 574 and a distal end 574b of the slot 574. Thus, the pin 568 and suture 580 can be used to bias or force the implant 502 to remain in contact with the catheter (for example, in contact with the core member 518 or the slot 570 formed in the core member) and to permit the user to move the securing element 510 from the first position to the second, engaged position (as shown in FIGS. 18-21).

Figure 19:
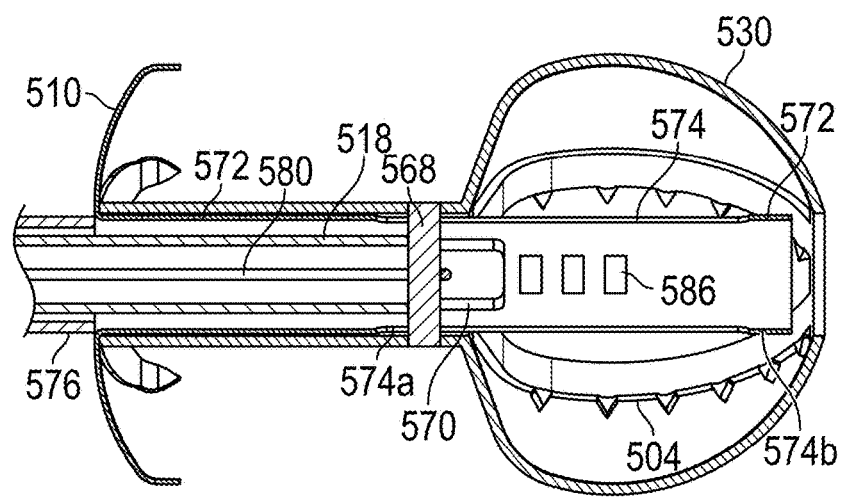
FIG. 19 is a section view of the treatment system shown in FIG. 18, taken through line 19-19 of FIG. 18.
Figure 20:
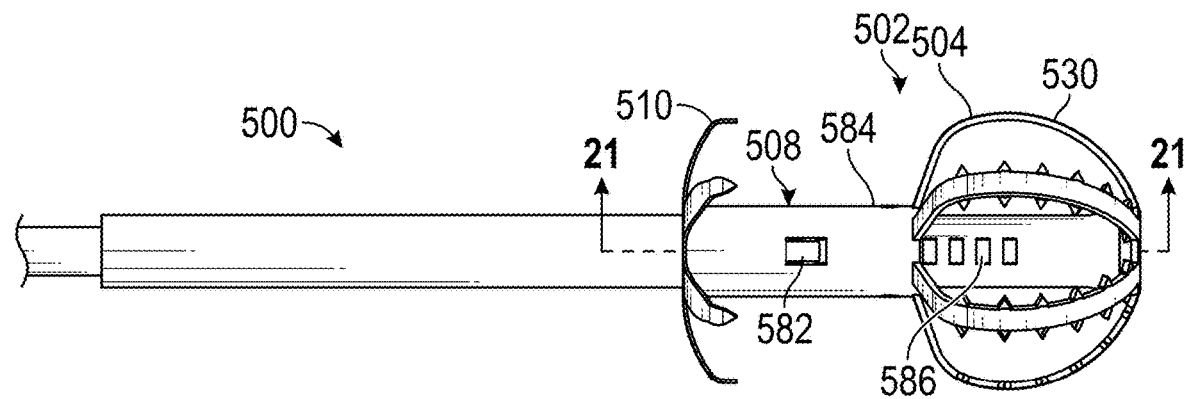
FIG. 20 is another side view of the treatment system shown in FIG. 18.
Figure 21:
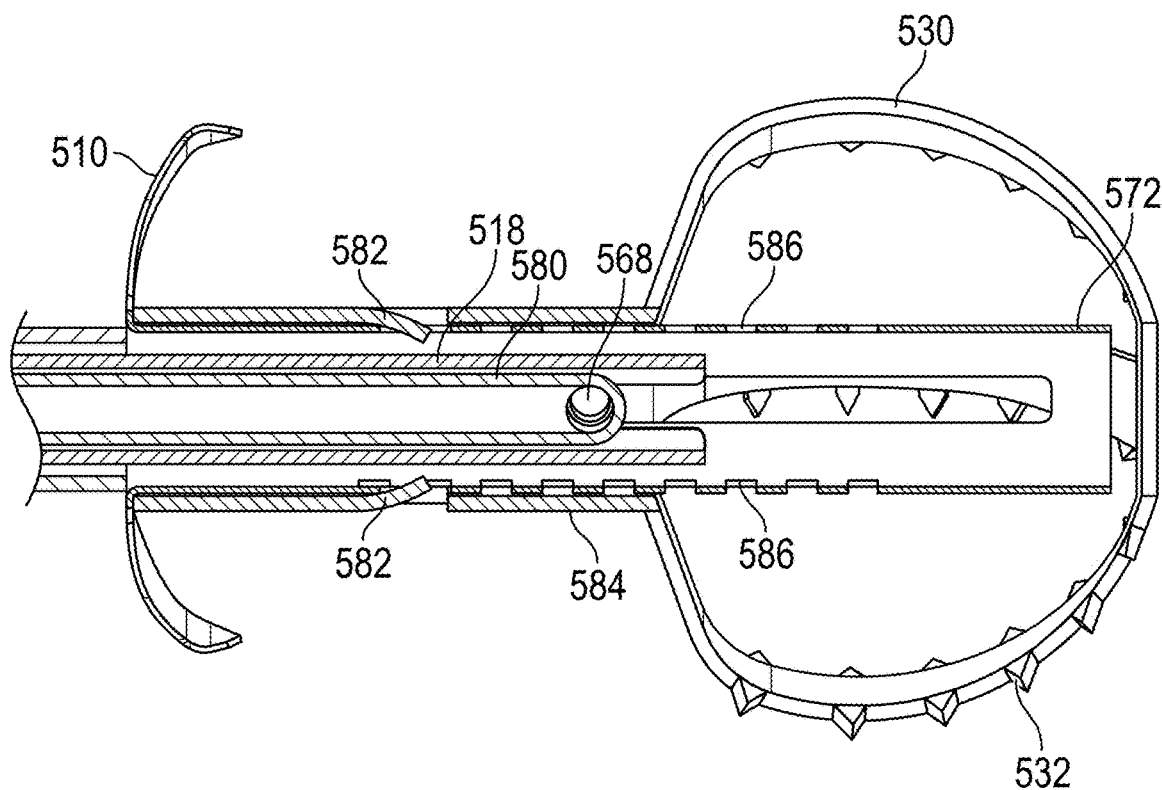
FIG. 21 is a section view of the treatment system shown in FIG. 18, taken through line 21-21 of FIG. 20.
Figure 24:
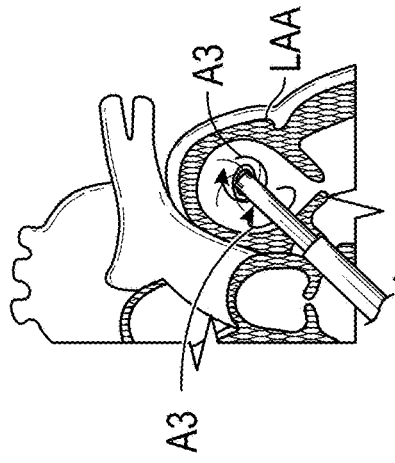
FIGS. 24-35 illustrate an embodiment of a deployment method for the embodiment of the treatment system illustrated in FIG. 22A.
Figure 26:
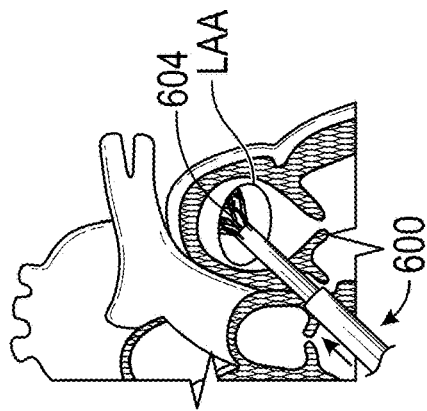

In some embodiments, if the contact member 504 is maintained in a fixed position using the catheter or the core member 518, the user can move the securing element 510 from the first position to the second position by pulling back on or withdrawing the suture 580 (again, while the contact member 504 is held in a fixed position within the LAA) and advancing an outer tube 576 of the deliver catheter in a distal direction so as to push the securing element 576 distally. This would be done after the desired level of twisting of the LAA has been achieved by torqueing or twisting the core member 518 or other portion of the catheter. With reference to FIG. 19, this can, in some embodiments, cause the securing element 510 and body portion 572 of the securing element to advance distally relative to the contact member 504, thereby forcing the securing element into the tissue of the LAA or LA so as to hold the tissue in the closed or contracted position.

Additionally, any embodiments of the device can be configured such that, as the securing element 510 is advanced into the second position, wherein the securing element 510 engages with the tissue and holds the LAA in an occluded or closed position, a retention member can be used to prevent the securing element from moving away from the second position toward the first position, thereby maintaining the position of the securing element and maintaining the occlusion in the LAA. For example and without limitation, one or more tabs 582 formed on or coupled with a body portion 584 of the contact member 504 can be biased to deflect into or engage with a respective depression or opening 586 of a plurality of depressions or openings 586 so as to prevent or inhibit the securing element 510 from moving back toward the first position relative to the contact member 504. The tabs 582 (which can be any other type of securing feature, such as ball and detent, or a zip tie type securing feature, or otherwise) can be configured such that the securing element 510 can freely move from the first, expanded position to the second, collapsed position, and to selectively prevent or inhibit movement from the second position to the first position, thereby essentially securing the securing element in the second position. Further, in any embodiments disclosed herein, the securing element and contact member can be held together using one or more sutures, wires, pins, or other components or fasteners, including, for example and without limitation, a suture with a slip knot which can be cinched during deployment. The suture can then be trimmed to length during final deployment, holding the securing element and contact member together to maintain the LAA in a closed or constricted state. Thereafter, the suture 580 can be removed, and the remaining components of the deployment device can be withdrawn from the patient's body, leaving the implant 502 in place.

In some embodiments, the implant device 502 can be configured such that the ratchet or retention mechanism formed by engagement of the tabs 582 and openings 586 is reversible or releasable, so that the securing element can be moved from the second to or toward the first position, for example, to disengage the securing element from the tissue for repositioning, for re-twisting the LAA, or otherwise. For example, some embodiments of the implant device 502 can be configured such that rotating or twisting the securing element (and, hence, the one or more tabs 582) relative to the body portion 584 of the contact member 504 so that the tabs 582 disengage the openings 586. Additionally, in some embodiments, the tabs can be positioned on the body portion 584 of the contact member 504 and the openings can be formed in a body portion of the securing element 510. Further, tabs can be formed in both directions so that the securing element can ratchet or be selectively securable in both axial movement directions. Further, in any embodiments disclosed herein, the tabs can be formed and configured so that the tabs can be moveable from a securing position or state to a non-securing (or sliding) state. Examples of these embodiments will be described below.

FIG. 22A shows another embodiment of a treatment system 600 having an implant device 602 wherein a contact member 604 is in a second, expanded state and a securing element 610 is in a first, retracted or pre-deployment state. FIG. 23 shows the embodiment of the implant device 602 wherein the securing element 610 has been moved to the second, deployed or locked state. FIGS. 24-35 illustrate an embodiment of a deployment method for the embodiment of the treatment system 600 illustrated in FIGS. 22-23. Any embodiments of the treatment system 600 or implant device 602 can have any of the components, features, or other details of any other implant device embodiments disclosed herein, including without limitation any of the embodiments of the implant device 100, 200, 300, 400, 500 described above, in any combination with any of the components, features, or details of the treatment system 600 or implant device 602 disclosed below. Similarly, any components, features, or other details of any of the other treatment system or implant device embodiments disclosed herein can have any of the components, features, or other details of any embodiments of the treatment system 600 or implant device 602 disclosed herein, in any combination, with any of the components, features, or details of the treatment system or implant device embodiments disclosed herein.

With reference to FIGS. 22A-22B, the securing element 610 can have a body portion 611 that can have a curved or helical (or corkscrew) shape that can extent from a proximal end portion 610a of the securing element 610 to a distal end portion 610b of the securing element 610, and can have a pointed distal tip 612 at the distal end portion 610b of the securing element 610 that can engage with (or, in some embodiments, penetrate at least partially through) the tissue of the LA and/or the LAA after the contact member 604 has been rotated to the second position, thereby securing the tissue and closing or occluding the opening of LAA about the implant device, such as about a body portion 614 that is integral with or coupled with the contact member 604 or other portion of the implant device.

The securing element 610 can define an axial opening 615 therethrough. In some embodiments, the opening 615 can be larger than a distal portion of an inner core member of the catheter and/or a body portion 614 of the implant, so that a body portion 611 of the securing element 610 wraps around or curves around (helically or otherwise) and/or is rotatable around the inner core member of the catheter and/or the body portion 614 of the implant.

FIGS. 23A-23B show another embodiment of a securing element 610 that can be used with any implant or delivery system embodiments and/or treatment methods disclosed herein. In any embodiments, a cross-section of the body portion 611 can be round, square (as shown), ovular, or have any other desired shape. In any embodiments, the body portion 611 can have from 2 to 15 or more coils (i.e., complete revolutions), or from 3 to 10 coils, or from 4 to 6 coils and can terminate at a distal end portion 610b of the securing element 610 in a sharp point, a blunt end, one or more tissue anchors or barbs, or otherwise. Additionally, any embodiments of the securing elements disclosed herein can have tissue anchors or barbs (not shown) along a length of the body portion 611 or body portions 611, in the embodiments having two or more body portions, such as described below, to engage with the tissue and prevent or inhibit the securing member 610 from backing out of the tissue after the securing element 610 has been advanced into such tissue. A proximal end portion 610a of the securing element 610 can have flanges 617, openings 619, and/or other features configured to connect the securing element 610 to the other portions of the implant 602.

Additionally, in any embodiments disclosed herein, the securing element 610 can also have rotational or axial lock features that can secure the securing element in a desired rotational position and/or desired axial position and/or inhibit the counter rotation of the securing element. The rotational or axial lock can be selectively reversible so that a user to return the securing element to a freely movable state, as desired. For example and without limitation, with reference to FIGS. 23C-23D, any embodiments of the securing elements disclosed herein can have one or more or a plurality of tissue anchors or barbs 621 extending away from a proximal end 610a of the securing element 610 that can improve the grip of the securing element in the target tissue, and/or prevent or inhibit the securing member 610 from backing out of the tissue after the securing element 610 has been advanced into such tissue. In any embodiments, the tissue anchors or barbs 621 can be axial facing, radially facing, or at an angle relative to the axial direction of the securing element 610. The tissue anchors or barbs 621 can be angled or otherwise configured to easily enter the tissue, and have a perpendicular face or otherwise be configured to engage with and/or lock with the tissue to prevent the counter-rotation of the securing element 610.

Further, with reference to FIGS. 23E-23F, any embodiments of the securing elements disclosed herein can have two or more or a plurality of body portions 611 extending away from a proximal end 610a of the securing element. The embodiment of the securing element 610 shown in FIGS. 23E-23F has a first body portion 611a and a second body portion 611b that are both helically shaped, have the same or similar pitch, and can both extend a full length of the securing element 610. In other embodiments, one of the body portions 611 can have a different length (e.g., be shorter) than the other body portion 611. Additionally, in any embodiments disclosed herein, the one or more body portions 611 can have a pitch that changes (increases or decreases) along a length thereof from a proximal portion to a distal portion of the securing element. A body portion 611 having a pitch that decreases along a length of the securing element (such that the spacing increases along a length of the body portion) can result in the tissue between the coils being compressed more near a proximal end portion of the securing element than near a distal end portion of the securing element. In some embodiments, this may increase the retaining force of the securing element in the tissue. The first body portion 611a can have a distal end portion 612a and the second body portion 611b can have a distal end portion 612b.

As mentioned, in some embodiments, the securing element 610 can have two or more curved or helical (or corkscrew) shaped body portions 611, each of which can have a pointed distal tip that can engage with (or, in some embodiments, penetrate at least partially through) the tissue of the LA and/or the LAA after the contact member has been rotated to the second position. In any embodiments disclosed herein, the securing element having a helical shape (such as the embodiment of the securing element 610 shown in FIGS. 22A-22B) can have two helically shaped body portions 611 that can be each configured to penetrate and engage the tissue that has constricted around a portion of the implant. In any embodiments, including the single and double helical securing element embodiments, the body portion or portions 611 can be long enough to engage contact member, or shorter and just engage all or just a proximal portion of the LA wall/LAA tissue, such as from approximately 1 mm to approximately 2 mm of the LA wall/LAA tissue, or from approximately 2 mm to approximately 5 mm or more of the LA wall/LAA tissue.

Further, in any embodiments, the one or more body portions 611 may define a cylindrical shape along a length of the securing member 610, as shown, define a conical shape along a length of the securing member 610, or otherwise. For example and without limitation, in any embodiments, the one or more body portions 611 may define a conical shape that increases along a length of the securing member 610 so that the opening 615 is larger at the distal end portion 610b of the securing element 610. The conical shape can result in the tissue being gathered wide and brought together (i.e., radially inwardly) as the securing element 610 is advanced into the LA wall/LAA tissue.

With reference to FIG. 22B, the securing element 610 (which can be any of the securing element embodiments or have any combination of any of the features of the securing element embodiments disclosed herein) can be rotated (such as in a corkscrew fashion) and advanced so as to penetrate into and/or pass through the tissue of the LA and/or LAA that has gathered and/or constricted about the body portion 614 or other portion of the implant device 602. In this configuration, the securing element 610 is configured to be rotatable relative to the contact member 604 so that the securing element 610 can be rotated and passed through the tissue of the LA and/or LAA while the LAA is held generally stationary in the second rotational position by holding the contact member 604 in the stationary position. In any embodiments, a sleeve or other component of the catheter or delivery system can be coupled with the securing element (including, without limitation, securing element 610) to enable a user to move the securing element between a first state and a second state (which should be interpreted to also include moving from the second state to the first state), to rotate the securing element in either direction, to move the securing element between a first position and a second position, and/or to otherwise manipulate the securing element. In some embodiments, the catheter or delivery system can be configured to perform these operations independently of any other movements or operations of the catheter so that, for example, the securing element can be axially advanced toward the contact member while the contact member is held in a fixed position by the catheter.

The securing element 610 can thereby hold the tissue of the LA and/or LAA to hold the tissue of the LA and/or LAA in the constricted state about the implant device, so as occlude the LAA. Additionally, in some embodiments, as shown, the securing element 610 can be configured to also pass through one or more of the openings 620 that can be formed in or result in the contact member 604 when the contact member 604 is in the second, expanded state, thereby further securing the securing element 610 to the contact member 604 and preventing or inhibiting the contact member 604 from rotating toward the first position. In any embodiments, the securing element 610 and/or the contact member 604 can have one or a plurality of teeth, cleats, barbs, nubs, texture, studs, anchors or other tissue engaging features or anchor members about an outside surface of the securing element 610 to prevent or inhibit the securing element 610 from disengaging from the tissue of the LA and/or LAA when in the second state. Further, in any embodiments, the securing element can be biased to the second positioned by a biasing member (not shown) such as an axially resilient member, or using one or more sutures, wires, ratchets, tabs and openings, or other securing features. However, in some embodiments, the engagement of the securing element 610 into the tissue of the LA and/or LAA can be sufficient to secure the securing element 610 in the second position and maintain the LAA in the occluded state.

Figure 28:
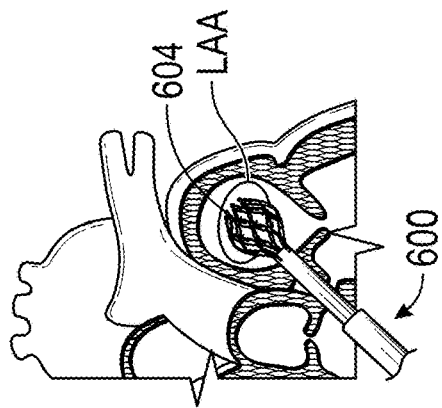
Figure 25:
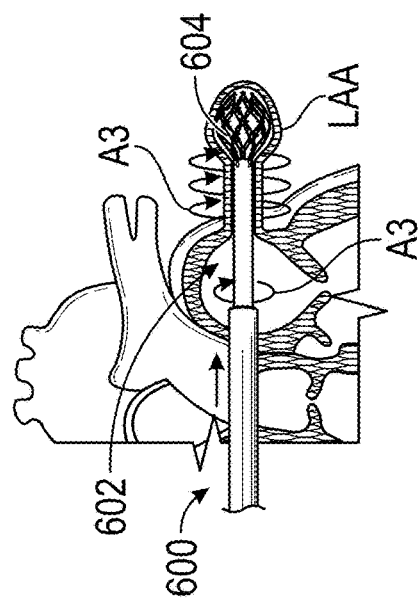
Figure 27:
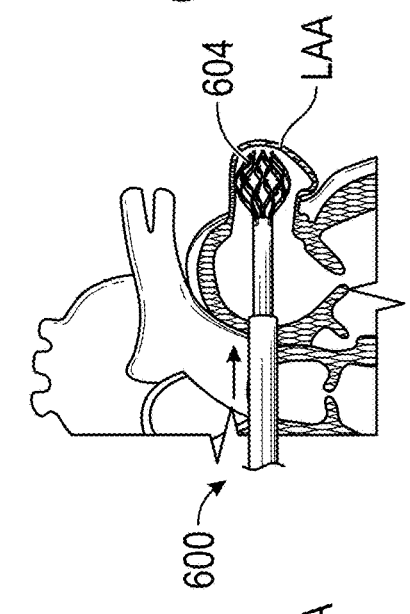
Figure 29:
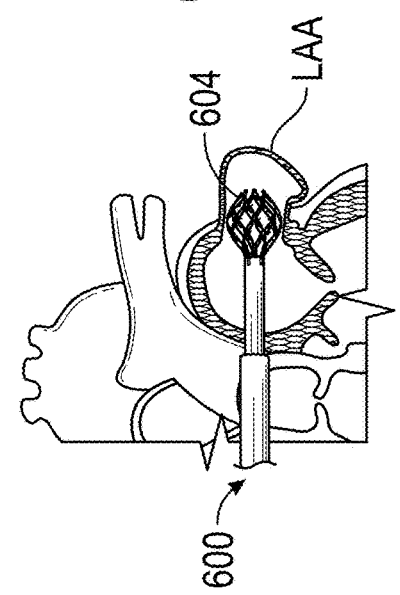

With respect to FIGS. 24-35, an embodiment of a deployment sequence will now be described. FIGS. 24-27 show the contact member 604 being advanced into the LAA. With reference to FIG. 27, the contact member 604 can be advanced to any desired depth, including to an end portion, of the LAA. In some embodiments, the contact member 610 can be advanced to the desired position relative to the LAA and then expanded to the second state so as to contact an inside surface or tissue of the LAA. Thereafter, the contact member 604 can be rotated in a first direction (represented by arrow A3 in FIGS. 28-29, which can be either the clockwise or counter-clockwise direction) toward the second position so as to twist the LAA in the first direction, as also indicated by arrow A3 in FIGS. 28-29, toward the second state. As described, the twisting can cause the ostium of the LAA to constrict around a portion of a body of the implant device 602, so as to occlude the LAA from the LA, as shown in FIGS. 28-29.

Figure 30:
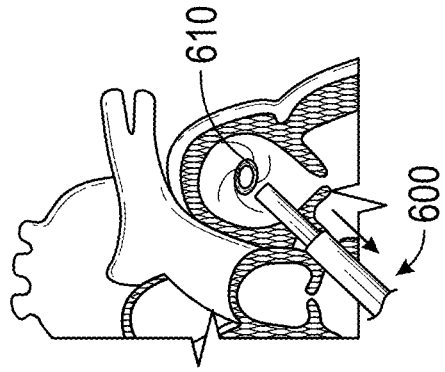
Figure 34:
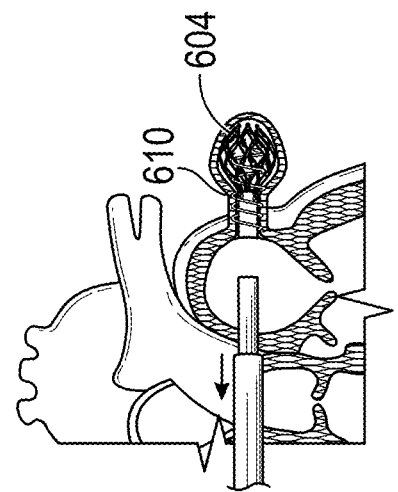
Figure 32:
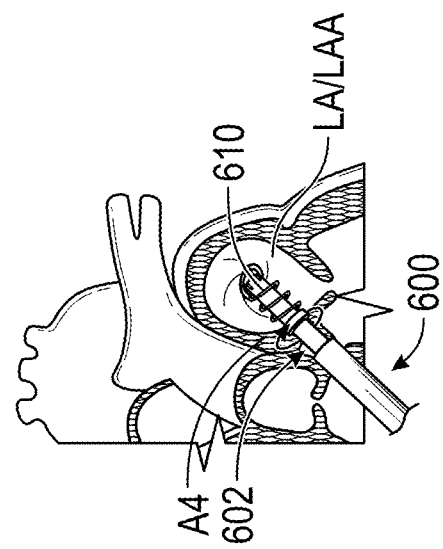
Figure 35:
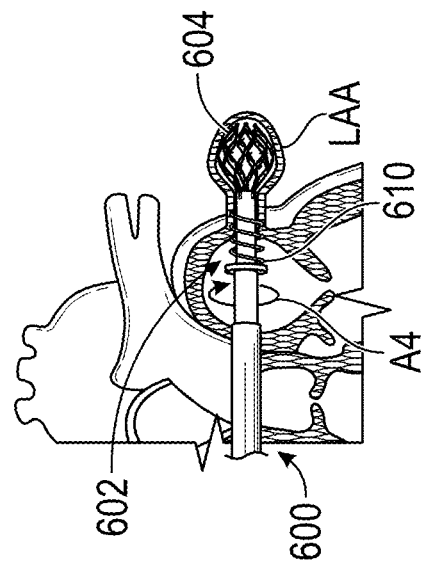
Figure 31:
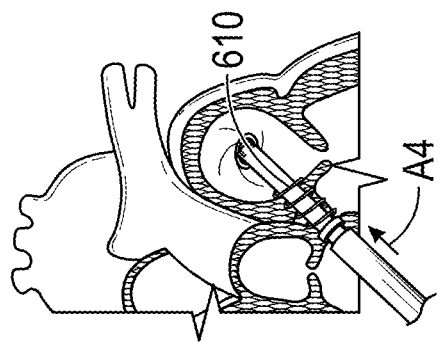
Figure 33:
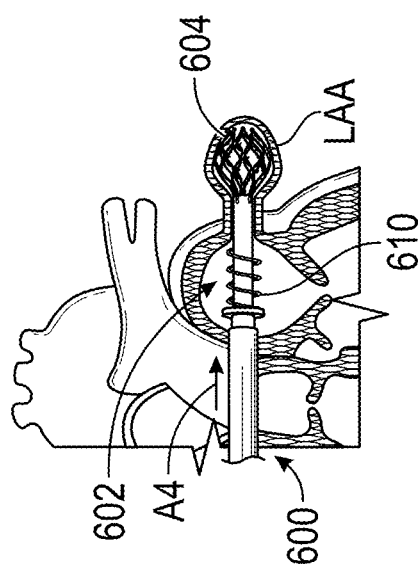

Thereafter, with reference to FIGS. 30-31, while maintaining the contact member 604 in the second rotational position and/or maintaining the tissue of the LA and/or LAA in the occluded or constricted state and the LAA in the twisted position, the securing element 610 can be advanced distally (as indicated by arrow A4 in FIGS. 30-31) toward the tissue of the LA and/or LAA that has constricted around the body of the implant device. Before a distal end of the securing element 610 reaches the tissue of the LA and/or LAA, the securing element 610 can be rotated in a first direction (such as the rotational direction indicated by arrow A5 shown in FIGS. 32-33) while the securing element 610 is being advanced distally to cause the securing element 610 to penetrate into and/or engage with the tissue of the LA and/or LAA that has constricted around the body portion of the implant device 602. In some embodiments, the securing element 610 can be advanced so as to penetrate completely through the tissue of the LA and/or LAA, as shown in FIGS. 34-35. In some embodiments, the securing element 610 can be configured so as to engage and/or only partially penetrate into the tissue of the LA and/or LAA. Thereafter, the implant device 602 can be released from the delivery catheter and the delivery catheter can be withdrawn from the patient's heart, as shown in FIGS. 34-35, leaving the LAA in the occluded position.

Figure 36:
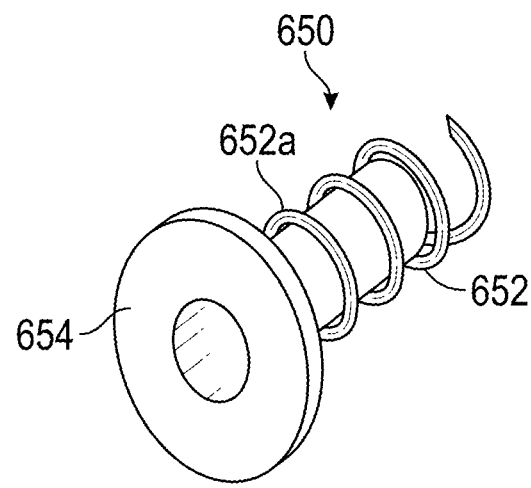
FIG. 36 shows another embodiment of an implant device wherein the retention member is engaging with a tissue surface surrounding an opening of the LAA.

FIG. 36 shows another embodiment of an implant device 650 having a different embodiment of a securing element 652 that can be used with any of the embodiments of the implant devices disclosed herein. As shown in FIG. 36, the securing element 650 can have a backing member 654 coupled with a proximal end 652a of the securing element 652 that can provide an additional seal against the tissue of the LA and/or LAA when the securing element is in the second or deployed position.

Figure 37:
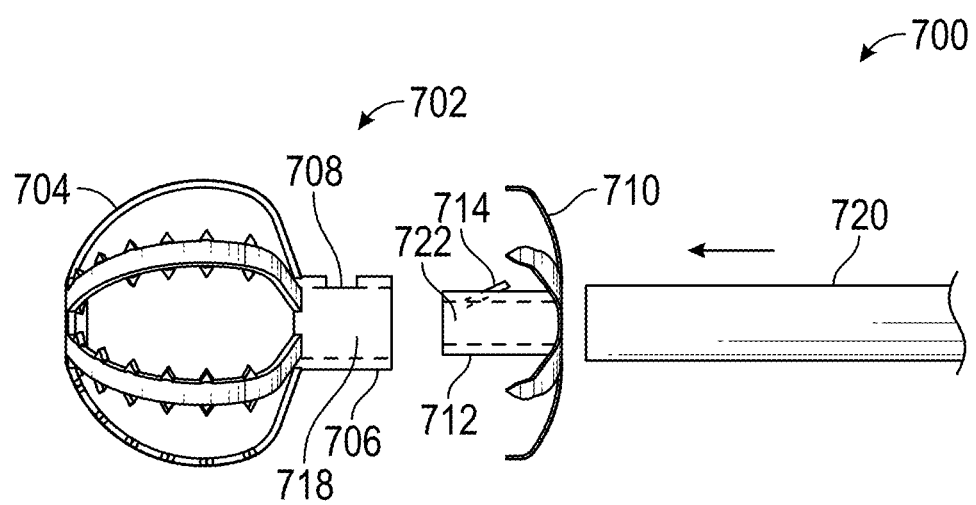
FIG. 37 shows another embodiment of a treatment system wherein a tab member of the securing element is in a first, engaged state.
Figure 38:
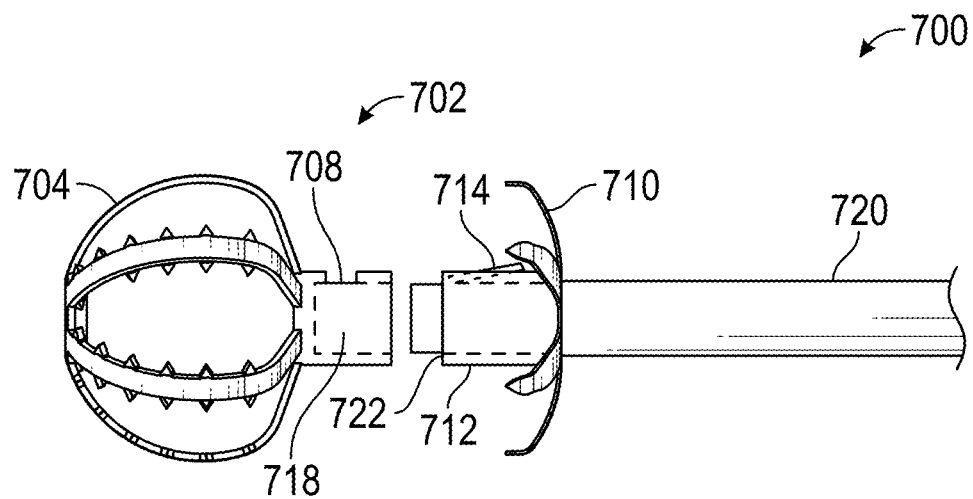
FIG. 38 shows the treatment system of FIG. 37, wherein the tab member is in a second, disengaged state.

FIGS. 37-38 show another embodiment of a treatment system 700 having an implant device 702 wherein the contact member 704 is in a second, expanded state, and the securing element 710 is in a second, open state. Any embodiments of the treatment system 700 or implant device 702 can have any of the components, features, or other details of any other treatment system or implant device embodiments disclosed herein, including without limitation any of the embodiments of the treatment system 100, 200, 300, 400, 500, 600 or implant device 102, 202, 302, 402, 502, 602 described above, in any combination with any of the components, features, or details of the treatment system 700 or implant device 702 disclosed below. Similarly, any components, features, or other details of any of the other treatment system or implant device embodiments disclosed herein can have any of the components, features, or other details of any embodiments of the treatment system 700 or implant device 702 disclosed herein, in any combination, with any of the components, features, or details of the treatment system or implant device embodiments disclosed herein.

In any embodiments, the contact member 704 can have a body portion 706 that can, but is not required to have, a cylindrical shape. An opening or recess 708 can be formed in the body portion 706 as part of a retaining element to retain the securing element 710 in a desired axial position relative to, or locked to, the coupling member 704. The securing element 710 can also have a body portion 712 that can, but is not required to have, a cylindrical shape. In some embodiments, the body portion 712 can extend into the body portion 706 of the contact member 704 even when the securing element 710 is in a first, retracted state. The body portion 706 can have an opening 708 extending therethrough, sized and configured to selectively receive the body portion 712 of the securing element 710. The body portion 712 can have an opening 722 extending therethrough, sized and configured to selectively receive a core member 720 of the delivery catheter of the treatment system 700.

Figure 39:
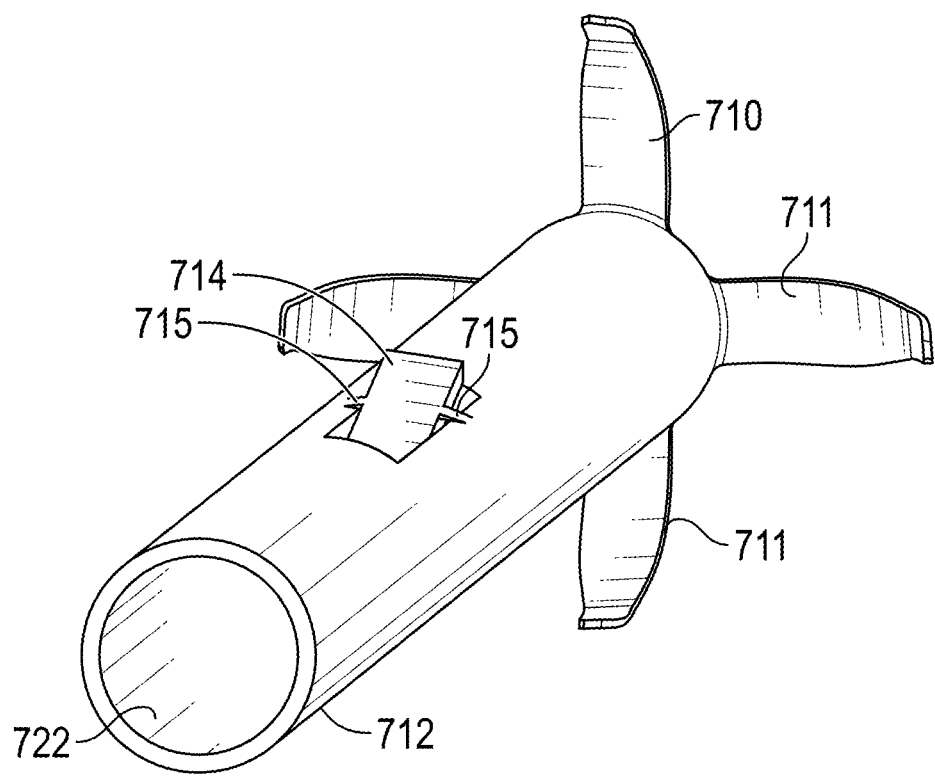
FIG. 39 shows the securing element of the treatment system of FIG. 37.

Additionally, with reference to FIG. 39, the securing element 710 can have a deflectable tab member 714 that can be movable or moved from a first, engaged position (as shown in FIG. 37) to a second, disengaged position (as shown in FIG. 38). The tab member 714 can be configured to rotate about a pin that can be coupled with the tab member 714 and the body portion 712, or can be configured to rotate about a thin strip of the material (referred to herein as a material strip 715) used to form the body portion 712 and/or the tab member 714. For example and without limitation, the body portion 712, the tab member 714, and the one or more material strips 715 (two being shown) can be integrally formed. Additionally, in some embodiments, the one or more arms 711 of the securing element 710 (four being shown) can also be integrally formed with the other features of the securing element 710. In some embodiments, the tab 714 can be biased toward the first, engaged position (as shown in FIGS. 37 and 39), but be physically deflectable or rotatable toward the second, disengaged position (as shown in FIG. 38) by advancing a core member 720 or other component through the opening 722 extending through the body portion 712 of the securing element 710. For example and without limitation, as shown in FIG. 38, the core member 720 can be advanced distally through the opening 722 of the securing element 710 to deflect or rotate the tab member 714, thereby moving the tab member 714 from the first, engaged position to the second, disengaged position.

When the tab member 714 is in the engaged position, the tab member 714 can engage with the opening 708 formed in the body portion 706 of the contact member to axially lock or couple the securing element 710 with the contact member 704, for example, after the contact member has twisted the LAA to a closed or occluded position or state, as described above. However, in some embodiments, if a user wishes to disengage or decouple the securing element 710 from the contact member 704, the user can achieve this by moving the tab member 714 to the second, disengaged position, such as, for example and without limitation, as described above, thereby disengaging the tab member 714 from the opening 708. Thereafter, the user can axially withdraw the securing element 710.

FIGS. 40-43 illustrate another embodiment of an implant device 732. Any embodiments of the implant device 732 can have any of the components, features, or other details of any other treatment system or implant device embodiments disclosed herein, including without limitation any of the embodiments of the treatment system 100, 200, 300, 400, 500, 600, 700 or implant device 102, 202, 302, 402, 502, 602 described above, in any combination with any of the components, features, or details of the implant device 732 disclosed below. Similarly, any components, features, or other details of any of the other treatment system or implant device embodiments disclosed herein can have any of the components, features, or other details of any embodiments of the implant device 732 disclosed herein, in any combination, with any of the components, features, or details of the treatment system or implant device embodiments disclosed herein.

Figure 40:
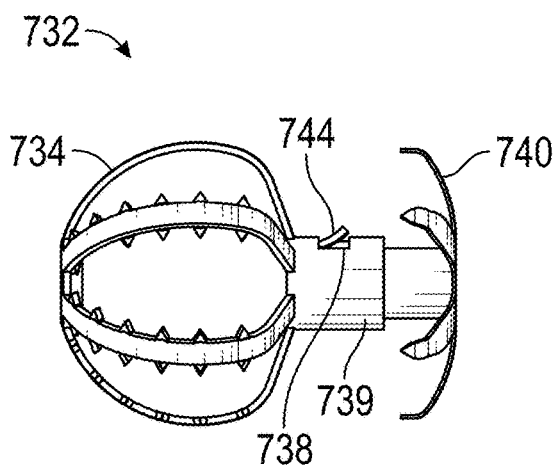
FIG. 40 shows the treatment system of FIG. 37, wherein the securing element is engaged with the contact member and the tab member of the securing element is in the first, engaged state.
Figure 41:
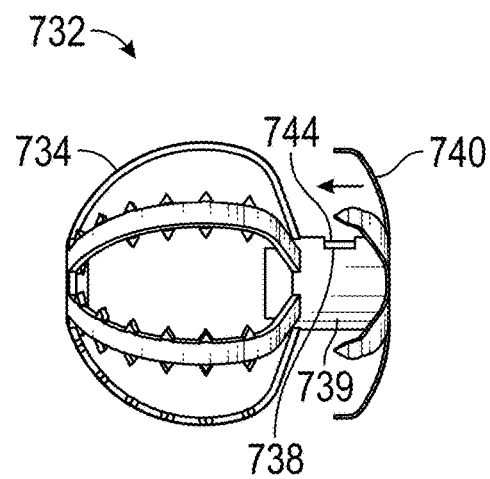
FIG. 41 shows the treatment system of FIG. 37, wherein the tab member of the securing element has been moved to the second, disengaged state by the axial advancement of a core member of the delivery system.
Figure 42:
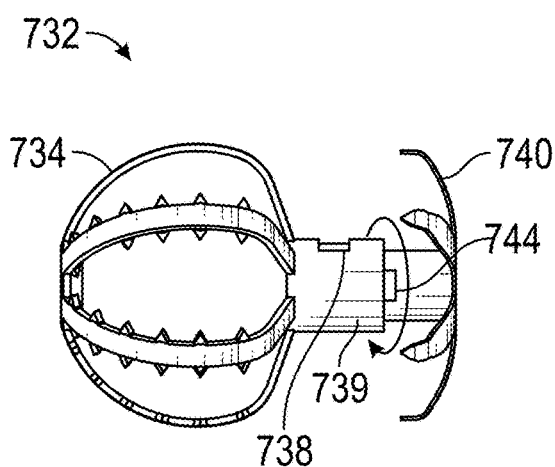
FIG. 42 shows the treatment system of FIG. 37, wherein the securing element has been rotated to misalign the tab member relative to the opening of the contact member and permit the withdrawal of the securing element from the contact member.
Figure 43:
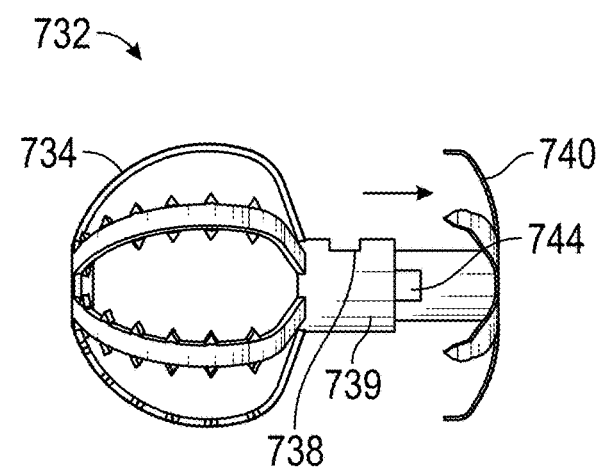
FIG. 43 shows the treatment system of FIG. 37, wherein the securing element has been withdrawn from the contact member.

As shown in FIG. 40, a deflectable tab member 744 of the implant device 732 is engaged with an opening 738 of the contact member 734, thereby causing the securing element 740 to be engaged with the contact member 734. In any embodiments, the deflectable tab member 744 can be movable or moved from a first, engaged position (as shown in FIG. 40) to a second, disengaged position (as shown in FIG. 41) by advancing the securing element 710 distally so that a body portion 739 of the contact member 734 causes the tab member 744 to deflect and move to the second, disengaged position, as shown in FIG. 41. Thereafter, the securing element 740 can be rotated in either direction (such as by 90 degrees) to a position in which the tab member 744 is not aligned with and therefore cannot engage with the opening 738, as shown in FIG. 42. The body portion 739 of the contact member 734 can hold the tab member 744 in the second, disengaged position while the securing element 740 is withdrawn away from or disengaged from the contact member, as shown in FIG. 43.

Figure 46A:
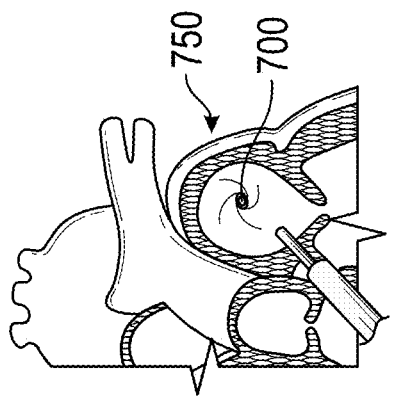
FIGS. 46A and 46B are a front view and a side view, respectively, of the treatment system of FIG. 44, showing the delivery device being removed from the implant device after the LAA has been occluded.
Figure 45A:
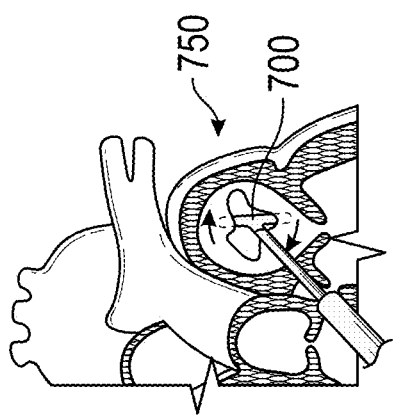
FIGS. 45A and 45B are a front view and a side view, respectively, of the treatment system of FIG. 44, showing the implant being used to twist the LAA to close or occlude the LAA at the ostium.
Figure 44A:
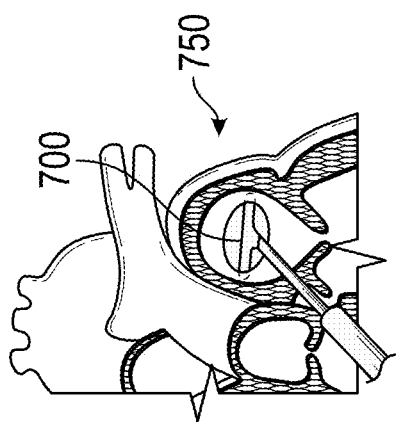
FIGS. 44A and 44B are a front view and a side view, respectively, of another embodiment of a treatment system configured to twist and close or occlude the LAA at the ostium of the LAA.
Figure 46B:
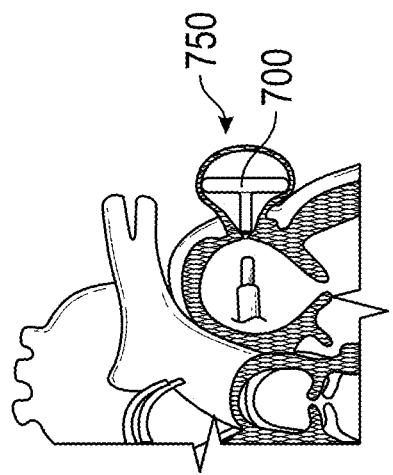
Figure 45B:
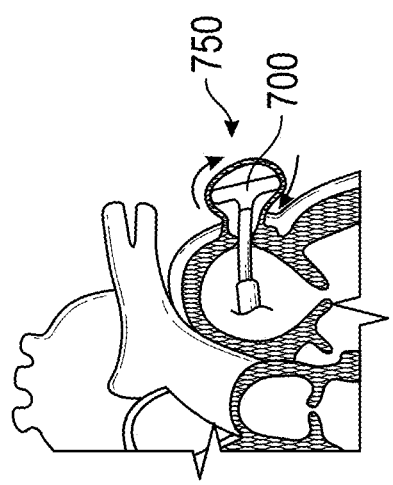
Figure 44B:
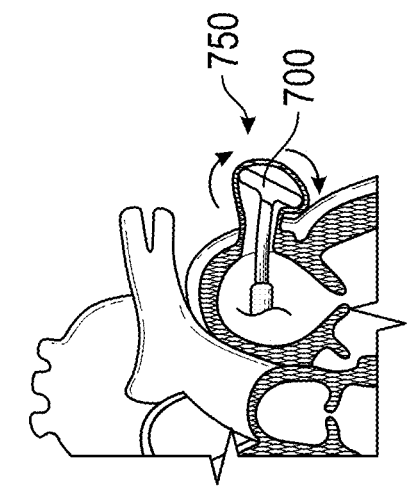
Figure 47C:
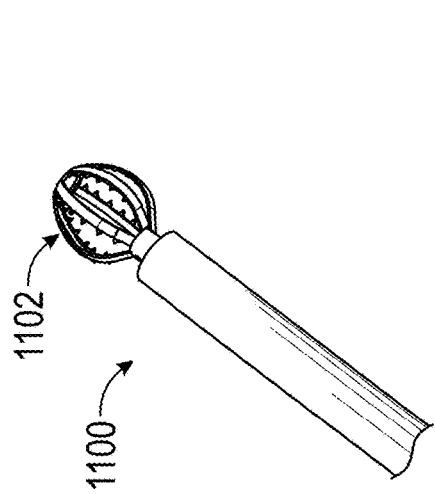
FIGS. 47A-47F show another embodiment of a treatment system for closing or occluding an LAA.
Figure 47B:
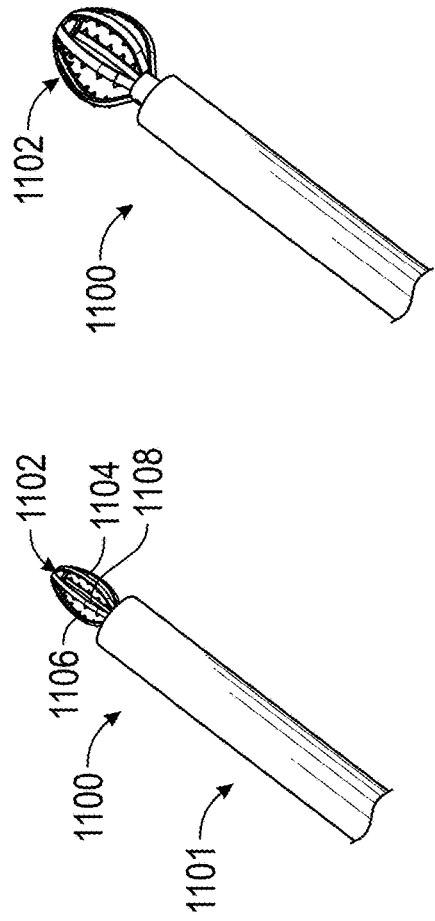
Figure 47A:
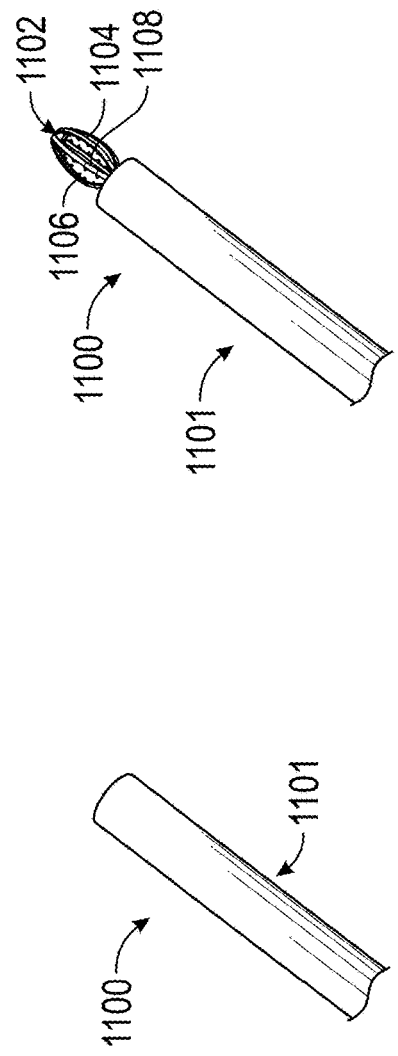
Figure 47F:
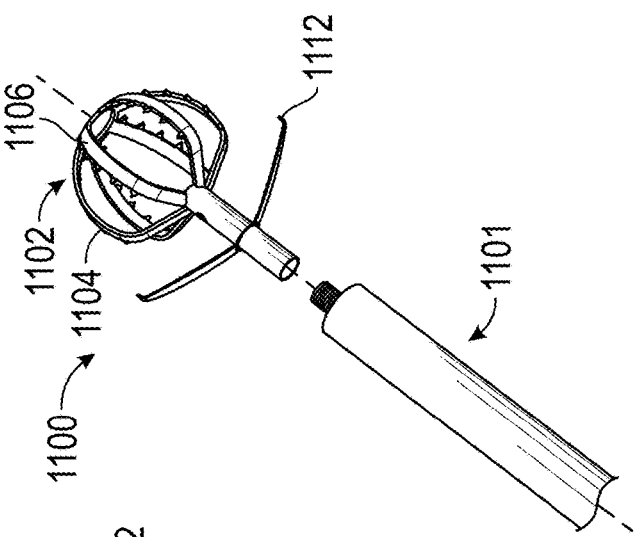
Figure 47E:
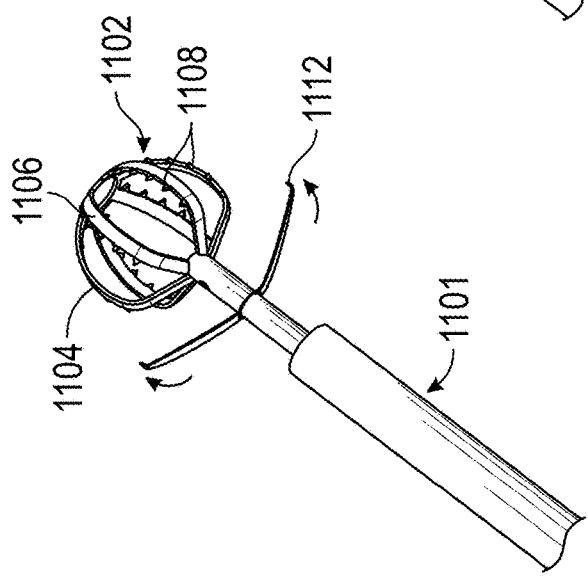
Figure 47D:
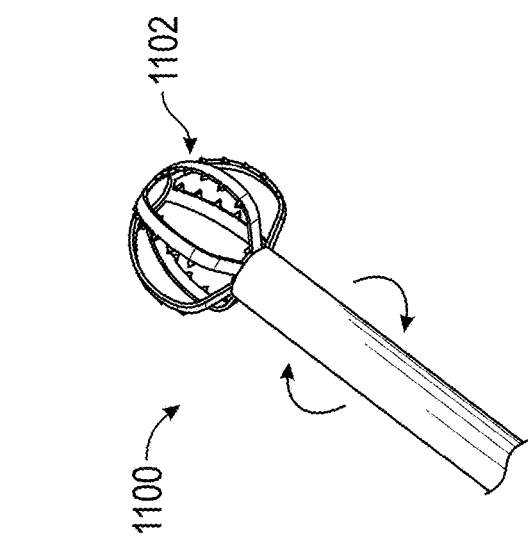
Figure 48C:
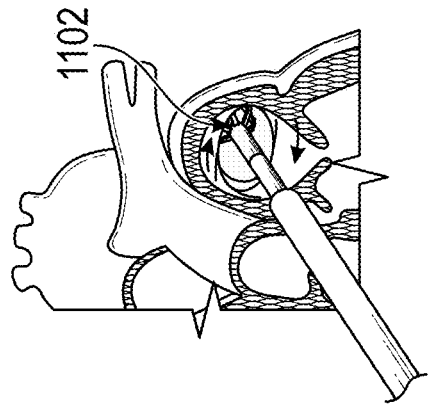
FIGS. 48A-48F show some stages or steps of an exemplifying deployment procedure of the expandable implant of FIGS. 47A-47F for treatment of an LAA.
Figure 48F:
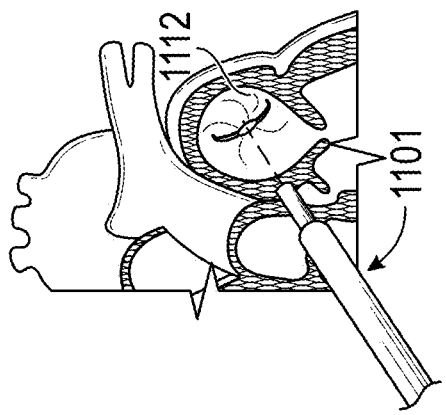
Figure 48B:
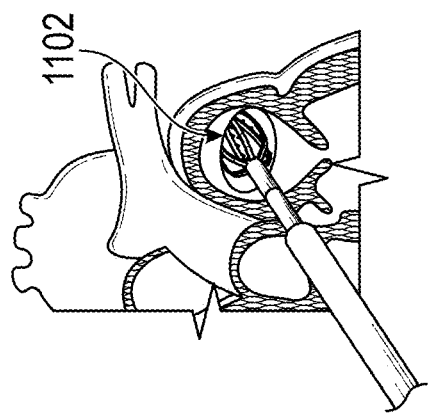
Figure 48E:
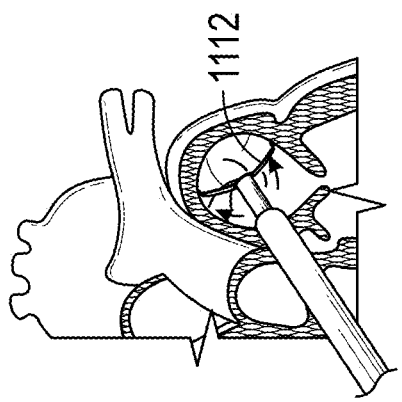
Figure 48A:
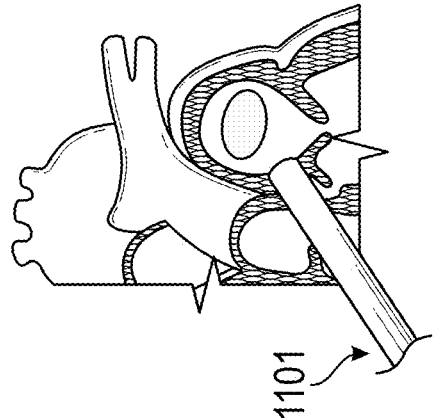
Figure 48D:
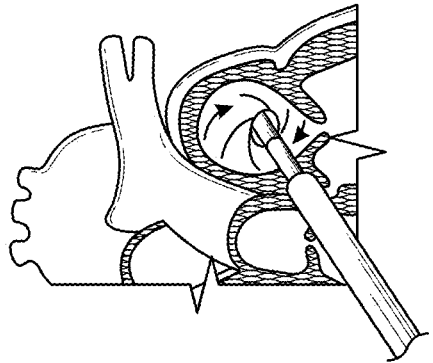

FIGS. 44A and 44B are a front view and a side view, respectively, of another embodiment of a treatment system 750 configured to twist and close or occlude the LAA at the ostium of the LAA. FIGS. 45A and 45B are a front view and a side view, respectively, of the treatment system 750 of FIG. 44, showing the implant being used to twist the LAA to close or occlude the LAA at the ostium. The ostium of the LAA or the material of the LA or LAA that has constricted around the implant device can then be clipped or locked in the constricted state, as in any embodiments disclosed herein and using any securing features or components disclosed herein. FIGS. 46A and 46B are a front view and a side view, respectively, of the treatment system of FIG. 44, showing the delivery device being removed from the implant device after the LAA has been occluded.

In some embodiments, the steps of deployment and implantation can include, in any combination and in any combination with any other steps: (a) inserting catheter and implant device through an ostium of the LAA; (b) rotating a contact member or other engaging component of the implant to twist the LAA, causing at least the ostium of the LAA to collapse on itself, thereby closing or occluding the ostium of the LAA; (c) clipping, holding, or securing the LA and/or LAA tissue in the occluded or closed state; and/or (d) releasing and withdrawing the delivery catheter from the implant. As illustrated, the treatment system twists and closes the LAA at the ostium, and then clip and hold that position, effectively closing the LAA. In some embodiments, the steps of deployment and implantation can include: Inserting catheter into middle of LAA ostium, rotating the paddle of the implant to twist LAA and self-collapsing the LAA on itself, clipping and holding position to atrial wall, and releasing the delivery catheter from the implant.

FIGS. 47A-47F show another embodiment of a treatment system 1100 for closing or occluding an LAA having an embodiment of a delivery device 1101 and an embodiment of an expandable implant or implant 1102 for the left atrial appendage, in particular, showing the implant 1102 in a plurality of exemplifying expansion and deployment stages.

The implant 1102 can have a body portion 1104 having a plurality of struts or arms 1106 that are expandable. The body portion 1104 can, in some embodiments, expand to an approximately spherical shape, or elongated spherical shape. The struts 1106 can each have a plurality of barbs or tissue anchors 1108 thereon (which can be or comprise any of the tissue anchors disclosed herein). Any embodiments of the implant disclosed herein can have a laser cut Nitinol body portion that is self-expanding and which is covered with micro-barbs.

The barbs 1108 can be configured to engage the tissue upon the twisting movement or motion of the body portion 1104 relative to an internal wall of the LAA after the body portion 1104 has been expanded from the first state to the second state, wherein, in the second state, the struts 1106 and barbs 1108 can be engaged with or in contact with the tissue on an inside wall of the LAA. Additionally, any embodiments of the implant 1102 can have one or more anchoring elements 1112 configured to engage with the tissue adjacent to or surrounding the LAA to prevent the implant 1102 from rotating back to the first rotational position after the implant 1102 has been rotated within the LAA to the second rotational position. In any embodiments, the anchoring elements 1112 can comprise two arms or members that can each engage a tissue surface and can each have a plurality of barbs thereon, configured to prevent the implant from rotating back to a first rotational position. FIGS. 48A-48E show some stages or steps of an exemplifying deployment procedure of the expandable implant 1102 of FIGS. 47A-47F as the implant 1102 is being deployed into an LAA.

FIGS. 49A-49G show an embodiment of an implant 1202 that can be used to close or substantially close an LAA. In some embodiments, the implant 1202 can be formed by laser cutting a tube of elastic material, such as Nitinol. The implant 1202 and any other implant embodiment disclosed herein can be self-expanding or mechanically expandable, such as using balloon expansion techniques. Further, any embodiment of the implant 1202 can have any of the same features, components, or details of any other implant embodiments disclosed herein in place of or in combination with any of the features, components, or other details of the embodiments of the implant 1202 disclosed herein. In some embodiments, the implant 1202 can have a contact member 1204 that can be covered with a plurality of micro-barbs or other tissue anchors 1208 and have a securing element 1212 (also referred to herein as an anchoring element) that can include a single folding clip anchor. The securing element 1212 can be configured to lock the implant 1202 in a fixed rotational position after the implant has rotated the LAA to the desired level of twist and closure or occlusion.

Figure 50C:
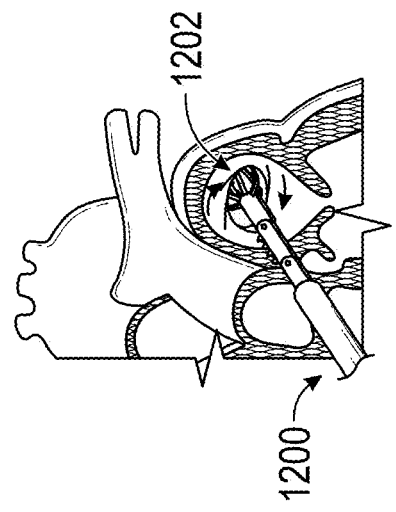
FIGS. 50A-50F show some stages or steps of an exemplifying deployment procedure of the expandable implant of FIGS. 49A-49G for treatment of an LAA.
Figure 50F:
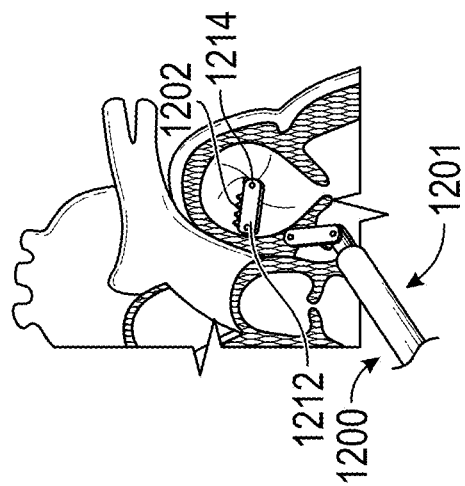
Figure 50B:
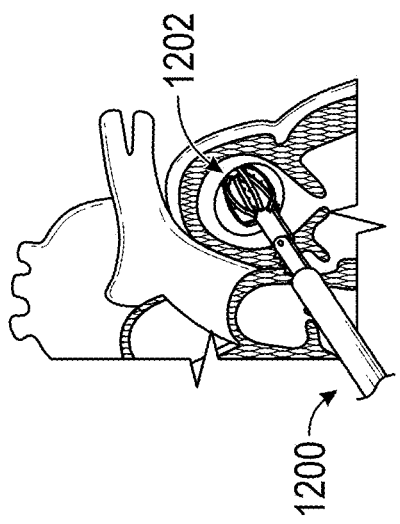
Figure 50E:
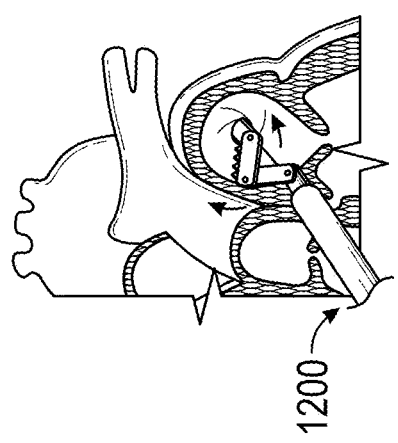
Figure 50A:
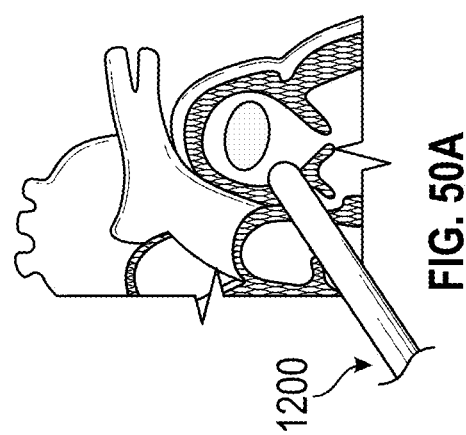
Figure 50D:
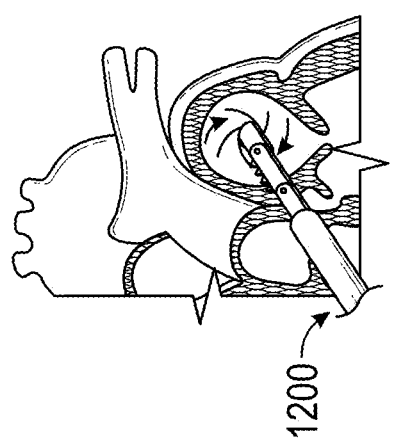

FIGS. 50A-50F show some exemplifying stages of an embodiment of a deployment procedure of the expandable implant 1202 of FIGS. 49A-49G as the implant 1202 is being deployed into an LAA. In any embodiments, the implant 1202 can be advanced into the LAA, expanded, and then rotated from a first rotational position to a second rotational position so as to twist the LAA and cause an ostium and/or other tissue of the LAA to constrict or occlude about a portion of the implant 1202. The implant or any implant disclosed herein can be configured to be rotated clockwise (and can be rotated clockwise and/or counterclockwise during any procedures disclosed herein) to twist and close or substantially close the ostium of the LAA or constrict the ostium of the LAA about a portion of the implant 1202. After the desired level of occlusion is reached, the securing element 1212 can be rotated or folded (such as, for example and without limitation, about an axis or a hinge 1214) to a lateral side of the LAA so as to be approximately perpendicular to the axial centerline of the implant, and forced into engagement with the tissue adjacent to the LAA adjacent to the ostium of the LAA to prevent unwinding of the implant and the ostium of the LAA. A body portion of the securing element 1212 can also have tissue anchors 1216 thereon or coupled or integrally formed therewith that can engage with, penetrate, and/or grip the tissue of the LA and/or LAA that has constricted as a result of the twisting of the LAA. In any embodiments disclosed herein, the securing element 1212 can be configured to be biased toward and/or securable in a second, locked state (such as is shown in FIG. 49G or FIG. 50F, using springs, shape memory material, sutures, ties, or other components. The delivery device can be disconnected from the implant and removed from the patient's body after deployment of the securing element 1212, as shown in FIG. 50F.

Figure 51:
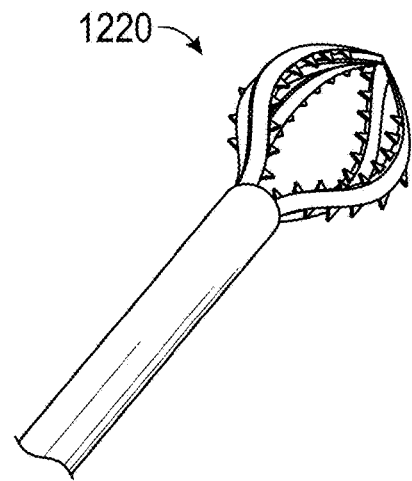
FIG. 51 shows another embodiment of a contact member that can be used with any treatment system embodiments disclosed herein.
Figure 52:
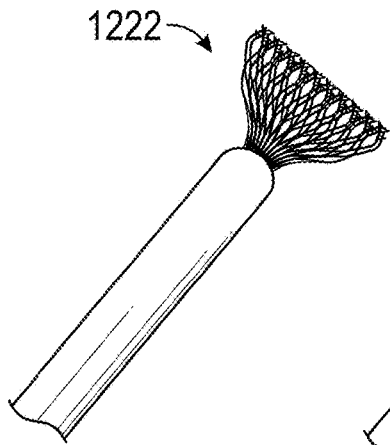
FIG. 52 shows another embodiment of a contact member that can be used with any treatment system embodiments disclosed herein.
Figure 53:
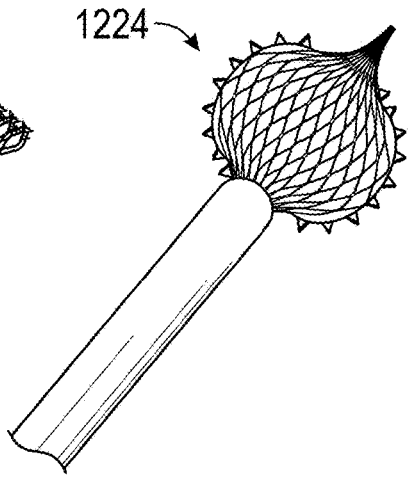
FIG. 53 shows another embodiment of a contact member that can be used with any treatment system embodiments disclosed herein.

FIGS. 51, 52, and 53 show additional embodiments of implant devices 1220, 1222, and 1224 (note that implant devices are also referred to herein as implants) that can be used with any of the embodiments of the treatment systems, delivery devices or procedures disclosed herein to treat an LAA. The implant device 1220 shown in FIG. 51 can have ribbons or struts made from Nitinol or any other suitable material which are configured to expand to an approximately spherical or elongated spherical shape, and which can be covered with small barbs or cleats (or other tissue anchors). The tissue anchors can be pointing in one or both circumferential directions. The implant device shown in FIG. 52 can have a stent-like body made from Nitinol or any other suitable material which can self-expand or be balloon expandable to an approximately spherical or elongated spherical shape. The body of the implant can be covered uniformly or otherwise with small barbs or cleats (or other tissue anchors). The implant device 1224 shown in FIG. 53 can have a woven wire body, which can be made from Nitinol or any other suitable material, and which can be configured to expand to an approximately spherical or elongated spherical shape. The body of the implant device 1224 can be covered uniformly or otherwise with small barbs or cleats (or other tissue anchors).

Figure 54:
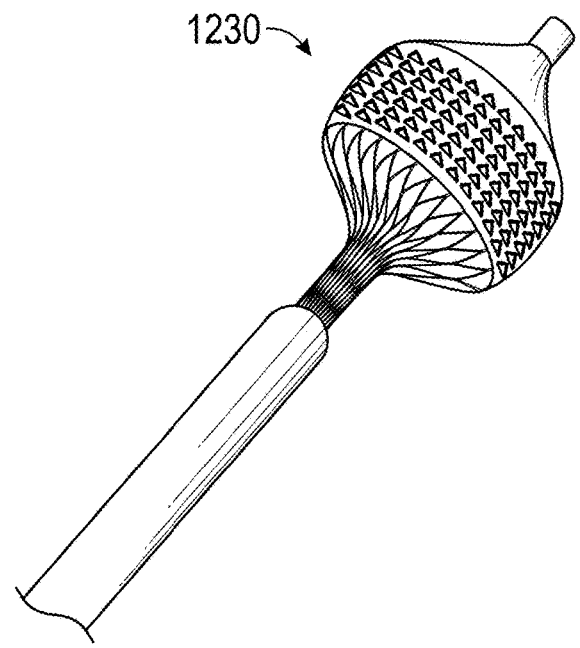
FIG. 54 shows another embodiment of a contact member that can be used with any treatment system embodiments disclosed herein.

FIG. 54 shows another embodiment of an implant device 1230 which can expand (or be expanded) to an approximately spherical or elongated spherical shape. For example and without limitation, the implant device 1230 can be configured to cover an inflatable balloon that can be inflated to expand the implant device 1230 into contact with the tissue of the LAA when the implant device 1230 is in a desired position within the LAA. The implant body 1230 covered with small barbs or cleats or other tissue anchors.

Figure 55:
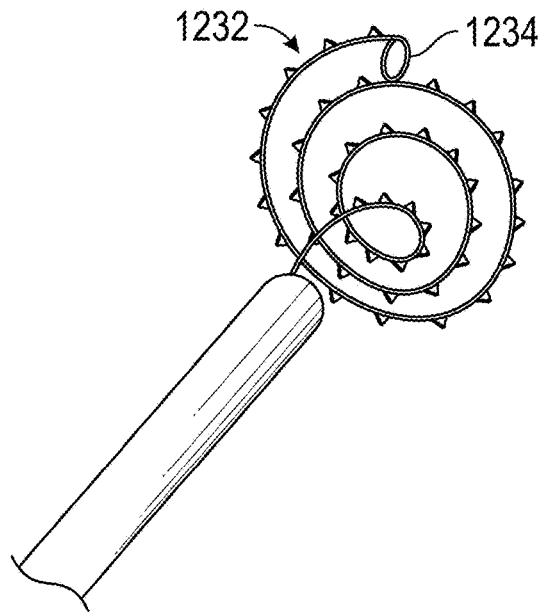
FIG. 55 shows another embodiment of a contact member that can be used with any treatment system embodiments disclosed herein.

FIG. 55 shows another embodiment of an implant device 1232 that can be used with any of the treatment system embodiments disclosed herein. In some embodiments, the implant device 1232 can have spiral shaped body at least when in a second, expanded state that can be used to exert the torque and twisting effect on the LAA. The implant device 1232 can be made from Nitinol, and can be covered with or have a plurality of small barbs, cleats, or other tissue anchors. The implant device 1232 can be self-expanding and can have a half-dome shape when in the second state. In some embodiments, the implant device 1232 can have a rounded end 1234 that can be approximately the same size as an internal lumen of the delivery system, or can be smaller, or larger and expandable.

Figures 56A, 56B:
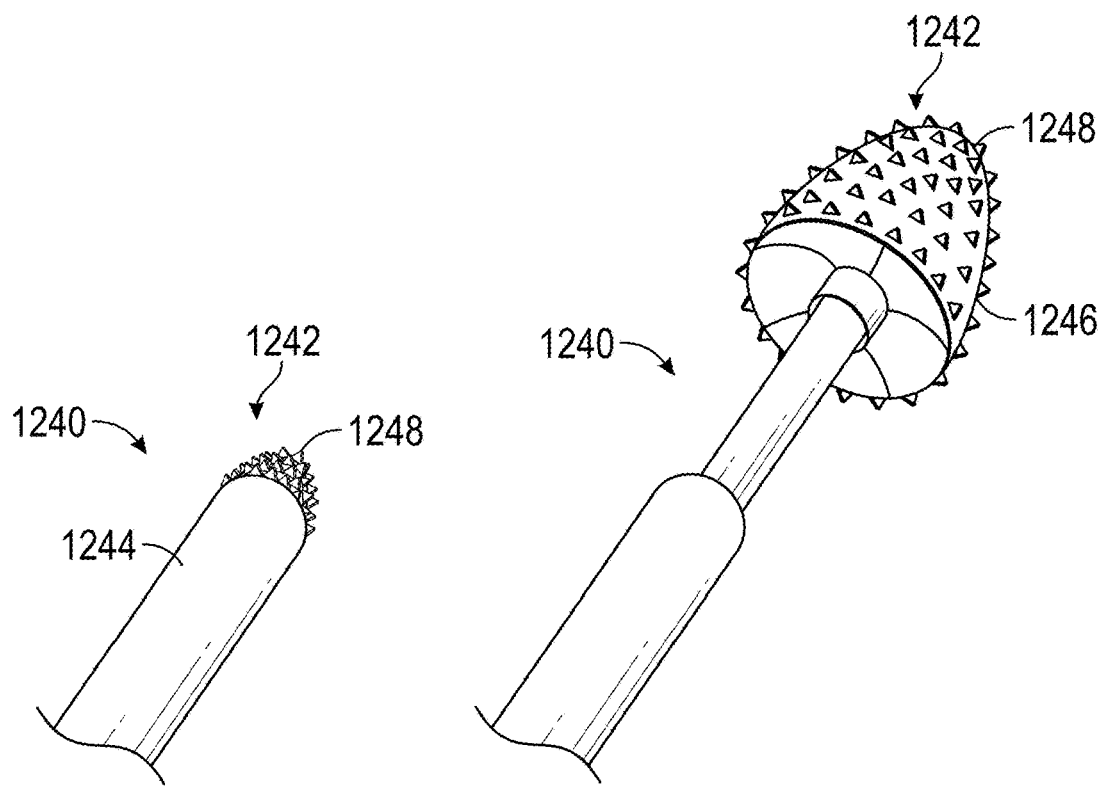
FIGS. 56A-56B show another embodiment of a contact member that can be used with any treatment system embodiments disclosed herein.
Figures 57A, 57B:
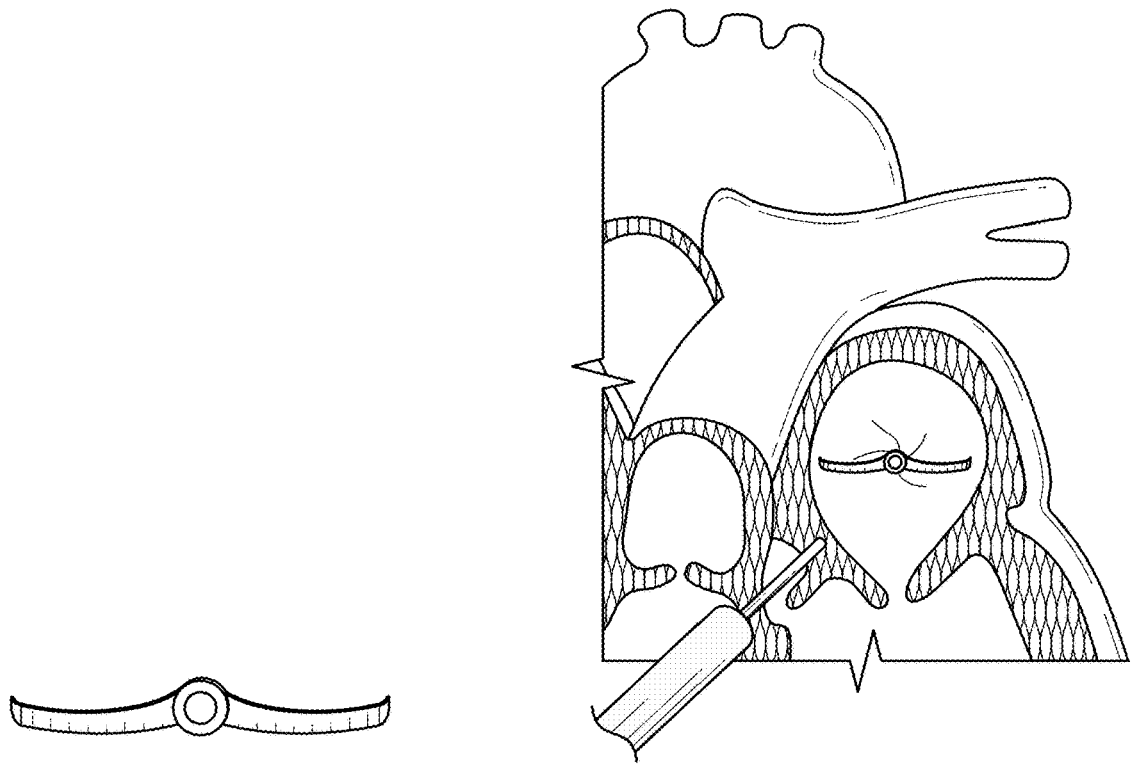
FIGS. 57A-57B show another embodiment of a securing element that can be used with any treatment system embodiments disclosed herein.

FIGS. 56A-56B show an embodiment of treatment system 1240 having an implant device 1242, with the implant device 1242 being mostly contained with a catheter body

1244 of the treatment system 1240 in FIG. 56A, and at least a contact member 1246 of the implant device 1242 being in a second, expanded state in FIG. 56B. The contact member 1246 can have a plurality of barbs or anchor members about an outside surface thereof, and can be configured to expand to an approximately spherical or elongated spherical shape. The contact member 1246 can be self-expanding, or mechanically expandable, and can have a half-dome shape with a rounded distal end portion 1248. In some embodiments, the rounded end portion 1248 can be approximately the same size as an internal lumen of the delivery system, or can be smaller, or larger and expandable.

FIGS. 57-61 show additional different embodiments of anchoring elements or securing elements that can be used with any of the other components of the implant device embodiments disclosed herein. FIG. 57A shows an embodiment of a double arm securing element. FIG. 57B shows the double arm securing element of FIG. 57A being advanced into the tissue of the LA and/or LAA adjacent to the ostium of the LAA that has constricted around a body portion of the implant device.

Figure 58A:
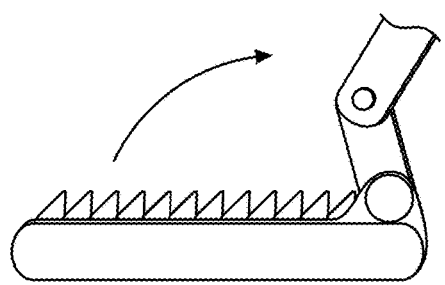
FIGS. 58A-58B show another embodiment of a securing element that can be used with any treatment system embodiments disclosed herein.
Figure 58B:
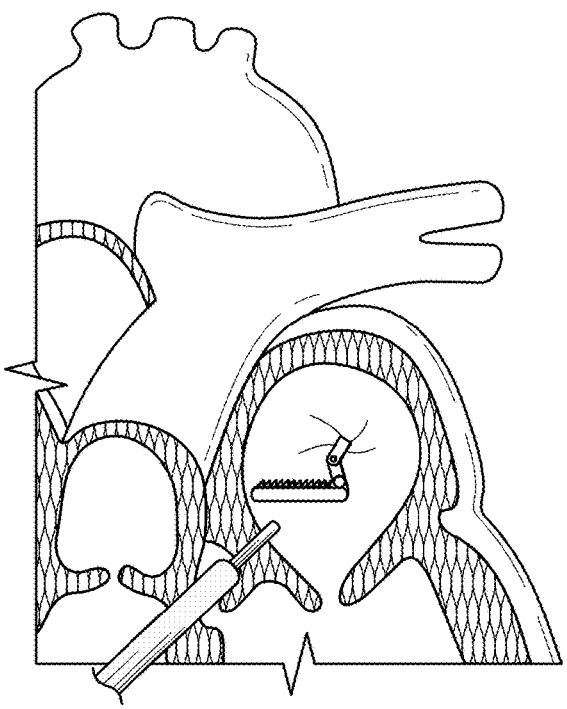
Figure 59A:
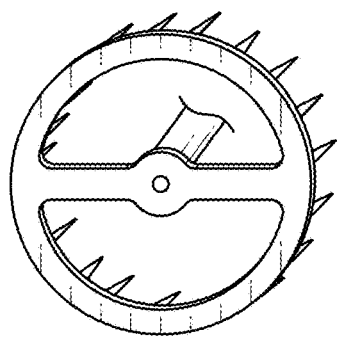
FIGS. 59A-59B show another embodiment of a securing element that can be used with any treatment system embodiments disclosed herein.
Figure 59B:
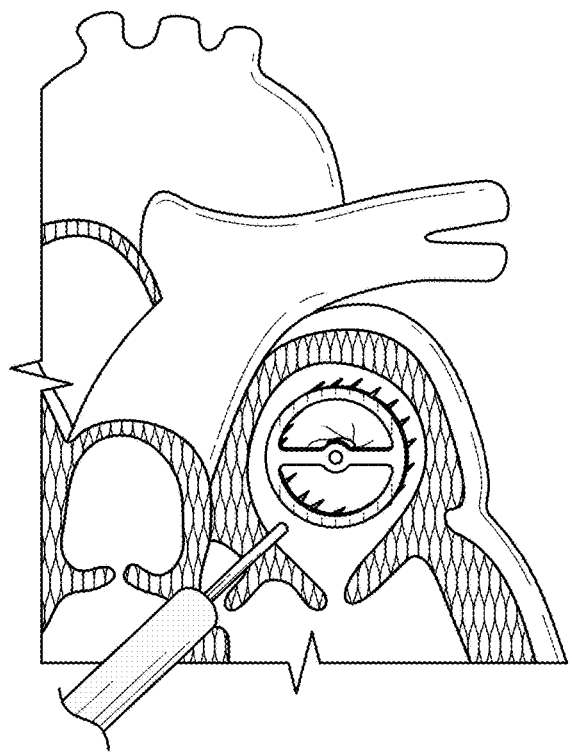

FIG. 58A shows an embodiment of a single folding clip anchor or securing element. FIG. 58B shows the single arm securing element of FIG. 58A being rotated against or clipped against the tissue of the LA and/or LAA adjacent to the ostium of the LAA that has constricted around a body portion of the implant device. In any embodiments, the securing element can be biased to remain in the secured or locked position. FIG. 59A shown an embodiment of a round disk anchor or securing element. FIG. 59B shows the round disk securing element of FIG. 59A being advanced toward the tissue of the LA and/or LAA adjacent to the ostium of the LAA that has constricted around a body portion of the implant device so that one or more tissue anchors of the securing element of FIG. 59A can engage with and/or penetrate into the tissue of the LA and/or LAA adjacent to the ostium of the LAA.

Figure 60A:
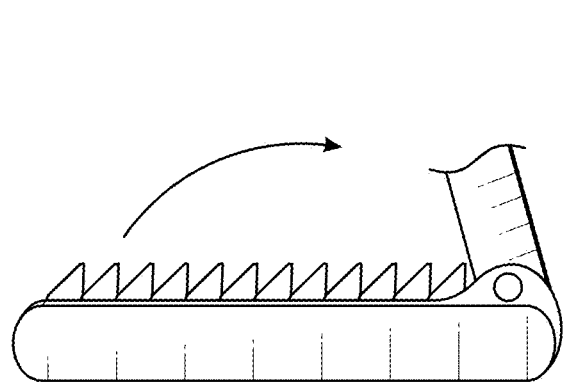
FIGS. 60A-60B show another embodiment of a securing element that can be used with any treatment system embodiments disclosed herein.
Figure 60B:
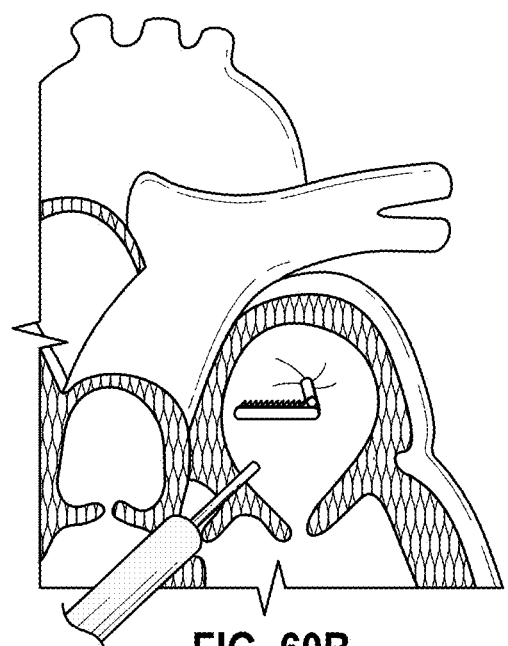
Figure 61A:
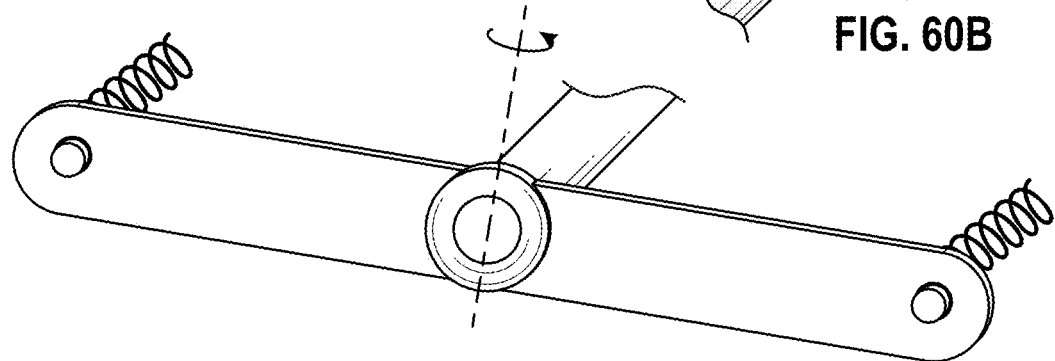
FIGS. 61A-61B show another embodiment of a securing element that can be used with any treatment system embodiments disclosed herein.
Figure 61B:
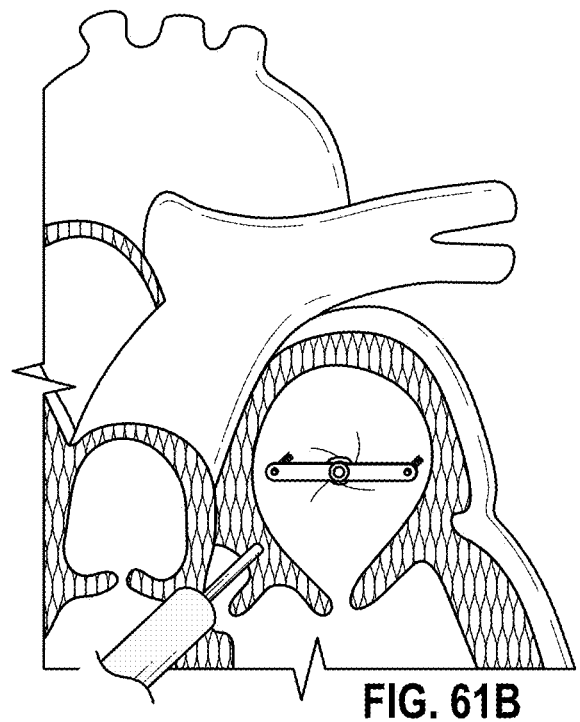

FIG. 60A shows an embodiment of a single folding clip anchor or securing element with a helical or screw type tissue anchor that can be used to engage with and/or penetrate into the tissue of the LA and/or LAA adjacent to the ostium of the LAA that has constricted around a body portion of the implant device. FIG. 60B shows the single folding clip anchor or securing element of FIG. 60A being rotated against or clipped against the tissue of the LA and/or LAA adjacent to the ostium of the LAA that has constricted around a body portion of the implant device. In any embodiments, the securing element can be biased to remain in the secured or locked position. FIG. 61A shows a double arm securing element with two helical or screw type tissue anchors. FIG. 61B shows the double arm securing element of FIG. 61A being rotated against the tissue of the LA and/or LAA adjacent to the ostium of the LAA that has constricted around a body portion of the implant device so that the tissue anchors on the arms can engage with and/or penetrate into the tissue. Both arms of the securing element of FIG. 61A-61B can collapse toward a body portion or axial centerline of the securing element, and can be configured to automatically deploy when extended past a distal end of the delivery catheter.

Figure 62A:
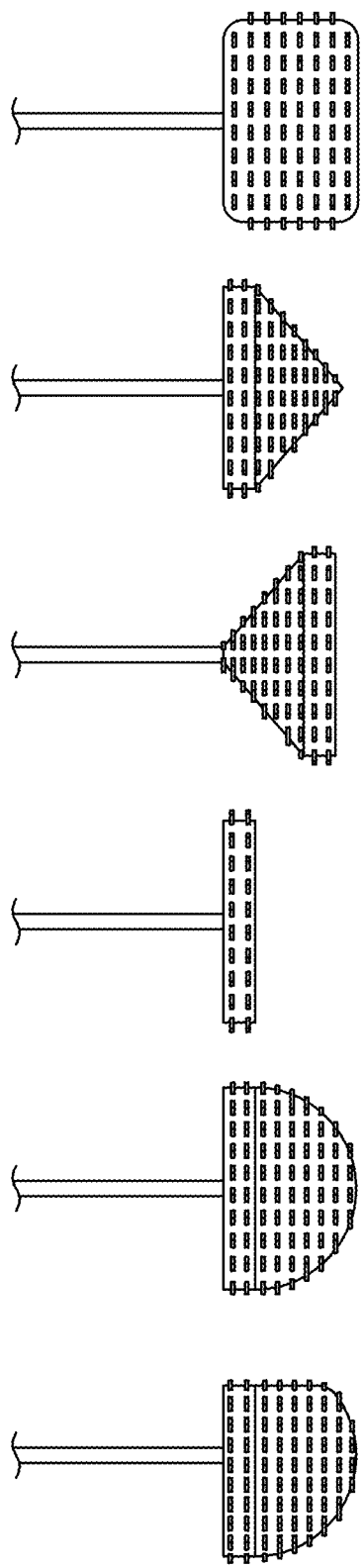
FIGS. 62A-62B show additional embodiments of contact members that can be used with any treatment system embodiments disclosed herein.
Figure 62B:
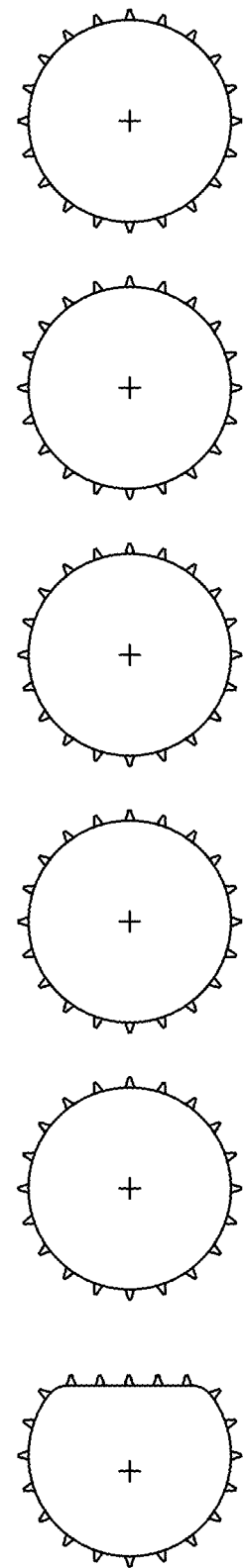
Figure 63:
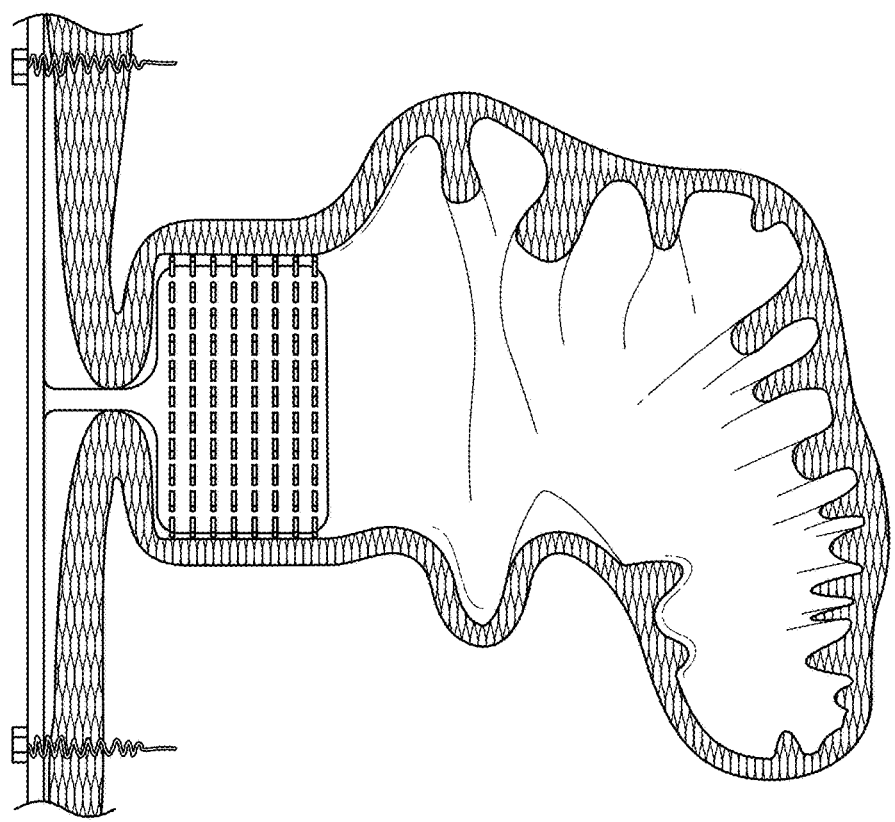
FIG. 63 shows a side view of an embodiment of a contact member.

FIGS. 62A-62B show side view and end views of different embodiments of contact member that can be deployed within the LAA to engage the tissue of the LAA so as to cause the LAA to twist when a torque is applied to the contact member. FIGS. 62A-62B show embodiments of contact members having cylindrical or thick disc shaped body portions, spherical shaped body portions, conical shaped body portions, and semi-spherical and/or half-spherical shaped body portions that are configured to better engage or couple with LAA tissue. Any of the embodiments of the contact members shown in FIGS. 62A-62B can have a plurality of barbs, micro-barbs, or other tissue anchors on an outside surface thereof. Additionally, any of the embodiments of the contact members shown in FIGS. 62A-62B can have outside surfaces that are uniformly covered with barbs, micro-barbs, or other tissue anchors. Further, any of the embodiments of the body portions disclosed herein, including without limitation the half-sphere shaped body portion shown in FIGS. 62A-62B, can have a flat area on one portion thereof to allow for a lower profile. FIG. 63 shows a side view of an embodiment of a contact member expanded against a tissue surface of the LAA, after a torque has been applied to the contact member that has caused a constriction of the tissue of the LA/LAA around a portion of the body of the implant device. FIG. 63 also shows the tissue anchors of the implant device advanced into the tissue of the LA/LAA to secure the LAA in the second position.

Additionally, any embodiment of the implant disclosed herein can have drug coatings, fabric or other at least substantially impermeable coverings (such as and similar to, without limitation, cover member 121 described above), electrical contacts to eliminate the conduction of electrical signals causing Afib, or other features to improve the performance of the implant. Some embodiments of the implant can be transseptally delivered via catheter and a disconnectable element between the implant element and the delivery system which would allow for permanent disconnection and therefore permanent implantation of the implant. Additionally, in any embodiments disclosed herein, the implant can be delivered without the use of a catheter, such as surgically, or otherwise.

Some embodiments include a device for closing or occluding an LAA, having an expandable implant that is configured to move between a first state in which the implant is substantially collapsed and a second state in which the implant is expanded, and a catheter configured to advance the implant into the left atrial appendage. The implant can be advanced into the LAA when the implant is in the first state and to cause the implant to move from the first state to the second state so that at least some of the plurality of tissue anchors engage an inner wall surface of the left atrial appendage after the implant has been advanced into the left atrial appendage. Any embodiments of the implant or insert can have a plurality of tissue anchors on an outside surface thereof.

Additionally, the catheter can be configured to rotate the implant in a first direction from a first rotational position to a second rotational position so that the implant can twist the wall of the left atrial appendage. As mentioned above, the catheter can rotate the implant from as little as a quarter turn to more than one turn. In any embodiments, the delivery device (which can be, in any embodiments disclosed herein, a catheter or can be any other suitable deployment or surgical device or system) can be configured such that a user can rotate the implant as many times as is necessary or desired to close, occlude, or collapse the LAA on itself or about an outside surface of the implant.

Any embodiments of the implant can be self-expandable such that the implant automatically expands when a restraint is removed from the implant, such as when the implant automatically expands when the implant is advanced past a distal end of an outer sleeve of the catheter. The implant can be biased to remain in an expanded state after deployment into the left atrial appendage.

Additionally, any embodiments of the implant or systems disclosed herein can be configured such that the implant can engage or automatically engage with a tissue or tissue surface when rotated or turned in one (or a first) direction. The implant of any embodiments disclosed herein can also be configured to disengage with any tissue that it is engaged with when turned in a second direction (the second direction being opposite to the first direction). In this embodiment, a user can engage the tissue or wall surface of the LAA by rotating the implant in a first direction, and disengage (if needed for any reason, including without limitation repositioning the implant) by rotating the implant in a second direction, the second direction being opposite to the first direction.

In any embodiments, as has been described, the implant can be configured to prevent the contact member from rotating back to the first rotational position after the contact member has been fully deployed. For example, as described above, any embodiments of the implant can have a securing element or anchoring element that can be configured to engage with tissue surrounding the LAA, such as the tissue of an internal wall of the heart outside of the left atrial appendage. Some embodiments of the implant can have a securing element having a plurality of tissue anchors configured to engage with an internal wall of the heart adjacent to the left atrial appendage.

For example and without limitation, the implant of any device, apparatus, and method embodiments disclosed herein can include a securing element configured to engage with an internal wall of the heart outside of or adjacent to the left atrial appendage. The securing element can have one or a plurality of arms and/or tissue anchors configured to engage with an internal wall of the heart adjacent to the left atrial appendage, or can be configured to be sutured to or otherwise coupled with an internal wall of the heart adjacent to the left atrial appendage. In any embodiments, the implant can be configured to prevent or inhibit counter-rotation of the contact member or other portions of the implant back to the first rotational position after the contact member or other portion(s) of the implant has been fully deployed. In any embodiments, the implant can be configured to rotate or permit rotation of the contact member in a first direction from the first rotational position to the second rotational position, and to prevent or inhibit rotation of the implant in a second direction after the contact member or other portion of the implant has been fully deployed, the second direction being opposite to the first direction.

Any embodiments disclosed herein can include an implant for deployment within a cavity or vessel, having an expandable body (which can, but is not required to, have any of the features or characteristics of the contact member), a plurality of tissue anchors on an outside surface of the expandable body configured to engage with an inner wall surface of the cavity or vessel, and an anchor element coupled with the expandable body configured to engage with a tissue surface adjacent to the inner wall surface of the cavity or vessel.

Some embodiments of methods of closing or occluding an LAA using any embodiments of the implants disclosed herein will now be described. The method or procedure can include advancing a deployment device having an implant having an expandable member or contact member into the patient's left atrium, moving or expanding a portion of the implant from a first state to a second state within the left atrial appendage, wherein the expandable member or contact member is substantially collapsed in the first state and expanded in the second state, engaging a wall portion on an inside of the left atrial appendage with the expandable member or contact member (which can, but is not required to have one or more tissue anchors on an outside surface thereof), rotating the expandable member or contact member from a first rotational position to a second rotational position to twist the wall portion on the inside of the left atrial appendage, and preventing the expandable member or contact member from rotating back to the first rotational position. Any portion of the implant, including but not limited to the expandable member or contact member, can be self-expanding, wherein moving the expandable member or contact member from the first state to the second state comprises advancing the expandable member or contact member out of a distal end of the deployment device.

Additionally, in any embodiments disclosed herein, engaging a wall portion on an inside of the left atrial appendage can include engaging a wall portion on an inside of the left atrial appendage with one or more tissue anchors positioned on an outside surface of the expandable member or contact member or other portion of the implant. Further, preventing the implant from rotating back to the first rotational position can include engaging a tissue wall outside of the left atrial appendage with an anchor element or securing element. In some embodiments, the anchor element or securing element can be rotationally fixed to the expandable member or contact member and/or other portion of the implant to prevent relative movement between the anchor element and the expandable member or contact member and/or other portion of the implant. Preventing the expandable member or contact member and/or other portion of the implant from rotating back to the first rotational position can include engaging a tissue wall of the heart with an anchor element or securing element, wherein the anchor element can be rotationally fixed relative to the implant and configured to prevent the expandable member or contact member and/or other portion of the implant from rotating back to the first rotational position, or engaging an internal wall of the heart outside of the left atrial appendage with an anchor element or securing element. In any embodiments, the anchor element or securing element can include a plurality of tissue anchors on at least one surface thereof, the tissue anchors configured to engage with the internal wall of the heart outside of the left atrial appendage.

In any embodiments disclosed herein, the implant can be configured to automatically rotate from the first rotational position to the second rotational position after the contact member and/or other portion of the implant is in the second state, or can be activated to self-rotate at any desired time. For example and without limitation, the implant could have a spring or other torsional member configured to rotate the contact member and/or other portion of the implant or other portion of the body of the implant upon release or activation of the spring, or could be configured to be pre-wound or pre-twisted when the implant or contact member and/or other portion of the implant is in a first state. The self-rotation or self-twisting could be done, for example, after the contact member and/or other portion of the implant has been secured to a wall portion surrounding the LAA, and after a portion of the implant has engaged with at least a portion of an inside wall surface of the LAA so that the rotation or twisting of a portion of the implant causes a twisting of the LAA, thereby causing the ostium of the LAA to close or substantially close.

Therefore, in any embodiments, the implant can be configured to automatically rotate or self-rotate from the first rotational position to the second rotational position upon a release of a restraint holding the implant in the first rotational position, or upon a triggering or actuation of the rotational mechanism, which can be a spring or other torsional member. In some embodiments, a shaft extending through the implant can be configured to be wound or rotated relative to a securing portion or base of the implant, or can have a spring around the shaft, so that a rotation of the shaft relative to the securing portion or base of the implant as a result of the release of the torsion in the shaft or the spring surrounding at least a portion of the shaft, can result in the twisting of the LAA.

In other embodiments, the implant can have a shaft or body portion that extends from a base, wherein the shaft can be rotated (either manually, by the catheter, or can be self-rotating) relative to the base from the first rotational position to the second rotational position, and wherein a ratchet mechanism or other securing mechanism can be used to secure the shaft or body portion in the second rotational position relative to the base. The base can be configured to engage with and be secured to a wall or tissue of the heart surrounding the LAA before the shaft or body portion engages an inner wall portion of the LAA and before the shaft or body portion is rotated to the second position.

Additionally, in any apparatus, implant device, method, or other embodiments disclosed herein, the second rotational position can be at least one-eighth or approximately one-eighth of a complete rotation (i.e., 45 degrees or approximately 45 degrees) relative to the first rotational position, one-quarter or approximately one-quarter of a complete rotation (i.e., 90 degrees or approximately 90 degrees) relative to the first rotational position, or at least one-half or approximately one-half of a complete rotation (i.e., 180 degrees or approximately 180 degrees) relative to the first rotational position, or wherein the second rotational position can be from one-eighth or approximately one-eighth of a complete rotation (i.e., 45 degrees or approximately 45 degrees) to one-half or approximately one-half of a complete rotation (i.e., 180 degrees or approximately 180 degrees) relative to the first rotational position. In any apparatus, implant device, method, or other embodiments disclosed herein, the second rotational position can be from one-quarter or approximately one-quarter of a complete rotation (i.e., 90 degrees or approximately 90 degrees) to one or more or approximately one or more complete rotations (i.e., 360 degrees or approximately 360 degrees or more) relative to the first rotational position, or from one-quarter or approximately one-quarter of a complete rotation (i.e., 90 degrees or approximately 90 degrees) to two, three, or more complete rotations or approximately one or more complete rotations (i.e., 360 degrees or approximately 360 degrees or more) relative to the first rotational position, one-eight or approximately one-eighth of a complete rotation (i.e., 45 degrees or approximately 45 degrees) to one, two, three, or more complete rotations or approximately one or more complete rotations (i.e., 360 degrees or approximately 360 degrees or more) relative to the first rotational position, or any value or ranges of values within any of the foregoing ranges. In any embodiments disclosed herein, the twisting movement or step can be accomplished by a torque catheter.

Further, in any apparatus, implant device, or method embodiments disclosed herein, the catheter can be configured to exert a torque on the implant to rotate the implant from the first rotational position until a threshold predetermined torque level is reached, or until the user decides to stop the rotation, whichever comes first. In some embodiments, the threshold predetermined torque level can be from 0.25 in-oz of torque or approximately 0.25 in-oz of torque to 10 in-oz of torque or approximately 10 in-oz of torque, or from 0.5 in-oz of torque or approximately 0.5 in-oz of torque to 5 in-oz of torque or approximately 5 in-oz of torque.

In any embodiments disclosed herein, without limitation, the contact member can have an outer diameter or size when in the first or collapsed state of from approximately 3 mm to approximately 8 mm (approximately 9 Fr to approximately 24 Fr), or from approximately 4 mm to approximately 6 mm, or of any values or ranges of values between any of the foregoing ranges, and/or a length (of the arm or strut members) from approximately 20 mm to approximately 60 mm, or from approximately 30 mm to approximately 50 mm, or of any values or ranges of values between any of the foregoing ranges. Further, in any embodiments disclosed herein, without limitation, the contact member can have an outer diameter or size when in the second or expanded state of from approximately 6 mm to approximately 14 mm (approximately 18 Fr to approximately 42 Fr), or of any values or ranges of values between any of the foregoing ranges, or from approximately 9 mm to approximately 11 mm, or of any values or ranges of values between any of the foregoing ranges, and/or a length (of the arm or strut members) from approximately 10 mm to approximately 40 mm, or from approximately 20 mm to approximately 30 mm, or of any values or ranges of values between any of the foregoing ranges.

In any embodiments disclosed herein, without limitation, the securing element can have an outer diameter or size when in the first or collapsed state of from approximately 3 mm to approximately 8 mm (approximately 9 Fr to approximately 24 Fr), or of any values or ranges of values between any of the foregoing ranges, or from approximately 4 mm to approximately 6 mm, and/or a length from approximately 4 mm to approximately 12 mm, or from approximately 6 mm to approximately 8 mm, or of any values or ranges of values between any of the foregoing ranges. Further, in any embodiments disclosed herein, without limitation, the securing element can have an outer diameter or size when in the second or expanded state of from approximately 6 mm to approximately 18 mm (approximately 18 Fr to approximately 54 Fr), or from approximately 9 mm to approximately 15 mm, or of any values or ranges of values between any of the foregoing ranges, and/or a length (of the arm or strut members) from approximately 4 mm to approximately 8 mm, or from approximately 4 mm to approximately 6 mm, or of any values or ranges of values between any of the foregoing ranges. Further, any embodiments of the securing elements disclosed herein can have tissue engaging tips or portions (i.e., the portion configured to penetrate or engage with the tissue) having a length of from approximately 0.2 mm to approximately 2 mm, or from approximately 0.5 mm to approximately 1 mm, or of any values or ranges of values between any of the foregoing ranges.

Some embodiments of the closure devices disclosed herein can be configured to more closely mimic the surgical type closure as compared to the conventional devices described above where the LAA in not plugged but closed with limited exposure of the device in the left atrium.

Figure 64:
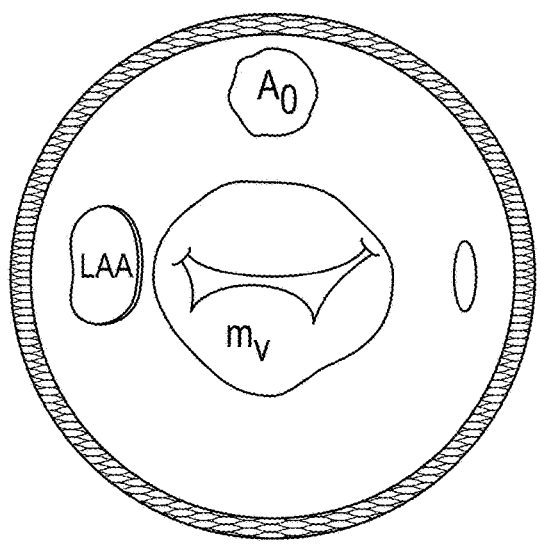
FIG. 64 shows a view of the left atrium (LA).
Figure 65:
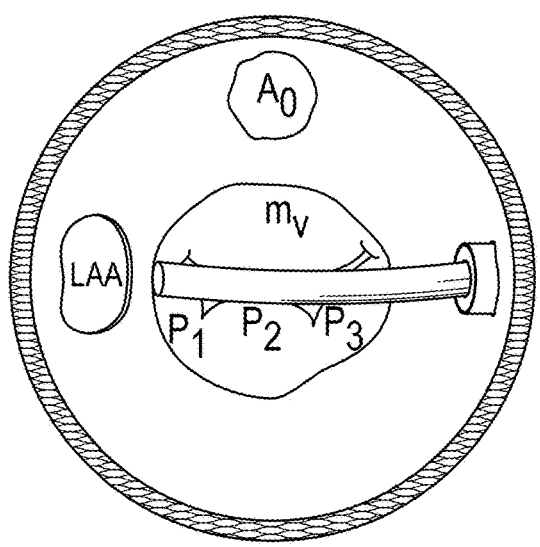
FIG. 65 shows an access path to the LAA.
Figure 67A:
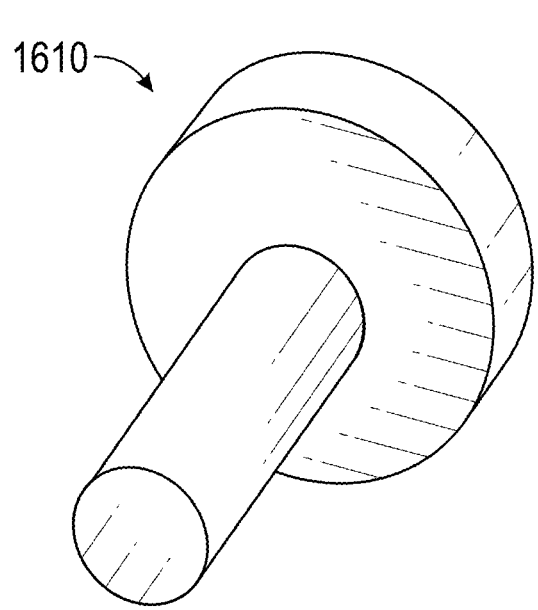
FIGS. 67A-67D show various embodiments of anchor members.
Figure 67B:
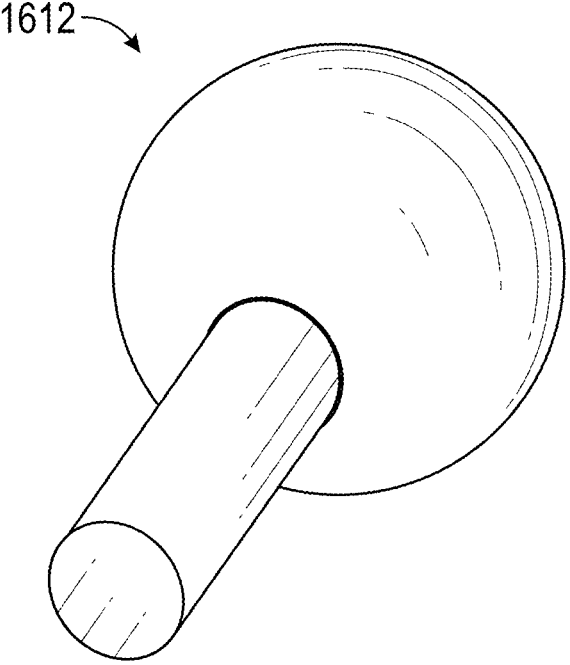
Figure 67C:
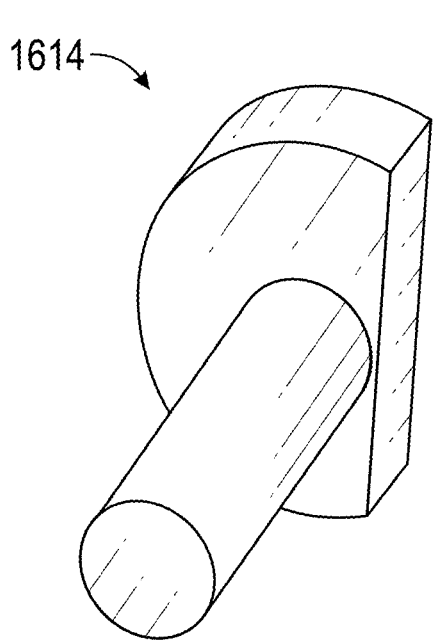
Figure 67D:
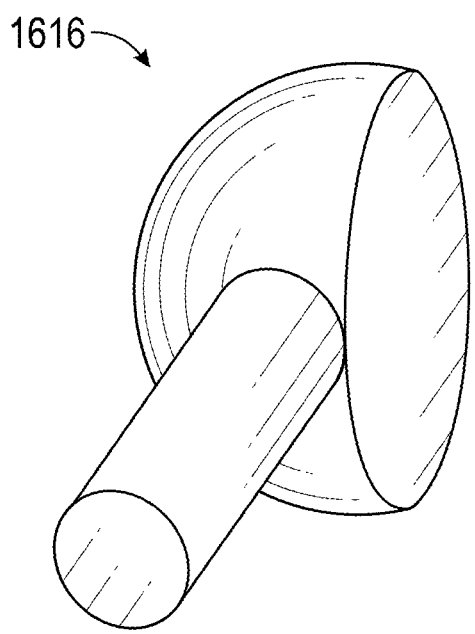
Figure 68A:
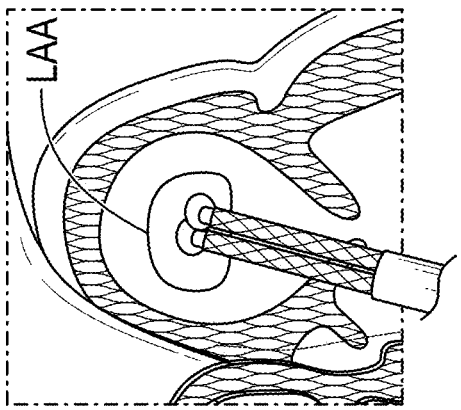
FIGS. 68A-68F show another embodiment of an implant and a method for occluding the LAA.
Figure 68B:
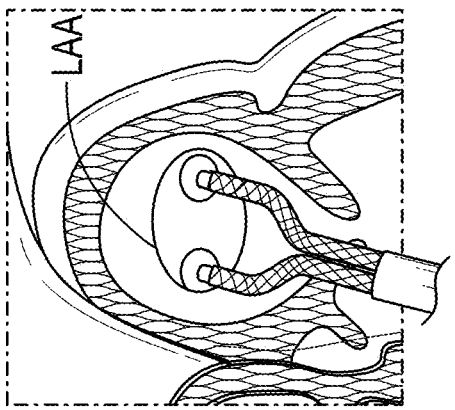
Figure 68C:
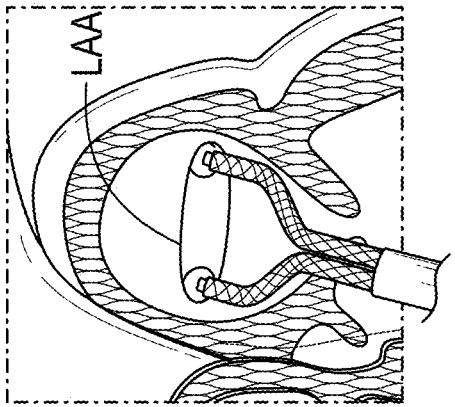
Figure 68D:
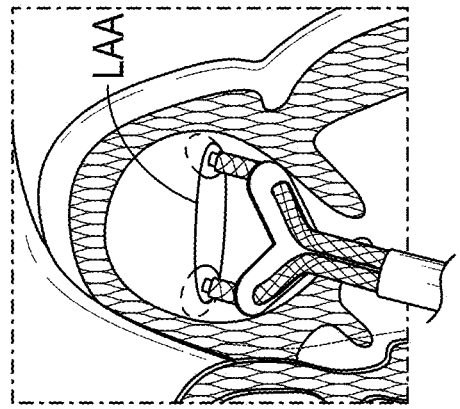
Figure 68E:
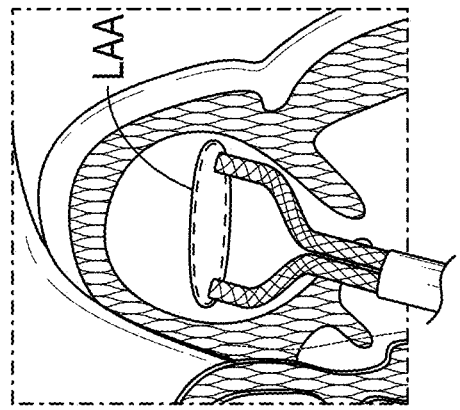
Figure 68F:
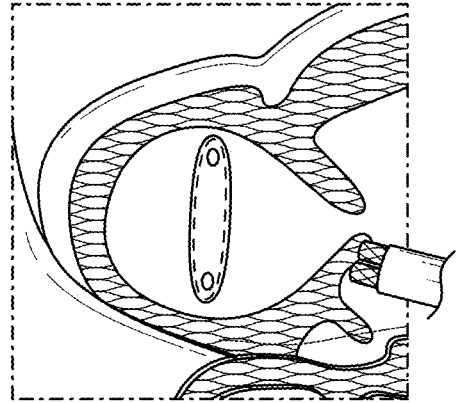
Figure 69A:
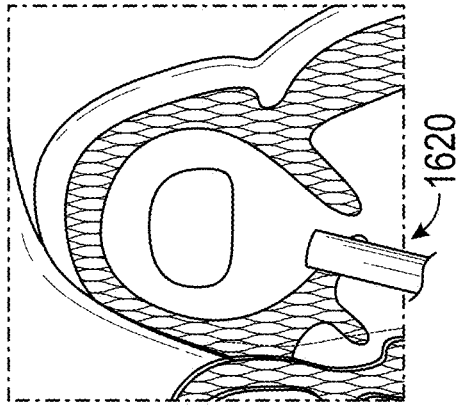
FIGS. 69A-69G show another embodiment of a device and a method for occluding the LAA.
Figure 69B:
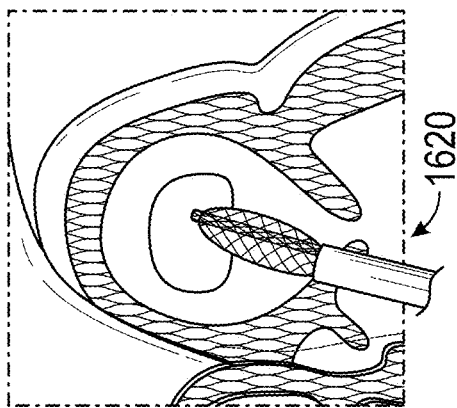
Figure 69C:
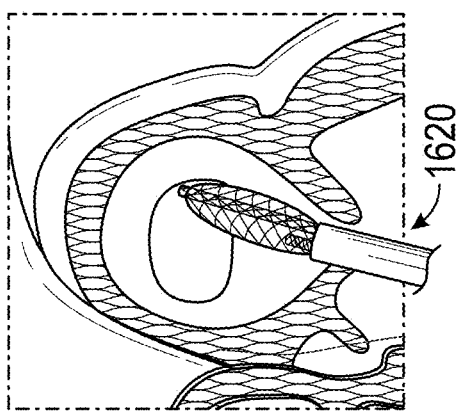
Figure 69D:
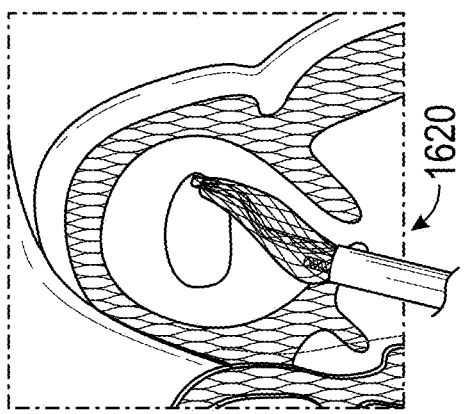
Figure 69E:
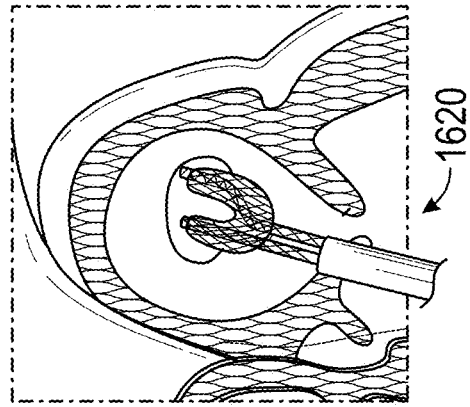
Figure 69F:
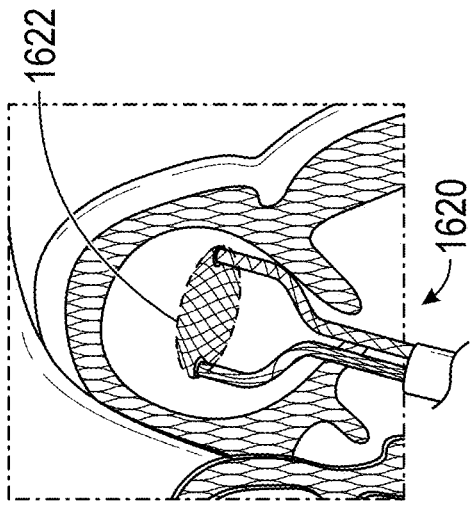
Figure 69G:
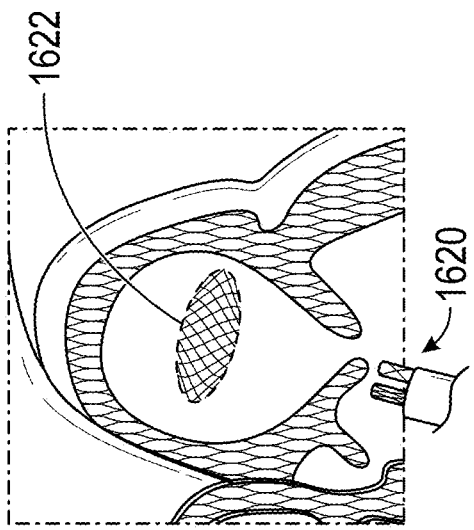
Figure 71D:
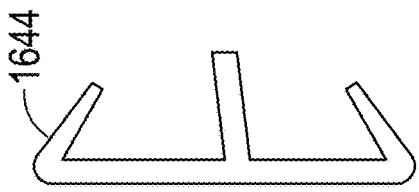
FIGS. 71A-71G show some details of some embodiments of a staple that can be used with any device disclosed herein for occluding the LAA.
Figure 71C:
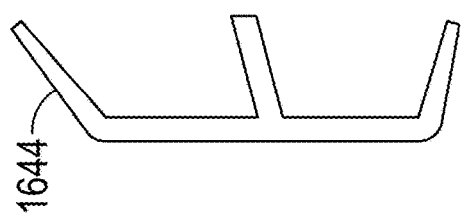
Figure 71B:
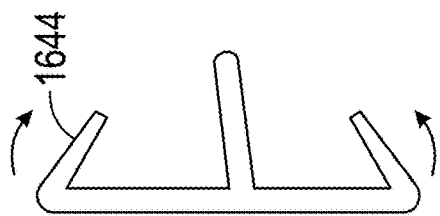
Figure 71A:
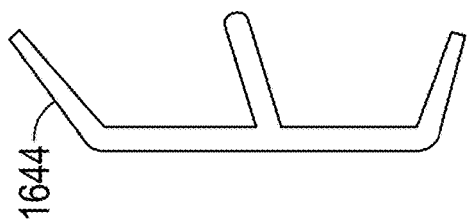
Figure 71G:
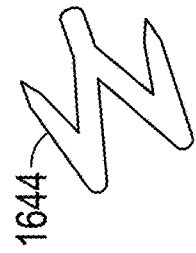
Figure 71F:
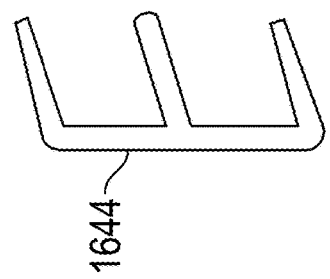
Figure 71E:
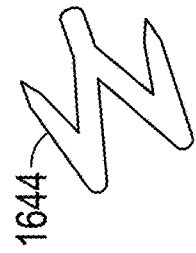
Figure 72A:
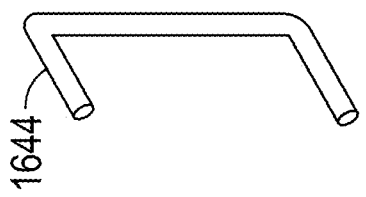
FIGS. 72A-72F show an embodiment of a device and a method for forming a staple.
Figure 72B:
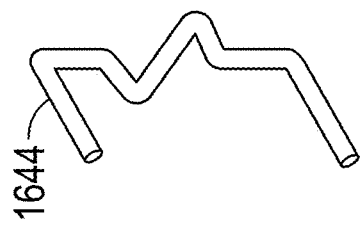
Figure 72C:
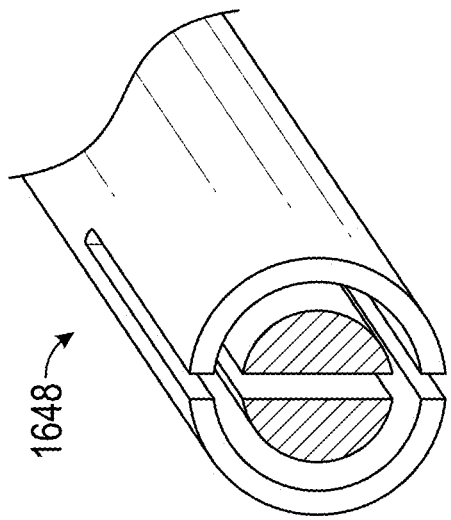
Figure 72D:
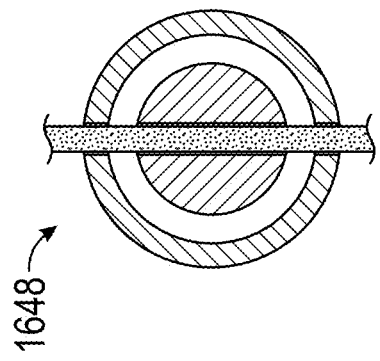
Figure 72E:
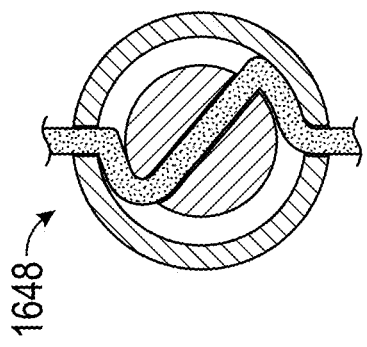
Figure 72F:
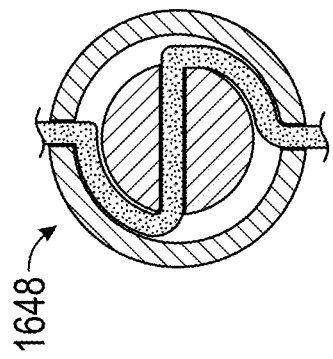

Entering through the venous system via femoral vein and a transseptal puncture into the left atrium, the access of the LAA (LAA) can be gained. Imaging could use both fluoroscopy and echo (TEE, ICE or transthoracic), the size, position, and location of the LAA for entry of the prosthesis for closure. FIGS. 1, 64, and 65 show at least a portion of a path from the access site to the LAA.

Some embodiments of the implant devices disclosed herein have two anchors that can be placed in the lateral ends of the LAA ostium and an oval mesh cover that can be attached to the two anchors. Steps of deployment and implantation for any embodiments disclosed herein can include: inserting catheter spreader into lateral ends of LAA ostium; placing anchors into appropriate positions; deploying mesh cover(s) along spreading catheters to anchors; and/or attaching the mesh cover(s) to the anchors.

In some embodiments, the mesh cover can be configured to maintain the stretched position of the anchors and cover the ostium of the LAA. An embodiment of an implant device 1600 of this design is shown in FIGS. 66A-66D and FIGS. 68A-68F. The lateral anchors 1601 of the implant device 1600 can, in some embodiments, have a larger backing which can encapsulate the atrial wall between this backing and the mesh 1602 later attached. Additional embodiments of anchors 1610, 1612, 1614, and 1616 are shown in FIGS. 67A-67D. Alternatively, the anchors can be connected and separated via a hinge type mechanism, therefore not requiring the mesh cover to provide that structural separation.

FIGS. 69A-69G show another embodiment of a device 1620 and a method for deploying an implant 1622 with one end coming out first and anchoring before the other end comes out. Some embodiments of this method and device 1620 have the following characteristics, including without limitation: (1) there may be more room to back the mesh by staggering the second anchoring catheter behind it in the delivery system, and (2) there may be more precision in the placement of the lateral anchors when they are positioned one at a time. Another option would be to have the anchors lock in position with a barb, spear, or corkscrew type mechanism, further securing their attachment to the atrial wall at the lateral ends of the LAA ostium.

FIGS. 70A-70F show another embodiment of a device 1640 and a method of deployment of such device, which can including deploying a plurality of staples, backing staples, clips, or other fasteners 1644 (collectively referred to herein as staples) in a sequential fashion after modifying the shape of the LAA ostium to a narrow oval. Some embodiments can include a series of custom staples 1644 which can be placed all along the LAA ostium after the shape of the ostium of the LAA has been modified to a narrow oval. These staples 1644 can have a backing on them which can provide the reaction force for the traumatic ends of the staple to piece the tissue and pull the top and bottom of the atrial wall together, closing the LAA ostium in a lateral fashion. The backing can also provide a large sealing area inside the LAA, something which a traditional staple is not capable of. As mentioned, FIGS. 70A-70F shows the deployment of the backing staples 1644 in a sequential fashion after modifying the shape of the LAA ostium to a narrow oval. When the staples are engaged and closed, they further bring the two ends of the tissue together, closing the LAA ostium.

In any embodiments disclosed herein, an implant can be deployed using any combination of the following steps: inserting catheter spreader into lateral ends of LAA ostium; applying one or more staples at one end of stretched LAA (or on both sides); removing catheter spreader from LAA ostium (or just one side); re-inserting catheter spreader into LAA ostium, between the last backing staple and far end; applying backing staple at one end of stretched LAA; and/or repeating any or all of the last three steps until LAA ostium is occluded or closed.

FIGS. 71A-71G show some details of some embodiments of a staple 1644 (which can be a backing staple). Any embodiments of the staple 1644 backing feature could be any shape and does not necessarily need to be made out of metal, or the same material as the staple. FIGS. 71A-71G and 72A-72F illustrate additional details of a device 1648 that would place a "z-bend" in the backing staple 1644 to further bring the two ends of atrial wall together. FIGS. 72A-72F also show an embodiment of a catheter mechanism device and a method to create this "z-bend" on the staple body, which would shorten the distance between the two prongs of the staple.

Figure 73A:
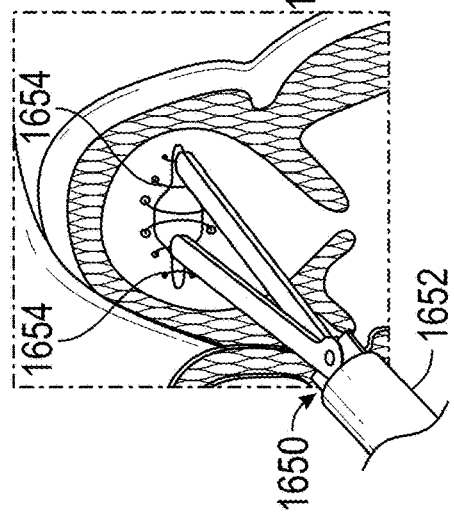
FIGS. 73A-73B show an embodiment of a device and a method for occluding the LAA.
Figure 73B:
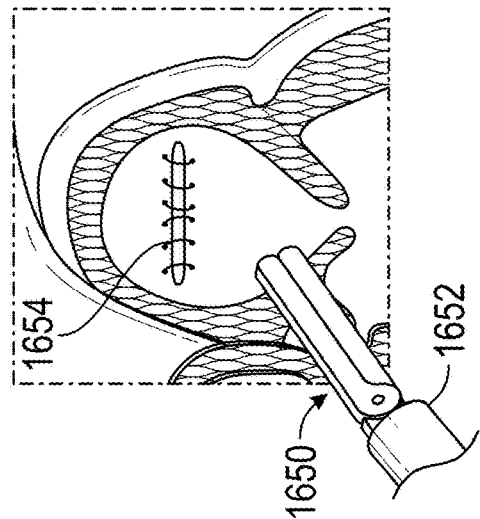
Figure 74A:
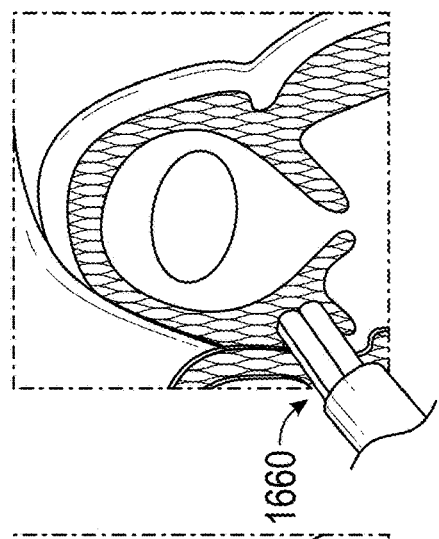
FIGS. 74A-74E show an embodiments of a device and a method for occluding the LAA.
Figure 74E:
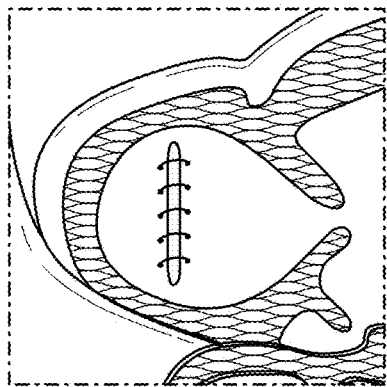
Figure 74D:
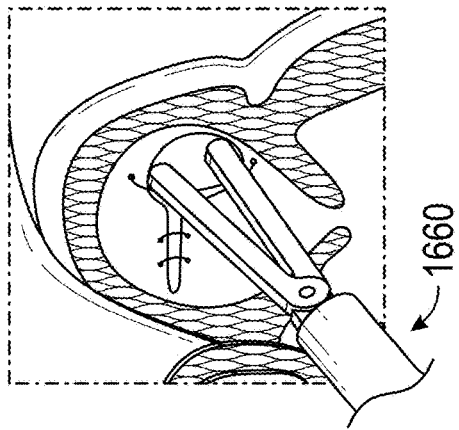
Figure 74C:
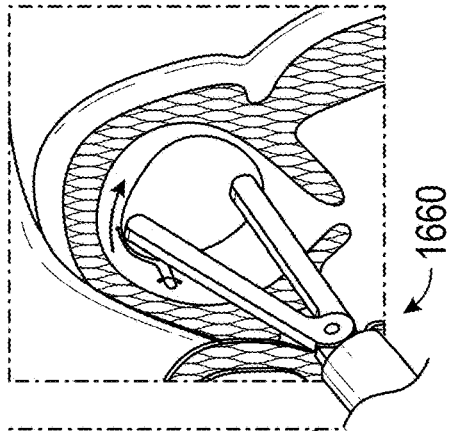
Figure 74B:
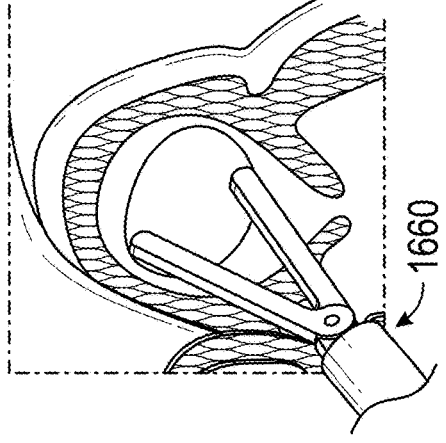
Figures 75A, 75B, 75C, 75D, 75E:
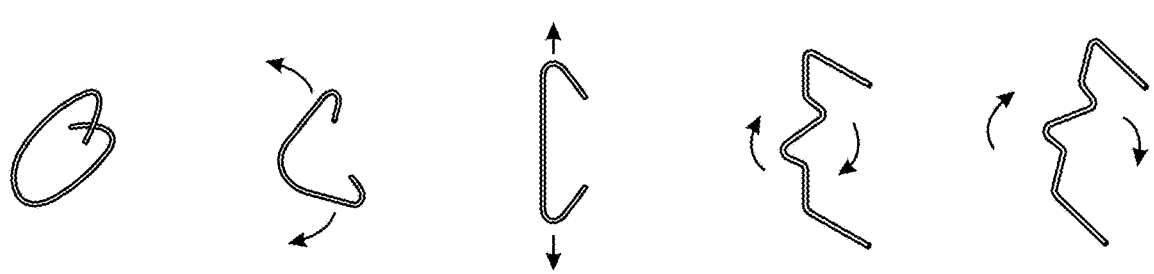
FIGS. 75A-75E show an embodiment of some stages of forming an embodiment of a staple that can be used with any of the devices or methods disclosed herein.
Figure 76A:
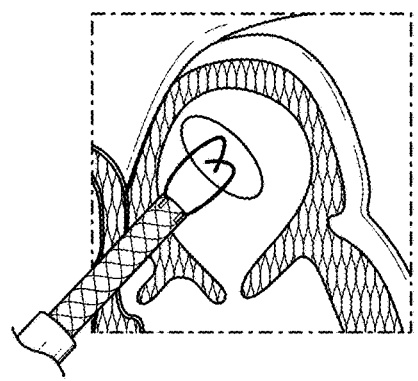
FIGS. 76A-76E show an embodiments of a device and a method for occluding the LAA.
Figure 76B:
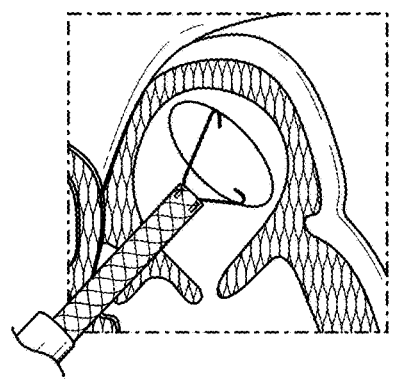
Figure 76C:
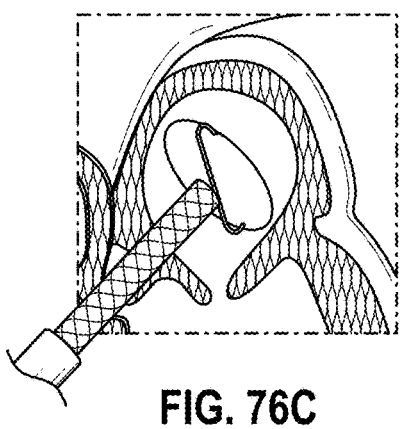
Figure 76D:
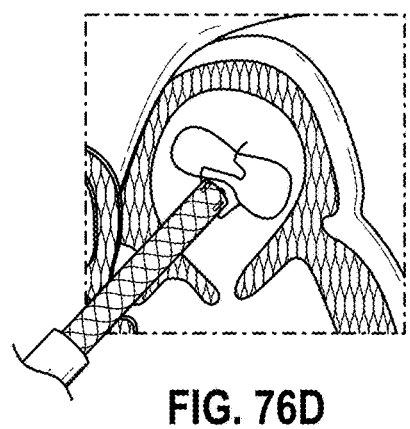
Figure 76E:
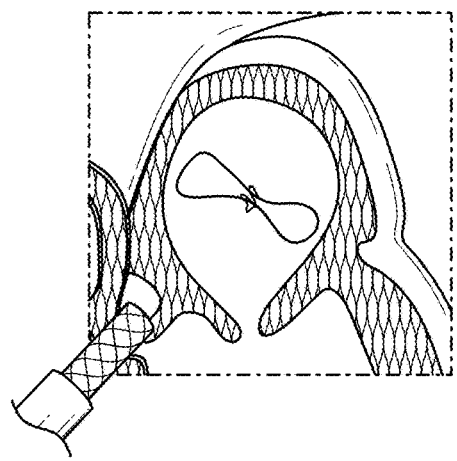
Figure 80A:
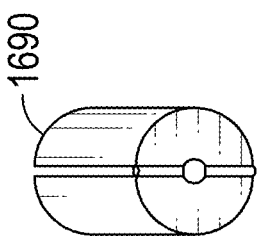
FIGS. 80A-80C show an embodiment of a device for treating the LAA.
Figure 80B:
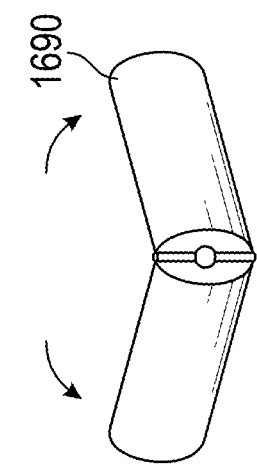
Figure 80C:
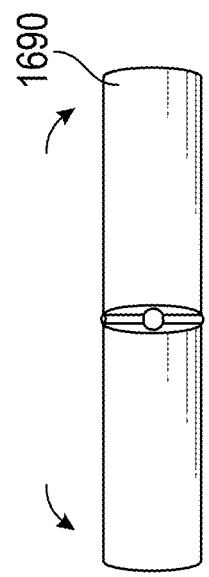
Figure 81A:
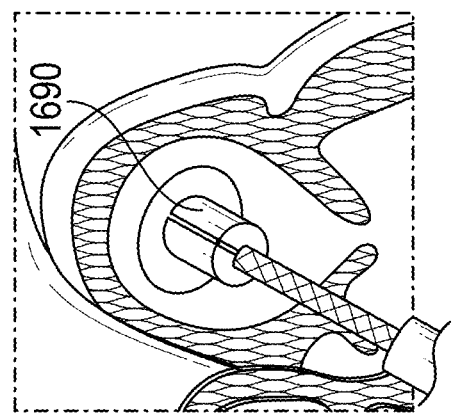
FIGS. 81A-81C show an embodiment of a method for using the device shown in FIGS. 80A-80C for occluding the LAA.
Figure 81B:
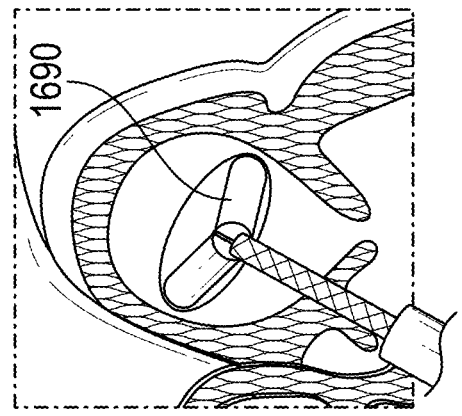
Figure 81C:
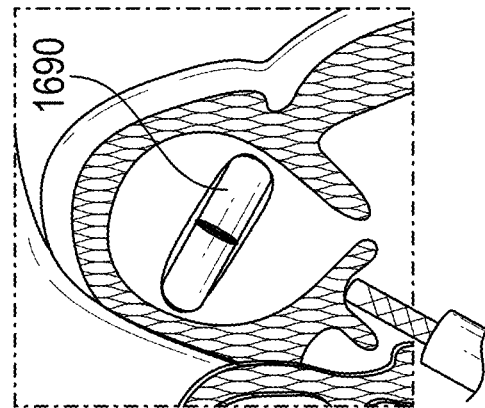
Figure 82A:
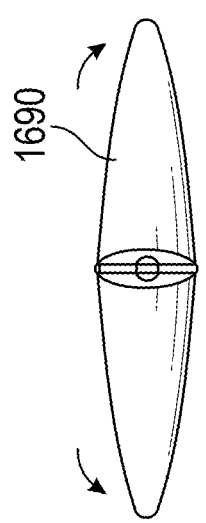
FIGS. 82A-82C show an embodiment of a device for treating the LAA.
Figure 82B:
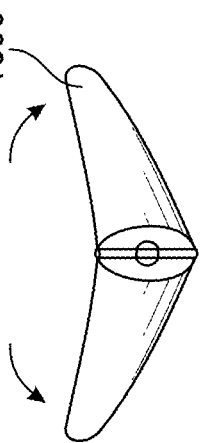
Figure 82C:
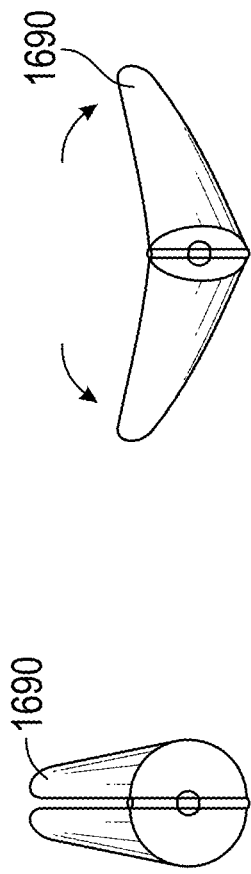
Figure 83A:
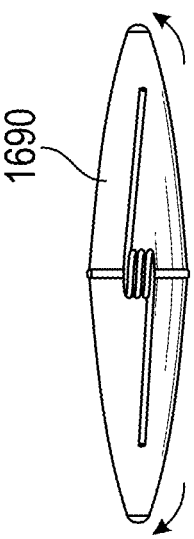
FIGS. 83A-83C show an embodiment of a device for treating the LAA.
Figure 83B:
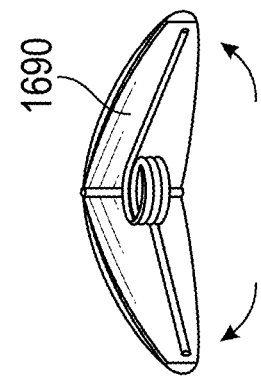
Figure 83C:
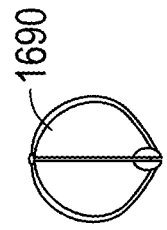
Figure 84A:
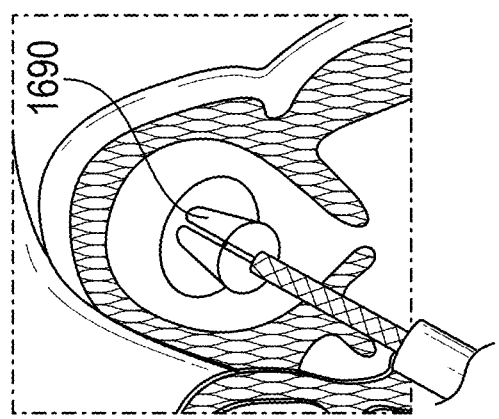
FIGS. 84A-84C show an embodiment of a method for using the device shown in FIGS. 83A-83C for occluding the LAA.
Figure 84B:
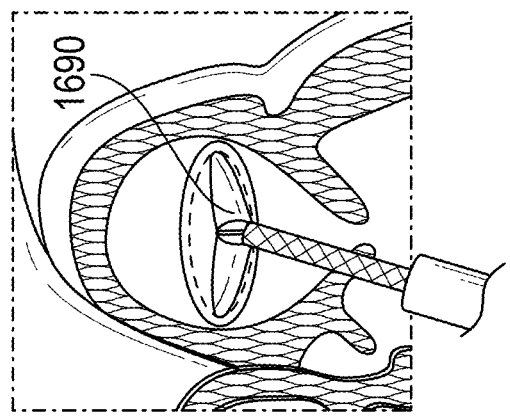
Figure 84C:
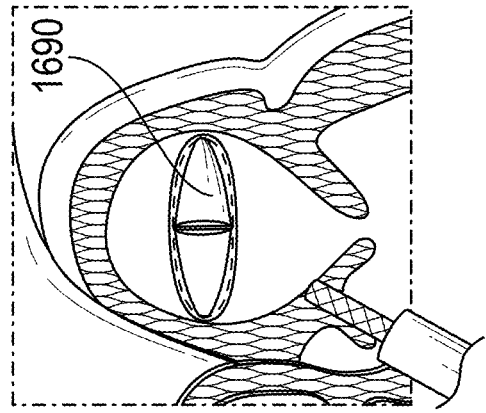

Another embodiment of an implant device and method can include a series of sutures or staples along the LAA ostium after the shape has been modified to a narrow oval, closing the LAA ostium in a lateral fashion. FIGS. 73A-73B show an example of a device 1650 and method for accomplishing that. The steps of deployment and implantation can include: inserting catheter spreader 1652 into lateral ends of LAA ostium; applying a stitch (or staple) 1654 along the inside edge of the spreader (on one or both sides); removing the catheter spreader from LAA ostium; re-inserting catheter spreader into LAA ostium, between the last stitches placed; applying a stitch along the inside edge of the spreader; and/or repeating last three steps until the LAA ostium is occluded or closed.

Another embodiment of an implant device 1660 and method can include a series of sutures or staples 1644 along the LAA ostium before the shape has been modified to a narrow oval, the placement and connection of the sutures are what modifies the shape to a narrow oval after tensioning, closing the LAA ostium in a lateral fashion. FIGS. 74A-74E show an embodiment of a device and method for accomplishing that. Some embodiments of a deployment and implantation method for such a device can include: inserting catheter spreader into middle of LAA ostium and spreading top-to-bottom; applying a stitch (or staple) along the edge of the spreader (on one or both sides); removing catheter spreader from LAA ostium; re-inserting catheter spreader into LAA ostium, between the last stitches placed and the lateral end; applying a stitch along the inside edge of the spreader; and/or repeating the last three steps until the LAA ostium is occluded or closed.

Any embodiments of the implant device and/or methods disclosed herein can include an implanting series of staples along the LAA ostium after the shape has been modified to a narrow oval, thereby closing the LAA ostium in a lateral fashion. FIGS. 75A-75E show an embodiment of some stages of forming of the staples 1670 (that can have any of the features, shapes, or other details of any of the other staple embodiments disclosed herein) from left to right as it would exit the catheter, be opened up and prepared for tissue engagement, applied and anchored to the atrial wall tissue, and z-bent to bring the ends of the tissue together. FIGS. 72A-72F, above, show one embodiment of a method for forming the z-bend. In any embodiments disclosed herein, the steps of deployment and implantation can include (with reference to FIGS. 76A-76E): inserting catheter into middle of the LAA; extending catheter with attached folded staple; unfolding (open up) staple; advancing staple into tissue; folding or z-bending staple to shorten and bringing tissue together; and/or repeating last four steps until the LAA ostium is occluded or closed. Any embodiments of the staples or delivery devices disclosed herein can be used in conjunction with other deliver device or implant embodiments to anchor or close other LAA covers or occlusion devices.

Another embodiment of an implant device comprises a compression spring which, when inserted into the LAA ostium, would modify its shape to a narrow oval, closing the LAA ostium in a lateral fashion. FIGS. 77A-77C show the compressed state of the spring 1680 and the following stages to expansion. FIGS. 78A-78C show the stages for deployment for this design. The steps of deployment and implantation in some embodiments can include: inserting catheter into middle of LAA ostium; releasing the tension on the cables constraining the compressed state of the spring; guiding the ends of the spring into the lateral ends of the LAA ostium; and/or releasing the delivery catheter from the implant.

FIGS. 79A-79C show the same embodiment of the spring device 1680 described above, but covered with a mesh or graft material 1682 which would promote ingrowth of tissue and ultimate closure/sealing of the LAA. The spring device 1680 can in some embodiments be made from metal or plastic, and can be formed from wire, strip, or sheet. Embodiments of the spring device 1680 can also incorporate some telescoping or sliding feature inside to guide its expansion trajectory and ensure its straightness.

Another embodiment of an implant device is a hinged or flexible member 1690 that can be folded to fit inside the delivery catheter. During implant delivery, some embodiments to deploy the implant 1690 includes withdrawal of the delivery catheter sheath, which allows the implant 1690 to partially hinge or flex open as it becomes unconstrained by the sheath. The ends of the implant 1690 can then be guided into each end (superior and inferior) of the LAA, each end of the implant 1690 can be held in place with any manner of frictional elements or force which will allow for stabilization of the device within the LAA as deployment is continued. Full deployment of the implant 1690 will result in stretching of the LAA ostium from an open orifice to a narrower orifice that can be brought down to seal around the implant. This reduction in height of the LAA effectively closes (substantially or completely) or occludes the opening of the LAA from the LA. In any embodiments disclosed herein, the term close or closed is also used herein to mean closed, substantially closed, and/or occluded. Closing the edges of the LAA would now eliminate the flow between the left atrium and the LAA and closing flow in either direction and stop potential thrombus from migrating into the circulatory system.

In some embodiments, the steps of deployment and implantation can include: inserting catheter into middle of LAA ostium; allowing the hinged implant to expand (aided with a spring or driven with a screw, pull cable, or hydraulic actuation); guiding the ends of the implant into the lateral ends of the LAA ostium; fully opening the implant and locking its position; and/or releasing the delivery catheter from the implant. The hinged or flexible implant 1690 can have a variety of shapes, from a very narrow line, if it were made from a wire which could be 0.020" in diameter to maybe 0.060" in diameter—shown in FIGS. 87A-87C, 88A-88C, and 89A-89C, to a thicker rectangular shape which could be 0.060" to maybe 0.25"—shown in FIGS. 80A-80C and 81A-81C, to an oval or "football" shape that can be thicker in the middle than at the ends—shown in FIGS. 82A-82C, 83A-83C, 84A-84C, 85A-85C, and 86A-86C.

The mechanism for opening the implant 1690 upon deployment can be passive or active. A passive mechanism would bias the implant 1690 to the normally open or normally expanded state and would be accomplished by something like a torsion spring—shown in FIGS. 84A-84C. Other spring like methods would also accomplish a similar result such as the implant itself having spring-like properties where it would bias itself to the normally open state. The implant could also be actively expanded into position with a screw type mechanism, a pull wire and lock mechanism, a hydraulic actuator, or other.

Figure 85A:
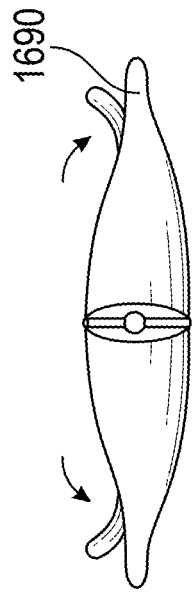
FIGS. 85A-85C show an embodiment of a device for treating the LAA.
Figure 85B:
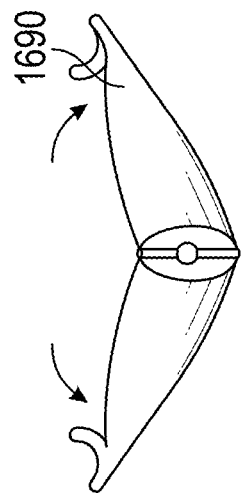
Figure 85C:
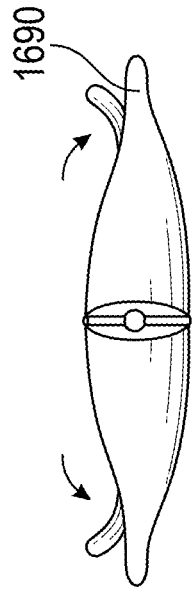
Figure 86A:
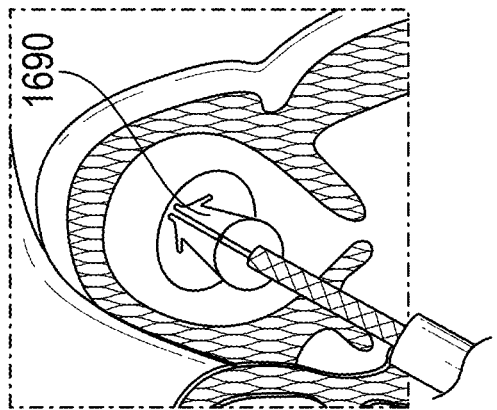
FIGS. 86A-86C show an embodiment of a method for using the device shown in FIGS. 85A-85C for occluding the LAA.
Figure 86B:
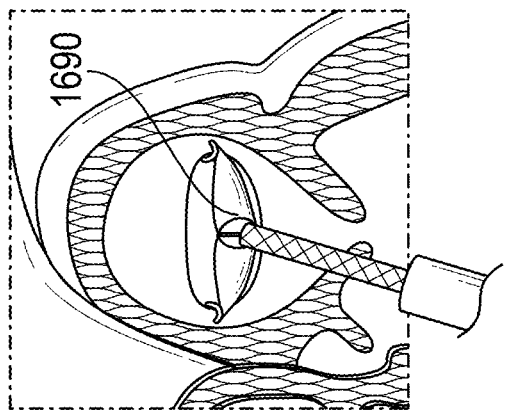
Figure 86C:
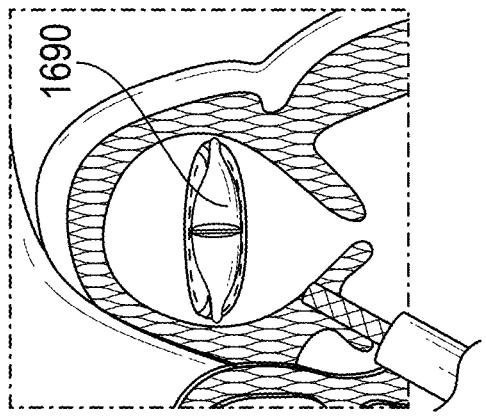
Figure 87A:
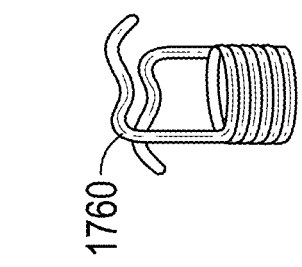
FIGS. 87A-87C show an embodiment of a device for treating the LAA.
Figure 87B:
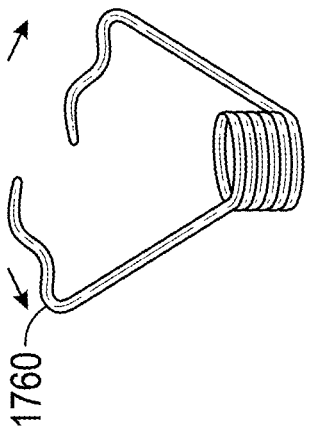
Figure 87C:
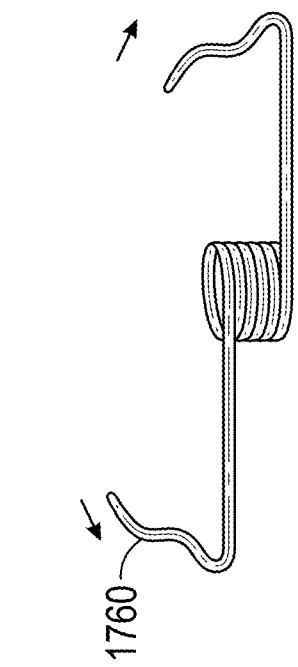
Figure 88C:
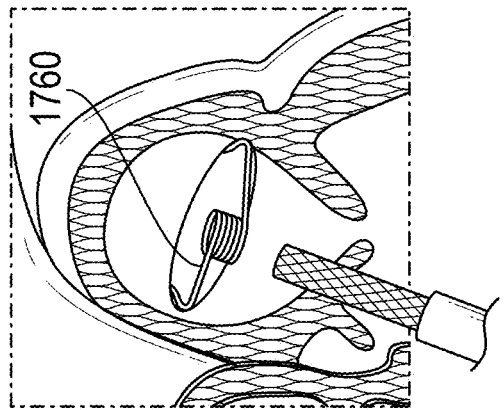
FIGS. 88A-88C show an embodiment of a method for using the device shown in FIGS. 87A-87C for occluding the LAA.

The hinged or flexible implant can also have features at the lateral ends to locate and engage with the LAA ostium for placement and secured engagement of the implant, aiding in deployment accuracy and long term migration resistance. An example of these engagement features is shown in FIGS. 85A-85C below where the "finger and thumb" features cup the lateral edges of the LAA ostium during deployment, as shown in FIGS. 86A-86C. Another embodiment of an implant 1750 having grip or engagement features on the edges of the implant is shown in FIGS. 95A-95C, 96A-96C, and 97A-97C, wherein texture, serrations, or teeth are used to engage the LAA lateral edges.

Another implant embodiment has a flexible or spring-like member that can be folded to fit inside the delivery catheter. FIGS. 87A-87C and 88A-88C show another embodiment where the implant 1760 can be constructed from a torsion spring with formed ends wherein, during implant delivery, the ends of the implant 1760 can be guided into each end (superior and inferior) of the LAA, each end of the implant 1760 can be held in place with any manner of frictional elements, specific shapes, or force which will allow for stabilization of the device within the LAA as deployment is continued. Full deployment of some of the embodiments of the device disclosed herein can result in stretching of the LAA ostium from an open orifice to a narrow slit of an orifice—this reducing in height of the LAA effectively closes the opening of the LAA from the LA. The gripping features at the ends of any of the implant embodiments disclosed herein can be formed from the torsion spring wire itself, or can be added on features like pads, grip plates, or other which provide adequate engagement to the tissue.

Figure 89C:
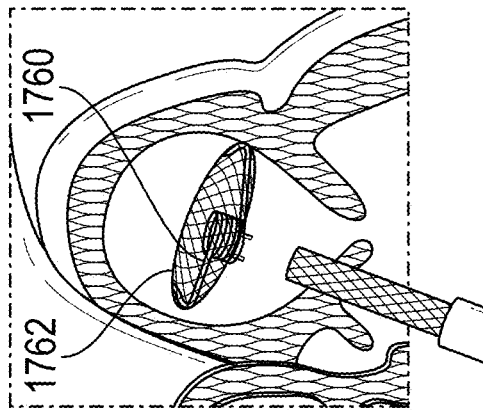
FIGS. 89A-89C show an embodiment of a method for using another embodiment of a device for occluding the LAA.
Figure 88B:
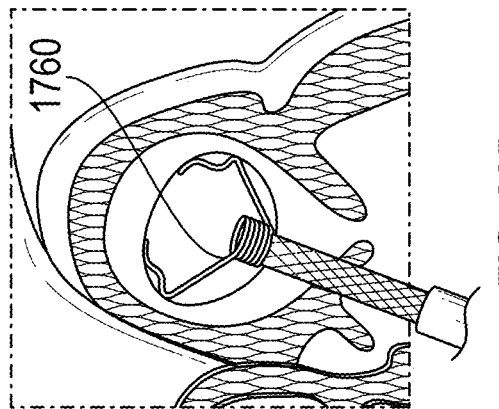
Figure 89B:
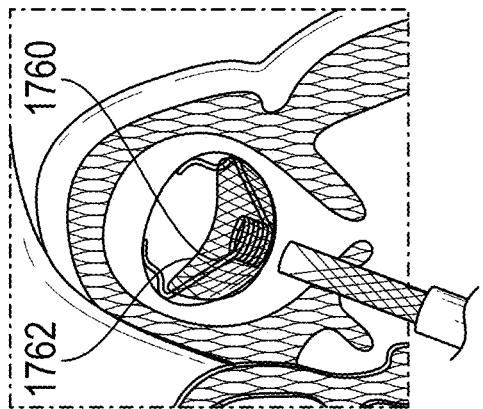
Figure 88A:
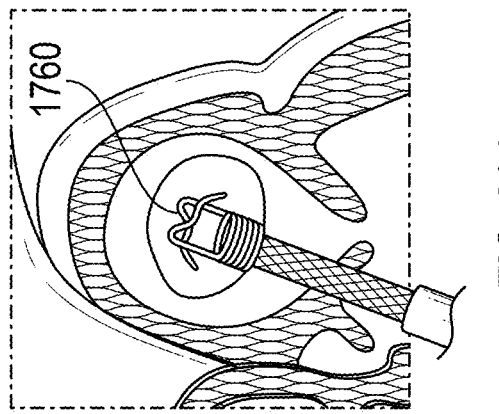
Figure 89A:
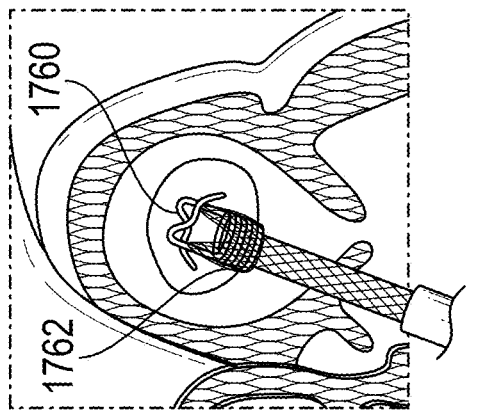
Figure 90C:
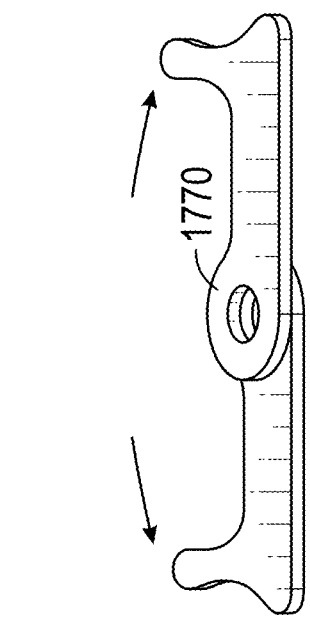
FIGS. 90A-90C show an embodiment of a device for treating the LAA.
Figure 90B:
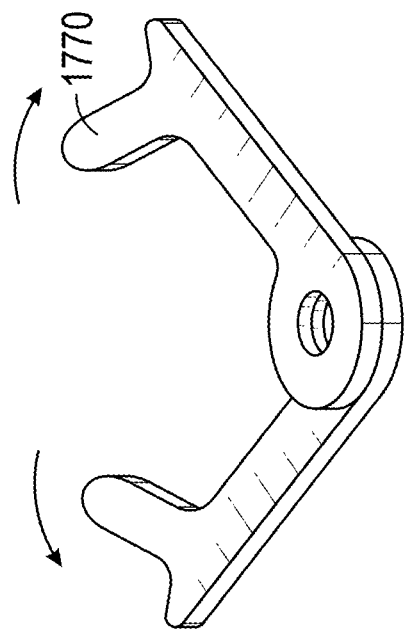
Figure 90A:
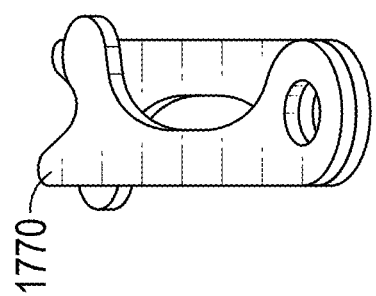
Figure 91C:
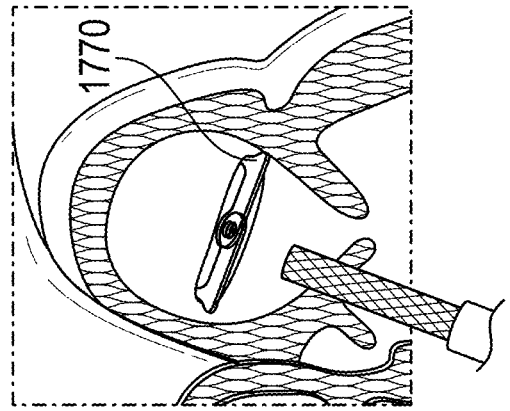
FIGS. 91A-91C show an embodiment of a method for using the device shown in FIGS. 90A-90C for occluding the LAA.
Figure 91B:
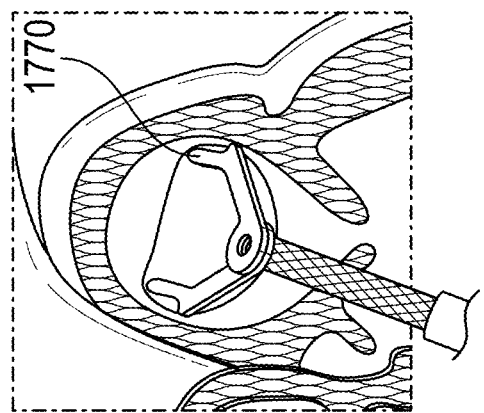
Figure 91A:
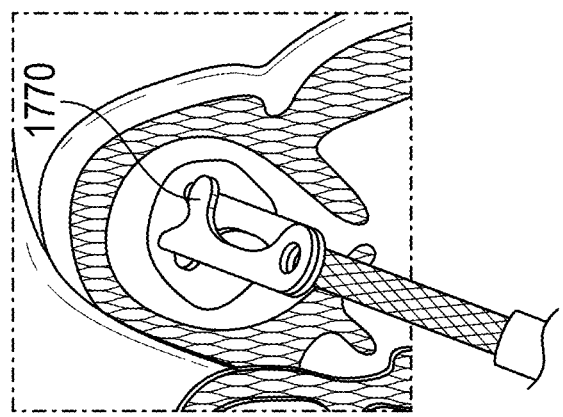
Figure 92A:
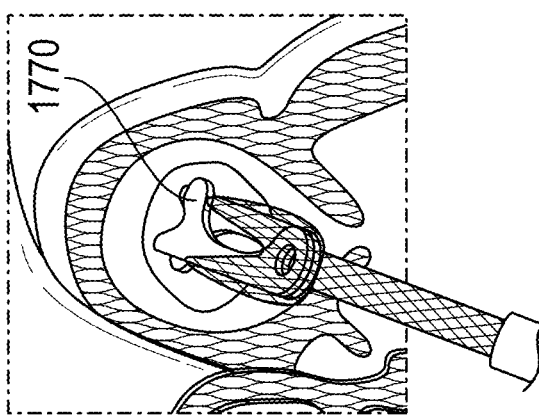
FIGS. 92A-92C show an embodiment of a method for using another embodiment of a device for occluding the LAA.
Figure 92B:
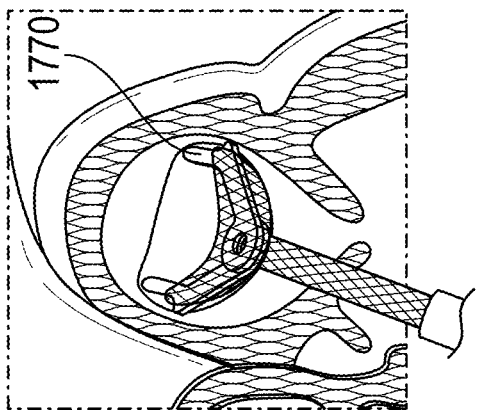
Figure 92C:
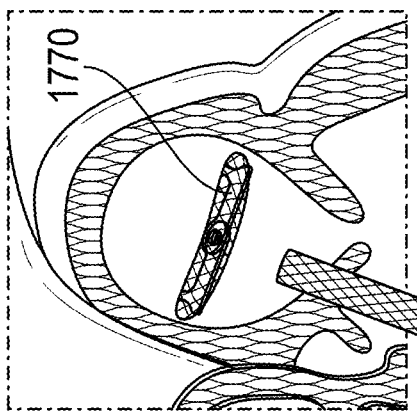
Figure 93A:
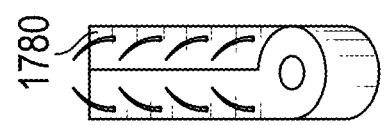
FIGS. 93A-93C show an embodiment of a device for treating the LAA.
Figure 93B:
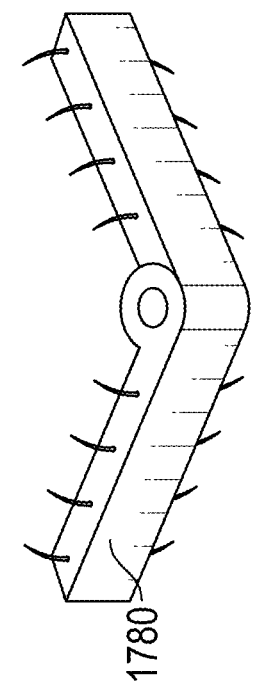
Figure 93C:
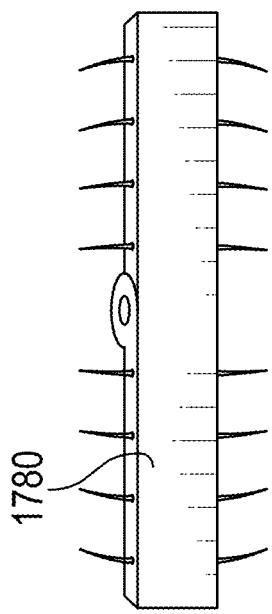
Figure 94A:
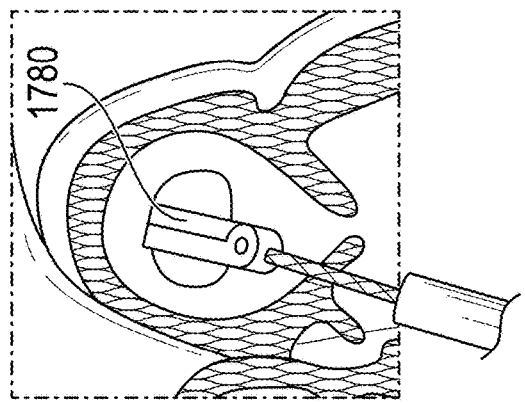
FIGS. 94A-94C show an embodiment of a method for using the device shown in FIGS. 93A-93C for occluding the LAA.
Figure 94B:
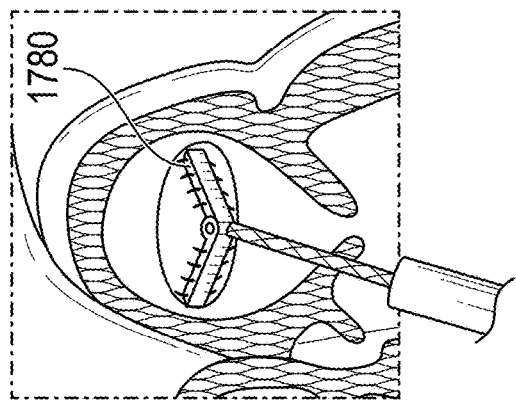
Figure 94C:
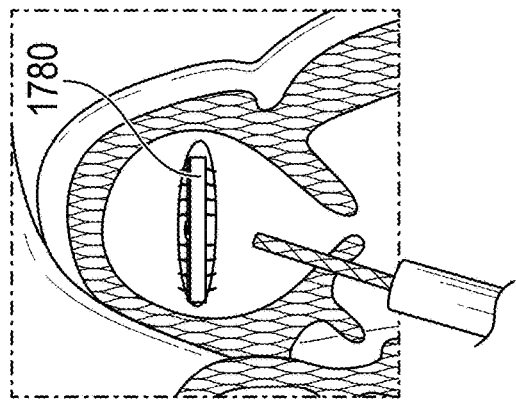
Figure 95A:
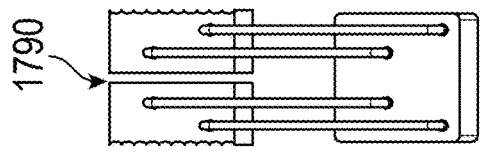
FIGS. 95A-95C show an embodiment of a device for treating the LAA.
Figure 95B:
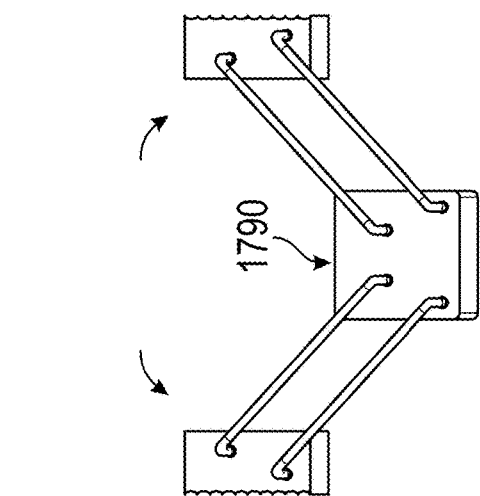
Figure 95C:
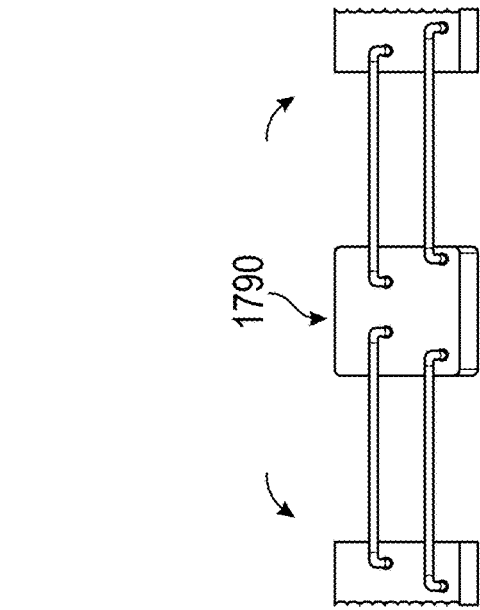
Figure 96C:
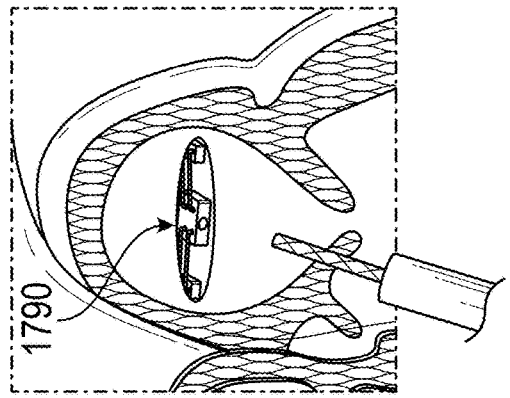
FIGS. 96A-96C show an embodiment of a method for using the device shown in FIGS. 95A-95C for occluding the LAA.
Figure 97C:
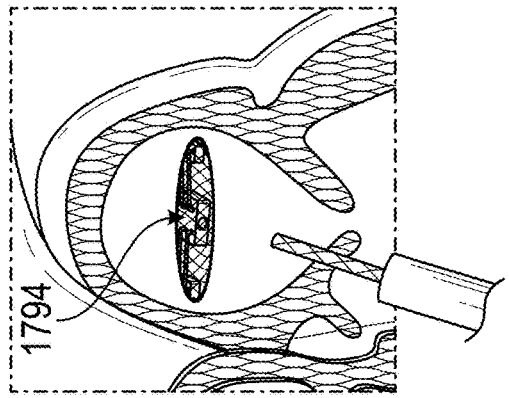
FIGS. 97A-97C show an embodiment of a method for using another embodiment of a device for occluding the LAA.
Figure 96B:
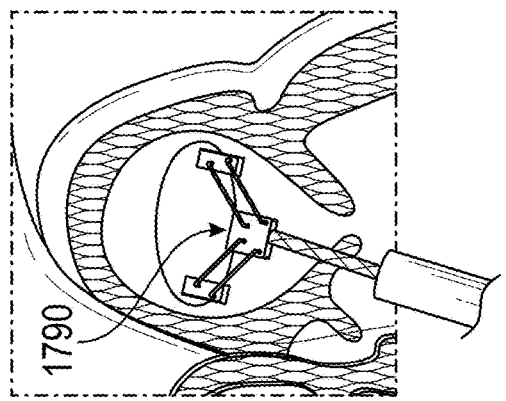
Figure 97B:
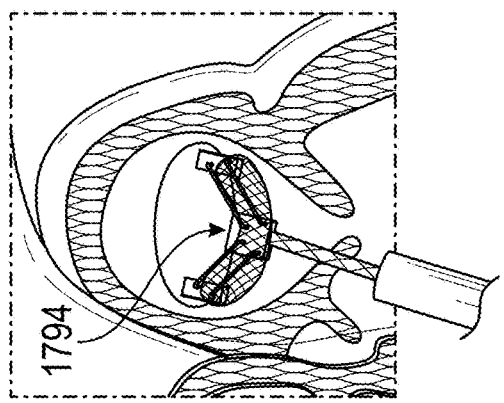
Figure 96A:
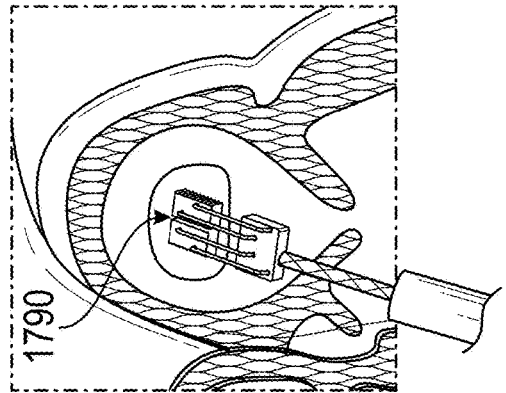
Figure 97A:
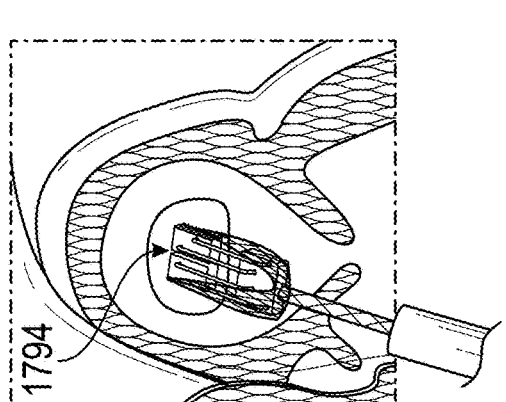
Figure 102A:
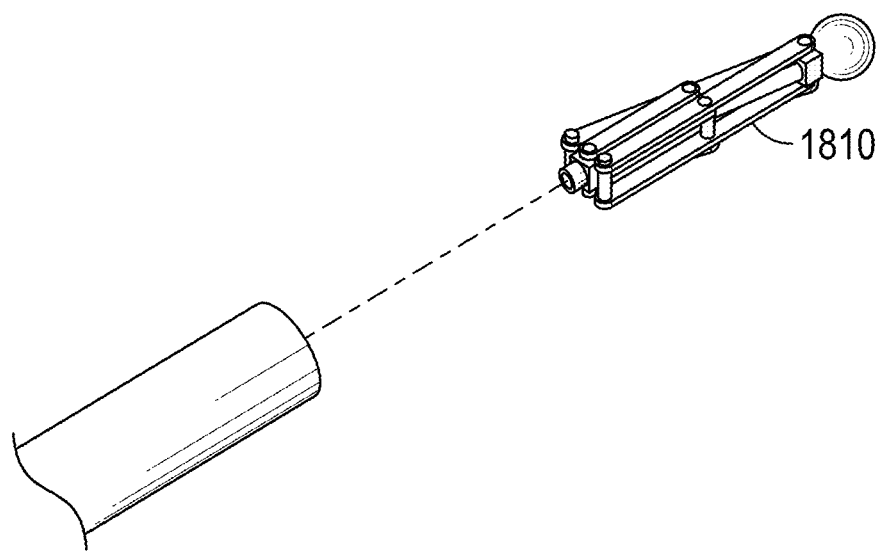
FIGS. 102A-102C show an embodiment of a method for deploying another embodiment of a device for treating the LAA.
Figure 102B:
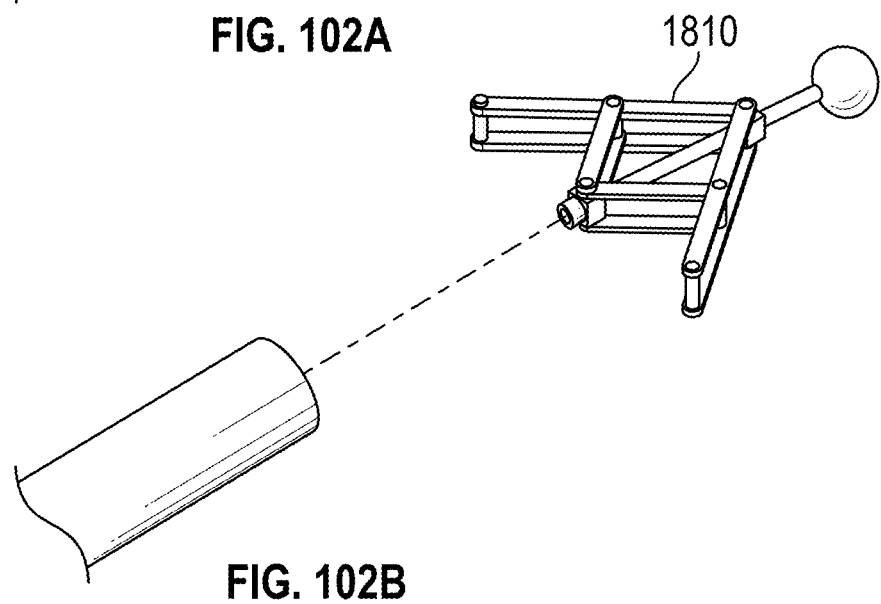
Figure 102C:
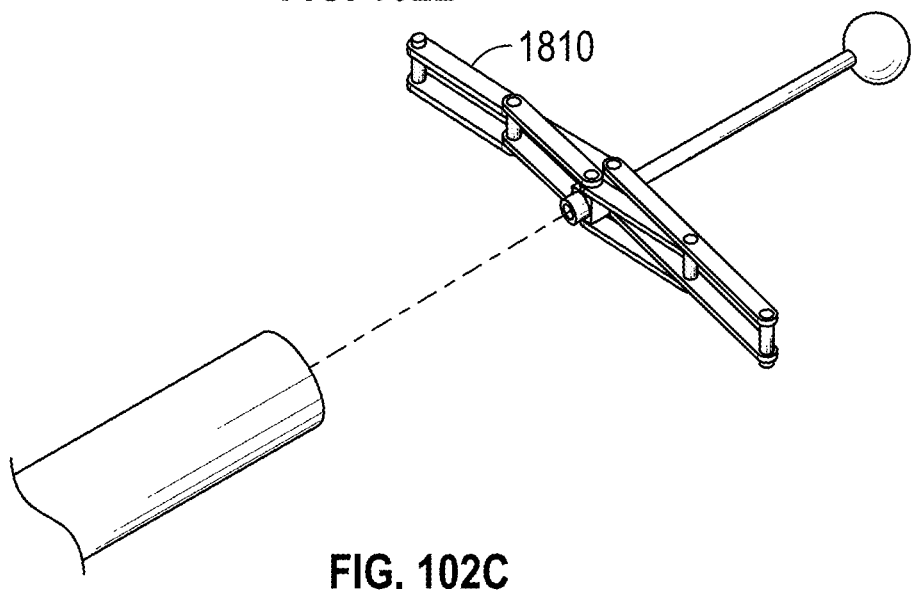
Figure 103A:
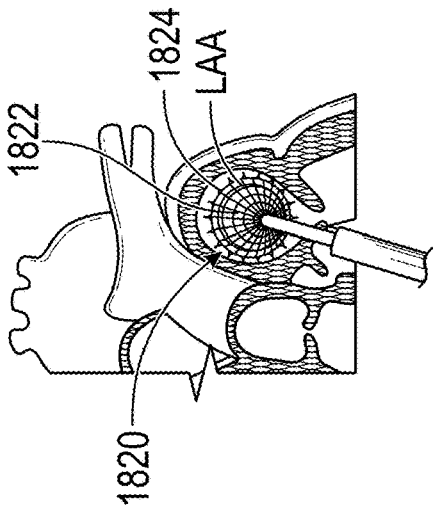
FIGS. 103A-103D show an embodiment of another implant device and an embodiment of a method for using such device for treating the LAA.
Figure 103B:
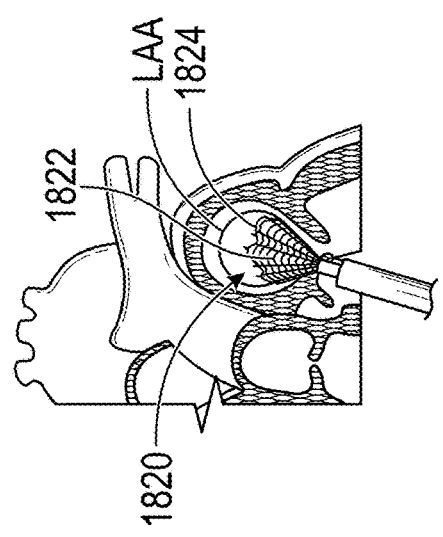
Figure 103C:
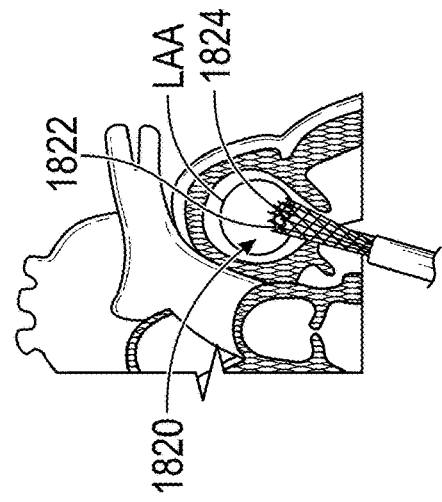
Figure 103D:
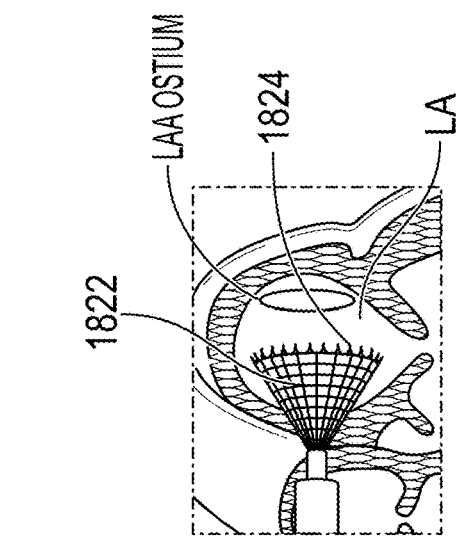
Figure 104A:
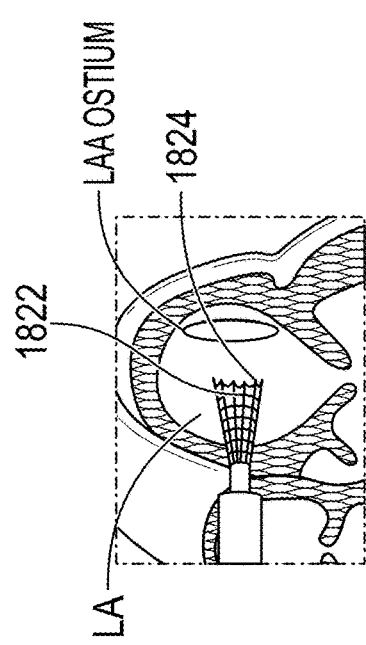
FIGS. 104A-104E show a side view of the embodiment of the implant device and method for using such device shown in FIGS. 103A-103D.
Figure 104B:
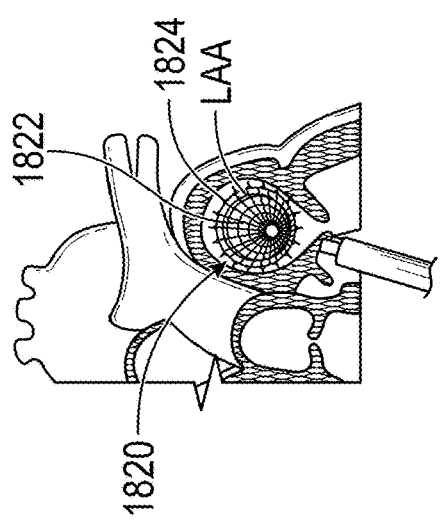
Figure 104C:
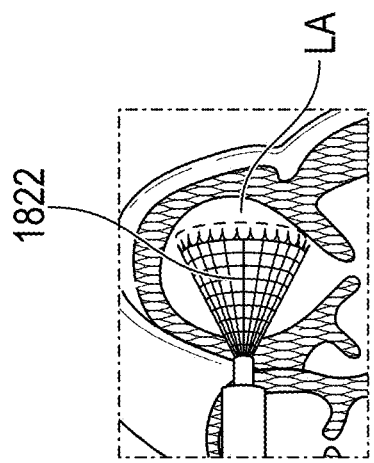
Figure 104D:
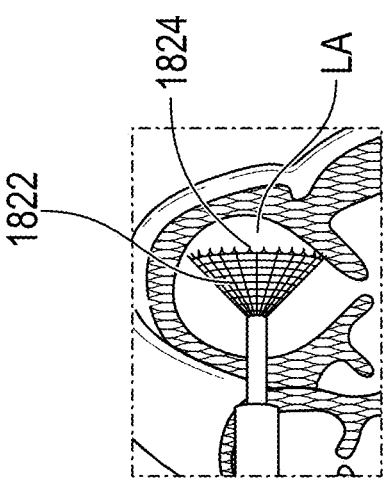
Figure 104E:
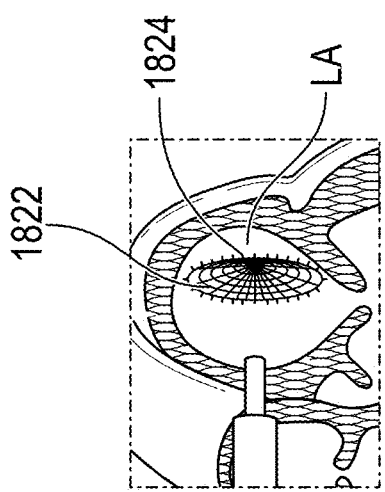
Figure 105A:
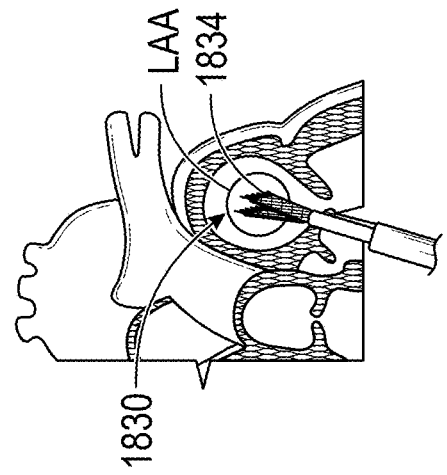
FIGS. 105A-105E show an embodiment of another implant device and an embodiment of a method for using such device for treating the LAA.
Figure 105B:
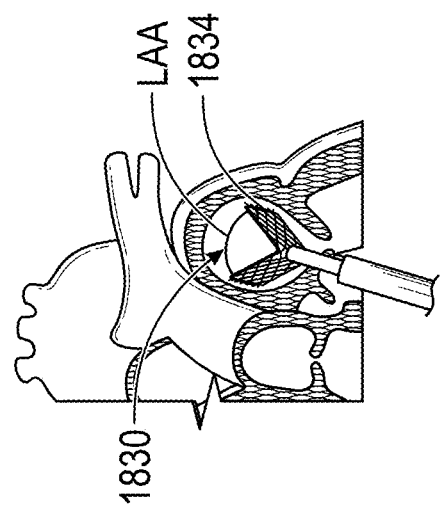
Figure 105C:
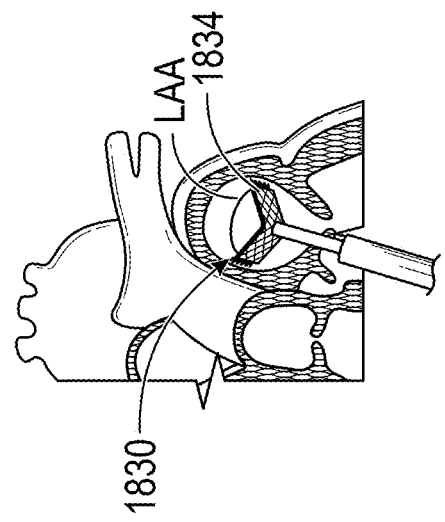
Figure 105D:
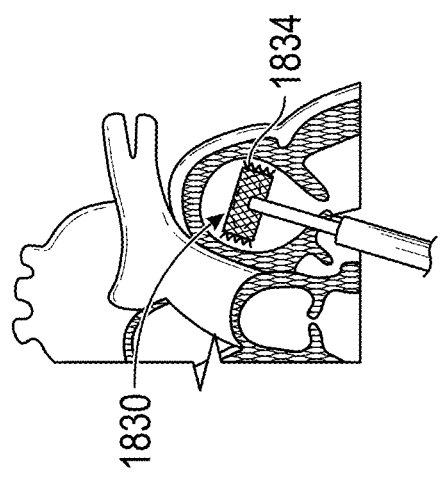
Figure 105E:
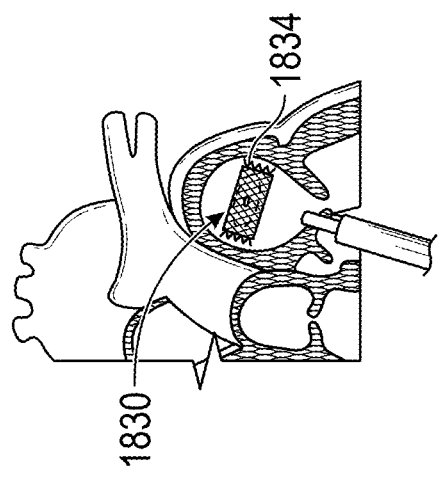
Figure 106A:
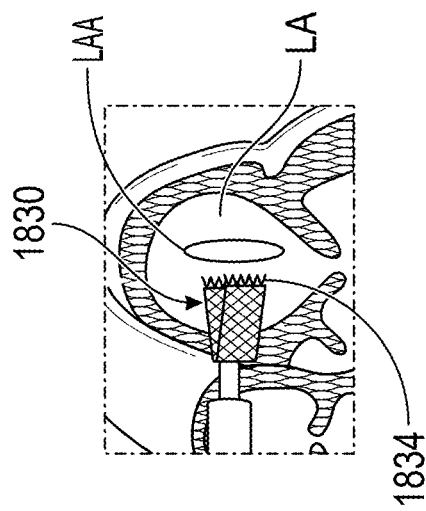
FIGS. 106A-106D show a side view of the embodiment of the implant device and method for using such device shown in FIG. 105A-105E.
Figure 106B:
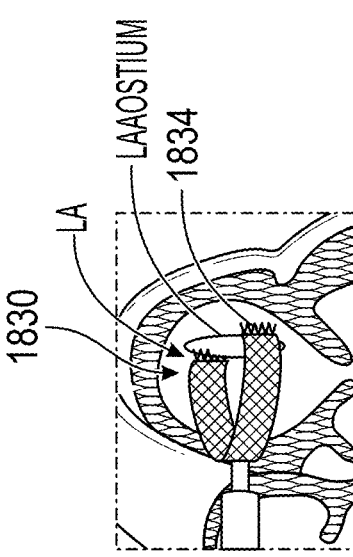
Figure 106C:
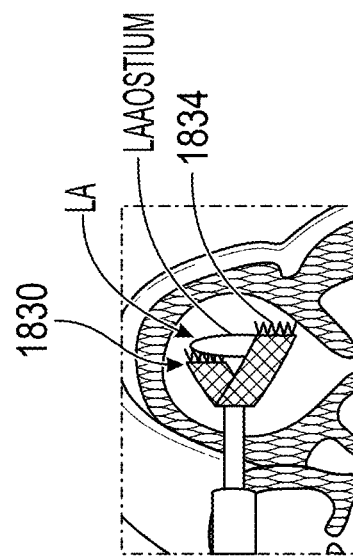
Figure 106D:
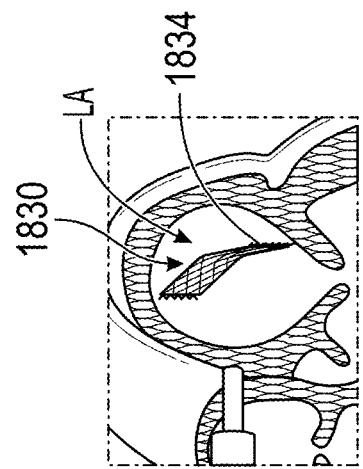

FIGS. 89A-89C show the same torsion spring implant 1760 but with a cover 1762 comprising a sealing material covering all or a portion of the implant 1760 to seal any remaining unclosed space in the LAA ostium after implantation and linearization. FIGS. 90A-90C, 91A-91C, and 92A-92C show a similar design of an implant 1770, wherein the implant 1770 does not have a spring in all embodiments thereof. The implant 1770 can be configured to achieve the locked out straight position through a stop at the hyperextended state.

FIGS. 93A-93C and 94A-94C show an embodiment of an implant 1780 having a hinge mechanism similar to that of implant 1770 but with added anchoring features or barbs to prevent the lateralized atrial wall tissue from drifting back up or down over time from relaxing, which could cause a leak. FIGS. 95A-95C, 96A-96C, 97A-97C, and 98A-98C show an implant 1790 having a similar hinge mechanism but accomplished with a 4-bar mechanism which has the characteristic of keeping the anchoring or gripping pads at the far lateral ends parallel to the catheter, potentially for better grip and easier engagement.

Another embodiment of an implant device is a multi-hinged or multi-strut flexible member that can be folded to fit inside the delivery catheter. During implant delivery, the multi-hinged mechanism can expand within the LAA ostium to expand and stretch the LAA ostium linear, closing the top atrial wall to the bottom atrial wall. The steps of deployment and implantation can include: inserting catheter into middle of LAA ostium; allowing expansion of the multi-hinged implant (driven with a screw, pull cable, or hydraulic actuation); guiding the ends of the implant into the lateral ends of the LAA ostium; fully opening the implant and locking its position; and/or releasing the delivery catheter from the implant. FIGS. 99A-99C, 100A-100C, and 101A-101C show an additional embodiment of an implant 1800 having a multi-hinged collapsing or folding mechanism. FIGS.

102A-102C show an additional embodiment of an implant 1810 having a multi-hinged collapsing or folding mechanism. There are a multitude of options for this type of a mechanism. FIGS. 101A-101C shows the implant 1800 having a mesh or graft cover 1802 to aid in tissue ingrowth into the atrium.

Another embodiment of an implant 1820 has a conical mesh 1822 with cleats or barbs at the perimeter of the implant 1820. There are two embodiments shown, one having a circular shape and another having an elongated shape. FIGS. 103A-103D and 104A-104E show the circular variation of the implant 1820 where the steps of deployment and implantation can include: inserting catheter into middle of LAA ostium; allowing expansion of the conical circular mesh barbed implant 1820; guiding the implant 1820 to completely cover the LAA ostium; applying forward pressure to the implant 1820 to both engaging perimeter barbs 1824 and inverting the implant 1820; and releasing the delivery catheter from the implant 1820. This implant can anchor or couple with the tissue of the LAA ostium and/or surrounding the LAA ostium via the cleats or barbs 1824 at the perimeter of the implant 1820 to the atrial wall, just outside the radius of the LAA ostium. Deployed in its conical shape and placed to cover the LAA ostium, when advanced, the anchors 1824 dig into the atrial wall in a radial outward motion as the cone shape of the implant flattens and then finally slightly inverts. Once inverted, the delivery system can be removed from the implant 1820. One characteristic of some embodiments of this design is that it is not dependent of a certain depth of the LAA, since no part of the delivery catheter or implant ever enters into the LAA. It would also lock itself in place still, even if not all the anchors were engaged.

FIGS. 105A-105E and 106A-106D show the elongated variation where the steps of an embodiment of deployment and implantation can include: inserting catheter into middle of LAA ostium; allowing expansion or unfolding of the elongated mesh barbed implant 1830; guiding the implant 1830 to completely cover the LAA ostium from the two lateral sides (the top and bottom will not be covered yet); applying forward pressure to the implant 1830 to both engaging perimeter barbs, stretching the LAA ostium wide and narrow, and finally inverting the implant 1830; and/or releasing the delivery catheter from the implant 1830. This implant can anchor or couple via the cleats or barbs 1834 at the ends of the implant 1830 to the atrial wall, just outside the lateral radius of the LAA ostium. Deployed in its folded shape and placed to cover the LAA ostium, when advanced, the anchors 1834 dig into the atrial wall in a lateral outward motion, stretching the LAA ostium to be narrow as the implant flattens and then finally inverts. Once inverted, the delivery system can be removed from the implant 1830. One characteristic of some of the embodiments of the implants disclosed herein is that they are not dependent of a certain depth of the LAA, since no part of the delivery catheter or implant ever enters into the LAA. Some embodiments of the implant are also configured to lock itself in place still, even if not all the anchors were engaged. This elongated embodiment can also leave less exposed material surface area than the circular embodiment.

Another embodiment of an implant device 1840 uses a radial reduction method to close the LAA ostium. In this design, several lumens are mounted to a balloon, expandable mesh, or other structure, which guide needles, anchors, or barbs 1842 with suture attached to the perimeter of the LAA ostium on the atrial wall. Once expanded to position, the anchors 1842 are advanced through the tubes into the atrial wall around the LAA ostium. The balloon can be deflated and the suture lines are crimped or tied off under tension, pulling the LAA ostium to a close. There may be a small plug of material left behind to close off any remaining space. FIGS. 107A-107G show an embodiment of the device 1840 and at least some of the steps for deployment of the device 1840. The steps of deployment and implantation can include: inserting a catheter into middle of LAA ostium and positioning for appropriate depth; expanding the balloon 1844 (could also be expandable mesh or other structure); advancing anchors 1842 each attached to a suture 1846 into the atrial wall surrounding LAA ostium through the lumens around the balloon; deflating the balloon 1844 and pulling the sutures under tension, closing the LAA ostium, and crimping or tying off the suture 1846 to hold the reduced diameter position (a plug can be inserted if necessary to close any remaining portion of the LAA ostium); and/or releasing the delivery catheter from the implant 1840.

Another embodiment of an implant device uses a radial reduction method to close the LAA ostium from the inside of the LAA. FIGS. 108A-108C, 109A-109C, 110A-110E, 111, 112, 113A-113C, and 114A-114C show additional embodiments of devices for treatment of the LAA. The embodiments of the devices shown in the foregoing figures can be configured to grip the atrial wall with anchors or barbs around the LAA ostium, and then pull them down (or inward) through a mechanism which is positioned inside the LAA. This mechanism can be activated by an attached delivery system, which once locked in the closed position, can be undocked from the implant and removed.

Figure 108A:
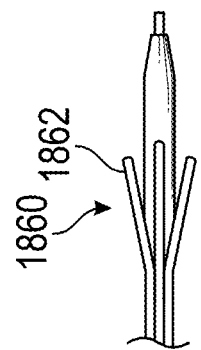
FIGS. 108A-108C show another embodiment of a device and an embodiment of a method for using such device for treating the LAA.
Figure 108B:
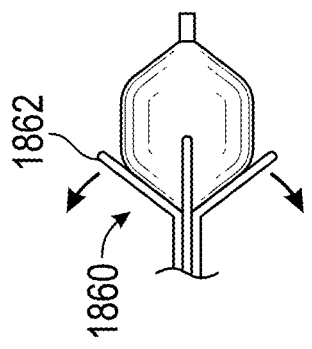
Figure 108C:
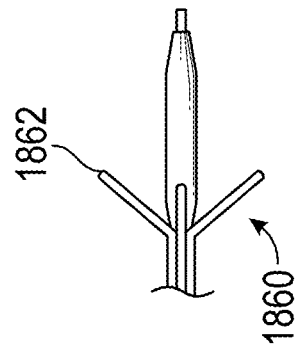
Figure 109A:
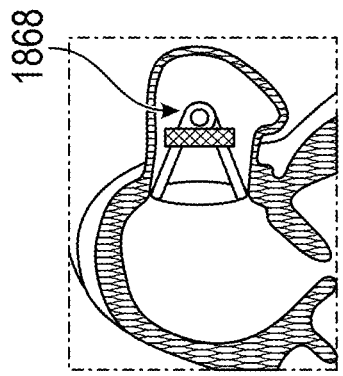
Figure 109B:
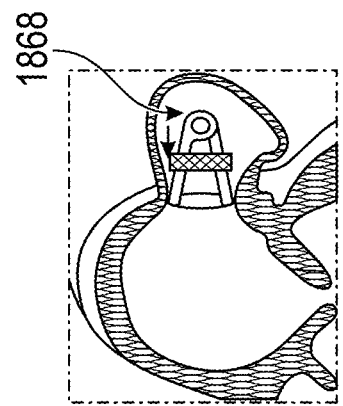
Figure 109C:
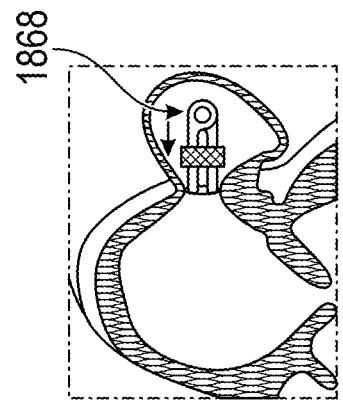
Figure 114A:
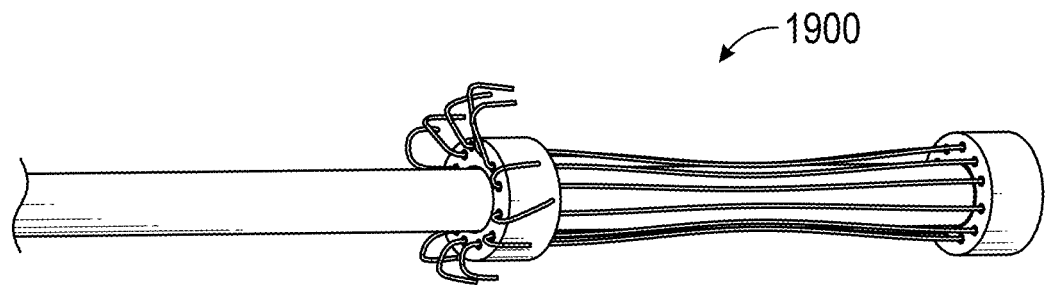
Figure 114B:
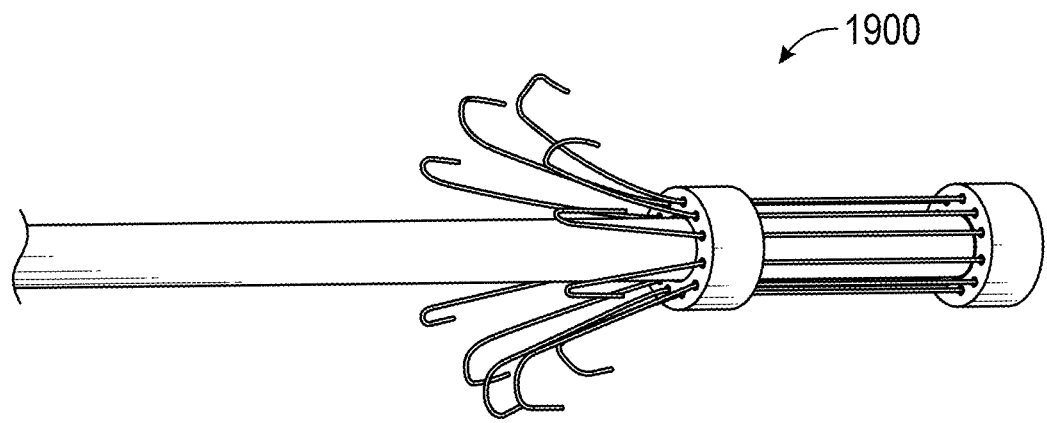
Figure 114C:
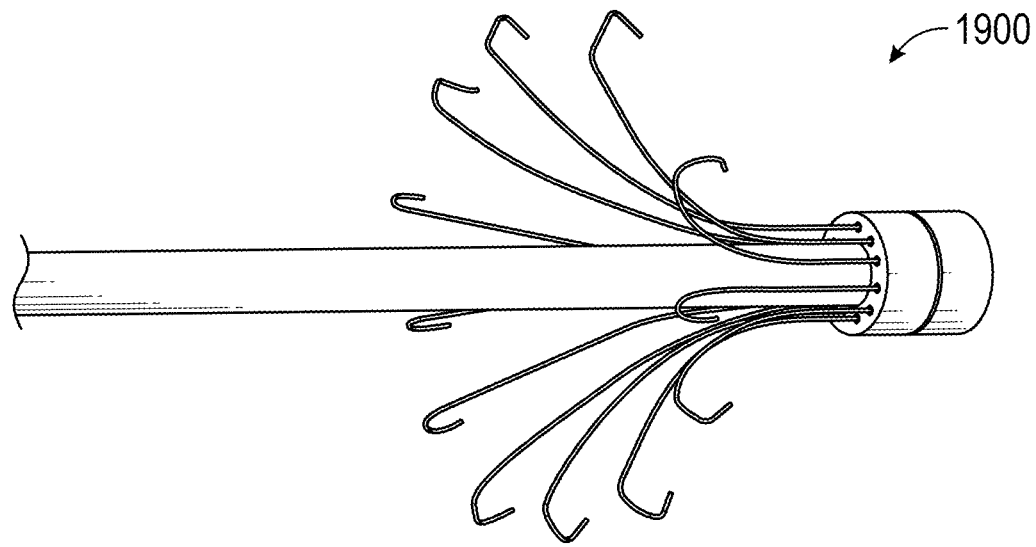
Figure 118A:
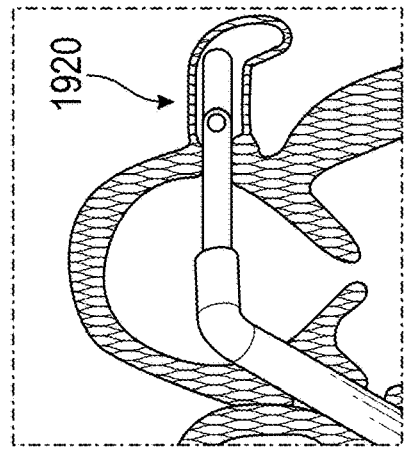
Figure 118B:
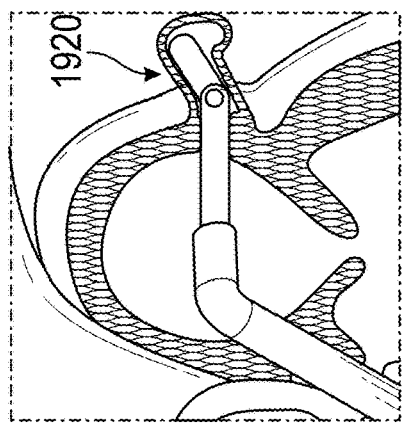
Figure 118C:
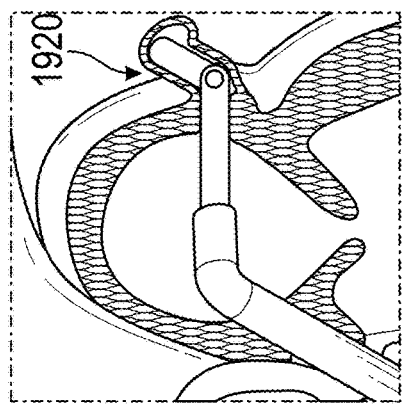
Figure 118D:
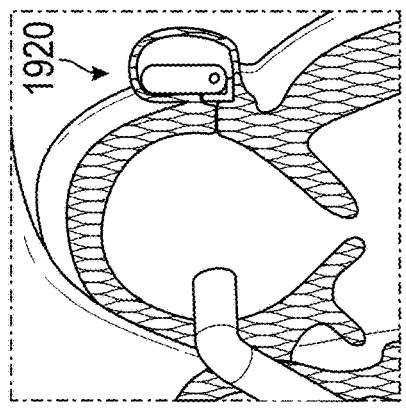
Figure 119A:
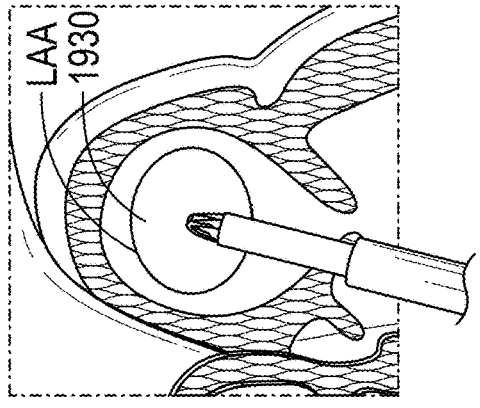
Figure 119B:
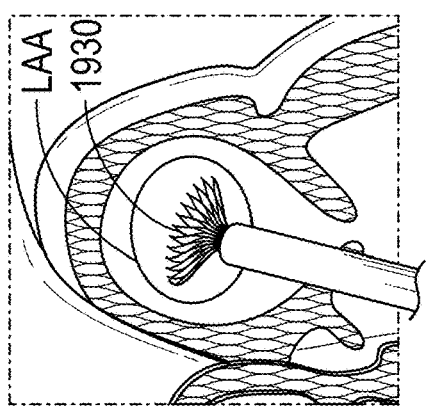
Figure 119C:
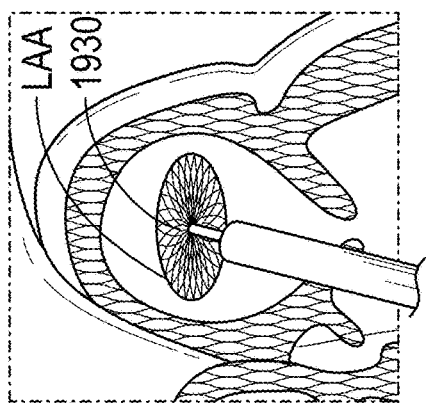
Figure 119D:
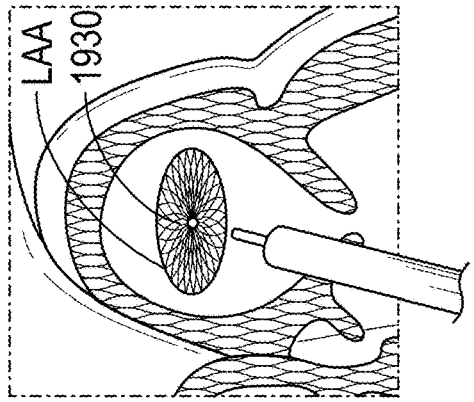

FIGS. 108A-108C show an embodiment of a device 1860 and some steps of a method for expanding the anchors 1862 and other portions of the device 1860, which could be accomplished by a balloon, or a spring, a mechanical actuator, or other expander. In other embodiments, the anchors 1862 can be self-expanding. FIGS. 110A-110C show some steps of an embodiment of the device 1860. FIGS. 109A-109C show another embodiment of a device 1868 that can be used to treat the LAA. FIGS. 111, 112, and 113A-113C show additional embodiments of devices 1870, 1880, and 1890, respectively, having a reduced cleat portion which can allow for several devices to be used to close the LAA ostium. In this manner, a lateral closure can be accomplished if, for example, 2, 3, 4, or more of these devices were used in a row, each pulling the atrial wall from top to bottom to close. The resultant closure would be a lateral closure of the LAA. FIGS. 114A-114C show an additional embodiment of an implant 1900 having more cleats so that the implant has more anchor points with the tissue. One or more of the implants 1900 can be used to occlude an LAA.

Additional embodiments of an implant 1910 use a method to spread the LAA ostium laterally, and then pinch or clip it closed, closing the atrial wall top-to-bottom from the inside of the LA. FIGS. 115A-115C, 116A-116C, and 117A-117C show some embodiments of the device 1910. One feature on some embodiments of the implant device 1910 (or could be on the delivery catheter), is the stretching or lateralizing bar which can be seen in the figures. This is a rounded bar 1912 which connects to each lateral end of the device 1910 and when advanced into the LAA, expands the LAA ostium, thereby also narrowing it. Once the hinged jaws or cleats are pressed against the atrial wall, just above the LAA ostium, the clip is occluded or closed. When closing the clip, the clip engages and pulls the atrial wall above and below the LAA together and locks portions of the atrial wall closed.

The steps of deployment and implantation of some embodiments of the implant devices disclosed herein can include: inserting catheter into middle of LAA ostium; advancing implant until clip jaws are contacting the atrial wall and stretch bar has stretched LAA ostium; actuating the closing of the jaws, can be actuated with a pull wire, or other mechanism (can also be spring actuated to the normally closed state where it is held open before deployment and simply released after); locking the jaws in the closed state; and/or releasing the delivery catheter from the implant.

Another embodiment of an implant device 1920 includes folding or kinking the LAA at the ostium, and then clipping and holding that position, effectively closing the LAA. FIGS. 118A-118D shows one variation of a sequence of steps to accomplish that. In some embodiments, the steps of deployment and implantation can include: inserting catheter into middle of LAA ostium; flexing a portion of the implant 1920 in a first direction (which can be up, as shown in the figures); clipping and holding the position of the bent portion of the implant 1920 to the atrial wall (additional anchoring can be used to anchor implant to lower atrial wall); and/or releasing the delivery catheter from the implant 1920.

Another embodiment of an implant device 1930, as shown in FIGS. 119A-119D and 120A-120C, uses a plug type closure but is not round and does not re-form the LAA to round. The implant can be instead oval or narrow where its length (represented by L in FIGS. 120A-120C) can be greater than its width or height (represented by W in FIGS. 120A-120C) through deliberate manipulation of the shape of the LAA with the implant device 1930. The implant 1930 shown in FIGS. 119A-119D and 120A-120C can have a metal scaffolding covered with a mesh or graft material. The implant 1930 can be self-expanding, balloon or mechanically expandable, or otherwise, and can have a shape biased to be wider (L) than it is tall (W). In any embodiments disclosed herein, the steps of deployment and implantation can include: inserting catheter into middle of LAA ostium; positioning the depth of the implant and deploying; once deployed, permitting the implant to re-shape the LAA anatomy to be an oval with the LAA ostium being wider than it is tall; implanting or imparting a radial force and/or cleats or anchors to hold the implant in position; and/or releasing the delivery catheter from the implant.

Any embodiments of the implant (such as implant 1950 shown in FIGS. 121A-121C) can also be a hybrid of a self-expanding LAA occlusion plug 1952 with a lateral expansion device 1954. The implant 1950 can first deploy round, and then be shape modified to oval through the expansion device which can be biased (for example and without limitation, spring biased) to the expanded position, or be actuated mechanism.

FIGS. 122 and 123 are a top view and side view, respectively, of another embodiment of an implant 2000 for treating or closing an opening, such as, but not limited to, an LAA. The implant 2000 can have a frame 2002 that is expandable from a collapsed state to an expanded state. FIG. 122 shows the expanded state of the frame 2002. The frame can be self-expanding, mechanically expandable using a balloon, or otherwise. The frame can be made from one or more wires or ribbons. In some embodiments, the frame 2002 can be laser cut from an extruded tube, a flat sheet, or otherwise. If laser cut from a flat sheet, the ends of the frame can be welded, brazed, or otherwise permanently joined together to form the continuous wall 2003 of the frame 2002.

The frame can have a plurality of members 2004 interconnected to form the frame 2002. The members 2004 can have a plurality of openings 2006 between the members 2004 of the frame 2002. A plurality of apexes 2010 can be formed between some of the adjacent members 2004. In some embodiments, the apexes 2010 can facilitate the bending of the members 2004 during expansion from a contracted or first state to an expanded or second state, the expanded, second state being shown in FIG. 123. In any embodiments disclosed herein, the members 2004 and apexes 2010 can form a zig-zag pattern.

With reference to FIGS. 122-123, the implant 2000 can have an elongated shape. In some embodiments, the implant 2000 can have an elongated shape along the entire length of the implant 2000. The term length is meant to refer to an axial direction of the implant, as identified with arrow AL in FIG. 123. The frame 2002 can have an opening 2014 extending through the frame in an axial direction from a proximal end 2002*a* to a distal end 2002*b* of the frame 2002. The opening 2014 can be continuously surrounded by a wall 2003 that is formed by the frame 2002.

With reference to FIG. 122, in any embodiments disclosed herein, the frame 2002 can be sized and configured such that the opening 2014 defines a first width or dimension W1 in a first direction (indicated by arrow A1) from a first portion 2020 across the opening 2014 of the frame 2002 to a second portion 2022 that is greater than a second width or dimension W2 of the opening 2014 in a second direction (indicated by arrow A2) that is perpendicular to the first direction A1 when the implant 2000 is in a deployed in-situ state in the LAA, or when the implant 2000 is in a naturally expanded state outside of the body. In any embodiments where the implant is self-expanding, the naturally expanded state outside of the body can be the unconstrained shape. The first and second directions (A1, A2) can be perpendicular to the direction AL or axial direction shown in FIG. 123. In some embodiments, without limitation, the first width can optionally be defined from an innermost portion of the first portion 2020 in the region configured to engage with or contact the ostium, whether or not the frame 2002 has a first recess 2032, to an innermost portion of the second portion 2022 in the region configured to engage with or contact the ostium, whether or not the frame 2002 has a second recess 2034.

In any embodiments disclosed herein, when the implant 2000 or any other implant embodiments or implementations disclosed herein are in a relaxed state, a naturally expanded state (i.e., expanded outside of the body, with no external forces from the LAA acting on the implant), and/or a mechanically expanded state, the first width W1 of the opening 2014 can In some embodiments be approximately three and a half times the second width W2 of the opening 2014, or at least approximately two times the second width W2 of the opening 2014 (i.e., the first width W1 of the opening 2014 can be double the second width W2 of the opening 2014), or In some embodiments from approximately two times to approximately eight times the second width W2 of the opening 2014, or In some embodiments two times to approximately four times the second width W2 of the opening 2014, or from approximately three times to approximately four times the second width W2 of the opening 2014, or from and to any values within these ranges.

In any embodiments disclosed herein, when the implant 2000 or any other implant embodiments or implementations disclosed herein are in the relaxed state, a naturally expanded state, and/or mechanically expanded state, the implant 2000 can define a ratio of the first width W1 of the opening 2014 to the second width W2 of the opening 2014 that is approximately 3.5:1, or at least approximately 2:1, or In some embodiments from approximately 2:1 to approximately 8:1, or In some embodiments from approximately 3:1 to approximately 4:1, or from and to any values within these ranges, either before or after one or more additional clips, staples, sutures, or other additional closure devices, if any, are deployed to further close the ostium of the LAA. For example, in some embodiments, such additional clips, staples, sutures, or other additional closure devices can be implanted in the patient after the implant has been fully expanded to any of the ratios or ranges of ratios stated above to further close or completely close the ostium of the LAA. In some embodiments, as stated above, the implant can be expanded to any of the ratios or ranges of ratios stated above without any additional closure devices being implanted thereafter.

In any embodiments disclosed herein, when the implant 2000 or any other implant embodiments or implementations disclosed herein are in a deployed in-situ state in the LAA, the first width W1 of the opening 2014 can In some embodiments be approximately three and a half times the second width W2 of the opening 2014, or at least approximately two times the second width W2 of the opening 2014 (i.e., the first width W1 of the opening 2014 can be double the second width W2 of the opening 2014), or In some embodiments from approximately two times to approximately eight times, or from approximately two times to approximately six times, or from approximately two times to approximately four times, or from approximately three times to approximately four times the second width W2 of the opening 2014, or from and to any values within these ranges.

In any embodiments disclosed herein, when the implant 2000 is in a deployed in-situ state in the LAA, the implant 2000 can define ratio of the first width W1 of the opening 2014 to the second width W2 of the opening 2014 that is approximately 3.5:1, or In some embodiments at least approximately 2:1, or In some embodiments from approximately 2:1 to approximately 8:1, from approximately 2:1 to approximately 6:1, or from approximately 3:1 to approximately 4:1, or from and to any values within these ranges.

In some embodiments, the implant 2000 and any other implant embodiments or implementations disclosed herein can be configured such that deploying the implant 2000 in the ostium of the LAA can increase a first width of the ostium (in the same direction as the first width W1 of the implant 2000) by at least approximately 40% (i.e., so as to increase the first width of the ostium by at least approximately 40% as compared to the first width of the ostium before the implant was deployed and expanded), or by approximately 65% or more, or by at most approximately 100%. Additionally, In some embodiments, deploying the implant 2000 in the ostium of the LAA can reduce a second width of the ostium (in the same direction as the second width W2 of the implant 2000) by at least approximately 50% (i.e., so as to cut the second width of the ostium in half), In some embodiments by approximately 25% to approximately 100%, or by approximately 40% to approximately 85%, or by approximately 40% to approximately 75%, either without any changes in the first width of the ostium or in combination with any of the aforementioned percentage increases of the first width of the ostium.

In any embodiments disclosed herein, the implant 2000 or any other implant embodiments or implementations disclosed herein can be configured such that deploying the implant 2000 in the ostium of the LAA when the implant 2000 is in a deployed in-situ state in the LAA can change a first width of the ostium (in the same direction as the first width W1 of the implant 2000) and the second width of the ostium (in the same direction as the second width W2 of the implant 2000) such that the ostium of the LAA defines a ratio of the first width of the ostium to the second width of the ostium (after deployment and expansion of the implant 2000 or any other implant embodiments or implementations disclosed herein) that is approximately 3.5:1, or at least approximately 2:1, or In some embodiments from approximately 2:1 to approximately 8:1, or In some embodiments from approximately 3:1 to approximately 4:1, or from and to any values within these ranges.

Any embodiments of the frame 2002 of the implant 2000 can be flared outwardly at the proximal end 2002a of the frame 2002 at least at the first portion and the second portion 2022 of the frame 2002 to enable better securement to the tissue surrounding the LAA and/or better positioning accuracy during deployment. For example and without limitation, the frame 2002 can have a first apex extension 2024 that extends away from the proximal end 2002a of the frame 2002 at the first portion 2020 of the frame 2002 or wall 2003. The first apex extension 2024 and/or a second apex extension 2026 can In some embodiments be configured to bias the proximal end 2002a of the frame 2002 to approximately align with the outside edge or surface E of the ostium (as shown in FIG. 124). In some embodiments, the first apex extension 2024 can extend away from the proximal end 2002a of the frame 2002 at the first portion 2024 of the wall, wherein the first apex extension 2024 is configured to prevent the frame from passing completely through an ostium O (as shown in FIG. 124) of an LAA. This can be achieved by overlapping a portion of the outside surface of the ostium O with at least one of the first apex extension 2024 and the second apex extension 2026.

Some embodiments of the implant 2000 can have a first apex extension 2024 that extends away from the proximal end 2002a of the frame 2002 at the first portion 2020 of the wall 2003. The first apex extension 2024 can be configured to overlap an outside surface E of a wall portion W surrounding an ostium O of the LAA when the implant 2000 is in an operable position within the LAA, a nonlimiting example of which is shown in FIG. 124. Additionally, the implant 2000 can in some embodiments have a second apex extension 2026 that extends away from the proximal end 2002a of the frame 2002 at the second portion 2022 of the wall 2003 of the frame 2002. In some embodiments, the second apex extension 2026 can be configured to bias the proximal end 2002a of the frame 2002 to approximately align with the outside edge E of the ostium O, be configured to prevent the frame 2002 from passing completely through an ostium O of the LAA, and/or be configured to overlap an outside surface of a wall 2003 portion surrounding an ostium O of the LAA when the implant 2000 is in an operable position within the LAA.

In this configuration, the first and/or second apex extensions can help during the implant procedures by providing a limit to the depth within the LAA that the implant can be advanced to. For example, a surgeon can advance a catheter into or adjacent to the LAA, expose the implant 2000 In some embodiments by advancing the implant 2000 relative to an outer sheath on the catheter or by withdrawing the outer sheath to expose the implant 2000. The implant 2000 can be moved into position within the LAA and then expanded to the second, expanded state. As the implant 2000 is being expanded to the expanded state, the first portion 2024 and second portion 2026 can exert a force on the LAA, causing the LAA to elongate in the first direction A1. The implant 2000 can in some embodiments be configured to spread a first portion of an ostium O of the LAA apart from a second portion 2022 of the ostium O that is opposite to the first portion so as to elongate the ostium O of the LAA in the first direction. For example, the first and second portions 2020, 2022 of the frame 2002 can be configured to spread a first portion of an ostium O of the LAA apart from a second portion of the ostium O that is opposite to the first portion so as to elongate the ostium O of the LAA in the first direction. This can result in the walls of the ostium of the LAA that are between the first and second portions to move toward one another, so as to substantially close the ostium or create a better seal of the ostium to the outside perimeter or surface of the implant, such as the wall 2003 of the implant 2000. This can be a particularly effective method of creating a better seal around the implant for irregularly shaped or non-smooth ostium.

During the deployment, the depth of the implant relative to the ostium can be adjusted by moving the implant distally and proximally. The first and/or second apex extensions 2024, 2026 can engage the outer surface E of the tissue surrounding the ostium O and prevent or inhibit the implant 2000 from being advanced further distally into the LAA, thereby ensuring the appropriate depth of the implant during the deployment procedure.

With reference to FIGS. 123-124, some embodiments of the frame 2002 can also have a first recess 2032 in a first portion 2020 of the frame 2002 and a second recess 2034 in a second portion 2022 of the frame 2002. The first recess 2032 and the second recess 2034 can each be configured to receive an edge E of a wall of the opening or ostium of the LAA therein when the implant 2000 is expanded against the wall of the opening of the LAA. In some embodiments, the first and second recesses 2032, 2034 can be sized, shaped, and/or otherwise configured to bias the edge E of the opening of the ostium or other tissue surface to remain in contact with the first and second recesses 2032, 2034. The first and second recesses 2032, 2034 can in some embodiments have a curved profile. The first and second recesses 2032, 2034 can help secure the implant to the ostium or body tissue.

Some embodiments of the implant 2000 can have a first recess 2032 in combination with the first apex extension 2024 and/or the second recess 2034 in combination with the second apex extension 2026. The first and/or second recess 2032, 2034 at the first end portion 2020 and/or the second end portion 2022 can bias the implant 2000 to remain in a generally fixed position relative to the wall of an ostium and/or can assist with a proper alignment of the implant 2000 relative to an ostium during implant procedures, which ostium can be the ostium of an LAA. Additionally, any embodiments of the implant 2000 can be configured to have a saddle or convex shape (such that, when viewed from the side as in FIG. 124, the first and second end portions 2020, 2022 are higher than a middle portion of the implant 2000, or otherwise be conformable so that, when the implant 2000 is deployed in the LAA, the implant 2000 can have a curved profile that substantially matches a curved profile of the wall of the heart surrounding the LAA.

Any embodiments of the implant 2000 can In some embodiments have an anchor for anchoring or securing the frame 2002 to the LAA located at least at the first portion and the second portion 2022 of the frame 2002. For example and without limitation, barbs, surface roughness, grips or grip features, or other surface features or securing features can be added to the frame or implant to secure the implant to the LAA, including without limitation adding such features to the first and second portions 2020, 2022. The frame 2002 can be configured to have a first coarse region and a second coarse region formed on, or on an outside surface of, the first and second portions 2020, 2022 of the frame 2002, respectively, the first and second coarse regions being configured to inhibit a movement of the frame 2002 relative to a tissue surface of the ostium O of the LAA.

With reference to FIG. 125, any embodiments of the implant 2000 can have a cover 2050 coupled with the frame 2002. The cover 2050 can at least partially cover the opening 2014 in the frame 2002. In some embodiments, the cover 2050 can completely or substantially completely cover the opening 2014 in the frame 2002. The cover 2050 can be made from any suitable material configured to block or inhibit a flow of blood, thrombus, or other objects or substances through the ostium of the LAA. The cover 2050 can be made from a mesh material, a graft material, or otherwise.

Due to the elongated shape of the implant 2000, some embodiments of the implant 2000 can have an overall cross-sectional area that is approximately 70% less than the cross-sectional area of some types of conventional closure devices that are designed to close a similarly sized ostium of an LAA, such as devices of the size and shape of the device 2060 shown in FIG. 126, and approximately 50% less than other types of conventional closure devices that are designed to close a similarly sized ostium of an LAA, such as devices of the size and shape of the device 2062, as shown in FIG. 126. For example, some embodiments of the implant 2000 have an elongated shape having an overall cross-sectional area that is from approximately 50% to approximately 70%, or from approximately 50% to at least approximately 80% less than implant devices having a circular shape that are designed to close a similarly sized ostium of an LAA. Additionally, some embodiments of the implant 2000 or any other implant disclosed herein can have an elongated shape having an overall cross-sectional area that is from approximately 50% to approximately 70%, or from approximately 50% to at least approximately 80% less than a cross-sectional area of the ostium of the LAA prior to implantation.

Such reduction in size can lead to significant improvements to the patient in terms of healing time which dictate the time a patient may be required to be on anticoagulation medication which have risks associated with taking them. As cross-sectional area of the opening of the implant and/or the distance to a center region of the implant from a wall of the LAA is reduced, the longest distance tissue cells have to migrate from atrial tissue to the cover of the implant is shortened, which should shorten healing times and reduce time on anticoagulation medications.

Some embodiments of the elongated implants disclosed herein can result in a shortening of the time a patient would need to be on anti-coagulation drugs for safe healing following an implant procedure for the LAA, which can shorten the overall healing time after a device is implanted. In some embodiments, this can be achieved by shortening a distance which cells need to migrate from atrial wall tissue to cover the opening (which can be covered by a cover) of the implant. An implant having a circular opening can result in the migration distance being maximum for an LAA, wherein the diameter is the distance that such cells must migrate. If the opening is elongated, such that portions of the wall are moved to a position where they are closer together, the migration distance for cells is reduced and, consequently, healing time can be reduced. An analogous example for this difference in healing time may be found in comparing a 1 inch long (narrow) cut to a 1 inch diameter gash in the skin. The 1 inch long cut would heal faster than the 1 inch diameter gash since the both the surface area and max distance from healthy tissue-to-healthy tissue is reduced, shortening the distance cells need to travel for wound healing.

Any embodiments of the implants and/or delivery systems disclosed herein can be configured to be partially or completely self-expanding, balloon expandable or otherwise mechanically expandable using any known or later developed expansion devices, including without limitation balloon expansion devices typically used for implants, stents, stent grafts, angioplasty devices, or otherwise, or any of the expansion devices disclosed herein. Similarly, any embodiments of the implants and/or delivery systems disclosed herein can be configured to be partially or completely self-elongating, balloon elongatable or otherwise mechanically elongatable, be configured to be partially self-elongating and partially balloon or mechanically elongatable using, without limitation, balloon expansion devices typically used for implants, stents, stent grafts, angioplasty devices, or any of the expansion devices disclosed herein, or otherwise. For example and without limitation, some implant embodiments can be configured to be self-expanding and/or self-elongating to an intermediate size or shape, and then balloon or otherwise mechanically expanded and/or elongated to a final size or shape. Similarly, any such balloon or mechanical expansion devices and/or such devices disclosed herein can, in several embodiments, be used to elongate or complete the elongation of the ostium of the LAA beyond the elongation, if any, resulting from a self-expansion and/or self-elongation of the implant.

FIG. 127 illustrates a non-limiting example of an expansion device 2100 that can be used to expand and/or elongate an implant 2102, which implant can have any of the features, components, or other details of any of the embodiments disclosed herein. The expansion device 2100 can have an expandable member 2104 (which can in some embodiments be an expandable balloon) and an expansion lumen 2106 in fluid communication with the expandable member 2104. Any embodiments of the expandable member 2104 can have an elongated shape and/or otherwise be configured to expand the implant 2102 to have an expanded and/or elongated shape through which an expansion fluid (such as air) can be communicated to the expandable member 2104. In some embodiments, the expandable member can include a plurality of separate or interconnected expandable members coupled together. For example and without limitation, FIG. 128 illustrates an expansion device 2120 that can be used to expand and/or elongate an implant 2102, which implant can have any of the features, components, or other details of any of the embodiments disclosed herein, and that can have an expandable member 2124 that can comprise multiple individual expandable elements. The expandable member 2124 can have any number or size of expandable elements that can, in some embodiments, be coupled together in a desired arrangement or orientation. As shown, the expandable member 2124 can have a first expandable element 2126 positioned in a center portion of the expandable member 2124, a second expandable element 2128 adjacent to and/or coupled with one side of the first expandable element 2126, a third expandable element 2128 adjacent to and/or coupled with a second, opposite side of the first expandable element 2126, a fourth expandable element 2130, and a fifth expandable element 2131.

The second and third expandable elements 2128, 2129 can In some embodiments have a similar size to one another and a smaller size than the first expandable element 2126. The fourth and fifth expandable elements 2130, 2131 can in some embodiments have a similar size to one another and a smaller size than the second and third expandable elements 2128, 2129. Any of the expandable elements 2126, 2128, 2129, 2130, and 2131 can in some embodiments have a spherical shape.

Without limitation, any embodiments of the expansion devices 2100 or 2120 can be configured to expand and elongate the implant to have any of the elongation ratios described herein for any of the implants described herein, including an approximately 3.5:1 first width to second width ratio, or at least approximately 2:1 first width to second width ratio, or In some embodiments from an approximately 2:1 to approximately 8:1 first width to second width ratio, or In some embodiments from approximately 3:1 to approximately 4:1 first width to second width ratio, or from and to any values within these ranges, either before or after one or more additional clips, staples, sutures, or other additional closure devices, if any, are deployed to further close the ostium of the LAA. For example, in some embodiments, such additional clips, staples, sutures, or other additional closure devices can be implanted in the patient after the implant has been fully expanded to any of the ratios or ranges of ratios stated above to further close or completely close the ostium of the LAA. In some embodiments, as stated above, the implant can be expanded to any of the ratios or ranges of ratios stated above without any additional closure devices being implanted thereafter.

FIGS. 129 and 130 illustrate a side view and FIGS. 131 and 132 illustrate an end view of another embodiment of a system 2200 having an implant 2202 and a delivery device 2204 having a movable core 2206 (which can be a cannula, a wire, or otherwise) that can be used to treat an LAA. The implant 2202 can In some embodiments comprise one or a plurality of wires formed in a wire mesh or weave that can be moved from a first, unexpanded state (as shown in FIG. 129) and a second, expanded state (as shown in FIG. 130) by decreasing a length of the implant 2202 from a first length L1 (shown in FIG. 129) to a second length L2 (shown in FIG. 130). In the second, expanded state, the implant 2202 can have any of the sizes, shapes, components (including, without limitation, the cover) and/or other details of any of the other implant embodiments disclosed herein, including without limitation being configured to be expandable to any of the elongation ratios described herein for any of the implants described herein. Similarly, the implant 2202 can be moved from the second, expanded state to the first, unexpanded state by increasing the length of the implant 2202 from the second length L2 to the first length L1.

The delivery device 2204 can have a distal support element 2210 that is releasably coupled with a distal end portion 2202a of the implant 2202 and a proximal support element 2212 that is releasably coupled with a proximal end portion 2202b of the implant 2202. The distal support element 2210 can be coupled with a distal end of the core 2206. The proximal support element 2212 can be slidable relative to the core 2206 and can In some embodiments be supported by at a distal end of a tube 2216 that can hold the proximal support element 2212 in a fixed position relative to the distal support element 2210 as the core 2206 is withdrawn proximally or advanced distally, respectively, relative to the tube 2216. In this configuration, as the core 2206 is withdrawn, the distal support element 2210 will be moved toward the proximal support element 2212 and the implant will be expanded from the first state (shown in FIG. 129) to the second state (shown in FIG. 130). Therefore, the implant 2202 can be advanced into the LAA in the first state and then expanded to the second, expanded state by withdrawing the core 2206, causing the implant 2202 to expand against the wall of the ostium of the LAA. The implant 2202 can thereafter be removed from the proximal and distal support elements 2212, 2210 and the delivery device 2204 can be withdrawn, leaving the implant 2202 positioned within the LAA in the second, expanded state.

FIGS. 133 and 134 illustrate a side view and FIGS. 135 and 136 illustrate an end view of another embodiment of a system 2240 having an implant 2242 and a delivery device 2244 having a movable core 2246 (which can comprise a pair of cannula or wires, or otherwise) that can be used to treat an LAA. The implant 2242 can In some embodiments comprise one or a plurality of wires formed in a wire mesh or weave that can be moved from a first, unexpanded state (as shown in FIG. 133) and a second, expanded state (as shown in FIG. 134) by decreasing a length of the implant 2242 from a first length L1 (shown in FIG. 133) to a second length L2 (shown in FIG. 134). In the second, expanded state, the implant 2242 can have any of the sizes, shapes, components (including, without limitation, the cover) and/or other details of any of the other implant embodiments disclosed herein, including without limitation being configured to be expandable to any of the elongation ratios described herein for any of the implants described herein. Similarly, the implant 2242 can be moved from the second, expanded state to the first, unexpanded state by increasing the length of the implant 2242 from the second length L2 to the first length L1.

The delivery device 2244 can have a pair of distal support elements 2250 that are releasably coupled with a distal end portion 2242*a* of the implant 2242 and a pair of proximal support elements 2252 that are releasably coupled with a proximal end portion 2242*b* of the implant 2242. The distal support elements 2250 can be coupled with a distal end of each of the wires of the core 2246. The proximal support elements 2252 can be slidable relative to the wires of the core 2246. The delivery device 2244 can be configured such that the proximal support elements 2252 can be held in a fixed position relative to the distal support elements 2250 as the core 2246 is withdrawn proximally or advanced distally, respectively, relative to the proximal support elements 2252 or, in another embodiment, as the wires of the core 2246 are spread apart from one another from the first state (shown in FIG. 133) to the second state (shown in FIG. 134).

In this configuration, as wires of the core 2246 are withdrawn and/or spread apart, the distal support element 2250 will move toward the proximal support element 2252 and the implant will be expanded from the first state (shown in FIG. 133) to the second state (shown in FIG. 134). Therefore, the implant 2242 can be advanced into the LAA in the first state and then expanded to the second, expanded state by withdrawing the wires of the core 2246 and/or spread in the wires of the core apart, causing the implant 2242 to expand against the wall of the ostium of the LAA. The implant 2242 can thereafter be removed from the proximal and distal support elements 2252, 2250 and the delivery device 2244 can be withdrawn, leaving the implant 2242 positioned within the LAA in the second, expanded state.

Another embodiment of an implant device 2300 features a wire-formed or laser-cut shape which, when deployed, can linearize and/or stretch the LAA ostium. This can bring a first and a second portion of the ostium of the LAA together, which can be opposing sides or portions of the ostium, for example a superior and an inferior portion. As the implant is deployed, the first-stage shape can be circular which can help in positioning for depth and angle, and the second-stage shape expands out laterally to engage the lateral ends of the LAA ostium and stretch it (shown in FIGS. 137A-137D and 138A-138C). Any embodiments of the devices disclosed herein (including device 2300) can be configured to deploy in a multi-stage or multi-step fashion. For example, in some embodiments, as the implant is deployed to a first stage, a first-stage shape (i.e., the shape of the implant after the user completes the first stage of deployment) can optionally be circular. The implant, when in the first stage shape and size, can be positioned for depth and angle relative to the LAA. During a second-stage of deployment of the implant, the implant can be expanded in a first and a second generally opposing direction (which can be a lateral direction relative to a reference frame of the user) to engage a first and a second portion (which can optionally be the lateral ends) of the LAA ostium and stretch the LAA in the first and second directions.

In any embodiments disclosed herein, the steps of deployment and implantation can include one or more of the following: advancing the delivery catheter into the proximal LAA, near an ostium of the LAA; deploying the implant to a stage one state (in which the first stage portion of the implant can optionally comprise a generally circular or spherical shape); moving or positioning the partially deployed form of the implant to the appropriate implant depth and angulation; positioning and deploying the implant to a stage two state to achieve apposition in a first direction and/or a second direction (which can, optionally, be a lateral direction); evaluating a position and/or an orientation of the implant; if the position and/or orientation are undesirable, recapturing all or a portion of the implant and repeating stage one or stage two of the deployment until the position and/or orientation of the implant is desirable; and/or detaching and removing the delivery catheter.

In any embodiments disclosed herein, the implant and delivery catheter (such as implant and delivery catheter 2310 shown in FIGS. 139A-139E) can have several means of holding the implant to the delivery catheter and controlling the expansion of the implant from the initial stage (stage 1), to the final stage (stage 2). One embodiment of the system can have a suture or tether which can constrain the proximal portion of the implant to control the full expansion and lateral apposition of the implant to the lateral LAA ostium (shown in FIGS. 139A-139E). This tether could also be configured to allow for retrieval, full implant recovery and removal, or redeployment.

Any embodiments or versions of the implants disclosed herein (including the implants 2320, 2322, 2324, 2326, 2328, 2330, and 2332 shown in FIGS. 140A, 140B, 140C, 140D, 140E, 140F, and 140G, respectively) can be formed in a plurality of different ways in order to achieve the spring-like mechanism which is configured to apply lateral expansion force on the LAA ostium. One embodiment of the implant, such as implant 2320, can have a length of wire in a U-shape configured to allow cantilever bending near the middle of the implant. Another embodiment of an implant, such as implant 2322, can have a torsion spring wire-form near the middle of the implant. Another embodiment of an implant, such as implant 2324, can have multiple U-shape cantilever sections or torsion spring forms. Another embodiment of an implant, such as implant 2326, can be formed from round wire. Another embodiment of an implant, such as implant 2332, can be formed from wire strip, or laser cut from a sheet, and/or can be made out of a shape memory alloy, stainless steel, a polymer (which can be an engineered polymer), a composite material, a metal, a super-elastic shape memory alloy, or any other suitable material.

Any embodiments of the implants disclosed herein can have gripping features (such as any of the gripping features 2340 shown in FIGS. 141A-141H) added to the shape or wireform to allow the implant to grip the anatomy better or be atraumatic at the implant-anatomy interfaces. One embodiment of the implant can optionally have cushions or bumpers at the lateral ends of the shape. The bumpers can optionally be textured or have features which provide grip. The bumpers can also have a conical or tapered shape configured to provide a different interface for the different tissues which it contacts. The tissue of the LAA is typically much thinner than the tissue of the LA wall. Accordingly, the bumper can have a first portion configured to contact the LAA that can be larger to distribute the expansion force or grip over a larger area and a second portion configured to contact the LA wall that can be smaller to facilitate a smaller residual opening of the LAA ostium after stretching. Several bumper shapes for atraumatic interfaces and grip are shown in FIGS. 141A-141H.

Any embodiments of the implants disclosed herein can have features added to the shape or wireform which allow the implant to clip or clamp closed a first and a second portion of the LAA (which can, optionally, be a superior and an inferior portion of the LAA ostium) after stretching, such as the embodiments of the clips 2350 shown in FIGS. 142A-142F. The clip 2350 can be an integrated part which can be attached to the implant and can be configured to stretch the LAA ostium. Alternatively, the clip can be a separate feature which can be deployed or attached after the expander is deployed. In an embodiment where the clip is an integrated feature to the expander, the clip can be configured to fold down to fit into the delivery catheter such that, after the expander is deployed, the clip would then deploy.

In any embodiments disclosed herein, the steps of deployment and implantation for any device embodiments disclosed herein can include one or more of the following: advancing the delivery catheter into the proximal LAA, near an ostium of the LAA; deploying the implant to a stage one state (in which the first stage portion of the implant can optionally comprise a generally circular or spherical shape); moving or positioning the implant to the appropriate implant depth and angulation; positioning or deploying the implant to a stage two state to achieve apposition in a first direction and/or a second direction (which can, optionally, be a lateral direction); optionally evaluating a position and/or an orientation of the implant; deploying the clip of the device; verifying the position of the clip (which can optionally be performed using imaging); if final position is undesirable, recapturing the implant and repeating stage one, stage two, and/or clip deployment; if the position and/or orientation are undesirable, recapturing all or a portion of the implant and repeating stage one, stage two, and/or clip deployment until the position and/or orientation of the implant and/or clip is desirable; and detaching and removing the delivery catheter. In any embodiments disclosed herein, the clip can be configured to atraumatically pinch the tissue together. In any embodiments disclosed herein, the clip can be configured to pierce or otherwise penetrate the tissue to achieve a more secure hold.

With reference to FIGS. 143A-143E, in any embodiments disclosed herein, the implant can have an integrated clip 2360, the clip 2360 can be located on the inside of the implant, such that when the implant is deployed, the clip 2360 can be configured to originate its closing motion from the side of the LAA and moves toward the Left Atrium (LA). The implant of any embodiments disclosed herein can also have a single clip arm which can be configured to pull the superior wall of the LA down to cross-over and cover the inferior wall of the LA at the LAA ostium.

With reference to FIGS. 144A-144F, in another embodiment of the implant with an integrated clip feature, the clip (such as clip 2370) can be located both on the inside and outside of the implant, such that when it is deployed, the inside clip feature originates its closing motion from the side of the LAA and moves toward the Left Atrium (LA) which creates a "back-stop" for the outside clip mechanism, which can be closed second or subsequently, to close against. When the outside clip 2370 is closed, it can be configured to close toward the LA wall, grab or engage the LA wall, and pull a first and a second side of the LA wall (which can be a superior and an inferior side) together.

With reference to FIGS. 145A-145F, in another embodiment of the implant with an integrated clip feature, the clip (such as clip 2380) can be located on the outside of the implant such that, when the clip 2380 is deployed, the outside clip feature originates its closing motion from the side of the LAA and moves toward the Left Atrium (LA). The clip can be configured to not pivot to its closed position but rather sides toward the LAA which grabs the LA wall tissue and pulls the LA wall tissue toward the center of the elastic wire expander, effectively closing the LAA ostium by bringing a first and a second side of the LA wall (which can be a superior and an inferior side) together.

In any embodiments disclosed herein, the implant (such as implant 2390 shown in FIGS. 146A-146D) can also have a 4-bar scissor mechanism incorporated in the middle of the expander form which can be configured to allow the implant to clamp closed a first and a second portion (which can be a superior and an inferior portion) of the LAA ostium after stretching. As the delivery catheter deploys the implant, the 4-bar clamp mechanism 2390 would be in a narrow or compressed state. As the 4-bar clamp mechanism is actively expanded or allowed to expand, the wire form would engage the latter ends of the LAA ostium, then the expansion would be permitted to continue to close the 4-bar clamp mechanism which is centered at the LAA ostium. FIG. 146A shows the implant 2390 before it has fully expanded. FIG. 146B shows the implant 2390 after it has fully or nearly fully expanded. As the implant finished deployment and closes the 4-bar mechanism, one or more cup-clamps on a distal portion of the mechanism can come from inside the LAA to meet the cup-clamps on the proximal portion of the mechanism which from the outside of the LA to pinch the tissue in between. The pinching of this tissue can hold the LAA ostium which was first stretched by the elastic wire form together, as shown in FIGS. 147A-147B.

Any embodiments of the implant disclosed herein can be configured for two-stage deployment wherein an expansion of a proximal portion of the implant and an expansion of a distal portion of the implant can each be controlled independently so that the expansion of the implant can be performed in two stages. The two-stage deployment mechanisms and steps described herein can result in a more accurate positioning and orientation of the implant. In any embodiments disclosed herein, the proximal and or distal portions of the implant can be self-expanding or can be mechanically expandable (such as, optionally, through the use of a balloon expander). In any embodiments disclosed herein, a proximal restraint can be used to restrain the proximal portion of the implant. Optionally, a sheath of the delivery catheter can be used to restrain the proximal portion of the implant such that the proximal portion of the implant can self-expand upon advancement past a distal end of the delivery catheter. Additionally, in any embodiments disclosed herein, a distal restraint can be used to restrain the distal portion of the implant. Optionally, the sheath of the delivery catheter can be used to restrain the distal portion of the implant.

With reference to FIGS. 148A-148B, when the distal portion of the implant 2500 (which can be self-expanding) is deployed, the distal end portion can comprise an enlarged atraumatic feature which can be larger than an outside diameter or dimension of the delivery catheter but smaller than the LAA ostium. This first stage shape can be used to center and position the implant in preparation of the second stage, in which the proximal portion of the implant is deployed (the completion of the deployment of the distal portion and the proximal portion of the implant is referred to herein as full deployment).

In any embodiments disclosed herein, the steps of deployment and implantation can include one or more of the following: inserting deployment catheter into the proximal LAA, near the ostium; deploying (i.e., expanding) the distal portion of the implant (this is referred to as the first stage of the deployment); positioning the partially expanded implant to the appropriate implant depth and angulation; deploying the proximal portion of the implant (this is referred to as the second stage of the deployment, or full deployment); evaluating a position and an orientation of the proximal and/or distal portions of the implant; if the position and/or orientation of the implant is undesirable, recapturing at least a portion of the implant (which can be all or a portion of the proximal portion of the implant) and repeating the first stage and/or the second stage deployments steps until the position and/or orientation of the implant is desirable; and/or detaching and removing the delivery catheter.

As described, any embodiments of the deployment system can have an implant (including the implant 2510 shown in FIGS. 149A-149B) that can have a proximal restraint selectively restrain a proximal portion of the implant and/or a distal restraint to selectively restrain a distal portion of the implant. This system can optionally allow for the sheath to be completely withdrawn, leaving the implant fully exposed to the anatomy, but not fully expanded or deployed. The proximal restraint can restrain or prevent the expansion of the proximal portion of the implant device. The optional distal restraint can restrain or prevent the expansion of the distal portion of the implant device. In this configuration, a distal portion of the implant device can be permitted to automatically expand when advanced beyond a distal end of the delivery catheter or by removing the distal restraint, or can be expanded (such as, optionally, using a balloon expander), while the proximal restraint can continue to restrain the proximal portion of the implant device in an unexpanded state.

In this configuration, a partially deployed two-stage implant can form an enlarged atraumatic feature at the distal end of the implant (which can, optionally, be positioned adjacent to the distal end of the LAA). The distal portion can optionally have a size/diameter that is larger than the delivery catheter but smaller than the LAA ostium. Upon activation of the proximal restraint, if any, the proximal portion can subsequently be released/expanded, which would allow full deployment and apposition of the implant to the LAA. In some embodiments, the proximal and/or distal restraints may be selectively reversible or resettable thereby allowing the surgeon to recapture and repeat any of the steps of the two-stage deployment process. For example, In any embodiments disclosed herein, the proximal portion of the implant can be restraint to the unexpanded state by retracting the proximal portion of the implant into the sheath of the delivery catheter, by advancing the sheath of the delivery catheter over the proximal portion of the implant, by resetting or changing the proximal restraint from the unrestrained states to the restrained state, or any combination of the foregoing.

In any embodiments disclosed herein, the steps of deployment and implantation can include one or more of the following: placing a delivery catheter into the proximal LAA, near the ostium; retracting an outer sheath of the catheter to fully expose the implant; expanding the distal portion of the implant (which is referred to as the first stage of deployment) (note that, in some embodiments, the distal portion can be self-expanding such that the distal portion of the implant expands upon advancement past the distal end of the delivery catheter or upon removal of a distal restraint, can be mechanically expandable optionally using a balloon, or otherwise); positioning the expanded distal portion of the implant to the appropriate implant depth and angulation relative to the LAA; expanding the proximal portion of the implant (which is referred to as the second stage of deployment) (note that, in some embodiments, the proximal portion can be self-expanding such that the expansion can be achieved by removing a proximal restraint or, alternatively, by advancing the proximal portion of the implant distantly past a distal end of the delivery catheter, or can be mechanically expanded such as, optionally, using an expansion balloon); evaluating a position and an orientation of the proximal and/or distal portions of the implant; if the position and/or orientation of the implant is undesirable, recapturing at least a portion of the implant (which can be all or a portion of the proximal portion of the implant) and repeating the first stage and/or the second stage deployments steps until the position and/or orientation of the implant is desirable; and detaching and removing the delivery catheter.

Any embodiments disclosed herein can have a proximal restraint, the distal restraint, or both a proximal and distal restraint. In many of the illustrated embodiments, for example, the implants only have a proximal restraint. Also, optionally, in any embodiments disclosed herein, the proximal and/or distal restraints can be provided by the sheath of the delivery catheter such that no separate restraints is/are required. In any embodiments disclosed herein, the proximal and/or distal restraints can include a removable lasso or configuration of suture material which can restrain the implant until the lasso or configuration of suture material released by the user at a device handle. This suture could be removed as the last step of detaching the implant from the delivery catheter.

Optionally, the proximal and/or distal restraints can include a tension tether or tethers which can attach to a series of features around the circumference of a frame of the implant to selectively restrain the desired portion of the implant. The tether or tethers can be advanced through a central lumen of the catheter, like chords of a parachute (as shown in FIGS. 149A-149B). When these tethers are in tension, the implant would be reduced in diameter and when tension is relaxed, the implant would expand to full diameter. These tethers could be removed or released as the last step of detaching the implant from the delivery catheter.

In another embodiment, the implant 2520 can include a mechanical linkage mechanism which, when actuated, would drive radial expansion of the implant and when deactivated or driven in the opposite direction would bring the implant back to the restrained size or state. An example of this embodiment is shown in FIGS. 150A-150C. This mechanism can include a scissor-jack mechanism or a sliding link mechanism for which linear motion is translated into radial expansion. This configuration can be used for the optional distal restraint also.

In another embodiment, the proximal restraint can include a frame which "snap fits" or has features which lock the restraint in a smaller configuration which can be over-come or unsnapped with some radial bias, such as a radial bias resulting from an expandable balloon. This would be a feature which produces a bi-stable implant configuration which is fully resettable when resheathed. This feature may look like barbs or cleats on a Nitinol strut frame which interlock with neighboring struts when crimped and when forced slightly above crimp stage, they release and allow implant expansion.

In another embodiment, the proximal restraint can include a handle (such as handle 2540) which can allow the user to carefully and/or precisely control the speed and motion at which the sheath which is withdrawn to expand and deploy the implant. Examples of embodiments of such devices is shown in FIGS. 151A-151B. An example of a method and a device control the deployment of the implant for accurate positioning via controlled withdrawal of the sheath is a screw gear mechanism on the handle where rotation of an actuator (nut) pulls the sheath back over a handle screw gear (screw) in a very controlled motion. This type of mechanism would provide both slow movement and mechanical advantage, which would aid in the controlled recapture of the implant as well. Note that any of the features, components, or details of any of the embodiments disclosed herein can be combined with any of features, components, or details of the other embodiments disclosed herein to form new combinations and new embodiments, all of which are contemplated as part of this disclosure.

Any of the device and method embodiments disclosed herein can be performed using one or more steerable implant positioning features, which can adjust the angulation of the implant attachment point to the delivery catheter to match the implant angle to the anatomy of the LAA ostium. In any embodiments disclosed herein, the steps of deployment and implantation can include one or more of the following: placing a delivery catheter into the proximal LAA, near the ostium; partially deploying the implant to the first stage, which can be achieved by expanding the distal portion of the implant; using the large partially deployed form (i.e., wherein only the distal portion of the implant has been expanded), positioning the implant to the appropriate or desired implant depth and angulation using the steering capability of the implant attachment mechanism; deploying implant to stage two, which can be achieved by expanding the proximal portion of the implant; evaluating a position and an orientation of the proximal and/or distal portions of the implant; if the position and/or orientation of the implant is undesirable, recapturing at least a portion of the implant (which can be all or a portion of the proximal portion of the implant) and repeating the first stage and/or the second stage deployments steps until the position and/or orientation of the implant is desirable; and detaching and removing the delivery catheter.

One mechanism that can be used to steer the implant angulation at the attachment mechanism includes a three-arm control mechanism 2550, examples of which are shown in FIGS. 152A-152C and 153A-153B. Three arms can provide enough control to fully define the plane which the face of the implant would lie in. By pushing or pulling each of the arms, the implant angle can be changed as desired. The control arms could be manipulated by the user at the handle and the desired angular position can be locked in place as the implant is taken to full deployment.

Another mechanism that can be used to steer the implant angulation at the attachment mechanism can include a multi-arm control mechanism, which can have two or more arms. A two arm mechanism could be used to control the implant in the anterior or posterior direction, the inferior or superior direction, or any combination in between. A four arm mechanism can be used to produce all the same motions as a three arm or more mechanism, but may be more intuitive for the user to control since manipulation would be in the inferior/superior and anterior/posterior directions. The control arms can be configured to be manipulable by the user at the handle and the desired angular position can be locked in place as the implant is taken to full deployment.

Any of the implant devices disclosed herein can be deployed using an implant and delivery catheter design having a steerable delivery catheter which can adjust the position and angulation of the distal end of the delivery catheter to center the implant in the LAA ostium during delivery. In any embodiments disclosed herein, the steps of deployment and implantation can include one or more of the following: placing a delivery catheter into the proximal LAA, near the ostium; steering the delivery catheter such that the distal end of the delivery catheter is perpendicular to a face/plane of the LAA ostium; deploying the implant (following any of the steps or using any of the devices disclosed above); evaluating a position and an orientation of the proximal and/or distal portions of the implant; if the position and/or orientation of the implant is undesirable, recapturing at least a portion of the implant (which can be all or a portion of the proximal portion of the implant) and repeating the first stage and/or the second stage deployments steps until the position and/or orientation of the implant is desirable; and detaching and removing the delivery catheter.

One mechanism which would steer the distal end of the delivery catheter could include a flexible braided catheter with embedded pull wires in the catheter for steering. An optional example of a delivery catheter or system 2560 having such capabilities and/or features is shown in FIGS. 154A-154B. The catheter can optionally flex and steer in more than one location to produce a compound steerable catheter (S-bend) within the single catheter. The catheter flex may also be made from a laser cut metal structure, again with flex and steer in more than one location so that the two locations can produce angulations in different directions to enable steering in different planes.

Another design which could be used to steer the distal end of the delivery catheter in multiple directions can include a dual catheter steerable design, an optional example of such catheter or delivery system 2570 is shown in FIGS. 155A-155B. This design can have nested steerable catheters, one inside another and slidably disposed relative to one another. The inner steerable catheter can also be steerable and rotatable within the outer steerable catheter. The catheter flexes can also be made from a laser cut metal structure and produce angulations in different directions which can enable steering in different planes.

In any of the embodiments disclosed herein, the implant can have one or more sealing features which can provide advanced sealing capabilities to prevent or reduce the likelihood of any leaks after the implant has been deployed into the LAA. The passive sealing feature would be attached to the outside proximal circumference of the implant and may be made from foam, graft material such as dacron, or a hydrogel coating which may swell after hydration to seal and gaps left after implantation, or otherwise.

In any embodiments disclosed herein, the steps of deployment and implantation can include one or more of the following: placing delivery catheter into the proximal LAA, near the ostium; positioning and deploying the implant (following any of the steps or using any of the devices disclosed above); evaluating a position and an orientation of the proximal and/or distal portions of the implant; if the position and/or orientation of the implant is undesirable, recapturing at least a portion of the implant (which can be all or a portion of the proximal portion of the implant) and repeating the first stage and/or the second stage deployments steps until the position and/or orientation of the implant is desirable; allowing the sealing mechanism to expand and sealing any remaining gaps; and detaching and removing delivery catheter.

One mechanism that can be used to provide additional implant sealing includes a foam material 2580 wrapped around the outer circumference of the implant, an optional example of which is shown in FIGS. 156A-156D. The foam can be covered with an additional covering or can be uncovered. The foam can act as a low force gap filler for any voids not sealed by the implant. Another mechanism which can be used to provide additional implant sealing is additional fabric material 2580 which can be made from graft material such as PTFE or dacron, biological tissue such as porcine or bovine pericardium, or other biocompatible textile materials, as shown in FIGS. 156A-156D. These materials can be attached to the outer perimeter of the implant as a means of thickening, or expanding into the void areas within the LAA not sealed by the implant. Another mechanism which can be used to provide additional implant sealing is a hydrogel coating applied around the outer circumference of the implant. This material can swell with time and blood contact, thereby expanding to fill any voids around the implant not already sealed by the device structure itself. In any of the embodiments disclosed herein, the implant can have one or more sealing features which can provide advanced sealing to prevent any leaks after the implant has been deployed into the LAA. The active sealing feature would be attached to the outside proximal circumference of the implant and may be activated by the user to fill any voids which may not have been sealed by the implant itself after implantation.

In any embodiments disclosed herein, the steps of deployment and implantation can include one or more of the following: placing delivery catheter into the proximal LAA, near the ostium; positioning and deploying the implant; if final position is undesirable, recapturing implant and repeating deployment; activating the sealing feature to seal any remaining gaps; and/or detaching and removing delivery catheter.

One mechanism which can be used to provide additional implant sealing activated by the user, that can be used with any of the embodiments of the devices disclosed herein, includes a bunching skirt or covering which could be made of PTFE or dacron, biological tissue such as porcine or bovine pericardium, or other biocompatible textile materials. The skirt or covering 2590 can be slidably attached to the implant and can be bunched or wrinkled when activated by the user to fill voids not filled by the implant, an optional example of which is shown in FIGS. 157A-157C. A simple pull wire or suture can be attached to this feature which when pulled, can cause the free end of the material to pile up to the fixed end, creating a mass of material which would expand radially outward and fill a void. This feature could be activated all at once, or could be selectively activated in certain sections around the circumference of the implant.

Another mechanism which can be used with any of the device embodiments disclosed herein to provide additional implant sealing activated by the user includes a driven expansion of the frame in all outward directions or in one or more selective radially outward directions. An example of an implant 2600 having an embodiment of a driven expansion device is shown in FIG. 158A-158C. This mechanism could include a mechanical linkage mechanism or expansion hinge which when actuated would drive radial expansion of the implant and when deactivated or driven in the opposite direction would relax or lessen that expansion. This mechanism could be a scissor-jack mechanism or a sliding link mechanism for which linear motion is translated into radial expansion.

One solution for implant sealing can include a separate implant which can provide a patch to seal a leak in an implant which was already deployed and has voids or gaps. This patch implant can include a foam insert, a coil insert, a graft, fabric, or biological tissue insert, or some hydrogel which could be accurately placed in the gap or void and anchored in place. The accurate placement could be facilitated through several cables, lines, or sutures which are pre-loaded to the implant and exist in place, radially spaced around the implant after delivery, an example of such an implant 2610 is shown in FIGS. 159A-159B. These cables could be used to guide filler inserts to the exact location of a leak after deployment but prior to implant release from the delivery catheter. Whichever line is closest to the leak, a filler would be run over the line to that location for targeted delivery. Any of the delivery catheter embodiments disclosed herein can include a through lumen, whether central or off-axis (i.e., eccentrically positioned), for an imaging catheter such as an Intra Cardiac Echo (ICE) probe. This lumen would allow the ICE probe to have a viewing perspective which is in-line with the trajectory of the catheter, providing a more direct view of the LAA ostium and implant during delivery.

In any embodiments disclosed herein, the steps of deployment and implantation can include one or more of the following: placing a delivery catheter into the proximal LAA, near the ostium; positioning and deploying the implant using ice imaging, which implant can comprise any of the features, components, or other details of any of the implant embodiments disclosed herein; evaluating a position and an orientation of the proximal and/or distal portions of the implant; if the position and/or orientation of the implant is undesirable, recapturing at least a portion of the implant (which can be all or a portion of the proximal portion of the implant) and repeating the first stage and/or the second stage deployments steps until the position and/or orientation of the implant is desirable; activating the sealing feature to seal any remaining gaps; and/or detaching and removing delivery catheter.

An embodiment of a delivery catheter 2620 that could be used to provide the through lumen for the imaging catheter central and co-axial to the delivery catheter is shown in FIGS. 160A-160D. In another embodiment, also shown in FIGS. 160A-160D, the lumen can be parallel and attached to the delivery catheter, also shown in FIGS. 160A-160D. Another embodiment can include an integrated imaging catheter that is part of the implant delivery catheter and can either be mounted co-axial or parallel to the implant delivery catheter.

One embodiment of an implant device includes a wire-formed or laser-cut shape device which, when deployed, can linearize and stretch the LAA ostium in a multi-stage deployment procedure. The embodiments of the multi-stage deployment procedures disclosed herein can facilitate a more accurate and effective deployment and/or placement of the implant. Some embodiments of the deployment procedure and the implants disclosed herein can bring a first and a second portion (which can optionally be the superior and inferior portions) of the LAA together or closer together.

In some embodiments, as the implant is deployed in a first stage of deployment by a user (who can be a surgeon), a first-stage shape (i.e., the shape of the implant after the user completes the first stage of deployment) can optionally be circular. The implant, when in the first stage shape and size, can be positioned for depth and angle relative to the LAA. During a second-stage of deployment of the implant, the implant can be expanded in a first and second generally opposing directions (which can be a lateral direction relative to a reference frame of the user) to engage a first and a second end (which can be the lateral ends) of the LAA ostium and stretch the LAA in the first and second directions. During a third stage of deployment, the user can activate a hinge mechanism or folding action which can fold the LAA ostium to occlude the opening of the ostium, nonlimiting examples of embodiments of a device 2630 are shown in FIGS. 161A-161C, 162A-162C, 163A-163D, and 164A-164C wherein the small circles indicate hinge points. The ostium can optionally be folded in an up and/or down direction.

In any embodiments disclosed herein, the steps of deployment and implantation can include one or more of the following: advancing the delivery catheter into the proximal LAA, near an ostium of the LAA; deploying the implant to a stage one state (in which the first stage portion of the implant can optionally comprise a generally circular or spherical shape); moving or positioning the implant to the appropriate implant depth and angulation; positioning or deploying the implant to a stage two state to achieve apposition in a first direction and/or a second direction (which can, optionally, be a lateral direction); deploying the implant to a stage three state by activating a hinge or tissue folding mechanism; evaluating a position and/or an orientation of the implant; if the position and/or orientation are undesirable, recapturing all or a portion of the implant and repeating stage one, stage two, and/or stage three steps until the position and/or orientation of the implant is desirable; and/or detaching and removing the delivery catheter.

The hinged or folding portion of the implant can cause the stretched LAA ostium to fold the face of the opening down on one side and up on the other, further occluding the opening. In a more extreme case, the LAA ostium could be folded so far as to face the atrial wall. In some embodiments and/or conditions, the lateral ends of the implant can be used to effect the folding action. In some embodiments and/or conditions, the folding action can occur at any point along the implant as to cause a change in the plane for which the ostium lies in to further occlude the opening. The hinge may be passively activated to move or change to the folded condition when fully deployed (which can, optionally, be achieved using an elastic material). Alternatively, any embodiments disclosed herein can have an active mechanism or actuation element that can be activated by the user to cause the implant and/or hinge to change into the final folded position.

One nonlimiting example of a hinge that can be used with any of the procedures or implant devices disclosed herein is shown in FIGS. 161A-161C, 162A-162C, 163A-163D, and 164A-164C. The hinge can be configured to fold with respect to the implant. Another optional embodiment of the implant is configured to fold with respect to the atrial wall. For example, a portion of the implant (which can be the implant bracing portion or mechanisms) can be supported against the atrial wall, thereafter the hinge and/or remainder of the implant can fold in the opposite direction.

Another embodiment of an implant device can have a wire-formed or laser-cut shape portion which, when deployed, can linearize and/or stretch the LAA ostium, which can, for example and without limitation, bring a first and a second portion (which can optionally be the superior and inferior portions) of the LAA together or closer together. The first and second portions can optionally be the superior and inferior portions of the LAA. As the implant is deployed, the first-stage shape (i.e., the shape of the implant following the first stage deployment procedures or steps) can optionally be circular. The implant, when in the first stage shape and size, can be positioned for depth and angle relative to the LAA. During a second-stage of deployment of the implant, the implant can be expanded in a first and second generally opposing directions (which can be a lateral direction relative to a reference frame of the user) to engage a first and a second end (which can be the lateral ends) of the LAA ostium and stretch the LAA in the first and second directions.

During a third stage of deployment, the user can activate a hinge mechanism or folding action which can fold the LAA ostium in a third and/or fourth direction to occlude the opening of the ostium (a nonlimiting example of a device 2635 having such a capability is shown in FIGS. 165A-165C, 166A-166C, and 167A-167D). The third and/or fourth directions can be in the up and/or down direction in the user's frame of reference.

In any embodiments disclosed herein, the steps of deployment and implantation can include one or more of the following: advancing the delivery catheter into the proximal LAA, near the ostium; deploying the implant to a stage one state (in which the first stage portion of the implant can optionally comprise a generally circular or spherical shape); positioning the implant to the appropriate implant depth and angulation; deploying implant to a stage two state to achieve apposition in a first direction and/or a second direction (which can, optionally, be a lateral direction); deploying the implant to a stage three state by activating a hinge or tissue folding mechanism to fold one end of the implant in a third direction and another opposite end of the implant in a fourth direction, the fourth direction being opposite to the third direction (which can, optionally, be the up and down directions); evaluating a position and/or an orientation of the implant; if the position and/or orientation are undesirable, recapturing all or a portion of the implant and repeating stage one, stage two, and/or stage three steps until the position and/or orientation of the implant is desirable; and/or detaching and removing the delivery catheter.

In any embodiments disclosed herein, the hinged portion of the implant can cause the stretched LAA ostium to twist a face of the opening of the LAA in one direction (for example, a first direction, which can optionally be a down direction on one side and up on the other side relative to a user's frame of reference), further occluding the opening. In any embodiments of the deployment procedures disclosed herein, the twisting action can occur at the first and second ends of the implant (which can optionally be the laterally oriented relative to a user's frame of reference) or can occur at any point along a length of the implant or arms thereof so as to cause a twist or wrinkle in the plane for which the ostium lies in to further occlude the opening. In any embodiments disclosed herein, the hinge may be passively activated though the use of an elastic material which can deform to the twisted condition when fully deployed or otherwise released from an untwisted initial state. Optionally, in any embodiments disclosed herein, the hinge deform to the twisted condition using an active mechanism that can be activated by the user to change the implant to the final, twisted state or position. Some embodiments of the hinge, such as the hinge shown in FIGS. 165A-165C and 167A-167D, is configured to fold with respect to the implant. Another embodiment of the implant can be configured to hinge with respect to the atrial wall, meaning the implant can have a portion of the implant bracing on the atrial wall in order to fold in the opposite direction and create a twist along the LAA ostium.

Certain embodiments of the disclosure herein can advantageously match the surgical type closure where the left atrial appendage is not plugged but closed or occluded with limited exposure of the device in the left atrium. Certain embodiments can include entering through the venous system via femoral vein and a transseptal puncture into the left atrium so that access of the left atrial appendage (LAA) can be gained. Imaging could use both fluoroscopy and echo (TEE, ICE or transthoracic), the size, position, and location of the LAA for entry of the prosthesis for closure. Placing the spreading device into each end (superior and inferior) of the LAA, each end-shoe will allow for stabilization of the device visa-a-vis the LAA. Connecting the shoes are struts with at least one pivot point between each shoe to connect the elements together for structural integrity and functionality to expand the shoes apart from one another and reduce the height of the LAA thus closing the opening of the LAA from the LA. By mechanical advancement of the main strut toward the pivot point the connecting struts and shoes are now forced laterally and expand the shoes left and right relative to the centerline of the LAA. With the shoes at each end (superior and inferior) of the LAA and the height decreased, the LAA would now be able to be closed via clips, staples, sutures or screws along the two approximated, adjacent edges of the tissue. Closing the edges of the LAA would now eliminate the flow between the left atrium and the LAA and closing flow in either direction and stopping potential thrombus from migrating into the circulatory system. The tissue approximation and attachment using clips, staples, or sutures would be completed using a delivery catheter along the tissue seam joining the tissue edges together and closing the LAA.

Locating the superior and inferior edges of the LAA using echo, flouro and mechanical means, the two ends (superior and inferior) can now be linearized and/or elongated for joining the edges together. The location of the superior and inferior edges using the shoes and a contrast dye injection with fluoroscopy would allow the radiopaque elements of the implant to be visible. The implant construction could use metallic materials such as stainless steel, Nitinol, Cobalt-Chromium or polymer or a combination of both implant grade quality materials. Ideally, the implant would use the least amount of material and leave the smallest footprint possible in the left atrium or the inner side of the LAA and the least surface area exposed to LA blood flow.

Dimensions of the superior and inferior ends of the LAA could range from about 30-50 mm in length. The implant could accommodate these lengths and allow for tissue ingrowth at each end and along the upper and lower ends of the LAA. Sealing the upper and lower ends from blood flow would be advantageous to limit any potential thrombus migration. A coiled wire could be advanced starting at one end and rotated to the other end of the implant embedding the coiling into the upper tissues.

Another means for joining the tissue together would be to join together the upper and lower portions of the LAA. Using the spreading device to separate the ends away from one another would allow the upper tissue to be joined. The joining could use screw-type anchors where the entry would penetrate one portion of the upper or lower tissue and then through the second portion of the upper or lower tissue. An example would be to penetrate the upper tissue with an anchor and then rotate the tip of the catheter moving the anchor from the upper portion to the lower portion thus overlapping the tissue while completing the rotation of the anchor embedment to complete the joining of the tissue together. This would require the catheter tip to be off-set where the anchor is exposed to allow for an offset when rotated with respect to the centerline of the catheter. An over rotation of the anchor could be possible so a stop similar to a slip-screw or drywall screw where the head and upper portion of the screw are allowed to rotate freely while the lower or distal portion would have a threaded portion to penetrate and grasp the tissue. This would draw the two tissues together pulling the near tissue toward the far tissue.

In some embodiments, steps for implantation can include any of the following: entry to the venous system in the groin; advancement of the delivery system up to the inferior vena cava; crossing into the left atrium through the septum; imaging the left atrium and left atrial appendage for positioning of the delivery catheter; positioning the delivery catheter near or in the left atrial appendage; an exposure of the spreading tool into the left atrium for linearization of the superior and inferior edges; an approximation and joining of the upper and lower portions of the left atrial appendage; securing and locking the now joined upper and lower portions of the left atrial appendage; a disconnection of the catheter from the spreading tool implant and joining tools of the upper and lower tissues; and/or removal of all catheters from the body.

The entry into the left atrium through a transseptal puncture with the delivery catheter and advancing a spreading tool to enter the semi-round left atrial appendage (LAA). The spreading tool would engage the edges of the LAA and spread them laterally changing the shape of the LAA from a circular shape to a long oval where the upper and lower edges of the tissue together and thus sealing the LAA from the circulatory system similar to a surgical suture closure. The catheter would have a plurality of lumens to allow for advancement of tools such as the spreading tool and screw anchors along with possible imaging tools such as intra cardiac echo and a guidewire for safe advancement.

The spreading tool could consist of a stainless steel, Nitinol or MP35N arms that pivot somewhere between two edge receiving pads located at the end of each arm. The arms would hold open the ends of the LAA while the attached. The mechanism of exposing the spreading tool into the LAA could be guided under live fluoroscopy and transesophageal, transthoracic, intracardiac or surface echo to position the receiving pads at each respective location. Once positioned the spreading tool can then be expanded by moving a pivot point closer toward the LAA forcing the two ends away from one another creating a linear shape to the LAA. The spreading tool could use spring force to maintain a constant force on either end of the arms. Additionally, a secondary adjustment could spread the pads to customize the spread distance for each patient. The pads could be covered in fabric or Gore-Tex materials to promote healing and tissue ingrowth and be a constructed of a metallic and polymer material. The pads could be allowed to pivot or be fixed to each arm.

The tissue anchors could be constructed from coiled wire, cut from a hypotube via laser, or machined from bar stock. The tissue anchors could be attached and detachable in vivo via catheter connection when ready for final deployment. The tissue anchors could be constructed from an implantable material such as stainless steel, MP35N, polymer or other suitable material. The anchors could measure about 5-20 mm in length but more preferably about 8-10 mm. The diameter would be about 1-5 mm but more preferably about 2-3 mm and could have a variable pitch but a measurement of about 10-30 threads per inch would be best for tissue capture.

Additionally, there could be anti-rotational features such as barbs or variable pitch changes along the length to hold intended position in the tissue. There could be a flange or washer at the thread head for resistance for the anchor to imbed into the tissue too far. A flush head configuration would allow for a smooth tissue formation in the left atrium so a receiver style acceptance in the screw may be beneficial. This receiver could be a slot, hex, square or other torque transmission connection to the driver housed in the catheter body. The head could be larger than the body of the screw as a machined flange, or an expandable disk or star to resist pullout through the tissue. Each anchor could be preloaded into the catheter or loaded individually in a single lumen traversing from the proximal end to the distal end. The connection could be a passive joint where longitudinal force would allow the connection to be maintained or an interlock could be used to hold the driver and screw together where a safety mechanism would resist premature disconnection. The driver could be constructed of a solid round wire, square or hex wire, or a hypotube with or without a flexible portion for adequate torque transmission to drive the anchors into the tissue. The flexible portion could consist of a laser cut pattern selectively removed to allow for torque transmission but also increase the flexibility in curved sections of the catheter. These patterns could be helix, slots or other known patterns for driver tubes. Additionally, a twisted-wire torque driver could also be used to deliver the anchor. Examples of these driver tubes are manufactured by Heraeus Medical Components in Hanau Germany and can be manufactured in lengths of about one meter and diameters of about one millimeter in solid or tubular configurations. Laser cut hypo tubes can also be uses and a continuous tube or with portions mechanically removed or selectively removed via laser cutting to provide additional flexibility while also providing adequate torque response. The pitch and pattern can vary from proximal to distal sections providing various degrees flexibility along the driver tubes. The driver tubes can be coated with a polymer and or hydrophilic layer to reduce transitional and rotational friction.

Another means for attaching the upper and lower tissue of the LAA is to use a zip-tie style attachment where the upper and lower tissues would be embedded with and anchor connecting the two ends to be approximated with a locking connection and or a final position lock to permanently secure the two elements together. The anchor means could be constructed of a screw type rotated into the upper and lower tissue or push-style anchor to be advanced into the tissue with barbs resisting migration. The joining of the two anchors could be a wire, flat ribbon, polymer suture, or cable using a locking means to hold the two ends during and after approximation. The locking means could use a ratcheting cam, tooth and pawl or other means for incrementally tightening the two ends. The anchors could also be connected through a series of sutures to gather or join the anchors together. The suture could be a polyethylene or pTFE (GoreTex) to allow for slippage through each anchor. To secure the ends, a cam style locking means or knotting could hold the ends from migrating or loosening. These anchors could be installed internal or external to the LAA.

An example of an internal anchoring implant would be a Nitinol formed element cut from a hypotube and heat-set to a shape to close the left atrial appendage. There would be a plurality of anchor elements and a screw driven slider to open and close the frame. In the closed position, the anchors could be hidden and in a first, reduced diameter and mounted at the distal end of the delivery system. There could be a screw mechanism to translate a collar along the delivery axis of the implant forcing the implant from a first, smaller delivery position to a second, larger implant position then returned to a smaller closure position. In these three steps the collar could start at the more proximal, delivery position and then translated to the distal position and finally returned to a more proximal finishing position by closing the implant and anchors thus closing the left atrial position. The implant could be cut from a Nitinol tube where the most distal portion of the implant is positioned in the left atrial appendage near the back and the more proximal portion of the implant is positioned in the more proximal portion of the left atrial appendage with anchors facing proximal and toward the opening of the left atrial appendage and are pulled into position with tension on the implant and delivery system thus imbedding the anchors into the internal edges of the left atrial appendage. The anchors could be formed, shaped or laser cut to better hold the tissue once imbedded in the internal tissue. One characteristic of this implant is that none of the material is exposed to the left atrium as the material is all housed internal to the left atrial appendage.

Another method for an internally located device could be to engage the tissue anchors in the left atrium where the device would have a first position, closed for delivery and a second open position where the struts are allowed to expand and contact the opening of the left atrial appendage no matter the shape or size and a third position where the device could be closed and thus halting the flow in an out of the left atrial appendage. The center of the device could block any flow between the struts, or the struts could be coated or covered with fabric or thrombogenic coatings. The importance of the covering would be to eliminate any free debris within the left atrial appendage would remain isolated and not cause a stroke or embolic event if released thus trapping the debris in the appendage. The entry into the LA could be a venous femoral stick to traverse up the inferior venacava to cross the septum into the LA. This has been a proven and standard technique to enter the left side of the heart for various other structural heart procedures.

Another method for closing the left atrial appendage would be to cut from a Nitinol hypo tube a diamond pattern, expandable device with a diameter between 20-50 mm but preferably about 30 mm. The length would be between 10-30 mm but preferably about 15 mm. The tube would start with a solid diameter of about 8-10 mm with a wall about 0.2-1.0 mm and a diamond or sinusoidal pattern for radial expansion of a round shape with a proximal flange angled outward to a larger diameter. The angle would be between 30-60 degrees but preferably about 45 degrees creating a taper from the base diameter. The first heat-set to this cylindrical shape with a flange would then go through a second heat-set to flatten the cylinder creating an elliptical shape with a minimal height on the minor axis and a maximal length on the major axis as its free shape. The flange and cylinder would remain along the flattened device and have distal facing barbs and or anchors to be inserted into the left atrial appendage ostium. Alternatively, the cylinder portion could be disconnected or a separate component from the angled flange portion thus could be removed from the body and leaving the flange and anchors only as an implant at the ostium of the left atrial appendage. Another shape would be a round, cylindrical shape to be expanded to a larger round cylindrical shape with a similar flange design to be anchored to the left atrial appendage. The round shape could have a blocking device in the center to prohibit central flow from the left atrium to the left atrial appendage. The blocking device could be a portion of the laser cut tube implant or a separate connected device to eliminate the passage of blood through or around the implant.

In some embodiments, a method of implantation can include: loading the device in a collapsed configuration inside a sheath at the distal end of a delivery catheter; advancing the delivery catheter into the left atrium; unsheathing the device allowing it to expand into a flattened cylinder with the flange at proximal end and barbs and or anchors forward or distal facing; inserting an expansion balloon inside the flattened cylinder device and inflate to create a round implant; advancing the delivery catheter, balloon expanded device into the left atrial appendage matching closely the diameter of the device and balloon to the ostium of the appendage; expanding the balloon and device to create a round shape of the left atrial appendage and implant so the cylinder is inside the appendage and the flange remains in the left atrium with the barbs and or anchors are exposed to the ostium; advancing the delivery system and implant to engage the barbs and or anchors into the ostial tissue for permanent securement; and/or deflating the balloon and allow the device to recover to its flat shape thus closing the left atrial appendage into a linear shape eliminating the blood circulation. The entry into the LA would be a venous femoral stick to travers up the inferior venacava to cross the septum into the LA. This has been a proven and standard technique to enter the left side of the heart for various other structural heart procedures.

Some embodiments of the delivery systems disclosed herein can include a 0.035 inch guidewire, dilator, and steerable guide and a delivery catheter to access the left atrium through a venous entry from the femoral vein. The guide could measure about 90 cm in length and about 24-34 French in diameter with a fixed or variable curve controlled outside the body. The steering is generally controlled via flexible distal section with a tensioning wire to bias the length of one diameter of the distal section by shortening one side of a laser cut tube pattern or a spiral wound ribbon or wire. The tension wire can be attached at the distal most tip of the guide and travers proximally where the wire can be pulled and maintained its relative tension and position with a rotational handle and clutch to resist unwinding when released. A series of gears and clutches could be used to increase the mechanical advantage. Radiopaque markers could provide positing inside the patient's body during introduction, positioning and removal. The shafting could preferably be constructed to be torqueable, and able to accept the delivery catheter through its inner lumen with a lubricious liner such as Teflon or other fluoropolymer and be laminated to a nylon product such as Pebax having a durometer of 50-70 on the Shore D scale with a possible softer distal section for less vessel trauma and easier entry across the septum. The dilator for guide introduction would be a very soft material with a low coefficient of friction to pass through the vein guiding the introduction of the delivery system and guide. Through the dilator could be a through lumen for a 0.035 inch guidewire and lure fitting for acceptance of a syringe for flushing and fluid introduction.

In some embodiments, the delivery system can measure about 120 cm in length and about 18-30 French in diameter and have a steerable distal section controlled outside the patient with a tensioned pullwire similar to the described guide where the distal section would be more flexible and constructed of a fluoropolymer inner liner with a multilumen to accept passage of wires, coils, hypotubes as needed to connect, actuate and deploy the implant into the left atrial appendage. Laminated together could be polymers, and metallic elements such as nylon (Pebax), coiled wire or ribbon or a laser cut hypo tube section for flexibility and torque response for positioning. Radiopaque markers and construction would be added for ease of positioning under live x-ray (fluoroscopy). Additional coatings could be added to inner and outer diameters to reduce friction between each catheter or dilator and vessel contact. The delivery and guide catheters could be constructed with handle assemblies to aid in delivery, positioning and curve actuation. Additional handle features could include flush ports for device preparation to evacuate air before patient instruction, or used to introduce radiopaque fluids for visualization inside the patient. Ports and lumens could also be used for the introduction of visualization catheters such and ICE (intra cardiac echo) or oblation catheters. The connection means between the delivery catheter and the implant could be via threaded connection, mechanical interlocking means, or other common device connections used in the interventional cardiology.

FIG. 168 illustrates a surgeons view with the sheath and delivery catheter 2700 across the left atrium and the spreader device 2702 entering the left atrial appendage with the shoes 2704 opposing the superior and inferior edges of the left atrial appendage to linearize the appendage thus approximating the upper and lower portions together for connection and elimination of blood flow into and out of the left atrial appendage. FIG. 169 illustrates the actuation and spreading of the left atrial appendage with the spreading device being advanced out of the delivery system and the superior and inferior edges now approximated relative to one another for connection. FIG. 170 illustrates the spreading of the left atrial appendage superior and inferior edges and the spreading device 2702 disconnected from the delivery catheter. The edges are now approximated and can be easily joined through sutures, clips, staples or other means for sealing the left atrial appendage from the blood circulation. The spreading device 2702 can be removed post joining of the upper and lower portions of the left atrial appendage or left as a permanent implant. The goal would be to leave the least amount of foreign material in the body and the least amount of surface area exposed in the left atrial circulation.

Figure 171A:
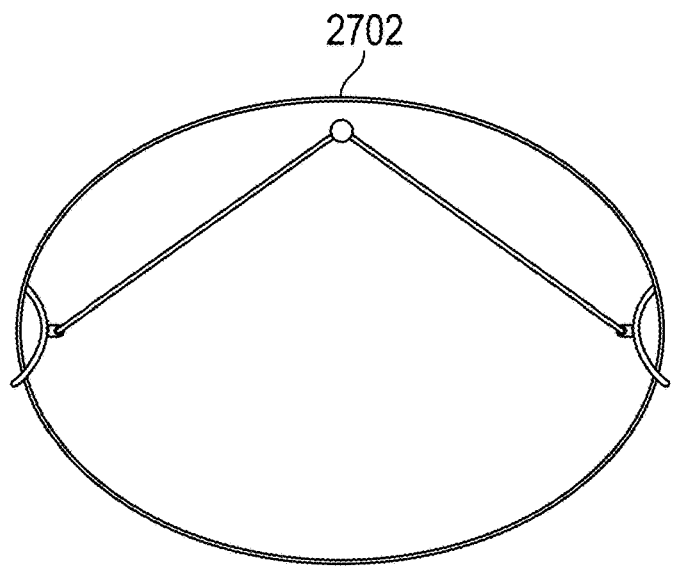
Figure 171B:
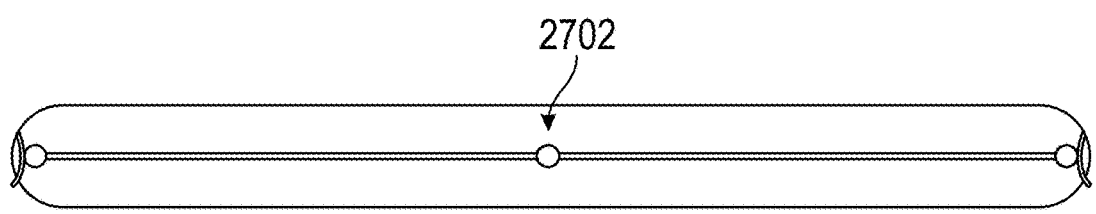
Figure 171C:
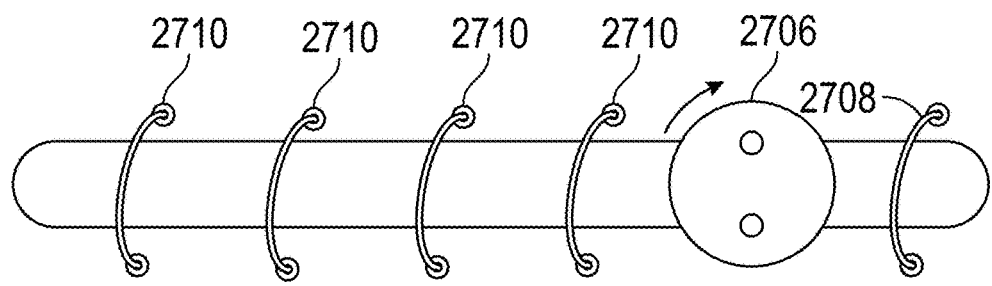
Figure 171D:
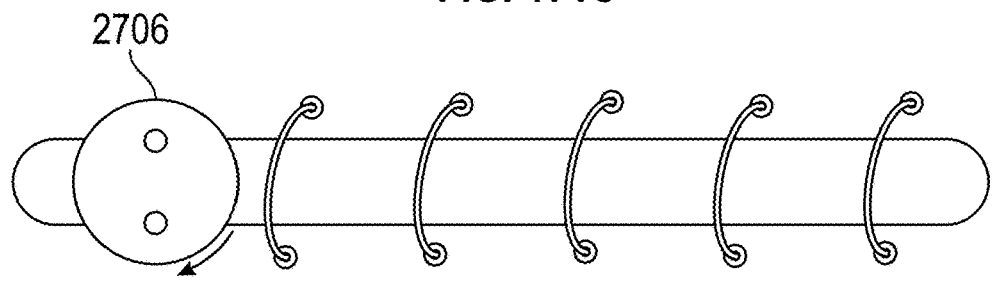

FIG. 171A illustrates an example of the spreading device 2702 partially implanted or installed into the left atrial appendage. FIG. 171B illustrates the spreading device 2702 now expanded and linearizing the left atrial appendage and this approximating the upper and lower portions of the left atrial appendage. FIG. 171C illustrates an example of the two edges joined via catheter where a first edge of the LAA has been joined and the adjacent upper anchor has been placed while then rotating the catheter 2706 180 degrees to lower tissue for another anchor placement to secure the anchors together thus stitching together the edges with sutures 2708. To the second side of the catheter, is illustrated additional anchor placement points 2710 along the tissue edges. To track the catheter 2706 along the tissue seam, the catheter 2706 could be tracked along the spreading device as a guide following the two edges. FIG. 171D illustrates the tissue seam nearly completely joined and the delivery catheter 2706 now at the second end of the tissue seam being rotated to join the anchors together.

FIG. 172A illustrates a side view of a treatment device 2720 implanting a tissue anchor 2722 by rotating the tissue anchor into the upper portion of the left atrial appendage. The anchor 2722 could be rotated like a cork screw or a barbed push-style anchor to resist tissue migration. FIG. 172B illustrates a side view of a tissue anchor 2722 being rotated into the lower portion of the left atrial appendage and connected via suture, wire or other attachment device 2724. FIG. 172C illustrates a side view of the tissue anchors 2722 being implanted into the upper portion of the left atrial appendage and the lower portion of the left atrial appendage and the attachment device 2724 being approximated thus joining the upper and lower portions of the left atrial appendage together and thus closing or occluding the appendage from the blood circulation.

Figure 173A:
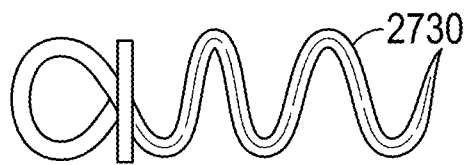
Figure 173B:
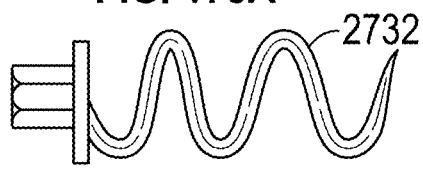
Figure 173C:
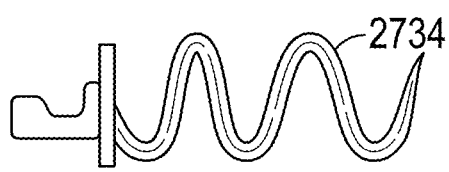
Figure 173D:
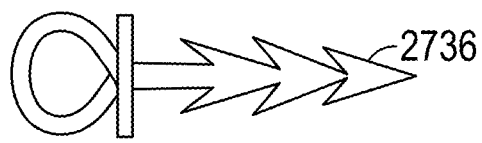

FIG. 173A illustrates an embodiment of a rotational anchor 2730 with a coiled loop wire at the left or proximal side and a flange below the middle portion with a helical coiled wire at the right or distal and for tissue penetration. FIG. 173B illustrates another embodiment of a rotational anchor 2732 with a hex-type driver at the proximal end. FIG. 173C illustrates another embodiment of a rotational anchor 2734 with an interlocking driver at the proximal end. FIG. 173D illustrates an embodiment of a push-style anchor 2736 with a coiled loop that can be formed from wire or otherwise at the proximal end. FIG. 174 illustrates another device 2740 for attaching the upper and lower tissues through the use of staples or clips to join together the upper and lower portions of the left atrial appendage after the edges have been spread longitudinally.

Figure 175A:
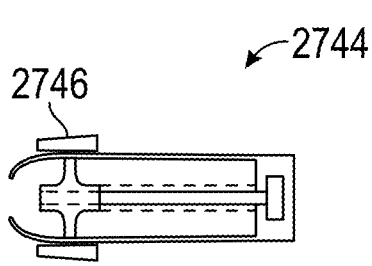
Figure 175B:
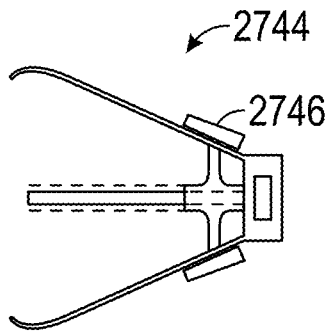
Figure 175C:
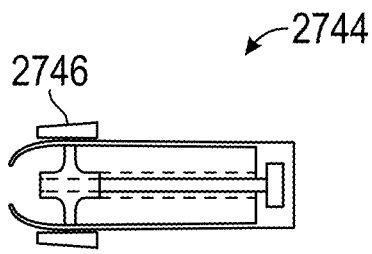
Figure 175D:
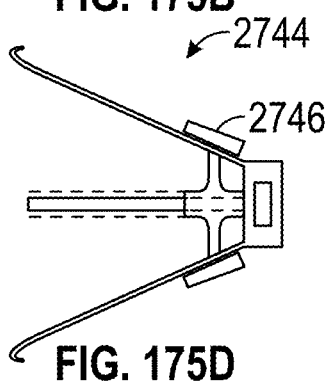

FIG. 175A illustrates an internally implanted and actuated device 2744 where the device 2744 is closed upon delivery and advanced into the left atrial appendage with the slider 2746 positioned most proximal holding the device in a first, smaller configuration to safely deliver via catheter. FIG. 175B illustrates an internally implanted and actuated device 2744 where the device 2744 is opened, exposing the anchors with the slider positioned most distally ready to be moved or pulled proximally to embed the anchors into the internal tissue of the left atrial appendage. FIG. 175C illustrates an internally implanted and actuated device 2744 where the device is attached to the tissue with the slider position now in its closed and final position ready for disconnection from the delivery system. FIG. 175D illustrates an internally implanted and actuated device 2744 where the device 2744 is attached to the external tissue in the left atrium and device is in an open position.

Figure 176B:
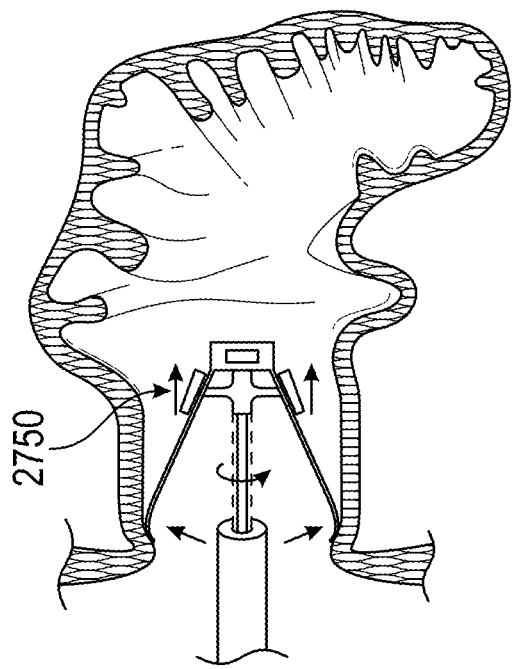
Figure 176D:
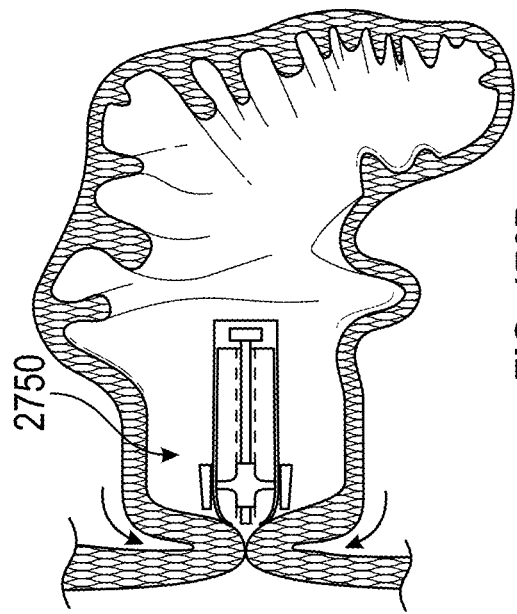
Figure 176A:
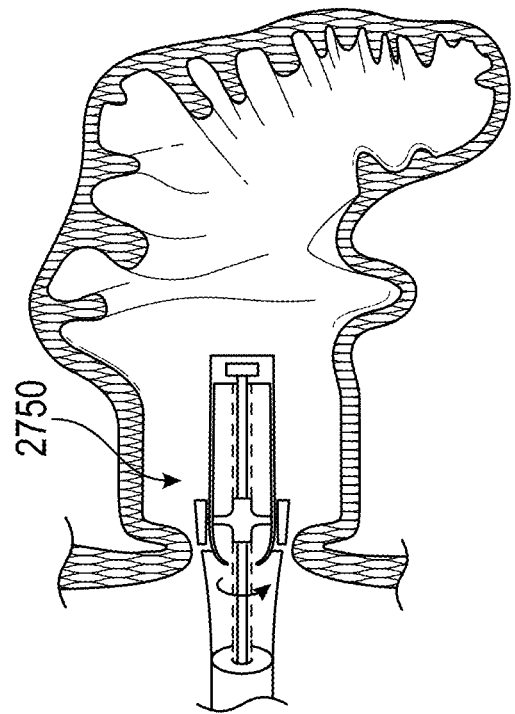
Figure 176C:
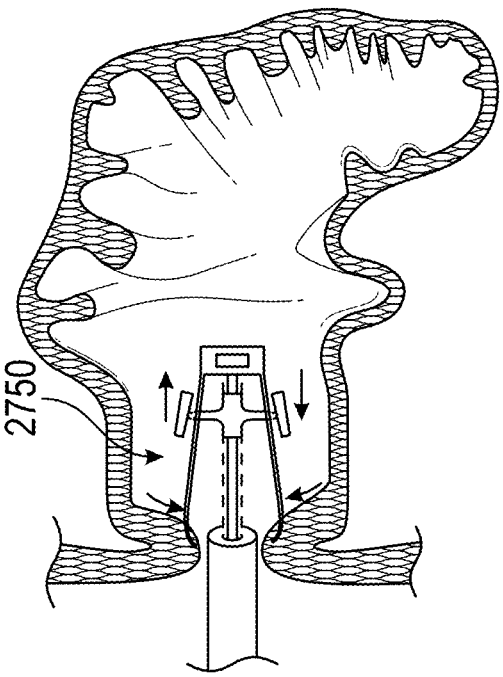

FIG. 176A illustrates an implant device 2750 wherein the device 2750 is closed and positioned inside the left atrial appendage in its closed, delivery configuration. FIG. 176B illustrates the device 2750 where the device 2750 is opened and retracted proximal thus imbedding the anchors into tissue. FIG. 176C illustrates the device 2750 where the device 2750 is beginning to be closed as the collar is retracted proximally via rotational screw and nut mechanism connected to the collar retracting proximally thus closing the anchors and attached tissue. FIG. 176D illustrates the device 2750 where the device 2750 is closed and in its final position and where the anchors are closed and the attached tissue where it is approximated and thus the left atrial appendage is now sealed from the blood circulation from the left atrium and the implant is disconnected from the delivery system.

FIG. 177 illustrates the surgeons view with the major structures in the left atrium on the relative clockface. FIG. 178A illustrates the spreading device 2760 entering the left atrial appendage and engaging the edges of the tissue laterally. The pivot points allow for actuation and expansion as the device is advanced distal the catheter thus opening and linearizing the left atrial appendage. FIG. 178B illustrates the spreading device 2760 in the left atrial appendage and engaging the edges of the tissue laterally. The pivot points are fully extended distal the catheter thus opening and linearizing the left atrial appendage and approximating the upper and lower tissue.

FIG. 179A illustrates an internally implanted and actuated device 2770 where the device 2770 is opened and advanced distally thus imbedding the anchors into left atrial tissue. FIG. 179B illustrates the internally implanted and actuated device 2770 where the device 2770 is closed and advanced distally thus imbedding the anchors into atrial tissue external to the left atrial appendage but rather in the left atrial tissue and the central portion is closed with the central area and material of the device.

Figure 180A:
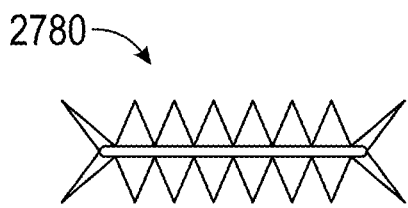
Figure 180B:
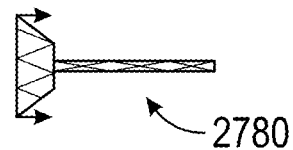
Figure 180C:
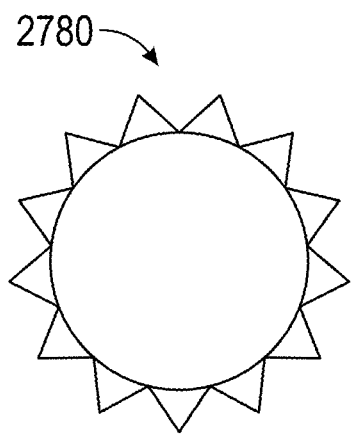
Figure 180D:
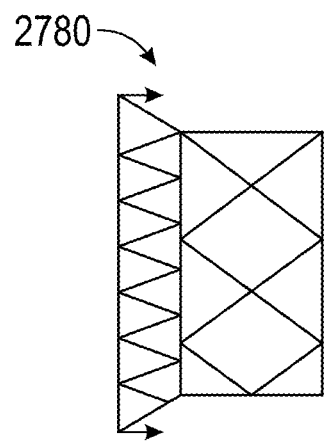

FIGS. 180A-180B are a front view and a side view of a device 2780 (that can be made from a shape memory material such as Nitinol) in a first, flattened and relaxed state. The device 2780 can be cut from a round hypotube, expanded to a larger diameter, and then flattened to an ellipse along its central axis where the major diameter verses the minor diameter has a large aspect ratio and the relaxed shape is essentially a flattened cylinder with distal facing tissue barbs or anchors around the periphery. FIGS. 180C-180D are a front view and a side view of the device 2780 in an expanded, round shape for delivery into the left atrial appendage to define the shape of the left atrial appendage ostium and the implant thus matching and sizing for the patient's specific anatomy.

Figure 181A:
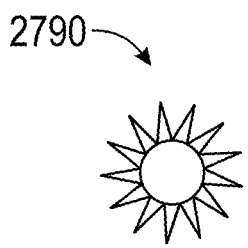
Figure 181B:
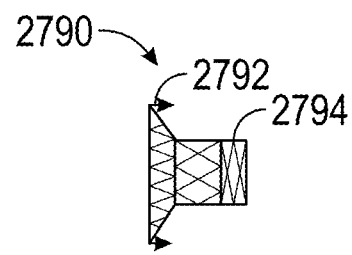
Figure 181C:
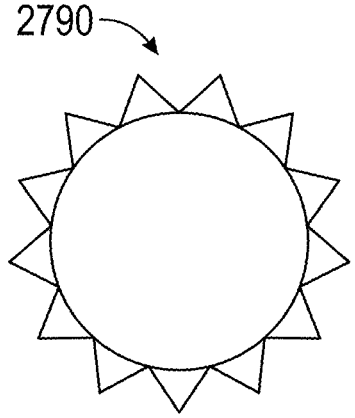
Figure 181D:
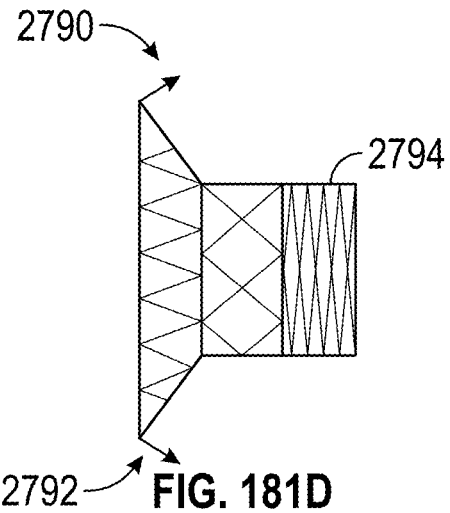

FIGS. 181A-181B are a front view and a side view of device 2790 (that can be made from a shape memory material such as Nitinol) in a first, round and relaxed state. The device 2790 can be cut from a round hypotube and expanded to a larger diameter. The device 2790 can have one or more distal facing tissue barbs or anchors 2792 around the periphery. FIGS. 181C-181D are a front view and a side view of the device 2790 in an expanded, round shape for delivery into the left atrial appendage to define the shape of the left atrial appendage ostium and the implant thus matching and sizing for the patient's specific anatomy. A blocking element 2794 can be attached to or cut from the same hypo tube to prohibit blood flow through the device and located at the proximal or distal end of the device or anywhere in between along the central axis.

Figure 182A:
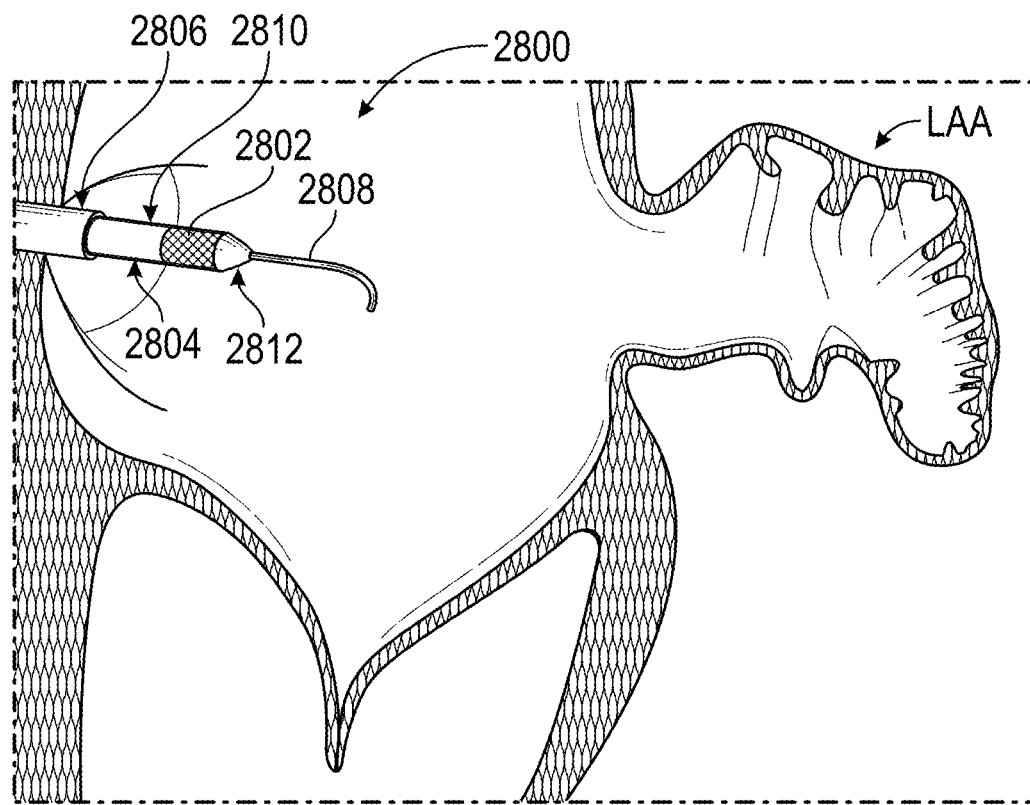
Figure 182B:
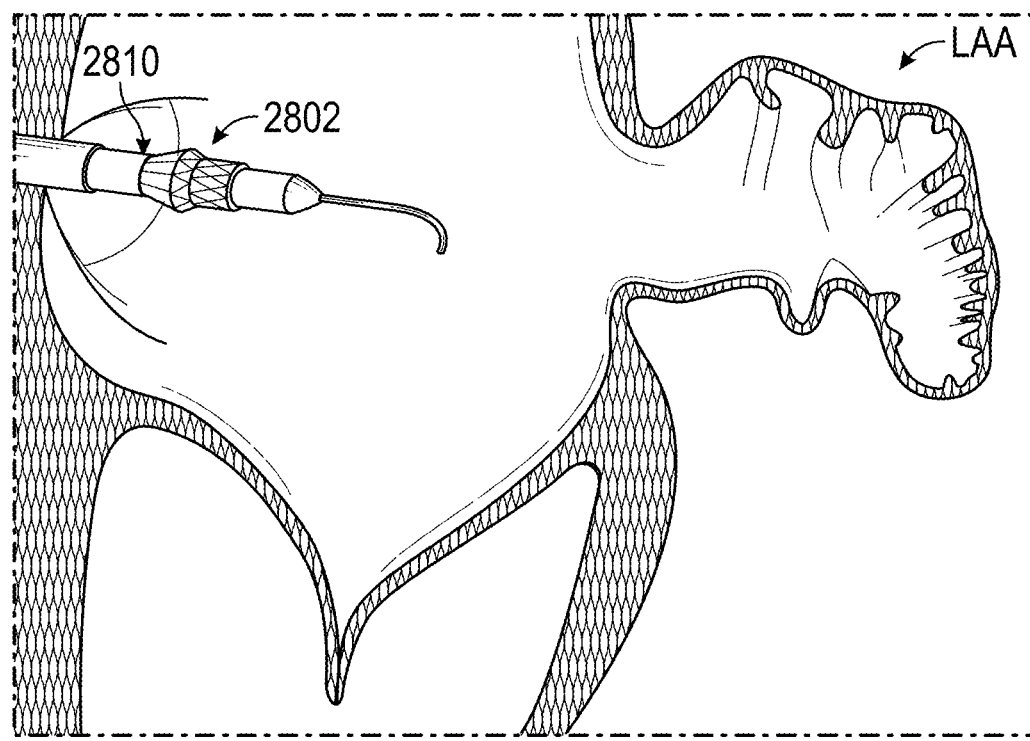
Figure 182C:
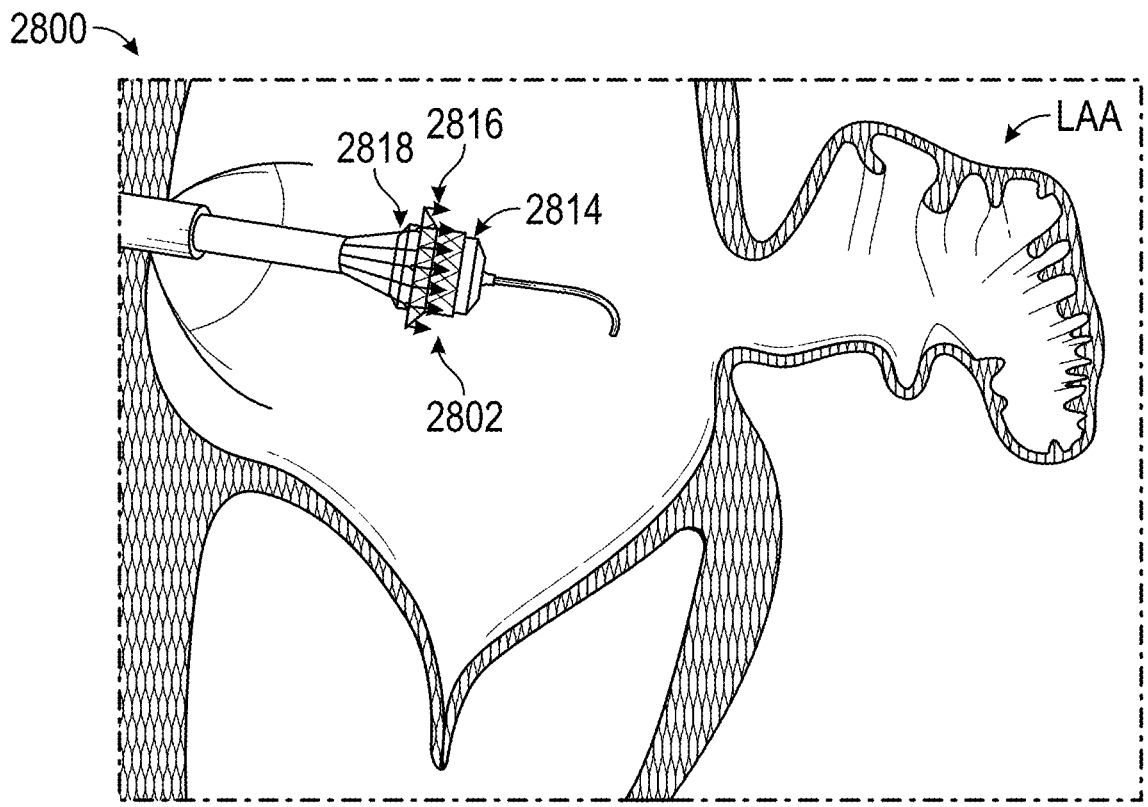
Figure 182D:
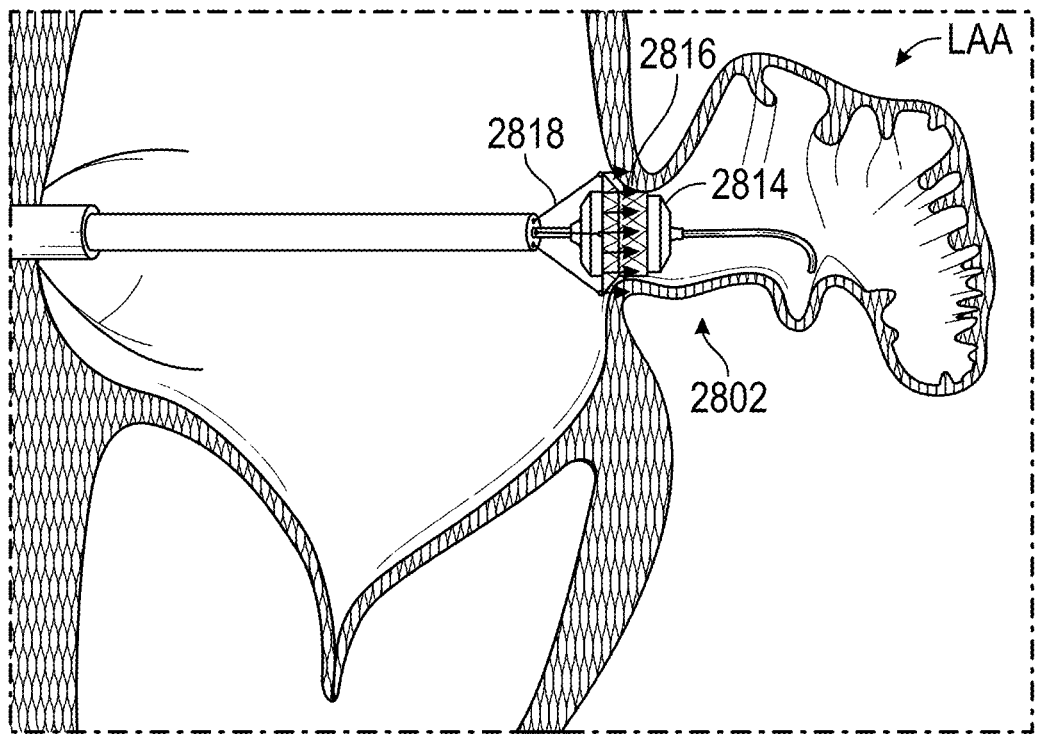
Figure 182E:
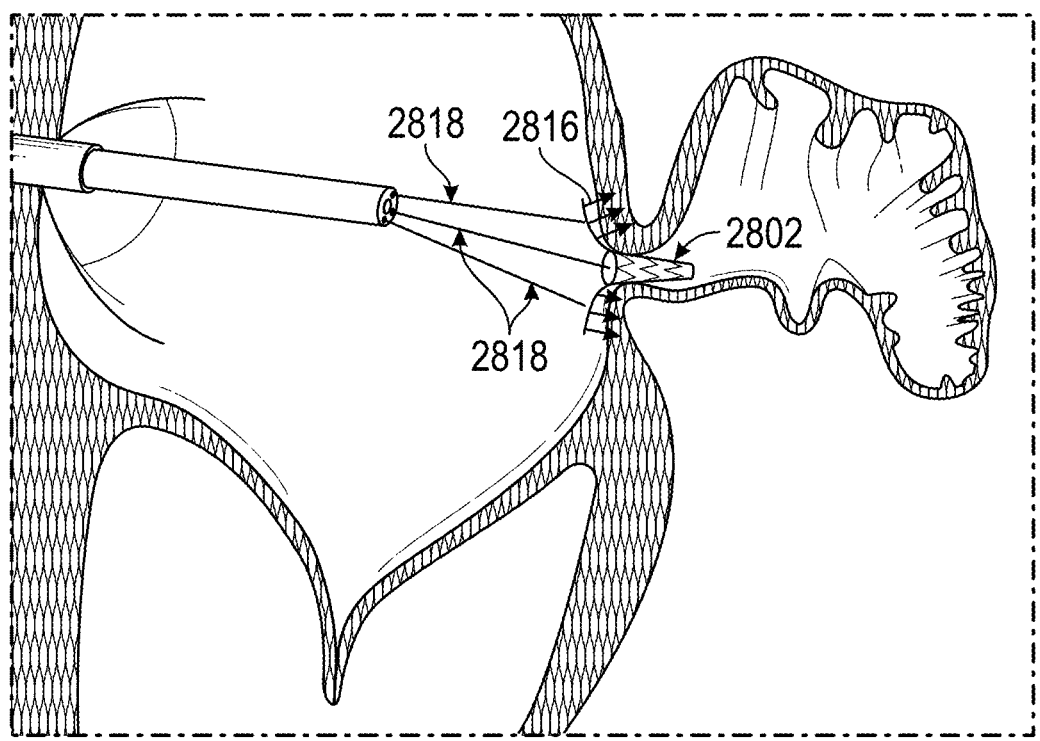
Figure 182F:
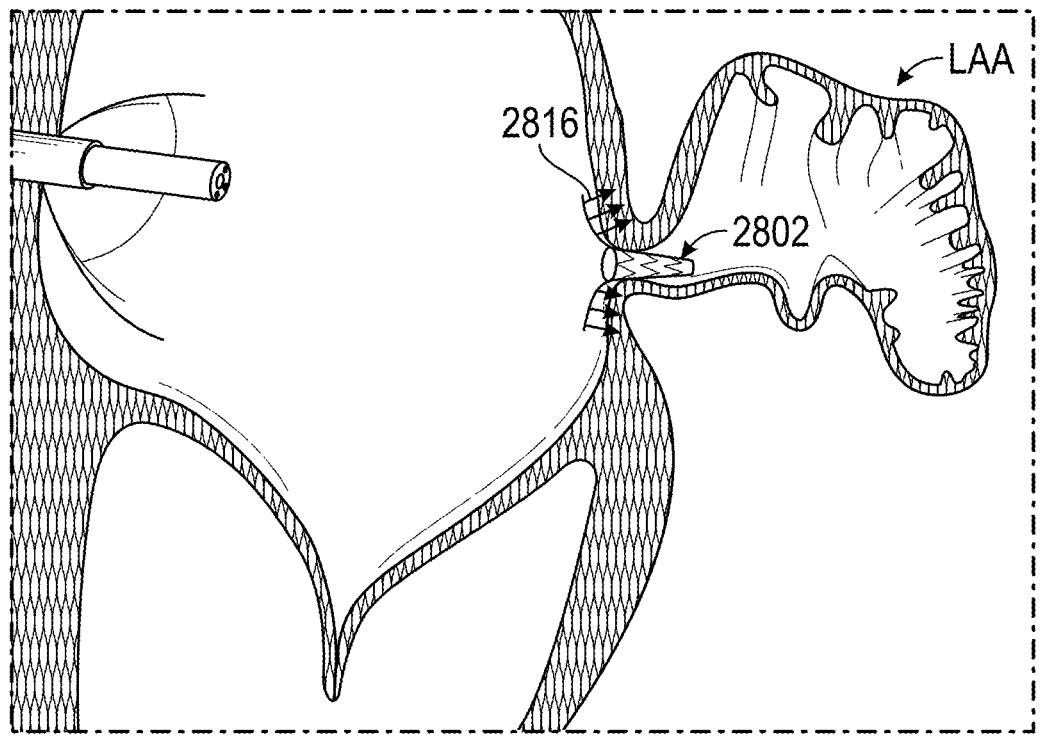

FIG. 182A illustrates a treatment system 2800 having an implant 2802 loaded into a delivery catheter 2804, coaxial and inside a guide catheter 2806 positioned in the left atrium with a guidewire 2808 also passing through the entire device and extending out the patient's body for vessel guidance. The implant 2802 is covered with a sheath 2810 for delivery and has an atraumatic tip 2812 to guide the delivery catheter through its delivery into the left atrial appendage. FIG. 182B illustrates a treatment system 2800 having a device 2802 loaded into a delivery catheter 2804 and the sheath being retracted proximally and the implant now beginning to be exposed in the left atrium with steering connections to position the device and retain its relative position with respect to the delivery catheter and anatomy. FIG. 182C illustrates the implant device 2802 fully exposed in the left atrium and partially expanded with a balloon 2814 which can be pre-mounted or introduced after the device is unsheathed. The distal facing tissue barbs 2816 are also exposed around the periphery. The device can also have one or more steering connectors 2818 coupled with a proximal end of the implant 2802, configured to assist in the manipulation and positioning of the device 2802. FIG. 182D illustrates a device 2802 now positioned into the left atrium with the balloon 2814 fully expanded and the barbs or anchors 2816 now at the ostium of the left atrial appendage ready for engagement into the surrounding tissue. FIG. 182E illustrates the device 2802 still connected to the delivery catheter, in the left atrium and left atrial appendage, the anchors and/or barbs 2816 engaged in the tissue at the ostium of the appendage with the balloon deflated and removed allowing the implant to be in its final heat-set, flat, relaxed shape thus closing the left atrial appendage from blood circulation with the left atrium. FIG. 182F illustrates the implant device 2802 now released from the delivery catheter, implanted and anchored at the ostium of the left atrial appendage with the shaped memory of the implant applying a force on the surrounding tissue to collapse the opening of the left atrial appendage with the tissue anchors and or barbs holding the surrounding engaged tissue closed to blood circulation from the left atrium.

Figure 183A:
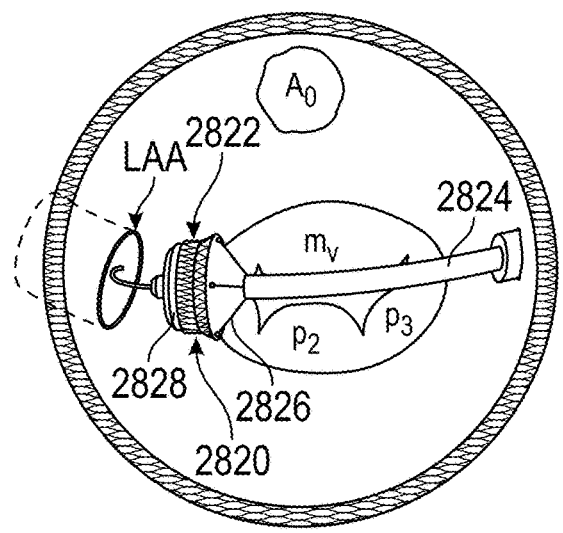
Figure 183B:
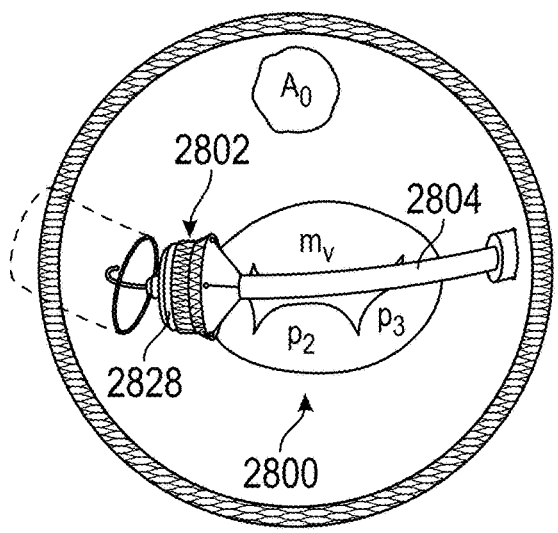
Figure 183C:
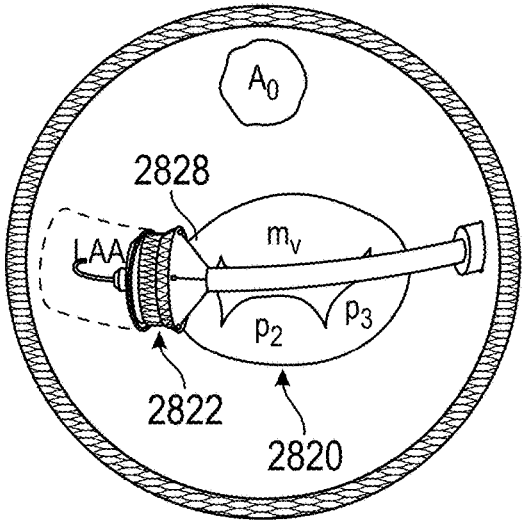
Figure 183D:
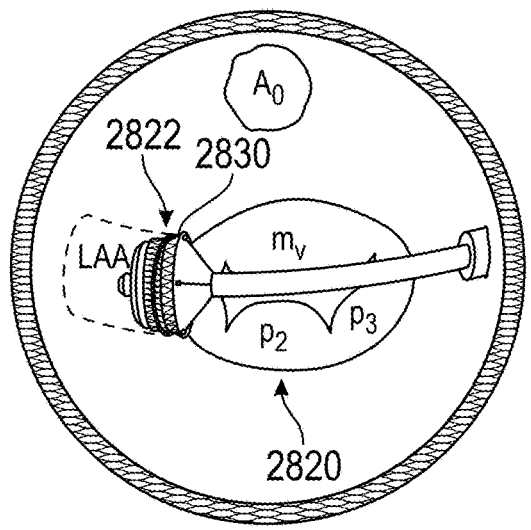
Figure 183E:
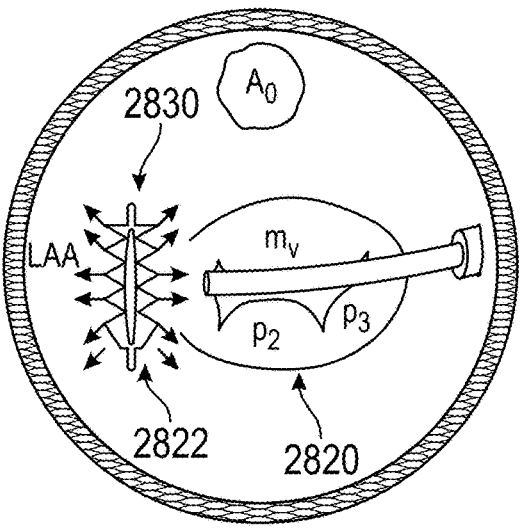

FIG. 183A illustrates an embodiment of a treatment system 2820 having an implant device 2822 unsheathed, expanded and from a surgeon's view looking into the left atrium. The implant 2822 can have any of the features or other details of the implant device 2802, and is shown connected to the delivery catheter 2824 via steering connections 2826 and the balloon 2828 is holding the implant partially open for delivery through the left atrium and in the direction of the left atrial appendage. FIG. 183B illustrates the device 2822 unsheathed, expanded and from a surgeon's view and notates the delivery catheter 2824. FIG. 183C illustrates the device 2822 unsheathed, expanded and from a surgeon's view and expanded to match the size of the left atrial appendage partially engaged into the appendage. FIG. 183D illustrates the device 2822 unsheathed, expanded and from a surgeon's view and fully engaged in the left atrial appendage with the distal facing barbs and/or anchors 2830 now penetrating the ostial tissue. FIG. 183E illustrates the device 2822 now released from the delivery catheter, implanted and anchored at the ostium of the left atrial appendage with the implant applying a force on the surrounding tissue to collapse the opening of the left atrial appendage with the tissue anchors and/or barbs 2830 holding the surrounding engaged tissue closed to blood circulation from the left atrium. In some embodiments, the inner diameter of the implant could be coated with a fabric, polymer or other sealing material to block the flow from the left atrium into the left atrial appendage.

Described herein are novel devices, systems, and methods for closing the left atrial appendage (LAA) by closing the LAA with a device applied to an outside surface of the LAA. In some embodiments, the device is applied to the LAA within the pericardial space, as will be described in greater detail. The improved devices for closing or clamping the LAA disclosed herein can be configured to flatten and/or elongate the opening of the LAA, thereby resulting in an improved seal across the ostium of the LAA. The clamp device embodiments disclosed herein can result in reduced leakage out of the LAA and potentially reduce tissue damage that may result from radially constricting devices. In some embodiments, the device can be applied across or over a neck portion of the LAA in the pericardial space, using guidewires or other devices to advance the closure device into the pericardial space and to the LAA.

FIG. 184 is an anterior view of a heart illustrating the right ventricle RV, the left ventricle LV, and the left atrial appendage LAA. The methods and apparatuses of the present disclosure are intended to place a closure mechanism over or otherwise close off the base region BR of the left atrial appendage. By closing off the base region BR, the exchange of materials between the left atrial appendage LAA and the left atrium LA can be significantly reduced or stopped. Thus, the release of emboli from the left atrial appendage into the left atrium can be significantly reduced or stopped. FIG. 185 illustrates the heart, located within the pericardial space PS located beneath the patient's rib cage RC. FIG. 185 also illustrates a possible percutaneous access site for performing the methods of the present disclosure. The sternum S is located in the center of the rib cage RC and terminates at its lower end in the Xiphoid X. On either side of the Xiphoid are the costal cartilage CC, and the percutaneous access points for performing the procedures of the present disclosure will be located beneath the rib cage RC, and preferably between the Xiphoid X and an adjacent costal cartilage CC, preferably at the access location AL shown by a broken line.

Any embodiments of the devices, systems, and methods disclosed herein can include one or more guide devices having alignment elements that can be advanced toward the target location of the LAA to aid in positioning of a closure device, as will be described in more detail below. Some embodiments comprise advancing a first guide having a first alignment member into the left atrial appendage, advancing a second guide having a second alignment member into the pericardial space, approximately axially aligning the first and second alignment members, advancing an LAA closure device into the pericardial space and adjacent to the left atrial appendage using the second alignment member, and closing the left atrial appendage with the closure device. In some embodiments, only a single guide device can be used.

Any of the devices used in any of the methods described here may be advanced under any of a variety of visualization techniques, e.g., fluoroscopic visualization, ultrasound, etc. For example, the first guide, the second guide, or both guides may be advanced under fluoroscopic visualization in some variations. Similarly, any of the devices used in any of the methods described herein can be configured to be advanced over a guide element or guide wire. For example and without limitation, the first guide, the second guide, the closure device, any additional guide, and/or any combination thereof, may be advanced over a guidewire. In some variations, the second guide can be coupled to the closure device for at least a portion of the method or procedure.

Figure 186E:
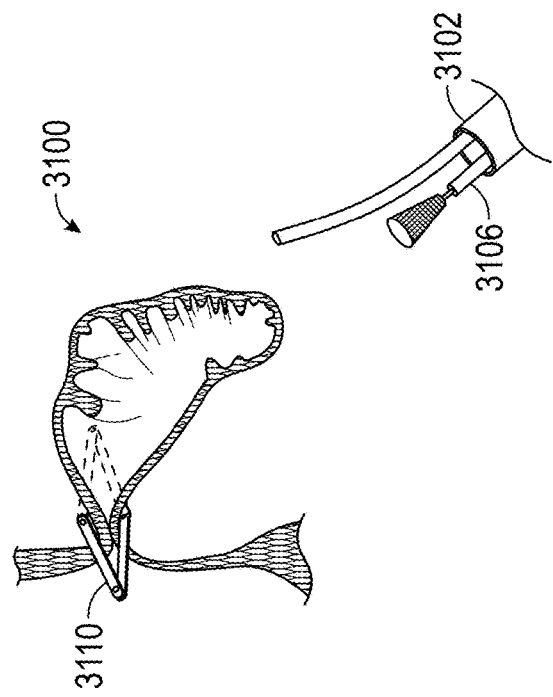

For example and without limitation, FIGS. 186A-186F show the delivery stages of an exemplifying system 3100 for closing an LAA. Some embodiments of the system 3100 can include a delivery catheter 3102, a first guide device 3104, a second guide device 3106, and a clamp device 3110. In some embodiments, the delivery catheter 3102 can have an outer sheath and a guide sheath 3103 or a guide lumen for tracking over the second guide device 3106. In any embodiments disclosed herein, the guide lumen can be formed as part of a catheter body, or can be the opening extending axially through the guide sheath. FIG. 186A shows the transseptal magnetic guidewire in the distal appendage connected to an epicardial magnetic guidewire on the outside of the distal appendage. The multi-link clamp delivery system 3100 in the nonlimiting example shown in FIGS. 186A-186F is using this guidewire system to track the clamp device to the LAA. FIG. 186A shows the system 3100 after the first guide device 3104 has been advanced into the LAA toward a distal end of the LAA and the second guide device 3106 has been advanced into the pericardial space PS to an outside surface of the LAA and into alignment (generally) with the first guide device 3104.

In any embodiments disclosed herein, the guide devices (such as guide devices 3102, 3104) can include alignment elements (such as alignment elements 3114, 3116) that can be used to approximately or generally align a portion (such as a distal portion) of a first guide device with a portion (such as a distal portion) of a second guide device. The alignment elements can be, or can comprise, any suitable device or component that is configured to align with a tissue location or another object, including another alignment element. In some embodiments, the alignment elements can be used for axial alignment through a tissue wall (including elements or devices that do and that do not penetrate the tissue wall). For example, the alignment members can each or both comprise magnets, radiopaque markers, echogenic markings, members configured to produce one or more audible signals, interconnecting or interlocking members, one or more vacuum members, or the like or any combination of the foregoing. In any embodiments disclosed herein, the alignment members can have magnets at distal ends of the alignment members that can be configured or biased to axially align with one another.

After the one or more guide devices have been advanced into the target or desired location, the delivery catheter 3102 and/or the clamp device 3110 can be advanced over the guide device (such as guide device 3106 shown in FIGS. 186A-186F) through the pericardial space toward the LAA. FIG. 186B shows the embodiment of the multi-link clamp device 3110 opening or moving from a first closed state (as shown in FIG. 186A) toward an open state to fit over the LAA. The multi-link clamp device 3110 can be configured in different sizes and may be mechanically actuated to clamp down when placed at the target location. In some embodiments, the clamp members 3120 can be straight or flat along a length thereof, or can be curved, or otherwise.

In some embodiments, the clamp device 3110 (or any other clamp devices disclosed herein) can be configured to be biased toward an open position (i.e., can be configured to be a normally open clamp device) such that, when a restraint is removed from the clamp device 3110, the clamp device with automatically move to an open position. Such normally open clamp devices can be configured to move to an open state automatically when they are advanced past a distal end of the delivery catheter. Sutures or other constricting devices or mechanisms can be used to move the clamp device to the closed position and to maintain the clamp device in the closed position.

In some embodiments, the clamp device 3110 can be at least partially housed within the elongate body of the delivery catheter 3102 during advancement of the clamp device 3110 into the pericardial space. In any embodiments disclosed herein, the clamp device (including, without limitation, the clamp device 3110) can have or define a continuous aperture therethrough or an open ended aperture. The clamp device of any embodiments disclosed herein can be configured to be clamped about or constricted over a neck portion of an LAA to isolate the LAA from the left atrium. The clamp device can have a generally flat configuration or clamping surface when the clamp is in the closed position, or can have a curved profile approximately or generally matching the contour of the closed neck portion of the LAA.

Figure 186F:
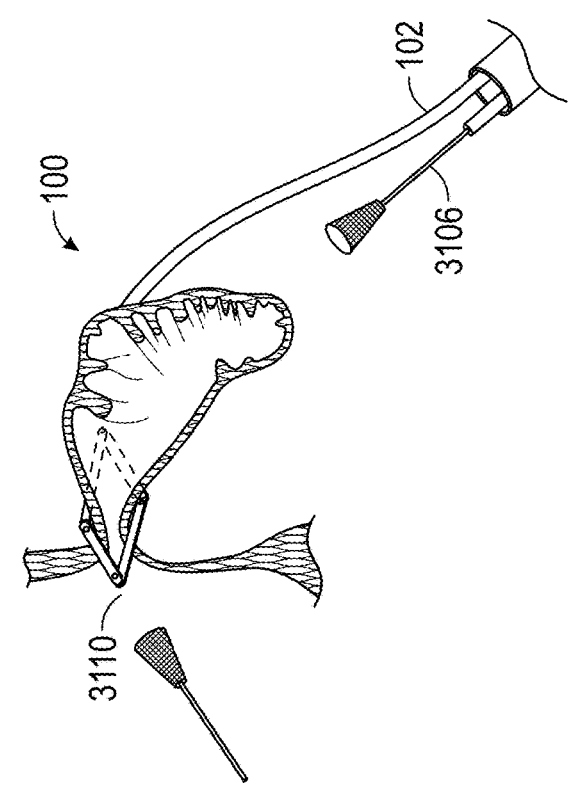

FIG. 186C shows the multi-link clamp device 3110 in an open position as the clamp device 3100 is being passed over the body of the LAA. FIG. 186D shows the multi-link clamp device 3110 positioned at a neck portion of the LAA. FIG. 186E shows the multi-link clamp device 3110 at least partially closed at the neck of the LAA. FIG. 186F shows the multi-link clamp device 3110 after the clamp device 3110 has been locked or secured about the neck portion of the LAA and released from the delivery catheter 3102.

FIGS. 187A-187E show the delivery stages of another embodiment of a clamp delivery system 3200 comprising a delivery catheter 3202, a first guide device 3204, a second guide device 3206, and a clamp device 3210 for closing an LAA. The deliver catheter 3202 can have a guide sheath 3203 or guide lumen. Any embodiments of the delivery system 3200 can have any of the same features, components, or other details of any other clamp delivery system embodiments disclosed herein, including without limitation any of the embodiments of the clamp delivery system 3200 disclosed above, in place of or in addition to any of the features, components, or other details disclosed below for delivery system 3200.

Figure 187A:
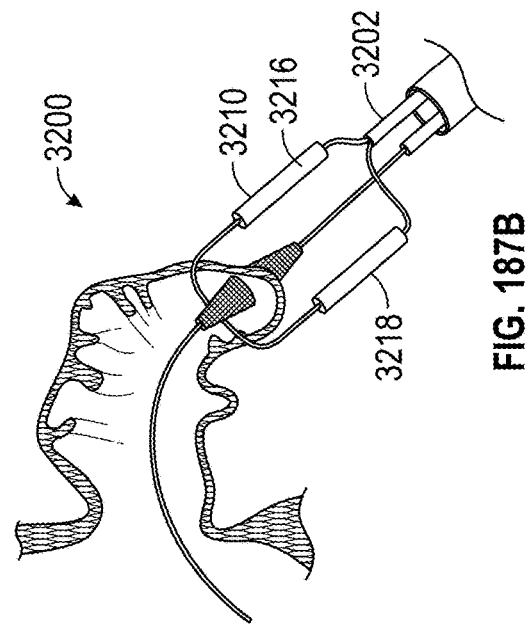
Figure 187B:
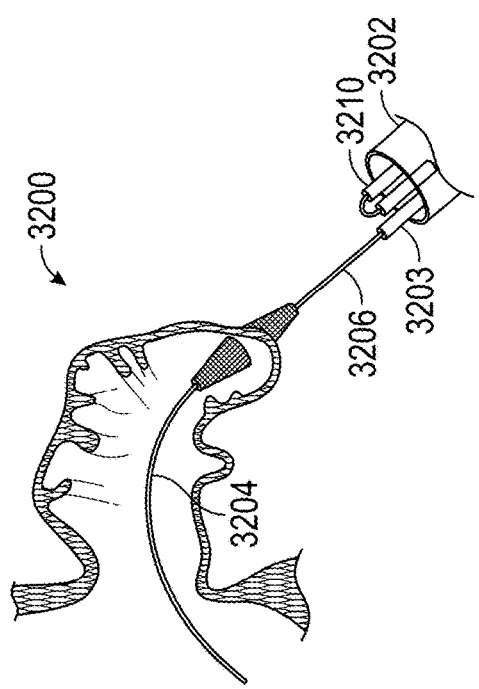
Figure 187D:
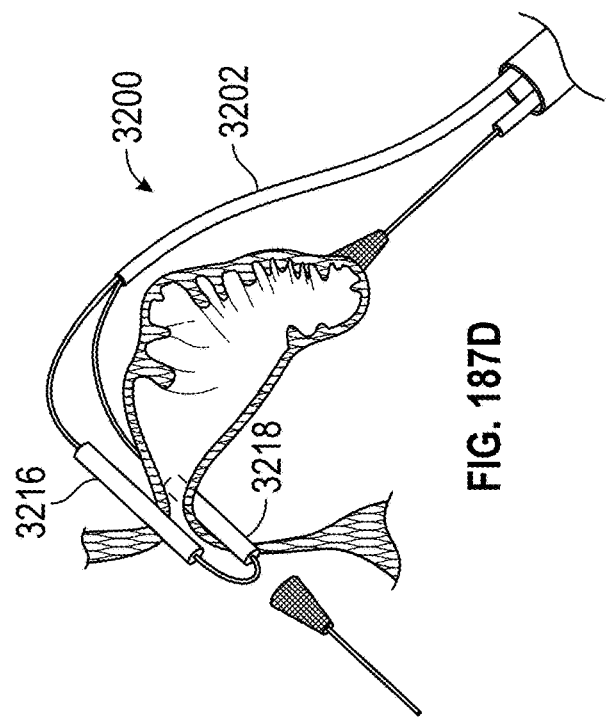
Figure 187C:
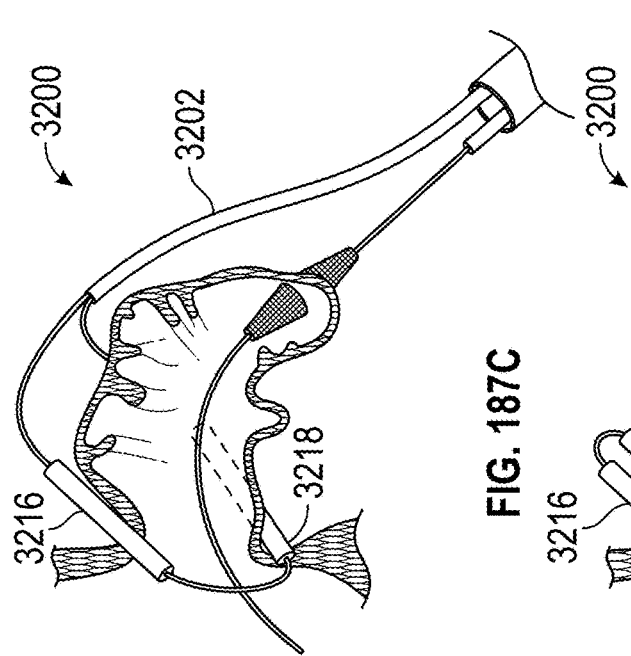
Figure 187E:
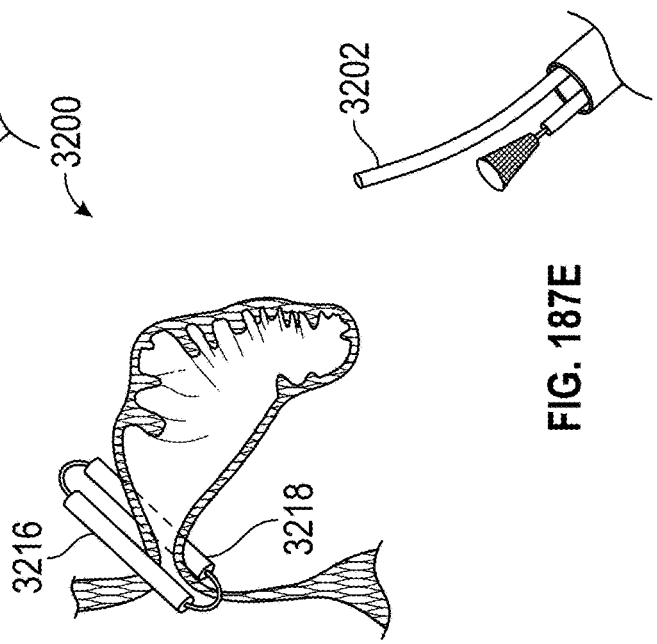

FIG. 187A shows the first guide device 3204 (which can be or comprise a transseptal magnetic guidewire) in the distal appendage aligned with or coupled with (through a distal wall of the LAA) the second guide device 3206 (which can be an epicardial magnetic guidewire) located on the outside of the distal appendage. The delivery catheter 3202 can track over the second guide device 3206 to direct the clamp device 3210 to the LAA. Any embodiments of the clamp device disclosed herein, such as without limitation claim device 3210, can have two bars or clamp members (for example, a first clamp member 3216 and a second clamp member 3218) that can be moved from a first open position, as shown in FIG. 187B to a closed position, as shown in FIG. 187D. As such, FIG. 187B shows the clamp device 3210 in an open position and being advanced toward the LAA. FIG. 187C shows the clamp device 3210 in an open position and being advanced over the body of the LAA toward the neck of the LAA. FIG. 187D shows the clamp device 3210 positioned at the neck of the LAA and partially collapsed or constricted about the neck of the LAA. FIG. 187E shows the clamp device 3210 after the clamp device 3210 has been locked or secured about the neck portion of the LAA and after the clamp device 3210 has been released from the delivery catheter.

Any embodiments of the clamp device 3210 can be provided in different sizes and/or shapes and can be mechanically actuated to clamp down when placed at the target location. Some embodiments of the clamp device 3210 can be adjustably cinched down at the lateral ends using a suture or otherwise to move the clamp device 3210 from the open state to the closed state. As such, any embodiments of the clamp device 3210 can include two rigid bars or clamping members (such as clamping members 3216, 3218) that can be configured to move together from an open state to a closed state. In the open state, the closure device can be passed over an outside surface of the LAA toward the neck region of the LAA. Once in the desired position, the clamp device 3210 can be moved from the open state to the closed state to flatten and substantially or completely close the opening of the LAA. The clamping members 3216, 3218 can be held together at the ends with a suture or other fastener, including a mechanical fastener, a spring, or otherwise, for maintaining the left atrial appendage in a flattened and substantially closed state after the LAA has been closed with the closure device. Alternatively, the closure device can comprise one or more multi-linkage rigid members held together at the ends with a suture for encircling the left atrial appendage after it has been closed with the closure device 3210.

FIGS. 188A-188E show the delivery stages of another embodiment of a clamp delivery system 3300 comprising a delivery catheter 3302, a first guide device 3304 (which can be a transseptal magnetic guidewire), a second guide device 3306 (which can be an epicardial magnetic guidewire), and a clamp device 3310 for closing an LAA. Any embodiments of the delivery system 3300 can have any of the same features, components, or other details of any other clamp delivery system embodiments disclosed herein, including without limitation any of the embodiments of the clamp delivery systems 100 or 200 disclosed above, in place of or in addition to any of the features, components, or other details disclosed below for delivery system 3300. Any embodiments of the clamp device 3310 can have a single bar clamp with a suture over a guidewire leading to the distal end of the LAA. The 1-bar clamp may come in different sizes, or shapes, and may be mechanically actuated through tensioning of the suture to clamp down when placed at the target location or may be adjustably cinched down at the lateral ends.

Figure 188A:
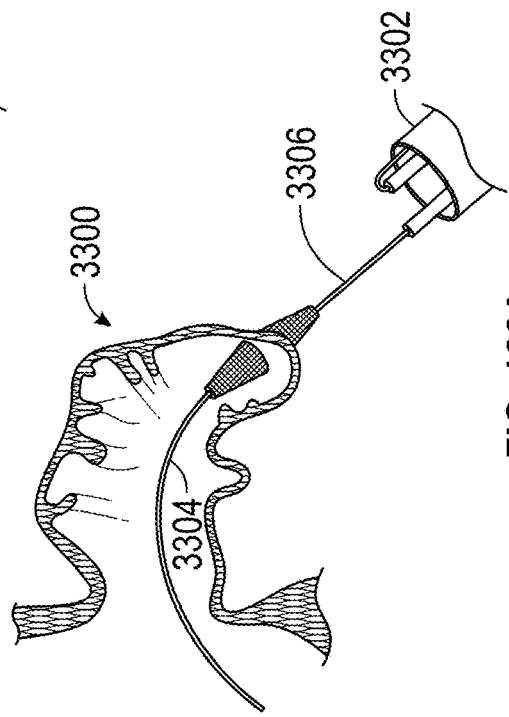

FIG. 188A shows the first guide device 3304 in the distal appendage connected to (through a distal wall of the LAA) or generally aligned with the second guide device 3306 positioned outside of the distal appendage. The embodiment of the one-bar suture clamp delivery system 3300 shown in FIG. 188A is using this guidewire system to track to the LAA. FIG. 188B shows the 1-bar clamp delivery system 3300 opening to fit over the LAA. FIG. 188C shows the embodiment of the clamp device 3310 in an open position and passing over the body of the LAA. FIG. 188D shows the embodiment of the clamp device 3310 closed at the neck of the LAA. FIG. 188E shows the embodiment of the clamp device 3310 locked, deployed, and released.

The clamp device 3310 can have a first rigid clamp member 3312 and a second flexible clamp member 3314. As shown, once in the desired position, the clamp device 3310 can be moved from the open state to the closed state by withdrawing the second flexible clamp member 3314 relative to the first rigid clamp member 3314 to flatten and substantially or completely close the opening of the LAA. The clamping members 3312, 3314 can be held together at the ends with a suture or other fastener, including a mechanical fastener, a spring, or otherwise, for maintaining the left atrial appendage in a flattened and substantially closed state after the LAA has been closed with the closure device.

Any embodiments of the clamp device disclosed herein can be configured to be movable between a first or open state and a second or closed state. In the first or open state, the clamp can have an opening therethrough that can be sized to enable the clamp to pass over the outside surface of the body of the LAA toward the neck of the LAA, as shown in FIG. 186C. Thereafter, as will be described, the clamp can be configured to be moved or be caused to automatically move to a second or closed state. In any embodiments disclosed herein, the clamp mechanism can be designed to be biased to the "normally open" state or condition where a spring (which can comprise or be a deformable wire, torsion spring, or other) can bias the clamp to be open. Activating the closure mechanism (which can be or can comprise a suture) can close the clamp. The clamp device can be configured such that, when tension is released from the closure mechanism, the clamp device can then return to the open state, or any configuration, state, or position between open and closed, based on the tension of the closure mechanism.

Any of the clamp device embodiments disclosed herein can be configured so that the clamp device can be held or maintained or locked in the closed or clamped position to maintain the LAA in a closed or substantially closed state after the procedure is completed. For example and without limitation, to lock or maintain any of the clamp device embodiments disclosed herein in the closed state, the suture can have a surgical slip knot on one end which can be tightened. This can also be done with two separate mechanisms where mechanism (1) can be used to open and close the clamp device, and mechanism (2) locks or secures the clamp device in the desired position. In this configuration, mechanism (2), which locks the clamp in the desired closed state can comprise or be a loop of suture with a surgical slip knot at the end which simply has sufficient slack in the line in the closed clamp configuration such that, when the clamp is open, the slack is removed. When this line is tightened, the slack is removed and the clamp is locked in the closed position. Then, in some embodiments, mechanism (1), which may just be a loop of suture without any slip knot, can be removed.

In some embodiments, closure of the clamping device could be achieved with just the locking suture alone. However, the addition of mechanism (1), which can be used to open and close the clamp device enables the surgeon to singularly or repeatedly reopen and reposition the clamp device after the clamp device has been closed. In some embodiments, the clamp can be configured to be a normally open type clamp, wherein the clamp is configured or biased to self-expand or automatically expand to the first or open state when the clamp is in a relaxed configuration. In this embodiment, for example and without limitation, the clamp can be configured to automatically move to the first or open state the clamp has been advanced past the distal end of the catheter sleeve.

In any embodiments disclosed herein, the clamp device (such as any embodiments of the clamp devices 3110, 3210, or 3310 disclosed herein) can be configured to be movable repeatedly between the open and closed states or positions. In this configuration, the clamp devices can be used to incrementally close or flatten the neck of the LAA, can be opened to release the LAA, repositioned, and then closed again, in any combination of steps.

In some embodiments, the clamp device can be configured to encircle the left atrial appendage without having a suture coupled to the clamp device. The closure element alone can be configured to capture and release the left atrial appendage (i.e., it can open and close around the left atrial appendage), which may help facilitate optimal closure of the left atrial appendage, prior to permanent exclusion. In any embodiments disclosed herein in which the clamp device comprises a suture, the suture can have a surgical slip knot. The slip knot can be used to hold or maintain the clamp device in the closed position, once the optimal position of the clamp device is achieved. The suture can optionally be coupled to the closure element or clamp device during advancement of the closure element or clamp device or, in other embodiments, the suture can be advanced into position about the clamp device after the clamp device has been positioned about the LAA.

Additionally, in any embodiments disclosed herein, the device can be configured so that the device has a low profile shape in the portion of the device that remains in the left atrium following implantation of the device and is otherwise configured to minimize the impact of the device on the overall volume of the left atrium and the flow of blood through the atrium. In some embodiments, the portion of the device that extends into the left atrium following implantation of the device can be minimized. For example and without limitation, the device of any embodiments disclosed herein can be configured such that only a small fraction of the overall length of the deployed device (for example and without limitation, approximately 10% or less, or approximately 15% or less, or in some embodiments approximately 20% or less of the overall length of the deployed device) extends into the left atrium following deployment.

Further, any embodiments of the devices and methods disclosed herein can be adapted or modified for use with robotic surgical devices or apparatuses. For example without limitation, any of the deployment catheters disclosed herein can be modified for use with such robotic surgical devices and apparatuses. All such applications of devices and methods disclosed herein for use with robotic systems are contemplated as forming part of the disclosure herein.

While certain embodiments of the inventions have been described, these embodiments have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure. Accordingly, the scope of the present inventions is defined only by reference to the appended claims.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a sub combination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A device for treating a left atrial appendage, comprising:
   an implant comprising:
      a contact member configured to move between a first state and a second state; and
      a securing element;
   wherein:
      at least a portion of the contact member is larger in a radial direction when the implant is in the second state as compared to the first state;
      the contact member is configured to be rotatable at least in a first direction from a first position to a second position that is at least 45 degrees from the first position to twist at least a portion of a left atrial appendage in the first direction from a first position to a second position that is at least 45 degrees from the first position of the left atrial appendage when the contact member is engaged with an inner wall of the left atrial appendage; and
      the securing element is configured to engage a tissue of the left atrium and/or the left atrial appendage to prevent the left atrial appendage that has been twisted from untwisting back to the first position of the left atrial appendage.

2. The device of claim 1, wherein the contact member is self-expandable such that at least a portion of the contact member automatically expands from the first state to the second state when a restraint is removed from the contact member.

3. The device of claim 1, wherein the device is configured to cause a tissue of the left atrium and/or the left atrial appendage to constrict around an outer surface of a body portion of the implant when the contact member is rotated to the second position, and the securing element is configured to engage with the tissue that has constricted around the outer surface of the body portion of the implant to prevent untwisting of at least a portion of the left atrial appendage back to the first position of the left atrial appendage.

4. The device of claim 1, wherein the securing element has a plurality of tissue anchors configured to engage with an internal wall of the heart adjacent to the left atrial appendage.

5. The device of claim 1, wherein the securing element has a helical shape and is configured to rotate about a body portion of the implant during the implantation procedure.

6. The device of claim 1, wherein the contact member has a plurality of tissue engaging features on an outside surface thereof.

7. The device of claim 1, wherein the second position is at least one-half of a complete rotation relative to the first position.

8. The device of claim 1, comprising a catheter selectively coupled with the contact member and configured to exert a torque on the contact member to rotate the contact member from the first position until a threshold torque level is reached.

9. The device of claim 8, wherein a threshold torque level is from approximately 0.25 in-oz of torque to approximately 10 in-oz of torque.

10. The device of claim 1, comprising a retention member configured to bias the securing element toward the contact member.

11. The device of claim 1, comprising a retention member configured to couple the securing element with the contact member.

12. The device of claim 11, wherein the retention member comprises a threaded shaft.

13. The device of claim 11, wherein the device is configured such that a rotation of the retention member in a first direction causes the securing element to move toward the contact member.

14. The device of claim 1, wherein the device is configured such that the contact member can be removed from the left atrial appendage after the securing element has been deployed.

15. The device of claim 1, wherein the device is configured such that the contact member can be removed from the left atrial appendage after the securing element has been deployed.

16. The device of claim 1, wherein the device is configured to cause a tissue of the left atrium and/or the left atrial appendage to constrict around an outer surface of a body portion of the implant when the contact member is rotated to the second position, and the securing element is configured to compress the tissue that has constricted around the outer surface of the body portion of the implant between a distal surface of the securing element and the contact member to prevent untwisting of at least a portion of the left atrial appendage back to the first position of the left atrial appendage.

17. The device of claim 1, wherein the securing element is switchable between at least a first state in which the contact member is rotatable relative to the securing element and a second state in which the securing element prevents a rotation of the contact member relative to the securing element.

18. The device of claim 1, wherein the second position is at least one-quarter of a complete rotation relative to the first position.

19. The device of claim 1, comprising a catheter having an inner core selectively coupled with the contact member and configured to rotate the contact member from the first position to the second position when the inner core is rotated from a first position to a second position when the contact member is coupled with the inner core.

20. An implant for reducing a size of an ostium of a left atrial appendage, comprising:
   a contact member configured to engage a tissue surface of the left atrial appendage and to rotate at least a portion of the left atrial appendage in a first direction to at least cause tissue of a left atrium and/or the left atrial appendage to twist and gather radially inwardly at or adjacent to an ostium of the left atrial appendage;
   a securing element configured to secure at least a portion of the tissue that has twisted and gathered radially inwardly at or adjacent to the ostium of the left atrial appendage as a result of rotating at least a portion of the left atrial appendage in the first direction; and
   a retention member configured to couple the securing element with the contact member at any of a range of distances between the securing element and the contact member.

21. The implant of claim 20, wherein the contact member is self-expandable such that at least a portion of the contact member automatically expands from a first state to a second state when a restraint is removed from the contact member.

22. The implant of claim 20, wherein the implant is configured to cause a tissue of the left atrium and/or the left atrial appendage to constrict around an outer surface of a body portion of the implant when the contact member is rotated to a second position, and the securing element is configured to engage with the tissue that has constricted around the outer surface of the body portion of the implant to prevent untwisting of at least a portion of the left atrial appendage back to the first position of the left atrial appendage.

23. The implant of claim 20, wherein the contact member has a plurality of anchors or other tissue engaging features on an outside surface thereof.

24. The implant of claim 20, wherein the securing element has a plurality of tissue anchors configured to engage with an internal wall of a heart adjacent to the left atrial appendage.

25. The implant of claim 20, wherein the contact member is configured to rotate at least a portion of the left atrial appendage at least one-half of a complete rotation in a first direction.

26. The implant of claim 20, wherein the contact member is configured to engage a tissue surface of the left atrial appendage without changing a state or shape of the contact member.

27. An implant for reducing a size of an ostium of a left atrial appendage, comprising:
- a contact member configured to engage a tissue surface of the left atrial appendage and to rotate at least a portion of the left atrial appendage in a first direction to at least cause tissue of a left atrium and/or the left atrial appendage to twist and gather radially inwardly at or adjacent to an ostium of the left atrial appendage; and
- a securing element configured to secure at least a portion of the tissue that has twisted and gathered radially inwardly at or adjacent to the ostium of the left atrial appendage as a result of rotating at least a portion of the left atrial appendage in the first direction;
- wherein the implant is configured to cause a tissue of the left atrium and/or the left atrial appendage to constrict around an outer surface of a body portion of the implant when the contact member is rotated to a second position, and the securing element is configured to engage with the tissue that has constricted around the outer surface of the body portion of the implant to prevent untwisting of at least a portion of the left atrial appendage back to the first position of the left atrial appendage.

28. The implant of claim 27, wherein the contact member is self-expandable such that at least a portion of the contact member automatically expands from a first state to a second state when a restraint is removed from the contact member.

29. The implant of claim 27, wherein the securing element has a plurality of tissue anchors configured to engage with an internal wall of a heart adjacent to the left atrial appendage.

30. The implant of claim 27, wherein the contact member is configured to rotate at least a portion of the left atrial appendage at least one-half of a complete rotation in a first direction.

* * * * *